US006492412B2

(12) United States Patent
Cameron et al.

(10) Patent No.: US 6,492,412 B2
(45) Date of Patent: Dec. 10, 2002

(54) PREVENTION OF LOSS AND RESTORATION OF BONE MASS BY CERTAIN PROSTAGLANDIN AGONISTS

(75) Inventors: Kimberly O. Cameron, East Lyme, CT (US); Hua Z. Ke, Ledyard, NY (US); Bruce A. Lefker, Gales Ferry, CT (US); Robert L. Rosati, Mystic, CT (US); David D. Thompson, Gales Ferry, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/897,824

(22) Filed: Jun. 29, 2001

(65) Prior Publication Data

US 2002/0016368 A1 Feb. 7, 2002

Related U.S. Application Data

(62) Division of application No. 09/331,081, filed as application No. PCT/IB97/01417 on Nov. 10, 1997, now Pat. No. 6,288,120.
(60) Provisional application No. 60/033,451, filed on Dec. 20, 1996.

(51) Int. Cl.$^7$ .................. A61K 31/40; A61K 31/38; A61K 31/19; C07D 207/00; C07C 303/00
(52) U.S. Cl. .................. 514/423; 514/448; 514/570; 514/605; 548/531; 549/72; 564/99; 561/470
(58) Field of Search .................. 514/605, 570, 514/448, 423; 564/99; 562/470; 549/72; 548/531

(56) References Cited

U.S. PATENT DOCUMENTS

| | | |
|---|---|---|
| 3,442,890 A | 5/1969 | Larsen et al. |
| 3,894,065 A | 7/1975 | Cragoe, Jr. et al. |
| 3,987,091 A | 10/1976 | Cragoe, Jr. et al. |
| 3,989,749 A | 11/1976 | Cragoe, Jr. et al. |
| 3,991,087 A | 11/1976 | Cragoe, Jr. et al. |
| 3,991,106 A | 11/1976 | Cragoe, Jr. et al. |
| 4,018,802 A | 4/1977 | Cragoe, Jr. et al. |
| 4,020,177 A | 4/1977 | Cragoe, Jr. et al. |
| 4,033,996 A | 7/1977 | Cragoe, Jr. et al. |
| 4,055,596 A | 10/1977 | Cragoe, Jr. et al. |
| 4,055,597 A | 10/1977 | Cragoe, Jr. et al. |
| 4,066,692 A | 1/1978 | Cragoe, Jr. et al. |
| 4,087,435 A | 5/1978 | Cragoe, Jr. et al. |
| 4,091,107 A | 5/1978 | Cragoe, Jr. et al. |
| 4,092,356 A | 5/1978 | Cragoe, Jr. et al. |
| 4,097,504 A | 6/1978 | Cragoe, Jr. et al. |
| 4,112,236 A | 9/1978 | Bicking et al. |
| 4,150,235 A | 4/1979 | Cragoe, Jr. et al. |
| 4,175,203 A | 11/1979 | Cragoe, Jr. et al. |
| 4,210,749 A | 7/1980 | Shetty |
| 4,243,678 A | 1/1981 | Krastinat |
| 4,803,197 A | 2/1989 | Wasley |
| 4,911,888 A | 3/1990 | Fikentscher et al. |
| 5,140,038 A | 8/1992 | Witte et al. |
| 5,332,730 A | 7/1994 | Chan |
| 5,407,951 A | 4/1995 | Witte et al. |
| 5,605,814 A | 2/1997 | Abramovitz et al. |
| 5,607,978 A | 3/1997 | Woodward et al. |
| 5,658,897 A | 8/1997 | Burk |
| 5,759,789 A | 6/1998 | Abramovitz et al. |
| 6,020,193 A | 2/2000 | Prockop et al. |

FOREIGN PATENT DOCUMENTS

| | | |
|---|---|---|
| AU | 632086 | 8/1990 |
| AU | 682026 | 9/1994 |
| AU | 716788 | 11/1997 |
| BE | 0897566 | 12/1983 |
| CL | 31853 | 1/1979 |
| DE | 512251 | 8/1989 |
| EP | 0528172 | 2/1993 |
| EP | 0605193 | 7/1994 |
| EP | 0606046 | 7/1994 |
| GB | 1478281 | 6/1977 |
| GB | 1479156 | 7/1977 |
| GB | 2233644 | 1/1991 |
| JP | 5019756 | 3/1975 |
| NZ | 336394 | 6/1999 |
| WO | 95056664 | 8/1993 |
| WO | WO 9636595 | 11/1995 |
| WO | WO 9727174 | 7/1997 |
| WO | 9827976 | 11/1997 |
| WO | WO 9827976 | 7/1998 |

OTHER PUBLICATIONS

Barker, et al., *Novel Thiophene–based Macrocycles related to Azacrown Ethers*, J. Chem. Soc. Chem. Commun., (1993)(23), pp. 1733–1734.

Sartori, et al., *Synthesis and activities of new arylsulfonamiko thromboxane $A_2$ receptor antagonists*, Eur.J. Med.Chem., (1993), 28(7–8), pp. 625–332.

Bicking, et al., *11, 12 Secoprostaglandins, 6. Interphenylene Analogues of Aclyhydroxyalkanoic Acids and Related Compounds as Renal Vasodilators*, J. Med. Chem., 1983, 26, 335–341.

Ludwig, B. et al., "J. Med. Chem." Jul. 1967. vol. 10, No. 4, pp 556–564, "The Synthesis of Hydroxylamine Derivatives Possessing Hypocholesteremic Activity".

Busetti, V. et al., "Recueil des Travaux Chimiques des Pays–Bas" May 1987. vol. 106, No. 5, pp 151–156, "Crystal and molecular structure of N–acetyl N–hydroxy α–amino acids".

Jones, J. H. et al., "J. Med. Chem." Oct. 1977, vol. 20, No. 10 pp 1299–1304, "11,12–Secoprostaglandins. 4. 7–(N–Aikylmethanesulfonamido)heptanoic Acids".

(List continued on next page.)

*Primary Examiner*—Deborah C. Lambkin
(74) *Attorney, Agent, or Firm*—Peter C. Richardson; Gregg C. Benson; A. Dean Olson

(57) ABSTRACT

Prostaglandin agonists, methods of using such prostaglandin agonists, pharmaceutical compositions containing such prostaglandin agonists and kits containing such prostaglandin agonists. The prostaglandin agonists are useful for the treatment of bone disorders including osteoporosis.

104 Claims, No Drawings

OTHER PUBLICATIONS

Bicking, J.B. et al., "J. Med. Chem." Oct. 1978, vol. 21, No. 10 pp 1011–1018, "11, 12–Secoprostaglandins. 5. 8–Acetyl–or 8–(1–Hydroxyethyl)–12–hydroxy–13–aryloxytridecanoic Acids and Sulfonamide Isosteres as Inhibitors of Platelet Aggregation".

Billman, J. H. et al., "J. Org. Chem." May 1961, vol. 26, pp 1437–1440, "Reduction of Schiff Bases. III. Reduction with Dimethylamine Borane".

Bolander, M. E. et al., "38th Annual Mtg Orthopaedic Research Society" Feb. 17–20, 1992, Washington D.C., pp 138, "Estrogen treatment during fracture repair strengthens healing callus in an osteoporotic model".

Regan, J. W. et al., "American Society for Pharmacology and Experimental Therapeutics" 1994, vol. 46, pp 213–220, "Cloning of a Novel Human Prostaglan din Receptor with Characteristics of the Pharmacologically Defined $EP_2$Subtype".

Bicking, J. B. et al., "J. Med. Chem." 1983, 26, pp. 335–341, "11, 12–Secoprostaglandins. 6. Interphenylene Analogues of Acylhydroxyalkanoic Acids and Related Compounds as Renal Vasodilators".

Smith, R. L. et al., "Journal of Medicinal Chemistry", 1977, vol. 20, No. 4, pp 540–547, "11, 12–Secoprostaglandins. 3. 8–Alkylthio(sulfinyl and sulfonyl)– 12–hydroxyalkanoic Acids and Related Compounds".

Jones, J. H. et al., "Journal of Medicinal Chemistry", 1977, vol. 20, No. 1, pp 44–48, 11, 12–Secoprostaglandins. 2. N–Acyl–*N*–alkyl–7–aminoheptanoic Acids.

Bicking, J.B. et al., "Journal of Medicinal Chemistry", 1977, vol. 20, No. 1, pp 35–43, 11, 12–Secoprostaglandins. 1. Acylhydroxyalkanoic Acids and Related Compounds.

Smith, R. L. et al., "Journal of Medicinal Chemistry", 1977, vol. 20, No. 10, pp 1292–1299, "Prostaglandin Isosteres. 1. (8–Aza–a, 8, 10–Diaza–, and 8–Aza–11–thia)–9–oxoprostanoic Acids anf Their Derivatives".

Fukumoto, S, et al., "Journal of Medicinal Chemistry", 1992, vol. 35, No 13, pp 2202–2209, "Antagonistic Activity of Phenol Derivatives".

Florence N. Woodiel, et al., "Anabolic Effects of Prostaglandins in Cultured Fetal Rate Calvariae: Structure–Activity Relations and Signal Transduction Pathway" Journal of Bone and Mineral Research, vol. 11 No. 9, 1996, pp 1249–1255.

A. Scutt, et al., "$PGE_2$ Induces the Transition from Non–Adherent to Adherent Bone Marrow Mesenchymal Precursor Cells Via a cAMP/$EP_2$–Mediated Mechanism" Prostaglandins 49:383–395, 1995.

PREVENTION OF LOSS AND RESTORATION OF BONE MASS BY CERTAIN PROSTAGLANDIN AGONISTS

This application is a divisional application of U.S. application Ser. No. 09/331,081 filed on Jun. 11, 1999. U.S. Pat. No. 6,288,120, which was filed under 35 U.S.C. §371 based on PCT/IB97/01417 which was filed on Nov. 10, 1997 which claims priority from U.S. provisional application no. 60/033,451 which was filed on Dec. 20, 1996 and is now abandoned.

BACKGROUND OF INVENTION

This invention relates to prostaglandin agonists, pharmaceutical compositions containing such agonists and the use of such agonists to prevent bone loss or restore or augment bone mass including the treatment of conditions which present with low bone mass in mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being physically impaired.

The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen failed to restore bone back to young adult levels in the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton.

U.S. Pat. No. 4,112,236 discloses certain interphenylene 8-aza-9-dioxothia-11,12-secoprostaglandins for the treatment of patients with renal impairment.

Certain prostagladin agonists are disclosed in GB 1478281, GB1479156 and U.S. Pat. Nos. 4,175,203, 4,055, 596, 4,175,203, 3,987,091 and 3,991,106 as being useful as, for example, renal vasodilators.

U.S. Pat. No. 4,033,996 discloses certain 8-aza-9-oxo(and dioxo)-thia-1 1,12- secoprostaglandins which are useful as renal vasodilators, for the prevention of thrombus formation, to induce growth hormone release, and as regulators of the immune response.

French patent no. 897,566 discloses certain amino acid derivatives for the treatment of neurological, mental or cardiovascular disease. J. Org. Chem. 26; 1961; 1437 discloses N-acetyl-N-benzyl-p-aminophenylmercaptoacetic acid.

In addition to osteoporosis, approximately, 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population. While there are several promising therapies (bis-phosphonates, etc.) in development to prevent bone loss with age and thus reduce the probability of incurring debilitating fractures, these therapies are not indicated for restoration of bone mass once the fracture has occurred.

Estrogens have been shown (Bolander et al., 38th Annual Meeting Orthopedic Research Society, 1992) to improve the quality of the healing of appendicular fractures. Therefore, estrogen replacement therapy might appear to be a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. Clearly the need exists for a therapy which would be beneficial to patients who have suffered debilitating bone fractures or who have low bone mass and which would increase patient compliance.

Although there are a variety of osteoporosis therapies there is a continuing need and a continuing search in this field of art for alternative osteoporosis therapies. In addition, there is a need for bone fracture healing therapies.

SUMMARY OF THE INVENTION

This invention is directed to a compound of Formula I

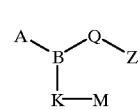

Formula I or a pharmaceutically-acceptable salt or prodrug thereof wherein either (i):

B is N;

A is $(C_1-C_6)$alkylsulfonyl, $(C_3-C_7)$cycloalkylsulfonyl, $(C_3-C_7)$cycloalkyl$(C_1-C_6)$ alkylsulfonyl, said A moieties optionally mono-, di- or tri-substituted on carbon independently with hydroxy, $(C_1-C_4)$alkyl or halo;

Q is

—($C_2$–$C_6$)alkylene-W—($C_1$–$C_3$)alkylene-,

—($C_3$–$C_8$)alkylene-, said —($C_3$–$C_8$)alkylene- optionally substituted with up to four substituents independently selected from fluoro or ($C_1$–$C_4$)alkyl, —X—($C_1$–$C_5$)alkylene-, —($C_1$–$C_5$)alkylene-X-, —($C_1$–$C_3$)alkylene-X—($C_1$–$C_3$)alkylene-, —($C_2$–$C_4$)alkylene-W-X—($C_0$–$C_3$)alkylene-, —($C_0$–$C_4$)alkylene-X-W—($C_1$–$C_3$)alkylene-, —($C_2$–$C_5$)alkylene-W-X-W—($C_1$–$C_3$)alkylene-, wherein the two occurrences of W are independent of each other, —($C_1$–$C_4$)alkylene-ethenylene—($C_1$–$C_4$)alkylene-, —($C_1$–$C_4$)alkylene-ethenylene—($C_0$–$C_2$)alkylene-X—($C_0$–$C_5$)alkylene-, —($C_1$–$C_4$)alkylene-ethenylene—($C_0$–$C_2$)alkylene-X-W—($C_1$–$C_3$)alkylene-, —($C_1$–$C_4$)alkylene-ethynylene—($C_1$–$C_4$)alkylene-, or —($C_1$–$C_4$)alkylene-ethynylene-X—($C_0$–$C_3$)alkylene-;

W is oxy, thio, sulfino, sulfonyl, aminosulfonyl-, -mono-N—($C_1$–$C_4$) alkyleneaminosulfonyl-, sulfonylamino, N—($C_1$–$C_4$)alkylenesulfonylamino, carboxamido, N—($C_1$–$C_4$)alkylenecarboxamido, carboxamidooxy, N—($C_1$–$C_4$) alkylenecarboxamidooxy, carbamoyl, -mono-N—($C_1$–$C_4$)alkylenecarbamoyl, carbamoyloxy, or -mono-N—($C_1$–$C_4$)alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, or di- substituted independently with halo, ($C_1$–$C_3$)alkyl, trifluoromethyl, trifluoromethyloxy, difluoromethyloxy, hydroxyl, ($C_1$–$C_4$)alkoxy, or carbamoyl;

Z is carboxyl, ($C_1$–$C_6$)alkoxycarbonyl, tetrazolyl, 1,2,4-oxadiazolyl, 5-oxo-1,2,4- oxadiazolyl, ($C_1$–$C_4$) alkylsulfonylcarbamoyl or phenylsulfonylcarbamoyl;

K is a bond, ($C_1$–$C_8$)alkylene, thio($C_1$–$C_4$)alkylene or oxy($C_1$–$C_4$)alkylene, said ($C_1$–$C_8$)alkylene optionally mono-unsaturated and wherein K is optionally mono-, di- or tri-substituted independently with fluoro, methyl or chloro;

M is —Ar, —$Ar^1$—V—$Ar^2$, —$Ar^1$—S—$Ar^2$ or —Ar—O—$Ar^2$ wherein Ar, $Ar^1$ and $Ar^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, $Ar^1$ and $Ar^2$ moieties optionally substituted, on one ring if the moiety is monocycic, or one or both rings if the moiety is bicyclic, on carbon with up to three substituents independently selected from $R^1$, $R^2$ and $R^3$ wherein $R^1$, $R^2$ and $R^3$ are hydroxy, nitro, halo, ($C_1$–$C_6$)alkoxy, ($C_1$–$C_4$)alkoxy($C_1$–$C_4$)alkyl, ($C_1$–$C_4$) alkoxycarbonyl, ($C_1$–$C_7$)alkyl, ($C_3$–$C_7$)cycloalkyl, ($C_3$–$C_7$)cycloalkyl($C_1$–$C_4$)alkyl, ($C_3$–$C_7$)cycloalkyl ($C_1$–$C_4$) alkanoyl, formyl, ($C_1$–$C_8$)alkanoyl, ($C_1$–$C_6$) alkanoyl($C_1$–$C_6$)alkyl, ($C_1$–$C_4$) alkanoylamino, ($C_1$–$C_4$)alkoxycarbonylamino, sulfonamido, ($C_1$–$C_4$) alkylsulfonamido, amino, mono-N- or di-N,N—($C_1$–$C_4$)alkylamino, carbamoyl, mono-N- or di-N,N—($C_1$–$C_4$)alkylcarbamoyl, cyano, thiol, ($C_1$–$C_6$) alkylthio, ($C_1$–$C_6$)alkylsulfinyl, ($C_1$–$C_4$)alkylsulfonyl or mono-N- or di-N,N—($C_1$–$C_4$)alkylaminosulfinyl;

$R^1$, $R^2$ and $R^3$ are optionally mono-, di- or tri-substituted on carbon independently with halo or hydroxy; and V is a bond or ($C_1$–$C_3$)alkylene optionally mono- or di-substituted independently with hydroxy or fluoro with the proviso that when K is ($C_2$–$C_4$)alkylene and M is Ar and Ar is cyclopent-1-yl, cyclohex-1-yl, cyclohept-1-yl or cyclooct-1-yl then said ($C_5$–$C_8$) cycloalkyl substituents are not substituted at the one position with hydroxy;

or (ii):

B is N;

A is ($C_1$–$C_6$)alkanoyl, or ($C_3$–$C_7$)cycloalkyl($C_1$–$C_6$) alkanoyl, said A moieties optionally mono-, di- or tri-substituted independently on carbon with hydroxy or halo;

Q is

—($C_2$–$C_6$)alkylene-W—($C_1$–$C_3$)alkylene-,

—($C_4$–$C_6$)alkylene-, said —($C_4$–$C_8$)alkylene-optionally substituted with up to four substituents independently selected from fluoro or ($C_1$–$C_4$)alkyl, —X—($C_2$–$C_5$)alkylene-, —($C_1$–$C_5$)alkylene-X-, —($C_1$–$C_3$)alkylene-X—($C_1$–$C_3$)alkylene-, —($C_2$–$C_4$)alkylene-W-X—($C_0$–$C_3$)alkylene-, —($C_0$–$C_4$)alkylene-X-W—($C_1$–$C_3$)alkylene-, —($C_2$–$C_5$)alkylene-W-X-W—($C_1$–$C_3$)alkylene-, wherein the two occurrences of W are independent of each other, —($C_1$–$C_4$)alkylene-ethenylene—($C_1$–$C_4$)alkylene-, —($C_1$–$C_4$)alkylene-ethenylene—($C_0$–$C_2$)alkylene-X—($C_0$–$C_5$)alkylene-, —($C_1$–$C_4$)alkylene-ethenylene—($C_0$–$C_2$)alkylene-X-W—($C_1$–$C_3$)alkylene-, —($C_1$–$C_4$)alkylene-ethynylene—($C_1$–$C_4$)alkylene-, or —($C_1$–$C_4$)alkylene-ethynylene-X—($C_0$–$C_3$)alkylene-;

W is oxy, thio, sulfino, sulfonyl, aminosulfonyl-, -mono-N—($C_1$-$_4$)alkyleneaminosulfonyl-, sulfonylamino, N—($C_1$–$C_4$)alkylenesulfonylamino, arboxamido, N—($C_1$–$C_4$)alkylenecarboxamido, carboxamidooxy, N—($C_1$–$C_4$) alkylenecarboxamidooxy, carbamoyl, -mono-N—($C_1$–$C_4$)alkylenecarbamoyl, carbamoyloxy, or -mono-N—($C_1$–$C_4$)alkylenecarbamoyloxy, wherein said W alkyl groups are optionally substituted on carbon with one to three fluorines;

X is a five or six membered aromatic ring optionally having one or two heteroatoms independently selected from oxygen, nitrogen, and sulfur; said ring optionally mono-, or di- substituted independently with halo, ($C_1$–$C_3$)alkyl, trifluoromethyl, trifluoromethyloxy, difluoromethyloxy, hydroxyl, ($C_1$–$C_4$)alkoxy, or carbamoyl;

Z is carboxyl, ($C_1$–$C_6$)alkoxycarbonyl, tetrazolyl, 1,2,4-oxadiazolyl, 5-oxo-1,2,4- oxadiazolyl, ($C_1$–$C_4$) alkylsulfonylcarbamoyl or phenylsulfonylcarbamoyl;

K is ($C_1$–$C_8$)alkylene, thio($C_1$–$C_4$)alkylene or oxy ($C_1$–$C_4$)alkylene, said ($C_1$–$C_8$) alkylene optionally mono-unsaturated and wherein K is optionally mono-, di- or tri-substituted independently with fluoro, methyl or chloro;

M is —Ar, —Ar$^1$—V—Ar$^2$, —Ar$^1$—S—Ar$^2$ or —Ar$^1$—O—Ar$^2$ wherein Ar, Ar$^1$ and Ar$^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, Ar$^1$ and Ar$^2$ moieties optionally substituted, on one ring if the moiety is monocyclic, or one or both rings if the moiety is bicyclic, on carbon with up to three substituents independently selected from R$^1$, R$^2$ and R$^3$ wherein R$^1$, R$^2$ and R$^3$ are H, hydroxy, nitro, halo, (C$_1$–C$_6$)alkoxy, (C$_1$–C$_4$)alkoxy(C$_1$–C$_4$)alkyl, (C$_1$–C$_4$)alkoxycarbonyl, (C$_1$–C$_7$)alkyl, (C$_3$–C$_7$)cycloalkyl, (C$_3$–C$_7$)cycloalkyl(C$_1$–C$_4$)alkyl, (C$_3$–C$_7$)cycloalkyl(C$_1$–C$_4$) alkanoyl, formyl, (C$_1$–C$_8$)alkanoyl, (C$_1$–C$_6$)alkanoyl(C$_1$–C$_6$)alkyl, (C$_1$–C$_4$)alkanoylamino, (C$_1$–C$_4$)alkoxycarbonylamino, sulfonamido, (C$_1$–C$_4$) alkylsulfonamido, amino, mono-N- or di-N,N—(C$_1$–C$_4$)alkylamino, carbamoyl, mono-N- or di-N,N—(C$_1$–C$_4$)alkylcarbamoyl, cyano, thiol, (C$_1$–C$_6$)alkylthio, (C$_1$–C$_6$)alkylsulfinyl, (C$_1$–C$_4$)alkylsulfonyl or mono-N- or di-N,N—(C$_1$–C$_4$)alkylaminosulfinyl;

R$^1$, R$^2$ and R$^3$ are optionally mono-, di- or tri-substituted on carbon independently with halo or hydroxy; and V is a bond or (C$_1$–C$_3$)alkylene optionally mono- or di-substituted independently with hydroxy or fluoro with the proviso that when K is (C$_2$–C$_4$)alkylene and M is Ar and Ar is cyclopent-1-yl, cyclohex-1-yl, cyclohept-1-yl or cycloct-1-yl then said (C$_5$–C$_8$) cycloalkyl substituents are not substituted at the one position with hydroxy and with the proviso that 6-[(3-Phenyl-propyl)-(2-propyl-pentanoyl)-amino]- hexanoic acid and its ethyl ester are not included or (iii):

B is C(H);

A is (C$_1$–C$_6$)alkanoyl, or (C$_3$–C$_7$)cycloalkyl(C$_1$–C$_6$) alkanoyl, said A moieties optionally mono-, di- or tri-substituted on carbon independently with hydroxy or halo;

Q is

—(C$_2$–C$_6$)alkylene-W—(C$_1$–C$_3$)alkylene-,

—(C$_4$–C$_8$)alkylene-, said —(C$_4$–C$_8$)alkylene-optionally substituted with up to four substituents independently selected from fluoro or (C$_1$–C$_4$)alkyl, —X—(C$_1$–C$_5$)alkylene-, —(C$_1$–C$_5$)alkylene-X-, —(C$_1$–C$_3$)alkylene-X—(C$_1$–C$_3$)alkylene-, —(C$_2$–C$_4$)alkylene-W-X—(C$_0$–C$_3$)alkylene-, —(C$_0$–C$_4$)alkylene-X-W—(C$_1$–C$_3$)alkylene-, —(C$_2$–C$_5$)alkylene-W-X-W—(C$_1$–C$_3$)alkylene-, wherein the two occurrences of W are independent of each other, —(C$_1$–C$_4$)alkylene-ethenylene—(C$_1$–C$_4$)alkylene-, —(C$_1$–C$_4$)alkylene-ethenylene—(C$_0$–C$_2$)alkylene-X—(C$_0$–C$_5$)alkylene-, —(C$_1$–C$_4$)alkylene-ethenylene—(C$_0$–C$_2$)alkylene-X-W—(C$_1$–C$_3$)alkylene-, —(C$_1$–C$_4$)alkylene-ethynylene—(C$_1$–C$_4$)alkylene-, or —(C$_1$–C$_4$)alkylene-ethynylene-X—(C$_0$–C$_3$)alkylene-;

W is oxy, thio, sulfino, sulfonyl, aminosulfonyl-, -mono-N—(C$_1$–C$_4$) alkyleneaminosulfonyl-, sulfonylamino, N—(C$_1$–C$_4$)alkylenesulfonylamino, carboxamido, N—(C$_1$–C$_4$)alkylenecarboxamido, carboxamidooxy, N—(C$_1$–C$_4$) alkylenecarboxamidooxy, carbamoyl, -mono-N—(C$_1$–C$_4$)alkylenecarbamoyl, carbamoyloxy, or -mono-N—(C$_1$–C$_4$)alkylenecarbamoyloxy, wherein said W alkyl groups are optionally substituted on carbon with one to three fluorines;

X is a five or six membered aromatic ring optionally having one or two heteroatoms selected independently from oxygen, nitrogen and sulfur; said ring optionally mono-, or di- substituted independently with halo, (C$_1$–C$_3$)alkyl, trifluoromethyl, trifluoromethyloxy, difluoromethyloxy, hydroxyl, (C$_1$–C$_4$)alkoxy, or carbamoyl;

Z is carboxyl, (C$_1$–C$_6$)alkoxycarbonyl, tetrazolyl, 1,2,4-oxadiazolyl, 5-oxo-1,2,4-oxadiazolyl, (C$_1$–C$_4$) alkylsulfonylcarbamoyl or phenylsulfonylcarbamoyl;

K is a bond, (C$_1$–C$_8$)alkylene, thio(C$_1$–C$_4$)alkylene, (C$_4$–C$_7$)cycloalkyl(C$_1$–C$_6$) alkylene or oxy(C$_1$–C$_4$) alkylene, said (C$_1$–C$_8$)alkylene optionally mono-unsaturated and wherein K is optionally mono-, di- or tri-substituted independently with fluoro, methyl or chloro;

M is —Ar, —Ar$^1$—V—Ar$^2$, —Ar$^1$—S—Ar$^2$ or —Ar$^1$—O—Ar$^2$ wherein Ar, Ar$^1$ and Ar$^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, Ar$^1$ and Ar$^2$ moieties optionally substituted, on one ring if the moiety is monocyclic, or one or both rings if the moiety is bicyclic, on carbon with up to three substituents independently selected from R$^1$, R$^2$ and R$^3$ wherein R$^1$, R$^2$ and R$^3$ are H, hydroxy, nitro, halo, (C$_1$–C$_6$)alkoxy, (C$_1$–C$_4$)alkoxy(C$_1$–C$_4$)alkyl, (C$_1$–C$_4$)alkoxycarbonyl, (C$_1$–C$_7$)alkyl, (C$_3$–C$_7$)cycloalkyl, (C$_3$–C$_7$)cycloalkyl(C$_1$–C$_4$)alkyl, (C$_3$–C$_7$)cycloalkyl(C$_1$–C$_4$) alkanoyl, formyl, (C$_1$–C$_8$)alkanoyl, (C$_1$–C$_6$)alkanoyl(C$_1$–C$_6$)alkyl, (C$_1$–C$_4$)alkanoylamino, (C$_1$–C$_4$)alkoxycarbonylamino, sulfonamido, (C$_1$–C$_4$) alkylsulfonamido, amino, mono-N- or di-N,N—(C$_1$–C$_4$)alkylamino, carbamoyl, mono-N- or di-N,N—(C$_1$–C$_4$)alkylcarbamoyl, cyano, thiol, (C$_1$–C$_6$)alkylthio, (C$_1$–C$_6$)alkylsulfinyl, (C$_1$–C$_4$) alkylsulfonyl or mono-N- or di-N,N—(C$_1$–C$_4$) alkylaminosulfinyl;

R$^1$, R$^2$ and R$^3$ are optionally mono-, di- or tri-substituted independently on carbon with halo or hydroxy; and V is a bond or (C$_1$–C$_3$)alkylene optionally mono- or di-substituted independently with hydroxy or fluoro with the proviso that when K is (C$_2$–C$_4$)alkylene and M is Ar and Ar is cyclopent-1-yl, cyclohex-1-yl, cyclohept-1-yl or cyclooct-1-yl then said (C$_5$–C$_8$) cycloalkyl substituents are not substituted at the one position with hydroxy.

A preferred group of compounds, designated the A Group, contains those compounds having the Formula I as shown above wherein B is N;

A is $(C_1–C_6)$alkylsulfonyl, $(C_3–C_6)$cycloalkylsulfonyl or $(C_3–C_6)$cycloalkyl$(C_1–C_6)$ alkylsulfonyl, said A moieties optionally mono-, di-, or tri-substituted on carbon with fluoro;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethoxy;

W is oxy, thio or sulfonyl;

Z is carboxyl, $(C_1–C_4)$alkoxycarbonyl or tetrazolyl;

K is methylene or ethylene;

Ar, $Ar^1$ and $Ar^2$ are each independently $(C_5–C_7)$ cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, $(C_1–C_6)$alkoxy, $(C_1–C_7)$alkyl, $(C_3–C_7)$ cycloalkyl, or $(C_3–C_7)$ cycloalkyl$(C_1–C_4)$alkyl, said $(C_1–C_6)$alkoxy, $(C_1–C_7)$alkyl, $(C_3–C_7)$cycloalkyl or $(C_3–C_7)$ cycloalkyl$(C_1–C_4)$alkyl, optionally mono-, di- or tri-substituted independently with hydroxy, fluoro or chloro; and $R^2$ and $R^3$ are chloro, fluoro, methyl, methoxy, difluoromethoxy, trifluoromethoxy or trifluoromethyl.

A group of compounds which is preferred among the A Group of compounds designated the B Group, contains those compounds wherein A is $(C_1–C_3)$alkylsulfonyl;

Q is

—$(C_2–C_6)$alkylene-W—$(C_1–C_3)$alkylene-,

—$(C_4–C_8)$alkylene-, said —$(C_4–C_8)$alkylene-optionally substituted with up to four substituents independently selected from fluoro or $(C_1–C_4)$alkyl, —X—$(C_2–C_5)$alkylene-, —$(C_1–C_5)$alkylene-X-, —$(C_1–C_3)$alkylene-X—$(C_1–C_3)$alkylene-, —$(C_2–C_4)$alkylene-W-X—$(C_0–C_3)$alkylene-, or —$(C_0–C_4)$alkylene-X-W—$(C_1–C_3)$alkylene-;

M is —$Ar^1$—V—$Ar^2$ or —$Ar^1$—O—$Ar^2$ wherein $Ar^1$ and $Ar^2$ are each independently phenyl, pyridyl or thienyl;

V is a bond or $(C_1–C_2)$alkylene;

$R^1$ is chloro, fluoro, $(C_1–C_4)$alkyl or $(C_1–C_4)$alkoxy, said $(C_1–C_4)$alkyl and $(C_1–C_4)$ alkoxy optionally mono-, di- or tri-substituted independently with hydroxy or fluoro; and $R^2$ and $R^3$ are each independently chloro or fluoro.

Especially preferred compounds within the B Group of compounds are

7-[(2'-Hydroxymethyl-biphenyl-4-ylmethyl)-methanesulfonyl-amino]-heptanoic acid, 7-{[4-(3-Hydroxymethyl-thiophen-2-yl)-benzyl]-methanesulfonyl-amino}-heptanoic acid, and 7-[(2'-Chloro-biphenyl-4-ylmethyl)-methanesulfonyl-amino]-heptanoic acid.

Especially preferred compounds within the B Group of compounds are compounds wherein a. A is methylsulfonyl;
   Q is n-hexylene;
   Z is carboxyl;
   K is methylene; and
   M is 4-(2-hydroxymethylphenyl)phenyl;

b. A is methylsulfonyl;
   Q is n-hexylene;
   Z is carboxyl;
   K is methylene; and
   M is 4-(3-hydroxymethylthien-2-yl)phenyl; and c. A is methylsulfonyl;
   Q is n-hexylene;
   Z is carboxyl;
   K is methylene; and
   M is 4-(2-chlorophenyl)phenyl.

A preferred group of compounds, designated the C Group, contains those compounds having the Formula I as shown above wherein B is N;

A is $(C_1–C_6)$alkylsulfonyl, $(C_3–C_6)$cycloalkylsulfonyl, $(C_3–C_6)$cycloalkyl$(C_1–C_6)$ alkylsulfonyl;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethyloxy;

W is oxy, thio or sulfonyl;

Z is carboxyl, $(C_1–C_4)$alkoxycarbonyl or tetrazolyl;

K is $(C_1–C_8)$alkylene or oxy$(C_1–C_4)$alkylene, said $(C_1–C_8)$alkylene optionally mono-unsaturated and wherein K is optionally mono-, di- or tri-substituted independently with methyl, fluoro or chloro;

M is —Ar, said —Ar is phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, imidazolyl, quinolinyl, isoquinolinyl, benzoxazolyl, benzothiazolyl, indolyl, 1,2,3,4-tetrahydronaphthalenyl, cyclohexyl, cyclopentyl, cyclobutyl, cycloheptyl or chromanyl;

$R^1$ is halo, $(C_1–C_6)$alkoxy, $(C_1–C_7)$alkyl, $(C_3–C_7)$ cycloalkyl, $(C_1–C_7)$alkanoyl or $(C_3–C_7)$cycloalkyl $(C_1–C_4)$alkyl, said $(C_1–C_6)$alkoxy, $(C_1–C_7)$alkyl, $(C_3–C_7)$cycloalkyl, $(C_1–C_7)$ alkanoyl or $(C_3–C_7)$ cycloalkyl$(C_1–C_4)$alkyl, optionally mono-, di- or tri-substituted independently with hydroxy, fluoro or chloro; and $R^2$ and $R^3$ are each independently hydroxy, halo, trifluoromethyl, $(C_1–C_7)$alkyl, $(C_1–C_4)$alkoxy, $(C_1–C_5)$ alkanoyl, cyano, $(C_3–C_7)$cycloalkyl, $(C_3–C_7)$cycloalkyl $(C_1–C_4)$alkyl, formyl, difluoromethoxy, trifluoromethoxy or carbamoyl.

It is especially preferred for Group C compounds that K is not optionally mono-, di- or tri-substituted independently with methyl, fluoro or chloro.

A group of compounds which is preferred among the C Group of compounds, designated the D Group, contains those compounds wherein K is methylene;

A is $(C_1–C_3)$alkylsulfonyl;

M is —Ar and —Ar is phenyl, thiazolyl, pyridyl, thienyl, oxazolyl, furanyl, cyclopentyl or cyclohexyl wherein —Ar is substituted with at least $R^1$;

$R^1$ is $(C_1–C_7)$alkyl or $(C_1–C_5)$alkoxy, said $(C_1–C_7)$alkyl or $(C_1–C_5)$alkoxy optionally mono-, di- or tri-substituted independently with hydroxy or fluoro; and $R^2$ and $R^3$ are each independently chloro, fluoro, methyl, difluoromethoxy, trifluoromethoxy or trifluoromethyl.

Especially preferred among the D Group of compounds are

7-{[4-(1-Hydroxy-hexyl)-benzyl]-methanesulfonyl-amino}-heptanoic acid,

7-[(4-Butyl-benzyl)-methanesulfonyl-amino]-heptanoic acid,

7-{[5-(1-Hydroxy-hexyl)-thiophen-2-ylmethyl]-methanesuffonyl-amino}- heptanoic acid and (3-{[(4-Butyl-benzyl)-methanesulfonyl-amino]-methyl}-phenyl)-acetic acid.

A group of compounds which is preferred among the D Group of compounds, designated the E Group, contains those compounds wherein Q is —$(C_2–C_6)$alkylene-W—$(C_1–C_3)$alkylene-; and W is oxy.

A group of compounds which is preferred among the D Group of compounds, designated the F Group, contains those compounds wherein Q is —$(C_3–C_8)$alkylene-, said —$(C_3–C_8)$alkylene- optionally substituted with from one to four fluorines.

Especially preferred compounds among the F Group of compounds are compounds wherein a. A is methylsulfonyl;
   Q is n-hexylene;
   Z is carboxyl;
   K is methylene; and
   M is 4-(1-hydroxy-n-hexylene-1-yl)phenyl;
b. A is methylsulfonyl;
   Q is n-hexylene;
   Z is carboxyl;
   K is methylene; and
   M is 4-(n-butylene-1-yl)phenyl; and
c. A is methylsulfonyl;
   Q is n-hexylene;
   Z is carboxyl;
   K is methylene; and
   M is 5-(1-hydroxy-n-hexylene-1-yl)thien-2-yl.

A group of compounds which is preferred among the D Group of compounds, designated the G Group, contains those compounds wherein Q is —X—$(C_1–C_5)$alkylene-; and X is thienyl or phenyl; said phenyl and thienyl optionally mono- or di- substituted independently with fluoro, chloro, trifluoromethyl or methoxy.

A group of compounds which is preferred among the D Group of compounds, designated the H Group, contains those compounds wherein Q is —$(C_1–C_5)$alkylene-X—; and X is thienyl or phenyl; said phenyl and thienyl optionally mono- or di- substituted independently with fluoro, chloro, trifluoromethyl or methoxy.

A group of compounds which is preferred among the D Group of compounds, designated the I Group, contains those compounds wherein Q is —$(C_1–C_3)$alkylene-X—$(C_1–C_3)$alkylene-; and X is thienyl or phenyl; said phenyl and thienyl optionally mono- or di- substituted independently with fluoro, chloro, trifluoromethyl or methoxy.

An especially preferred compound within the I Group of compounds is a compound wherein A is methylsulfonyl;
Q is 3-methylenephenylmethyl;
Z is carboxyl;
K is methylene; and
M is 4-(n-butylene-1-yl)phenyl.

A group of compounds which is preferred among the D Group of compounds, designated the J Group, contains those compounds wherein Q is —$(C_2–C_4)$alkylene-W-X—$(C_0–C_3)$alkylene-;

X is thienyl or phenyl; said phenyl and thienyl optionally mono- or di- substituted independently with fluoro, chloro, trifluoromethyl or methoxy; and W is oxy.

A group of compounds which is preferred among the D Group of compounds, designated the K Group, contains those compounds wherein Q is —$(C_0–C_4)$alkylene-X-W—$(C_1–C_3)$alkylene-;

X is thienyl or phenyl; said phenyl and thienyl optionally mono- or di- substituted independently with fluoro, chloro, trifluoromethyl or methoxy; and W is oxy.

A group of compounds which is preferred among the D Group of compounds, designated the L Group, contains those compounds wherein Q is —$(C_2–C_4)$alkylene-W-X-W—$(C_1–C_3)$alkylene-;

W is oxy; and

X is thienyl or phenyl; said phenyl and thienyl optionally mono- or di- substituted independently with fluoro, chloro, trifluoromethyl or methoxy.

A group of compounds which is preferred among the D Group of compounds, designated the M Group, contains those compounds wherein Q is —$(C_1–C_4)$alkylene-ethenylene—$(C_1–C_4)$alkylene-; and M is —Ar and —Ar is phenyl, thiazolyl, pyridyl or thienyl.

A group of compounds which is preferred among the D Group of compounds, designated the N Group, contains those compounds wherein Q is —$(C_1–C_4)$alkylene-ethenylene—$(C_0–C_2)$alkylene-X—$(C_0–C_3)$alkylene-; and X is thienyl or phenyl; said phenyl and thienyl optionally mono- or di- substituted independently with fluoro, chloro, trifluoromethyl or methoxy.

A group of compounds which is preferred among the D Group of compounds, designated the O Group, contains those compounds wherein Q is —$(C_1–C_3)$alkylene-ethenylene—$(C_0–C_2)$alkylene-X-W—$(C_1–C_3)$alkylene-;

W is oxy; and

X is thienyl or phenyl; said phenyl and thienyl optionally mono- or di- substituted independently with fluoro, chloro, trifluoromethyl or methoxy.

A group of compounds which is preferred among the D Group of compounds, designated the P Group, contains those compounds wherein Q is —$(C_1–C_4)$alkylene-ethynylene—$(C_1–C_4)$alkylene-.

A group of compounds which is preferred among the D Group of compounds designated the Q Group, contains those compounds wherein Q is —$(C_1–C_4)$alkylene-ethynylene-X—$(C_0–C_3)$alkylene-; and X is thienyl or phenyl; said phenyl and thienyl optionally mono- or di- substituted independently with fluoro, chloro, trifluoromethyl or methoxy.

A group of compounds which is preferred among the C Group of compounds designated the R Group, contains those compounds wherein A is $(C_1–C_3)$alkylsulfonyl;

K is $(C_1–C_8)$alkylene;

—Ar is phenyl, thiazolyl, pyridyl, thienyl, benzofuranyl, benzo[1,3]dioxolyl, 2,3-dihydrobenzo[1,4]dioxine, 2,3-dihydrobenzofuranyl, benzimidazolyl, benzo[b]thiophenyl, cyclopentyl or cyclohexyl; and $R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

Preferred compounds among the R Group are

7-{[3-(3-Chloro-phenyl)-propyl]-methanesulfonyl-amino}-heptanoic acid,

7-{[3-(3,5-Dichloro-phenyl)-propyl]-methanesulfonyl-amino}-heptanoic acid and 5-(3-{[3-(3-Chloro-phenyl)-propyl]-methanesulfonyl-amino}-propyl)-thiophene-2-carboxylic acid.

A group of compounds which is preferred among the R Group of compounds, designated the S Group, contains those compounds wherein Q is —($C_2$–$C_6$)alkylene-W—($C_1$–$C_3$)alkylene-; and W is oxy.

A group of compounds which is preferred among the R Group of compounds, designated the T Group, contains those compounds wherein Q is —($C_3$–$C_8$)alkylene-, said —($C_3$–$C_8$)alkylene- optionally substituted with from one to four fluorines.

Especially preferred compounds among the T Group are compounds wherein a. A is methylsulfonyl;
Q is n-hexylene;
Z is carboxyl;
K is propylene; and
M is 3-chlorophenyl; and b. A is methylsulfonyl;
Q is n-hexylene;
Z is carboxyl;
K is propylene; and
M is 3,5-dichlorophenyl.

A group of compounds which is preferred among the R Group of compounds, designated the U Group, contains those compounds wherein Q is —X—($C_1$–$C_5$)alkylene-; and X is thienyl or phenyl; said phenyl and thienyl optionally mono- or di- substituted independently with fluoro, chloro, trifluoromethyl or methoxy.

A group of compounds which is preferred among the R Group of compounds, designated the V Group, contains those compounds wherein Q is —($C_1$–$C_5$)alkylene-X—; and X is thienyl or phenyl; said phenyl and thienyl optionally mono- or di- substituted independently with fluoro, chloro, trifluoromethyl or methoxy.

An especially preferred compound among the V group is a compound wherein

A is methylsulfonyl;
Q–Z is 3-(2-carboxylthien-5-yl)-n-propylene
K is propylene; and
M is 3-chlorophenyl.

A group of compounds which is preferred among the R Group of compounds, designated the W Group, contains those compounds wherein Q is —($C_1$–$C_3$)alkylene-X—($C_1$–$C_3$)alkylene-; and X is thienyl or phenyl; said phenyl and thienyl optionally mono- or di- substituted independently with fluoro, chloro, trifluoromethyl or methoxy.

A group of compounds which is preferred among the R Group of compounds, designated the X Group, contains those compounds wherein Q is —($C_2$–$C_4$)alkylene-W-X—($C_0$–$C_3$)alkylene-;

X is thienyl or phenyl; said phenyl and thienyl optionally mono- or di- substituted independently with fluoro, chloro, trifluoromethyl or methoxy; and W is oxy.

A group of compounds which is preferred among the R Group of compounds, designated the Y Group, contains those compounds wherein Q is —($C_0$–$C_4$)alkylene-X-W—($C_1$–$C_3$)alkylene-;

X is thienyl or phenyl; said phenyl and thienyl optionally mono- or di- substituted independently with fluoro, chloro, trifluoromethyl or methoxy; and W is oxy.

A group of compounds which is preferred among the R Group of compounds, designated the Z Group, contains those compounds wherein Q is —($C_2$–$C_4$)alkylene-W-X-W—($C_1$–$C_3$)alkylene-;

W is oxy; and

X is thienyl or phenyl; said phenyl and thienyl optionally mono- or di- substituted independently with fluoro, chloro, trifluoromethyl or methoxy.

A group of compounds which is preferred among the R Group of compounds, designated the A1 Group, contains those compounds wherein Q is —($C_1$–$C_4$)alkylene-ethenylene—($C_1$–$C_4$)alkylene-; and M is —Ar and —Ar is phenyl, thiazolyl, pyridyl or thienyl.

A group of compounds which is preferred among the R Group of compounds, designated the B1 Group, contains those compounds wherein Q is —($C_1$–$C_4$)alkylene-ethenylene—($C_0$–$C_2$)alkylene-X—($C_0$–$C_3$)alkylene-; and X is thienyl or phenyl; said phenyl and thienyl optionally mono- or di- substituted independently with fluoro, chloro, trifluoromethyl or methoxy.

A group of compounds which is preferred among the R Group of compounds, designated the C1 Group, contains those compounds wherein Q is —($C_1$–$C_3$)alkylene-ethenylene—($C_0$–$C_2$)alkylene-X-W—($C_1$–$C_3$)alkylene-;

W is oxy; and

X is thienyl or phenyl; said phenyl and thienyl optionally mono- or di- substituted independently with fluoro, chloro, trifluoromethyl or methoxy.

A group of compounds which is preferred among the R Group of compounds, designated the D1 Group, contains those compounds wherein Q is —($C_1$–$C_4$)alkylene-ethynylene—($C_1$–$C_4$)alkylene-.

A group of compounds which is preferred among the R Group of compounds, designated the E1 Group, contains those compounds wherein Q is —($C_1$–$C_4$)alkylene-ethynylene-X—($C_0$–$C_3$)alkylene-; and X is thienyl or phenyl; said phenyl and thienyl optionally mono- or di- substituted independently with fluoro, chloro, trifluoromethyl or methoxy.

A group of compounds which is preferred among the C Group of compounds, designated the F1 Group, contains those compounds wherein A is ($C_1$–$C_3$)alkylsulfonyl;

K is oxy($C_1$–$C_4$)alkylene;

—Ar is phenyl, thienyl, thiazolyl, pyridyl, benzo[1,3]dioxolyl, cyclopentyl or cyclohexyl; and $R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

Especially preferred compounds within the F1 Group are
7-{[2-(3,5-Dichloro-phenoxy)-ethyl]-methanesulfonyl-amino}-heptanoic acid,
5-(3-{[2-(3,5-Dichloro-phenoxy)-ethyl]-methanesulfonyl-amino}-propyl)-thiophene-2-carboxylic acid and
N-[2-(3,5-Dichloro-phenoxy)-ethyl]-N-[6-(1H-tetrazol-5-yl)-hexyl]-methanesulfonamide.

A group of compounds which is preferred among the F1 Group of compounds, designated the G1 group, contains those compounds wherein Q is —($C_2$–$C_6$)alkylene-W—($C_1$–$C_3$)alkylene-; and
W is oxy.

A group of compounds which is preferred among the F1 Group of compounds, designated the H1 Group, contains those compounds wherein Q is —($C_3$–$C_8$)alkylene-, said —($C_3$–$C_8$)alkylene- optionally substituted with from one to four fluorines.

An especially preferred compound among the Hi group of compounds is a compound wherein A is methylsulfonyl;
Q is n-hexylene;
Z is carboxyl;
K is oxyethylene; and
M is 3,5-dichlorophenyl.

A group of compounds which is preferred among the F1 Group of compounds, designated the I1 Group, contains those compounds wherein Q is —X—($C_1$–$C_5$)alkylene-; and
X is thienyl or phenyl; said phenyl and thienyl optionally mono- or di- substituted independently with fluoro, chloro, trifluoromethyl or methoxy.

A group of compounds which is preferred among the F1 Group of compounds, designated the J1 Group, contains those compounds wherein Q is —($C_1$–$C_5$)alkylene-X—; and
X is thienyl or phenyl; said phenyl and thienyl optionally mono- or di- substituted independently with fluoro, chloro, trifluoromethyl or methoxy.

An especially preferred compound among the J1 group is a compound wherein

A is methylsulfonyl;
Q–Z is 3-(2-carboxylthien-5-yl)-n-propylene;
K is oxyethylene; and
M is 3,5-dichlorophenyl.

A group of compounds which is preferred among the F1 Group of compounds, designated the K1 Group, contains those compounds wherein Q is —($C_1$–$C_3$)alkylene-X—($C_1$–$C_3$)alkylene-; and
X is thienyl or phenyl; said phenyl and thienyl optionally mono- or di- substituted independently with fluoro, chloro, trifluoromethyl or methoxy.

A group of compounds which is preferred among the F1 Group of compounds, designated the L1 Group, contains those compounds wherein Q is —($C_2$–$C_4$)alkylene-W-X—($C_0$–$C_3$)alkylene-;
X is thienyl or phenyl; said phenyl and thienyl optionally mono- or di- substituted independently with fluoro, chloro, trifluoromethyl or methoxy; and
W is oxy.

A group of compounds which is preferred among the F1 Group of compounds, designated the M1 Group, contains those compounds wherein Q is —($C_0$–$C_4$)alkylene-X-W—($C_1$–$C_3$)alkylene-;
X is thienyl or phenyl; said phenyl and thienyl optionally mono- or di- substituted independently with fluoro, chloro, trifluoromethyl or methoxy; and
W is oxy.

A group of compounds which is preferred among the F1 Group of compounds, designated the N1 Group, contains those compounds wherein Q is —($C_2$–$C_4$)alkylene-W-X-W—($C_1$–$C_3$)alkylene-;
W is oxy; and
X is thienyl or phenyl; said phenyl and thienyl optionally mono- or di- substituted independently with fluoro, chloro, trifluoromethyl or methoxy.

A group of compounds which is preferred among the F1 Group of compounds, designated the O1 Group, contains those compounds wherein Q is —($C_1$–$C_4$)alkylene-ethenylene—($C_1$–$C_4$)alkylene-; and
M is —Ar and —Ar is phenyl, thiazolyl, pyridyl or thienyl.

A group of compounds which is preferred among the F1 Group of compounds, designated the P1 Group, contains those compounds wherein Q is —($C_1$–$C_4$)alkylene-ethenylene—($C_0$–$C_2$)alkylene-X—($C_0$–$C_3$)alkylene-; and
X is thienyl or phenyl; said phenyl and thienyl optionally mono- or di- substituted independently with fluoro, chloro, trifluoromethyl or methoxy.

A group of compounds which is preferred among the Fl Group of compounds, designated the Q1 Group, contains those compounds wherein Q is —($C_1$–$C_3$)alkylene-ethenylene—($C_0$–$C_2$)alkylene-X-W—($C_1$–$C_3$)alkylene-;
W is oxy; and
X is thienyl or phenyl; said phenyl and thienyl optionally mono- or di- substituted independently with fluoro, chloro, trifluoromethyl or methoxy.

A group of compounds which is preferred among the F1 Group of compounds, designated the $R^1$ Group, contains those compounds wherein Q is —($C_1$–$C_4$)alkylene-ethynylene—($C_1$–$C_4$)alkylene-.

A group of compounds which is preferred among the F1 Group of compounds, designated the S1 Group, contains those compounds wherein Q is —($C_1$–$C_4$)alkylene-ethynylene-X—($C_0$–$C_3$)alkylene-; and
X is thienyl or phenyl; said phenyl and thienyl optionally mono- or di- substituted independently with fluoro, chloro, trifluoromethyl or methoxy.

A group of compounds which is preferred among the C1 Group of compounds, designated the T1 Group, contains those compounds wherein A is ($C_1$–$C_3$)alkylsulfonyl;
K is ($C_3$–$C_8$)alkylene, said ($C_3$–$C_8$)alkylene being mono-unsaturated;
—Ar is phenyl, thienyl, thiazolyl, pyridyl, cyclopentyl or cyclohexyl; and
$R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

Especially preferred compounds among the T1 Group are
Trans-(4-{[3-(3,5-Dichloro-phenyl)-allyl]-methanesulfonyl-amino}-butoxy)-acetic acid, Trans-N-[3-(3,5-Dichloro-phenyl)-allyl]-N-[6-(1H-tetrazolyl-5-yl)-hexyl]- methanesulfonamide, Trans-5-(3-{[3-(3,5-Dichloro-phenyl)-allyl]-methanesulfonyl-amino}-propyl)-thiophene-2-carboxylic acid and Trans-[3-({[3-(3,5-Dichloro-phenyl)-allyl]-methanesulfonyl-amino}-methyl)-phenyl]- acetic acid.

A group of compounds which is preferred among the T1 Group of compounds, designated the U1 Group, contains those compounds wherein Q is —($C_2$–$C_6$)alkylene-W—($C_1$–$C_3$)alkylene-; and W is oxy.

An especially preferred compound among the U1 group is a compound wherein

A is methylsulfonyl;

Q is methyloxy-n-butylene;

Z is carboxyl;

K is trans-2-n-propenylene; and

M is 3,5-dichlorophenyl.

A group of compounds which is preferred among the T1 Group of compounds, designated the V1 Group, contains those compounds wherein Q is —($C_3$–$C_8$)alkylene-, said —($C_3$–$C_8$)alkylene- optionally substituted with from one to four fluorines.

A preferred compound among the V1 group of compound is a compound wherein

A is methylsulfonyl;

Q is n-hexylene;

Z is 5-(1H-tetrazolyl);

K is trans-2-n-propeneylene; and

M is 3,5-dichlorophenyl.

A group of compounds which is preferred among the T1 Group of compounds, designated the W1 Group, contains those compounds wherein Q is —X—($C_1$–$C_5$)alkylene-; and X is thienyl or phenyl; said phenyl and thienyl optionally mono- or di- substituted independently with fluoro, chloro, trifluoromethyl or methoxy.

A group of compounds which is preferred among the T1 Group of compounds, designated the X1 Group, contains those compounds wherein Q is —($C_1$–$C_5$)alkylene-X—; and X is thienyl or phenyl; said phenyl and thienyl optionally mono- or di- substituted independently with fluoro, chloro, trifluoromethyl or methoxy.

A preferred compound among the X1 Group is a compound wherein

A is methylsulfonyl;

Q–Z is 3-(2-carboxylthien-5-yl)-n-propylene;

K is trans-2-n-propeneylene; and

M is 3,5-dichlorophenyl.

A group of compounds which is preferred among the T1 Group of compounds, designated the Y1 Group, contains those compounds wherein Q is —($C_1$–$C_3$)alkylene-X—($C_1$–$C_3$)alkylene-; and X is thienyl or phenyl; said phenyl and thienyl optionally mono- or di- substituted independently with fluoro, chloro, trifluoromethyl or methoxy.

A group of compounds which is preferred among the T1 Group of compounds, designated the Z1 Group, contains those compounds wherein Q is —($C_2$–$C_4$)alkylene-W-X—($C_0$–$C_3$)alkylene-;

X is thienyl or phenyl; said phenyl and thienyl optionally mono- or di- substituted independently with fluoro, chloro, trifluoromethyl or methoxy; and W is oxy.

A group of compounds which is preferred among the T1 Group of compounds, designated the A2 Group, contains those compounds wherein Q is —($C_0$–$C_4$)alkylene-X-W—($C_1$–$C_3$)alkylene-;

X is thienyl or phenyl; said phenyl and thienyl optionally mono- or di- substituted independently with fluoro, chloro, trifluoromethyl or methoxy; and W is oxy.

A group of compounds which is preferred among the T1 Group of compounds, designated the B2 Group, contains those compounds wherein Q is —($C_2$–$C_4$)alkylene-W-X-W—($C_1$–$C_3$)alkylene-;

W is oxy; and

X is thienyl or phenyl; said phenyl and thienyl optionally mono- or di- substituted independently with fluoro, chloro, trifluoromethyl or methoxy.

A group of compounds which is preferred among the T1 Group of compounds, designated the C2 Group, contains those compounds wherein Q is —($C_1$–$C_4$)alkylene-ethenylene—($C_1$–$C_4$)alkylene-; and M is —Ar and —Ar is phenyl, thiazolyl, pyridyl or thienyl.

A group of compounds which is preferred among the T1 Group of compounds, designated the D2 Group, contains those compounds wherein Q is —($C_1$–$C_4$)alkylene-ethenylene—($C_0$–$C_2$)alkylene-X—($C_0$–$C_3$)alkylene-; and X is thienyl or phenyl; said phenyl and thienyl optionally mono- or di- substituted independently with fluoro, chloro, trifluoromethyl or methoxy.

A group of compounds which is preferred among the T1 Group of compounds, designated the E2 Group, contains those compounds wherein Q is —($C_1$–$C_3$)alkylene-ethenylene—($C_0$–$C_2$)alkylene-X-W—($C_1$–$C_3$)alkylene-;

W is oxy; and

X is thienyl or phenyl; said phenyl and thienyl optionally mono- or di- substituted independently with fluoro, chloro, trifluoromethyl or methoxy.

A group of compounds which is preferred among the T1 Group of compounds, designated the F2 Group, contains those compounds wherein Q is —($C_1$–$C_4$)alkylene-ethynylene—($C_1$–$C_4$)alkylene-.

A group of compounds which is preferred among the T1 Group of compounds, designated the G2 Group, contains those compounds wherein Q is —($C_1$–$C_4$)alkylene-ethynylene-X—($C_0$–$C_3$) alkylene-; and X is thienyl or phenyl; said phenyl and thienyl optionally mono- or di- substituted independently with fluoro, chloro, trifluoromethyl or methoxy.

A preferred group of compounds, designated the H2 Group, contains those compounds having the Formula I as shown above wherein B is N;

A is ($C_1$–$C_6$)alkanoyl, or ($C_3$–$C_7$)cycloalkyl($C_1$–$C_6$) alkanoyl, said A moieties optionally mono-, di- or tri-substituted on carbon independently with hydroxy or halo;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethoxy;

W is oxy, thio or sulfonyl;

Z is carboxyl, $(C_1-C_4)$alkoxycarbonyl or tetrazolyl;

K is $(C_1-C_8)$alkylene or oxy$(C_1-C_4)$alkylene, said $(C_1-C_8)$alkylene optionally mono-unsaturated and wherein K is optionally mono-, di- or tri-substituted independently with methyl, fluoro or chloro;

Ar is $(C_5-C_7)$cycloalkyl, phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, pyrazinyl, imidazolyl, quinolinyl, isoquinolinyl, benzoxazolyl, benzothiazolyl, indolyl, 1,2,3,4-tetrahydronaphthalenyl, cyclohexyl, cyclopentyl, or chromanyl;

$Ar^1$ and $Ar^2$ are each independently $(C_5-C_7)$cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, $(C_1-C_6)$alkoxy, $(C_1-C_7)$alkyl, $(C_3-C_7)$cycloalkyl, $(C_1-C_7)$alkanoyl or $(C_3-C_7)$cycloalkyl $(C_1-C_4)$alkyl, said $(C_1-C_6)$alkoxy, $(C_1-C_7)$alkyl, $(C_3-C_7)$cycloalkyl, $(C_1-C_7)$ alkanoyl or $(C_3-C_7)$cycloalkyl$(C_1-C_4)$alkyl, optionally mono-, di- or tri-substituted independently with hydroxy, fluoro or chloro; and $R^2$ and $R^3$ are each independently hydroxy, halo, difluoromethoxy, trifluoromethoxy, trifluoromethyl, $(C_1-C_7)$alkyl, $(C_1-C_4)$alkoxy, $(C_1-C_5)$alkanoyl, cyano, $(C_3-C_7)$cycloalkyl, $(C_3-C_7)$cycloalkyl$(C_1-C_4)$alkyl, formyl or carbamoyl.

It is especially preferred for the H2 Group that K is not optionally mono-, di- or tri-substituted independently with methyl, fluoro or chloro.

A group of compounds which is preferred among the H2 Group of compounds, designated the I2 Group, contains those compounds wherein A is $(C_1-C_6)$alkanoyl, said $(C_1-C_6)$alkanoyl optionally mono-, di- or tri-substituted on carbon independently with halo;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-, K is methylene or ethylene;

M is —$Ar^1$—V—$Ar^2$ or —$Ar^1$—O—$Ar^2$ wherein $Ar^1$ and $Ar^2$ are each independently phenyl, pyridyl or thienyl;

V is a bond or $(C_1-C_2)$alkylene;

$R^1$ is chloro, fluoro, $(C_1-C_4)$alkyl or $(C_1-C_6)$alkoxy, said $(C_1-C_4)$alkyl and $(C_1-C_6)$alkoxy optionally mono-, di-or tri-substituted independently with hydroxy or fluoro; and $R^2$ and $R^3$ are each independently chloro or fluoro.

A group of compounds which is preferred among the H2 Group of compounds, designated the J2 Group, contains those compounds wherein A is $(C_1-C_6)$alkanoyl said $(C_1-C_6)$alkanoyl optionally mono-, di- or tri-substituted independently on carbon with hydroxy or halo;

K is methylene;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-;

M is —Ar and —Ar is phenyl, thiazolyl, pyridyl, thienyl, oxazolyl, furanyl, cyclopentyl or cyclohexyl wherein —Ar is substituted with at least $R^1$;

$R^1$ is $(C_1-C_7)$alkyl or $(C_1-C_5)$alkoxy, said $(C_1-C_7)$alkyl or $(C_1-C_5)$alkoxy optionally mono-, di- or tri-substituted independently with hydroxy or fluoro; and $R^2$ and $R^3$ are each independently chloro, fluoro, methyl, difluoromethoxy, trifluoromethoxy or trifluoromethyl.

A group of compounds which is preferred among the H2 Group of compounds, designated the K2 Group, contains those compounds wherein A is $(C_1-C_6)$alkanoyl, said $(C_1-C_6)$alkanoyl optionally mono-, di- or tri-substituted on carbon independently with halo;

K is $(C_1-C_8)$alkylene;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-;

M is —Ar and —Ar is phenyl, thienyl, benzofuranyl, benzo[1,3]dioxolyl, 2,3-dihydrobenzo[1,4]dioxinyl, 2,3-dihydrobenzofuranyl, benzimidazolyl, benzo[b]thiophenyl, cyclopentyl or cyclohexyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

A group of compounds which is preferred among the H2 Group of compounds, designated the L2 Group, contains those compounds wherein A is $(C_1-C_6)$alkanoyl, said $(C_1-C_6)$alkanoyl optionally mono-, di- or tri-substituted on carbon independently with halo;

K is oxy$(C_1-C_4)$alkylene;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—($C_2$–$C_5$)alkylene-,
—($C_1$–$C_5$)alkylene-X-,
—($C_1$–$C_3$)alkylene-X—($C_1$–$C_3$)alkylene-,
—($C_2$–$C_4$)alkylene-W-X—($C_0$–$C_3$)alkylene-, or
—($C_0$–$C_4$)alkylene-X-W—($C_1$–$C_3$)alkylene-;

M is —Ar and —Ar is phenyl, thienyl, benzo[1,3]dioxolyl, cyclopentyl or cyclohexyl; and $R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

A group of compounds which is preferred among the H2 Group of compounds, designated the M2 Group, contains those compounds wherein A is ($C_3$–$C_6$)alkanoyl said ($C_3$–$C_6$)alkanoyl optionally mono-, di- or tri-substituted on carbon independently with halo;

K is ($C_3$–$C_8$)alkylene, said ($C_3$–$C_8$)alkylene being mono-unsaturated;

Q is
—($C_2$–$C_6$)alkylene-W—($C_1$–$C_3$)alkylene-,
—($C_4$–$C_8$)alkylene-, said —($C_4$–$C_8$)alkylene-optionally substituted with up to four substituents independently selected from fluoro or ($C_1$–$C_4$)alkyl,
—X—($C_2$–$C_5$)alkylene-,
—($C_1$–$C_5$)alkylene-X-,
—($C_1$–$C_3$)alkylene-X—($C_1$–$C_3$)alkylene-,
—($C_2$–$C_4$)alkylene-W-X—($C_0$–$C_3$)alkylene-, or
—($C_0$–$C_4$)alkylene-X-W—($C_1$–$C_3$)alkylene-;

M is —Ar and —Ar is phenyl, thienyl, cyclopentyl or cyclohexyl; and $R^1$, $R^2$ and $R^3$ are each independently hydroxy, halo, trifluoromethyl, trifluoromethoxy, ($C_1$–$C_4$)alkoxy or ($C_1$–$C_7$)alkyl.

A preferred group of compounds, designated the N2 Group, contains those compounds having the Formula I as shown above wherein B is C(H);

A is ($C_1$–$C_6$)alkanoyl, or ($C_3$–$C_7$)cycloalkyl($C_1$–$C_6$)alkanoyl, said A moieties optionally mono-, di- or tri-substituted on carbon independently with hydroxy or halo;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethoxy;

W is oxy, thio or sulfonyl;

Z is carboxyl, ($C_1$–$C_4$)alkoxycarbonyl or tetrazolyl;

K is ($C_1$–$C_8$)alkylene or oxy($C_1$–$C_4$)alkylene, said ($C_1$–$C_8$)alkylene optionally mono-unsaturated and wherein K is optionally mono-, di- or tri-substituted independently with hydroxy, fluoro or chloro;

Ar is ($C_5$–$C_7$)cycloalkyl, phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, pyrazinyl, imidazolyl, quinolinyl, isoquinolinyl, benzoxazolyl, benzothiazolyl, indolyl, 1,2,3,4-tetrahydronaphthalenyl, cyclohexyl, cyclopentyl, or chromanyl;

$Ar^1$ and $Ar^2$ are each independently ($C_5$–$C_7$)cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, ($C_1$–$C_6$)alkoxy, ($C_1$–$C_7$)alkyl, ($C_3$–$C_7$)cycloalkyl, ($C_1$–$C_7$)alkanoyl or ($C_3$–$C_7$)cycloalkyl($C_1$–$C_4$)alkyl, said ($C_1$–$C_6$)alkoxy, ($C_1$–$C_7$)alkyl, ($C_3$–$C_7$)cycloalkyl, ($C_1$–$C_7$) alkanoyl or ($C_3$–$C_7$)cycloalkyl($C_1$–$C_4$)alkyl, optionally mono-, di- or tri-substituted independently with hydroxy, fluoro or chloro; and $R^2$ and $R^3$ are each independently hydroxy, halo, difluoromethoxy, trifluoromethoxy, trifluoromethyl, ($C_1$–$C_7$)alkyl, ($C_1$–$C_4$)alkoxy, ($C_1$–$C_5$)alkanoyl, cyano, ($C_3$–$C_7$)cycloalkyl, ($C_3$–$C_7$)cycloalkyl($C_1$–$C_4$)alkyl, formyl or carbamoyl.

It is especially preferred for Group N2 that K is not optionally mono-, di- or tri-substituted independently with methyl, fluoro or chloro.

A group of compounds which is preferred among the N2 Group of compounds, designated the O2 Group, contains those compounds wherein A is ($C_1$–$C_6$)alkanoyl, said A optionally mono-, di- or tri-substituted on carbon independently with halo;

Q is
—($C_2$–$C_6$)alkylene-W—($C_1$–$C_3$)alkylene-,
—($C_4$–$C_8$)alkylene-, said —($C_4$–$C_8$)alkylene-optionally substituted with up to four substituents independently selected from fluoro or ($C_1$–$C_4$)alkyl,
—X—($C_2$–$C_5$)alkylene-,
—($C_1$–$C_5$)alkylene-X-,
—($C_1$–$C_3$)alkylene-X—($C_1$–$C_3$)alkylene-,
—($C_2$–$C_4$)alkylene-W-X—($C_0$–$C_3$)alkylene-, or
—($C_0$–$C_4$)alkylene-X-W—($C_1$–$C_3$)alkylene-;

K is methylene or ethylene;

M is —$Ar^1$—V—$Ar^2$ or —$Ar^1$—O—$Ar^2$ wherein $Ar^1$ and $Ar^2$ are each independently phenyl, pyridyl or thienyl;

V is a bond or ($C_1$–$C_2$)alkylene;

$R^1$ is chloro, fluoro, ($C_1$–$C_4$)alkyl or ($C_1$–$C_4$)alkoxy, said ($C_1$–$C_4$)alkyl and ($C_1$-$C_4$) alkoxy optionally mono-, di-or tri-substituted independently with hydroxy or fluoro; and $R^2$ and $R^3$ are each independently chloro or fluoro.

A group of compounds which is preferred among the N2 Group of compounds, designated the P2 Group, contains those compounds wherein A is ($C_1$–$C_6$)alkanoyl, said A optionally mono-, di- or tri-substituted on carbon independently with hydroxy or halo;

K is methylene;

Q is
—($C_2$–$C_6$)alkylene-W—($C_1$–$C_3$)alkylene-,
—($C_4$–$C_8$)alkylene-, said —($C_4$–$C_8$)alkylene-optionally substituted with up to four substituents independently selected from fluoro or ($C_1$–$C_4$)alkyl,
-X—($C_2$–$C_5$)alkylene-,
—($C_1$–$C_5$)alkylene-X-,
—($C_1$–$C_3$)alkylene-X—($C_1$–$C_3$)alkylene-,
—($C_2$–$C_4$)alkylene-W-X—($C_0$–$C_3$)alkylene-, or
—($C_0$–$C_4$)alkylene-X-W—($C_1$–$C_3$)alkylene-;

M is —Ar and —Ar is phenyl, thiazolyl, pyridyl, thienyl, oxazolyl, furanyl, cyclopentyl or cyclohexyl wherein —Ar is substituted with at least $R^1$;

$R^1$ is ($C_1$–$C_7$)alkyl or ($C_1$–$C_6$)alkoxy, said ($C_1$–$C_7$)alkyl or ($C_1$–$C_6$)alkoxy optionally mono-, di- or tri-substituted independently with hydroxy or fluoro; and $R^2$ and R are each independently chloro, fluoro, methyl, difluoromethoxy, trifluoromethoxy or trifluoromethyl.

A group of compounds which is preferred among the N2 Group of compounds, designated the Q2 Group, contains those compounds wherein A is $(C_1-C_6)$alkanoyl, said A optionally mono-, di- or tri-substituted on carbon independently with halo;

K is $(C_1-C_8)$alkylene;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-;

M is —Ar and —Ar is phenyl, thienyl, benzofuranyl, benzo[1,3]dioxolyl, -dihydrobenzo[1,4]dioxinyl, 2,3-dihydrobenzofuranyl, benzimidazolyl, benzo[b]thiophenyl, cyclopentyl or cyclohexyl; and $R^1$, $R^2$ and $R^3$ are each independently hydroxy, halo, trifluoromethyl, trifluoromethoxy, $(C_1-C_4)$alkoxy or $(C_1-C_7)$alkyl.

A group of compounds which is preferred among the N2 Group of compounds, designated the $R^2$ Group, contains those compounds wherein A is $(C_1-C_6)$alkanoyl said A optionally mono-, di- or tri-substituted on carbon independently with halo;

K is oxy$(C_1-C_4)$alkylene;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-;

M is —Ar and —Ar is phenyl, thienyl, benzo[1,3]dioxolyl, cyclopentyl or cyclohexyl; and $R^1$, $R^2$ and $R^3$ are each independently hydroxy, halo, trifluoromethyl, trifluoromethoxy, $(C_1-C_4)$alkoxy or $(C_1-C_7)$alkyl.

A group of compounds which is preferred among the N2 Group of compounds, designated the S2 Group, contains those compounds wherein A is $(C_1-C_6)$alkanoyl, said A optionally mono-, di- or tri-substituted on carbon independently with halo;

K is $(C_3-C_8)$alkylene, said $(C_3-C_8)$alkylene being mono-unsaturated;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, or —$(C_0-C_4)$alkylene-X-W—$(C_1-C_3)$alkylene-;

M is —Ar and —Ar is phenyl, thienyl, cyclopentyl or cyclohexyl; and $R^1$, $R^2$ and $R^3$ are each independently hydroxy, halo, trifluoromethyl, trifluoromethoxy, $(C_1-C_4)$alkoxy or $(C_1-C_7)$alkyl.

An especially preferred compound of the J2 Group of compounds is a compound wherein A is propanoyl;

Q is n-hexylene;

Z is carboxyl;

K is methylene; and

M is 4-(n-1-hydroxylhexyl)phenyl.

An especially preferred compound among the H1 Group of compounds is a compound wherein A is methylsulfonyl;

Q is n-hexylene;

Z is 5-(1H-tetrazolyl);

K is oxyethyl; and

M is 3,5-dichlorophenyl.

An especially preferred compound among the Y1 Group of compounds is a compound wherein A is methylsulfonyl;

Q is 3-methylenephenylmethyl;

Z is carboxyl;

K is trans-2-n-propenylene; and

M is 3,5-dichlorophenyl.

This invention is also directed to a method for augmenting, and maintaining bone mass and preventing further bone loss in a mammal comprising administering to a mammal a therapeutically effective amount of a compound of Formula I or a pharmaceutically acceptable salt or prodrug thereof.

This invention is also directed to a method for treating a mammal having a condition which presents with low bone mass comprising administering to a mammal having a condition which presents with low bone mass a therapeutically effective amount of a compound of Formula I or a pharmaceutically acceptable salt or prodrug thereof. Preferably post-menopausal women and men over the age of 60 are treated. Also included are individuals regardless of age who have significantly reduced bone mass, i.e., $\geq 1.5$ s.d. below young normal levels.

Yet another aspect of this invention is directed to methods for treating osteoporosis, bone fractures, osteotomy, bone loss associated with periodontitis, or prosthetic ingrowth in a mammal (including a human being) comprising administering to a mammal suffering from osteoporosis, bone fracture, osteotomy, bone loss associated with periodontitis, or prosthetic ingrowth an osteoporosis, bone fracture, osteotomy, bone loss associated with periodontitis, or prosthetic ingrowth treating amount of a Formula I compound or a pharmaceutically acceptable salt or prodrug thereof.

Yet another aspect of this invention is directed to a method for treating osteoporosis in a mammal (including a human being) by comprising administering to a mammal suffering from osteoporosis an osteoporosis treating amount of a Formula I compound or a pharmaceutically acceptable salt or prodrug thereof.

Yet another aspect of this invention is directed to a method for treating osteotomy bone loss in a mammal (including a human being) comprising administering to a mammal who underwent an osteotomy procedure to repair bone integrity a therapeutically effective amount of a Formula I compound or a pharmaceutically acceptable salt or prodrug thereof. In one aspect the Formula I compound is applied locally to a site of osteotomy.

Yet another aspect of this invention is directed to a method for treating alveolar bone loss in a mammal (including a human being) comprising administering to a mammal suffering from an alveolar bone loss an alveolar bone loss treating amount of a Formula I compound or a pharmaceutically acceptable salt or prodrug thereof.

Yet another aspect of this invention is directed to a method for treating bone loss associated with periodontitis in a mammal (including a human being) comprising administering to a mammal suffering from bone loss associated with periodontitis a bone loss associated with periodontitis treating amount of a Formula I compound or a pharmaceutically acceptable salt or prodrug thereof.

Yet another aspect of this invention is directed to a method for treating childhood idiopathic bone loss in a mammal comprising administering to a child suffering from childhood idiopathic bone loss a childhood idiopathic bone loss treating amount of a Formula I compound or a pharmaceutically acceptable salt or prodrug thereof.

Yet another aspect of this invention is directed to a method for treating "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a mammal (including a human being) by administering to a mammal suffering from "secondary osteoporosis" a "secondary osteoporosis" treating amount of a Formula I compound or a pharmaceutically acceptable salt or prodrug thereof.

Yet another aspect of this invention is directed to a method for treating glucocorticoid-induced osteoporosis in a mammal (including a human being) comprising administering to a mammal suffering from glucocorticoid-induced osteoporosis a glucocorticoid-induced osteoporosis treating amount of a Formula I compound or a pharmaceutically acceptable salt or prodrug thereof.

Yet another aspect of this invention is directed to a method for treating hyperthyroidism-induced osteoporosis in a mammal (including a human being) comprising administering to a mammal suffering from hyperthyroidism-induced osteoporosis a hyperthyroidism-induced osteoporosis treating amount of a Formula I compound or a pharmaceutically acceptable salt or prodrug thereof.

Yet another aspect of this invention is directed to a method for treating immobilization-induced osteoporosis in a mammal (including a human being) comprising administering to a mammal suffering from immobilization-induced osteoporosis a immobilization-induced osteoporosis treating amount of a Formula I compound or a pharmaceutically acceptable salt or prodrug thereof.

Yet another aspect of this invention is directed to a method for treating heparin-induced osteoporosis in a mammal (including a human being) comprising administering to a mammal suffering from heparin-induced osteoporosis a heparin-induced osteoporosis treating amount of a Formula I compound or a pharmaceutically acceptable salt or prodrug thereof.

Yet another aspect of this invention is directed to a method for treating immunosuppressive-induced osteoporosis in a mammal (including a human being) comprising administering to a mammal suffering from immunosuppressive-induced osteoporosis an immunosuppressive-induced osteoporosis treating amount of a Formula I compound or a pharmaceutically acceptable salt or prodrug thereof.

Yet another aspect of this invention is directed to a method for treating a bone fracture in a mammal (including a human being) comprising administering to a mammal suffering from a bone fracture a bone fracture treating amount of a Formula I compound or a pharmaceutically acceptable salt or prodrug thereof. In one aspect of this invention for treating a bone fracture the Formula I compound or a pharmaceutically acceptable salt or prodrug thereof is applied locally to the site of bone fracture. In another aspect of this invention the Formula I compound or a pharmaceutically acceptable salt or prodrug thereof is administered systemically.

Yet another aspect of this invention is directed to a method for enhancing bone healing following facial reconstruction or maxillary reconstruction or mandibular reconstruction in a mammal (including a human being) comprising administering to a mammal which has undergone facial reconstruction or maxillary reconstruction or mandibular reconstruction a bone enhancing amount of a Formula I compound or a pharmaceutically acceptable salt or prodrug thereof. In one aspect of this invention the Formula I compound or a pharmaceutically acceptable salt or prodrug thereof is applied locally to the site of bone reconstruction.

Yet another aspect of this invention is directed to a method for inducing prosthetic ingrowth in a mammal (including a human being) comprising administering to a mammal a therapeutically effective amount of a Formula I compound or a pharmaceutically acceptable salt or prodrug thereof.

Yet another aspect of this invention is directed to a method for inducing vertebral synostosis in a mammal (including a human being) comprising administering to a mammal undergoing surgery for vertebral synostosis a therapeutically effective amount of a Formula I compound or a pharmaceutically acceptable salt or prodrug thereof.

Yet another aspect of this invention is directed to a method for enhancing long bone extension in a mammal (including a human being) comprising administering to a mammal suffering from an insufficiently sized long bone a long bone enhancing amount of a Formula I compound or a pharmaceutically acceptable salt or prodrug thereof.

Yet another aspect of this invention is directed to a method for use in place of a bone graft in a mammal (including a human being) comprising administering to a mammal a therapeutically effective amount of a Formula I compound or a pharmaceutically acceptable salt or prodrug thereof. In one aspect of this method the Formula I compound or a pharmaceutically acceptable salt or prodrug thereof is applied locally to the site of a bone graft. Also, if bone graft is needed, an amount of a Formula I compound or a pharmaceutically acceptable salt or prodrug thereof can be applied to the site of a bone graft to restore bone.

A preferred dosage is about 0.001 to 100 mg/kg/day of the Formula I compound or a pharmaceutically acceptable salt or prodrug thereof. An especially preferred dosage is about 0.01 to 10 mg/kg/day of the Formula I compound or a pharmaceutically acceptable salt or prodrug thereof.

This invention is also directed to pharmaceutical compositions which comprise a therapeutically effective amount of a compound of Formula I or a pharmaceutically acceptable salt or prodrug thereof and a pharmaceutically acceptable carrier.

This invention is also directed to pharmaceutical compositions for the augmentation of bone mass which comprise a bone mass augmentating amount of a compound of Formula I or a pharmaceutically acceptable salt or prodrug thereof and a pharmaceutically acceptable carrier.

This invention is also directed to pharmaceutical compositions for the treatment of a condition which presents with low bone mass in a mammal (including a human being) which comprise a low bone mass condition treating amount of a compound of Formula I or a pharmaceutically acceptable salt or prodrug thereof and a pharmaceutically acceptable carrier.

This invention is also directed to pharmaceutical compositions for the treatment of osteoporosis, bone fractures, osteotomy, bone loss associated with periodontitis, bone graft substitution or prosthetic ingrowth in a mammal (including a human being) which comprises a therapeutically effective amount of a compound of Formula I or a pharmaceutically acceptable salt or prodrug thereof and a pharmaceutically acceptable carrier.

This invention is also directed to pharmaceutical compositions for the treatment of "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a mammal (including a human being) which comprise a "secondary osteoporosis" treating amount of a compound of Formula I or a pharmaceutically acceptable salt or prodrug thereof and a pharmaceutically acceptable carrier.

This invention is also directed to pharmaceutical compositions for the treatment of osteoporosis in a mammal (including a human being) which comprise an osteoporosis treating amount of a compound of the Formula I or a pharmaceutically acceptable salt or prodrug thereof and a pharmaceutically acceptable carrier.

This invention is also directed to pharmaceutical compositions for enhancing bone fracture healing in a mammal (including a human being) which comprise a bone fracture treating amount of a compound of the Formula I or a pharmaceutically acceptable salt or prodrug thereof and a pharmaceutically acceptable carrier.

This invention is also directed to pharmaceutical compositions for the treatment of osteotomy bone loss in a mammal (including a human being) which comprise an osteotomy bone loss treating amount of a compound of the Formula I or a pharmaceutically acceptable salt or prodrug thereof and a pharmaceutically acceptable carrier.

This invention is also directed to pharmaceutical compositions for the treatment of alveolar bone loss in a mammal (including a human being) which comprise an alveolar bone loss treating amount of a compound of the Formula I or a pharmaceutically acceptable salt or prodrug thereof and a pharmaceutically acceptable carrier.

This invention is also directed to pharmaceutical compositions for the treatment of childhood idiopathic bone loss in a child which comprises a childhood idiopathic bone loss treating amount of a compound of the Formula I or a pharmaceutically acceptable salt or prodrug thereof and a pharmaceutically acceptable carrier.

This invention is also directed to pharmaceutical compositions for the augmentation of bone healing following facial reconstruction or maxillary reconstruction or mandibular reconstruction in a mammal (including a human being) which comprise a bone healing treating amount of a compound of the Formula I or a pharmaceutically acceptable salt or prodrug thereof and a pharmaceutically acceptable carrier.

This invention is also directed to pharmaceutical compositions for the treatment of bone loss associated with periodontitis in a mammal (including a human being) which comprise a bone loss associated with periodontitis treating amount of a compound of the Formula I or a pharmaceutically acceptable salt or prodrug thereof and a pharmaceutically acceptable carrier.

This invention is also directed to pharmaceutical compositions for the treatment of prosthetic ingrowth in a mammal (including a human being) which comprise a prosthetic ingrowth treating amount of a compound of the Formula I or a pharmaceutically acceptable salt or prodrug thereof and a pharmaceutically acceptable carrier.

This invention is also directed to pharmaceutical compositions for inducing vertebral synostosis in a mammal (including a human being) which comprise a therapeutically effective amount of a compound of the Formula I or a pharmaceutically acceptable salt or prodrug thereof and a pharmaceutically acceptable carrier.

This invention is also directed to pharmaceutical compositions for the augmentation of long bone extension in a mammal (including a human being) which comprise bone mass augmentation treating amount of a compound of the Formula I or a pharmaceutically acceptable salt or prodrug thereof and a pharmaceutically acceptable carrier.

This invention is also directed to pharmaceutical compositions for the treatment of glucocorticoid-induced osteoporosis in a mammal (including a human being) which comprise a glucocorticoid-induced osteoporosis treating amount of a compound of the Formula I or a pharmaceutically acceptable salt or prodrug thereof and a pharmaceutically acceptable carrier.

This invention is also directed to pharmaceutical compositions for the treatment of hyperthyroidism-induced osteoporosis in a mammal (including a human being) which comprise a hyperthyroidism-induced osteoporosis treating amount of a compound of the Formula I or a pharmaceutically acceptable salt or prodrug thereof and a pharmaceutically acceptable carrier.

This invention is also directed to pharmaceutical compositions for the treatment of immobilization-induced osteoporosis in a mammal (including a human being) which comprise a immobilization-induced osteoporosis treating amount of a compound of the Formula I or a pharmaceutically acceptable salt or prodrug thereof and a pharmaceutically acceptable carrier.

This invention is also directed to pharmaceutical compositions for the treatment of heparin-induced osteoporosis in a mammal (including a human being) which comprise a heparin-induced osteoporosis treating amount of a compound of the Formula I or a pharmaceutically acceptable salt or prodrug thereof and a pharmaceutically acceptable carrier.

This invention is also directed to pharmaceutical compositions for the treatment of immunosuppressive-induced osteoporosis in a mammal (including a human being) which comprise a immunosuppressive-induced osteoporosis treating amount of a compound of the Formula I or a pharmaceutically acceptable salt or prodrug thereof and a pharmaceutically acceptable carrier.

Yet another aspect of this invention are combinations of the Formula I compounds or a pharmaceutically acceptable salt or prodrug thereof and other compounds as described below.

Yet another aspect of this invention is directed to a pharmaceutical compositions comprising a compound of Formula I or a pharmaceutically acceptable salt or prodrug thereof and an anti-resorptive agent and for the use of such compositions for the treatment (e.g., prevention) of conditions which present with low bone mass, including osteoporosis in mammals (e.g., humans, particularly women) or the use of such compositions for other bone mass augmenting uses.

The combinations of this invention comprises a therapeutically effective amount of a first compound, said first compound being a Formula I compound or a pharmaceutically acceptable salt or prodrug thereof; and a therapeutically effective amount of a second compound, said second compound being an anti-resorptive agent such as an estrogen agonist/antagonist or a bisphosphonate.

Preferred estrogen agonist/antagonists include droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]-naphthalen-2-ol, {4-[2-(2-Aza-bicyclo[2.2.1]hept-2-yl)-ethoxy]-phenyl}-[6-hydroxy-2-(4-hydroxy-phenyl]-benzo[b) thiophen-3-yl]-methanone,

- Cis-6-(4-fluoro-phenyl)-5-[4-(2-piperidin-1-yl-ethoxy)-phenyl]5, 6, 7, 8-tetrahydro-naphthalene-2-ol;
- (−)-Cis-6-phenyl-5-[4-(2-pyrrolidin-1-yl-ethoxy)-phenyl]-5,6,7,8-tetrahydro-naphthalene-2-ol;
- Cis-6-phenyl-5-[4-(2-pyrrolidin-1-yl-ethoxy)-phenyl]-5,6,7,8-tetrahydro-naphthalene-2-ol;
- Cis-1-[6'-pyrrolodinoethoxy-3'-pyridyl]-2-phenyl-6-hydroxy-1,2,3,4-tetrahydrohaphthalene;
- 1-(4'-Pyrrolidinoethoxyphenyl)-2-(4"-fluorophenyl)-6-hydroxy-1,2,3,4-tetrahydroisoquinoline;
- Cis-6-(4-hydroxyphenyl)-5-[4-(2-piperidin-1-yl-ethoxy)-phenyl]-5,6,7,8-tetrahydro-naphthalene-2-ol; and
- 1-(4'-Pyrrolidinolethoxyphenyl)-2-phenyl-6-hydroxy-1,2,3,4-tetrahydroisoquinoline and the pharmaceutically acceptable salts thereof.

Especially preferred estrogen agonist/antagonists include droloxifene;

- Cis-6-(4-fluoro-phenyl)-5-[4-(2-piperidin-1-yl-ethoxy)-phenyl]-5,6,7,8-tetrahydro-naphthalene-2-ol;
- (−)-Cis-6-phenyl-5-[4-(2-pyrrolidin-1-yl-ethoxy)-phenyl]-5,6,7,8-tetrahydro-naphthalene-2-ol;
- Cis-6-phenyl-5-[4-(2-pyrrolidin-1-yl-ethoxy)-phenyl]-5,6,7,8-tetrahydro-naphthalene-2-ol;
- Cis-1-[6'-pyrrolodinoethoxy-3'-pyridyl]-2-phenyl-6-hydroxy-1,2,3,4- tetrahydrohaphthalene;
- 1-(4'-Pyrrolidinoethoxyphenyl)-2-(4"-fluorophenyl)-6-hydroxy-1,2,3,4- tetrahydroisoquinoline;
- Cis-6-(4-hydroxyphenyl)-5-[4-(2-piperidin-1-yl-ethoxy)-phenyl]-5,6,7,8-tetrahydro- naphthalene-2-ol;
- 1-(4'-Pyrrolidinolethoxyphenyl)-2-phenyl-6-hydroxy-1, 2,3,4- tetrahydroisoquinoline; and the pharmaceutically acceptable salts thereof.

Preferred bisphosphonates include, tiludronic acid, alendronic acid, ibandronic acid, risedronic acid, etidronic acid, clodronic acid, and pamidronic acid and their pharmaceutically acceptable salts.

Another aspect of this invention is a method for treating mammals which present with low bone mass comprising administering to a mammal having a condition which presents with low bone mass a. a therapeutically effective amount of a first compound, said first compound being a Formula I compound or a pharmaceutically acceptable salt or prodrug thereof; and b. a therapeutically effective amount of a second compound, said second compound being an anti-resorptive agent such as an estrogen agonist/antagonist or a bisphosphonate.

Such compositions and methods may also be used for other bone mass augmenting uses.

Preferred estrogen agonist/antagonists in this method include droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]- naphthalen-2-ol, {4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone,

- Cis-6-(4-fluoro-phenyl)-5-[4-(2-piperidin-1-yl-ethoxy)-phenyl]-5,6,7,8-tetrahydro-naphthalene-2-ol;
- (−)-Cis-6-phenyl-5-[4-(2-pyrrolidin-1-yl-ethoxy)-phenyl]-5,6,7,8-tetrahydro-naphthalene-2-ol;
- Cis-6-phenyl-5-[4-(2-pyrrolidin-1-yl-ethoxy)-phenyl]-5,6,7,8-tetrahydro-naphthalene-2-ol;
- Cis-1-[6'-pyrrolodinoethoxy-3'-pyridyl]-2-phenyl-6-hydroxy-1,2,3,4-tetrahydrohaphthalene;
- 1-(4'-Pyrrolidinoethoxyphenyl)-2-(4"-fluorophenyl)-6-hydroxy-1,2,3,4-tetrahydroisoquinoline;
- Cis-6-(4-hydroxyphenyl)-5-[4-(2-piperidin-1-yl-ethoxy)-phenyl]-5,6,7,8-tetrahydro-naphthalene-2-ol;
- 1-(4'-Pyrrolidinolethoxyphenyl)-2-phenyl-6-hydroxy-1, 2,3,4-tetrahydroisoquinoline; and the pharmaceutically acceptable salts thereof.

Especially preferred estrogen agonist/antagonists include droloxifene;

- Cis-6-(4-fluoro-phenyl)-5-[4-(2-piperidin-1-yl-ethoxy)-phenyl]-5,6,7,8-tetrahydro-naphthalene-2-ol;
- (−)-Cis-6-phenyl-5-[4-(2-pyrrolidin-1-yl-ethoxy)-phenyl]-5,6,7,8-tetrahydro-naphthalene-2-ol;
- Cis-6-phenyl-5-[4-(2-pyrrolidin-1-yl-ethoxy)-phenyl]-5,6,7,8-tetrahydro-naphthalene-2-ol;
- Cis-1-[6'-pyrrolodinoethoxy-3'-pyridyl]-2-phenyl-6-hydroxy-1,2,3,4-tetrahydrohaphthalene;
- 1-(4'-Pyrrolidinoethoxyphenyl)-2-(4"-fluorophenyl)-6-hydroxy-1,2,3,4-tetrahydroisoquinoline;
- Cis-6-(4-hydroxyphenyl)-5-[4-(2-piperidin-1-yl-ethoxy)-phenyl]-5,6,7,8-tetrahydro-naphthalene-2-ol;
- 1-(4'-Pyrrolidinolethoxyphenyl)-2-phenyl-6-hydroxy-1, 2,3,4-tetrahydroisoquinoline and the pharmaceutically acceptable salts thereof Preferred bisphosphonates include, tiludronic acid, alendronic acid, ibandronic acid, risedronic acid, etidronic acid, clodronic acid, and pamidronic acid and their pharmaceutically acceptable salts.

A preferred aspect of this method is wherein the condition which presents with low bone mass is osteoporosis.

Another preferred aspect of this method is wherein the first compound and the second compound are administered substantially simultaneously.

Another preferred aspect of this method is wherein the first compound is administered for a period of from about one week to about three years.

Optionally the administration of the first compound is followed by administration of the second compound wherein the second compound is an estrogen agonist/antagonist for a period of from about three months to about three years without the administration of the first compound during the second period of from about three months to about three years.

Alternatively, the administration of the first compound is followed by administration of the second compound wherein the second compound is an estrogen agonist/antagonist for a period greater than about three years without the administration of the first compound during the greater than about three year period.

Another aspect of this invention is a kit comprising:

a. a therapeutically effective amount of a Formula I compound or a pharmaceutically acceptable salt or prodrug thereof and a pharmaceutically acceptable carrier in a first unit dosage form;

b. a therapeutically effective amount of an anti-resorptive agent such as an estrogen agonist/antagonist or a bisphosphonate and a pharmaceutically acceptable carrier in a second unit dosage form; and c. container means for containing said first and second dosage forms.

Preferred estrogen agonist/antagonists in this kit include droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]-naphthalen-2-ol, {4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone, Cis-6-(4-fluoro-phenyl)-5-[4-(2-piperidin-1-yl-ethoxy)-phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;

Cis-6-phenyl-5-[4-(2-pyrrolidin-1-yl-ethoxy)-phenyl]-5,6,7,8-tetrahydro-naphthalene-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalene-2-ol;

1-(4'-Pyrrolidinolethoxyphenyl)-2-phenyl-6-hydroxy-1,2,3,4-tetrahydroisoquinoline; and the pharmaceutically acceptable salts thereof.

Especially preferred estrogen agonist/antagonists include droloxifene;

Cis-6-(4-fluoro-phenyl)-5-[4-(2-piperidin-1-yl-ethoxy)-phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;

Cis-6-phenyl-5-[4-(2-pyrrolidin-1-yl-ethoxy)-phenyl]-5,6,7,8-tetrahydro-naphthalene-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalene-2-ol;

1-(4'-Pyrrolidinolethoxyphenyl)-2-phenyl-6-hydroxy-1,2,3,4-tetrahydroisoquinoline; and the pharmaceutically acceptable salts thereof Preferred bisphosphonates include, tiludronic acid, alendronic acid, ibandronic acid, risedronic acid, etidronic acid, clodronic acid, and pamidronic acid and their pharmaceutically acceptable salts.

Yet another aspect of this invention is directed to a pharmaceutical composition including a compound of Formula I or a pharmaceutically acceptable salt or prodrug thereof and another bone anabolic agent (although the other bone anabolic agent may be a different Formula I compound) and for the use of such compositions for the treatment of conditions which present with low bone mass, including osteoporosis in mammals (e.g., humans, particularly women) or the use of such compositions for other bone mass augmenting uses.

The combination comprises a therapeutically effective amount of a first compound, said first compound being a Formula I compound or a pharmaceutically acceptable salt or prodrug thereof; and a therapeutically effective amount of a second compound, said second compound being another bone anabolic agent.

Preferred bone anabolic agents include IGF-1 optionally with IGF-1 binding protein 3, prostaglandin, prostaglandin agonist/antagonist, sodium fluoride, parathyroid hormone (PTH), active fragments of parathyroid hormone, parathyroid hormone related peptides and active fragments and analogues of parathyroid hormone related peptides, growth hormone or growth hormone secretagogues and the pharmaceutically acceptable salts thereof.

Another aspect of this invention is a method for treating mammals which present with low bone mass comprising administering to a mammal having a condition which presents with low bone mass a. a therapeutically effective amount of a first compound, said first compound being a Formula I compound or a pharmaceutically acceptable salt or prodrug therof; and b. a therapeutically effective amount of a second compound, said second compound being another bone anabolic agent other than the Formula I compound.

Such compositions and methods may also be used for other bone mass augmenting uses.

Preferred bone anabolic agents include IGF-1 optionally with IGF-1 binding protein 3, prostaglandin, prostaglandin agonist/antagonist, sodium fluoride, parathyroid hormone (PTH), active fragments of parathyroid hormone, parathyroid hormone related peptides and active fragments and analogues of parathyroid hormone related peptides, growth hormone or growth hormone secretagogues and the pharmaceutically acceptable salts thereof.

A preferred aspect of this method is wherein the condition which presents with low bone mass is osteoporosis.

Another preferred aspect of this method is wherein the first compound and the second compound are administered substantially simultaneously.

Another aspect of this invention is a kit comprising:

a. a therapeutically effective amount of a Formula I compound or a pharmaceutically acceptable salt or prodrug thereof and a pharmaceutically acceptable carrier in a first unit dosage form;

b. a therapeutically effective amount of a second compound, said second compound being a bone anabolic agent other than the Formula I compound; and c. container means for containing said first and second dosage forms.

Preferred bone anabolic agents include IGF-1 optionally with IGF-1 binding protein 3, prostaglandin, prostaglandin agonist/antagonist, sodium fluoride, parathyroid hormone (PTH), active fragments of parathyroid hormone, parathyroid hormone related peptides and active fragments and analogues of parathyroid hormone related peptides, growth hormone or growth hormone secretagogues and the pharmaceutically acceptable salts thereof.

A preferred group of compounds, designated the T2 Group, contains those compounds having the Formula I as shown above wherein B is N;

A is $(C_1-C_3)$ alkylsulfonyl;

Q is

—$(C_3-C_5)$alkylene—O—$(C_1-C_3)$alkylene-,

—$(C_5-C_7)$alkylene-, said —$(C_5-C_7)$alkylene-optionally substituted with up to four substituents independently selected from fluoro or $(C_1-C_4)$alkyl, —$(C_2-C_4)$alkylene-X-, —(CH$_2$)-meta-phenylene—O—(CH$_2$)— optionally mono- or di- substituted independently with methoxy, trifluoromethyl, difluoromethoxy, trifluoromethoxy, chloro or fluoro or —(CH$_2$)-meta-phenylene-(CH$_2$)— optionally mono- or di- substituted independently with methoxy, trifluoromethyl, difluoromethoxy, trifluoromethoxy, chloro or fluoro;

M is —Ar$^1$—V—Ar$^2$ or —Ar$^1$—O—Ar$^2$;

V is a bond or —CH$_2$—;

Z is carboxyl, (C$_1$–C$_4$)alkoxycarbonyl or tetrazolyl;

X is thienyl, thiazolyl, or furanyl;

K is methylene;

Ar$^1$ is phenyl, (C$_5$–C$_7$)cycloalkyl, furanyl, thienyl, thiazolyl, or pyridyl;

Ar$^2$ is (C$_5$–C$_7$)cycloalkyl, phenyl, thienyl, thiazolyl, pyridyl, pyrimidyl, oxazolyl, furanyl, imidazolyl, isoxazolyl, pyrazinyl, triazolyl or pyrazolyl;

R$^1$ is chloro, fluoro, (C$_1$–C$_4$)alkyl or (C$_1$–C$_4$)alkoxy, said (C$_1$–C$_4$)alkyl and (C$_1$–C$_4$) alkoxy optionally mono-, di- or tri-substituted independently with hydroxy or fluoro; and R$^2$ and R$^3$ are each independently, methoxy, trifluoromethyl, difluoromethoxy, trifluoromethoxy, chloro or fluoro.

A group of compounds which is preferred among the T2 group of compounds, designated the U2 Group, contains those compounds wherein Q is —(CH$_2$)-meta-phenylene-(CH$_2$)—, M is —Ar$^1$—Ar$^2$, Ar$^1$ is phenyl;

Ar$^2$ is (C$_5$–C$_7$)cycloalkyl, phenyl, thienyl, thiazolyl, pyridyl, pyrimidyl, oxazolyl, furanyl, imidazolyl, isoxazolyl, pyrazinyl or pyrazolyl, said Ar$^2$ optionally mono- or di- substituted independently with R$^1$ or R$^2$;

R$^1$ is chloro, fluoro, methyl, methoxy, trifluoromethyl, difluoromethoxy or trifluoromethoxy; and R$^2$ is methoxy, chloro or fluoro.

A group of compounds which is preferred among the T2 group of compounds, designated the V2 Group, contains those compounds wherein Q is —(CH$_2$)-meta-phenylene-O—(CH$_2$)—, M is —Ar$^1$—Ar$^2$, Ar$^1$ is phenyl;

Ar$^2$ is (C$_5$–C$_7$)cycloalkyl, phenyl, thienyl, thiazolyl, pyridyl, pyrimidyl, oxazolyl, furanyl, imidazolyl, isoxazolyl, pyrazinyl or pyrazolyl, said Ar$^2$ optionally mono- or di- substituted independently with R$^1$ or R$^2$;

R$^1$ is chloro, fluoro, methyl, methoxy, trifluoromethyl, difluoromethoxy or trifluoromethoxy; and R$^2$ is methoxy, chloro or fluoro.

An especially preferred compound of the U2 Group of compounds is a compound wherein A is methylsulfonyl;

Z is carboxyl; and

M is 4-(cyclohexyl)phenyl.

An especially preferred compound of the U2 Group of compounds is a compound wherein A is methylsulfonyl;

Z is carboxyl; and

M is 4-(thiazol-2-yl)phenyl.

An especially preferred compound of the U2 Group of compounds is a compound wherein A is methylsulfonyl;

Z is carboxyl; and

M is 4-(pyrazin-2-yl)phenyl.

Especially preferred compounds among the U2 Group are a. (3-{[(4-Cyclohexyl-benzyl)-methanesulfonyl-amino]-methyl}-phenyl)-acetic acid;

b. (3-{[Methanesulfonyl-(4-thiazol-2-yl-benzyl)-amino]-methyl}-phenyl)-acetic acid; or c. (3-{[Methanesulfonyl-(4-pyrazin-2-yl-benzyl)-amino]-methyl}-phenyl)-acetic acid.

A preferred group of compounds, designated the W2 Group, contains those compounds having the Formula I as shown above wherein B is N;

A is (C$_1$–C$_3$)alkylsulfonyl;

Q is —(C$_2$–C$_4$)alkylene-X-;

X is thiazolyl or furanyl; said thiazolyl or furanyl optionally mono- or di- substituted independently with methyl, methoxy, fluoro, chloro, trifluoromethyl, difluoromethoxy or trifluoromethoxy;

K is oxy-ethylene or propylene, said propylene optionally being mono-unsaturated;

M is —Ar, said —Ar is phenyl, thienyl, pyridyl, thiazolyl, oxazolyl, isoxazolyl, pyrimidyl, imidazolyl, cyclohexyl, cyclopentyl, cyclobutyl, or cycloheptyl;

R$^1$ is halo, (C$_1$–C$_6$)alkoxy, (C$_1$–C$_7$)alkyl, (C$_3$–C$_7$)cycloalkyl, (C$_1$–C$_7$)alkanoyl or (C$_3$–C$_7$)cycloalkyl(C$_1$–C$_4$)alkyl, said (C$_1$–C$_6$)alkoxy, (C$_1$–C$_7$)alkyl, (C$_3$–C$_7$)cycloalkyl, (C$_1$–C$_7$) alkanoyl or (C$_3$–C$_7$)cycloalkyl(C$_1$–C$_4$)alkyl, optionally mono-, di- or tri-substituted independently with hydroxy, fluoro or chloro; and R$^2$ and R$^3$ are each independently methoxy, trifluoromethyl, difluoromethoxy, trifluoromethoxy, chloro or fluoro.

A group of compounds which is preferred among the W2 group of compounds, designated the X2 Group, contains those compounds wherein A is methylsulfonyl;

Z is carboxyl, or (C$_1$–C$_4$)alkoxycarbonyl;

Q is -propylene-X-;

X is thiazolyl;

K is oxy-ethylene or propylene;

M is phenyl optionally mono- or di- substituted independently with fluoro, chloro, methoxy, methyl, difluoromethoxy, trifluoromethoxy or trifluoromethyl.

An especially preferred compound of the X2 Group of compounds is a compound wherein Z is carboxyl;

K is propylene; and

M is 3-(chloro)phenyl.

An especially preferred compound of the X2 Group of compounds is a compound wherein Z is carboxyl;

K is oxy-ethylene; and

M is 3,5-dichlorophenyl.

Especially preferred compounds among the X2 Group are
a. 2-(3-{[2-(3,5-Dichloro-phenoxy)-ethyl]-methanesulfonyl-amino}-propyl)-thiazole-4-carboxylic acid; or
b. 2-(3-{[3-(3-Chloro-phenyl)-propyl]-methanesulfonyl-amino}-propyl)-thiazole-4-carboxylic acid.

Another aspect of this invention is directed to a compound of Formula IA

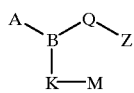

Formula IA or a pharmaceutically acceptable salt or prodrugs thereof wherein either (I):

B is N;

A is $(C_1-C_6)$alkylsulfonyl, $(C_3-C_7)$cycloalkylsulfonyl, $(C_3-C_7)$cycloalkyl$(C_1-C_6)$ alkylsulfonyl, said A moieties optionally mono-, di- or tri-substituted on carbon independently with hydroxy, $(C_1-C_4)$alkyl or halo;

Q is

—$(C_2-C_6)$alkylene-W—$(C_1-C_3)$alkylene-,

—$(C_3-C_8)$alkylene-, said —$(C_3-C_8)$alkylene- optionally substituted with up to four substituents independently selected from fluoro or $(C_1-C_4)$alkyl, —X—$(C_1-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, —$(C_0-C_4)$alkylene-X-W—$(C_1-C_3)$alkylene-, —$(C_2-C_5)$alkylene-W-X-W—$(C_1-C_3)$alkylene-, wherein the two occurrences of W are independent of each other, —$(C_1-C_4)$alkylene-ethenylene—$(C_1-C_4)$alkylene-, —$(C_1-C_4)$alkylene-ethenylene—$(C_0-C_2)$alkylene-X—$(C_0-C_5)$alkylene-, —$(C_1-C_4)$alkylene-ethenylene—$(C_0-C_2)$alkylene-X-W—$(C_1-C_3)$alkylene-, —$(C_1-C_4)$alkylene-ethynylene—$(C_1-C_4)$alkylene-, or —$(C_1-C_4)$alkylene-ethynylene-X—$(C_0-C_3)$alkylene-;

W is oxy, thio, sulfino, sulfonyl, aminosulfonyl-, -mono-N—$(C_1-C_4)$ alkyleneaminosulfonyl-, sulfonylamino, N—$(C_1-C_4)$alkylenesulfonylamino, carboxamido, N—$(C_1-C_4)$alkylenecarboxamido, carboxamidooxy, N—$(C_1-C_4)$ alkylenecarboxamidooxy, carbamoyl, -mono-N—$(C_1-C_4)$alkylenecarbamoyl, carbamoyloxy, or -mono-N—$(C_1-C_4)$alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, or di- substituted independently with halo, $(C_1-C_3)$alkyl, trifluoromethyl, trifluoromethyloxy, difluoromethyloxy, hydroxyl, $(C_1-C_4)$alkoxy, or carbamoyl;

Z is carboxyl, $(C_1-C_6)$alkoxycarbonyl, tetrazolyl, 1,2,4-oxadiazolyl, 5-oxo-1,2,4-oxadiazolyl, $(C_1-C_4)$ alkylsulfonylcarbamoyl or phenylsulfonylcarbamoyl;

K is a bond, $(C_1-C_8)$alkylene, thio$(C_1-C_4)$alkylene or oxy$(C_1-C_4)$alkylene, said $(C_1-C_8)$alkylene optionally mono-unsaturated and wherein K is optionally mono-, di- or tri-substituted independently with fluoro, methyl or chloro;

M is —Ar, —Ar¹—V—Ar², —Ar¹—S—Ar², —Ar¹—O—Ar², —Ar¹—S—$(C_1-C_3)$—Ar²—, —Ar¹—$(C_1-C_3)$—S—Ar²— or —Ar¹—$(C_1-C_3)$—S—$(C_1-C_3)$—Ar², wherein Ar, Ar¹ and Ar² are each independently a partially saturated, fully saturated or fully unsaturated five to eight membered ring optionally having one to four heteroatoms selected independently from oxygen, sulfur and nitrogen, or a bicyclic ring consisting of two fused partially saturated, fully saturated or fully unsaturated five or six membered rings, taken independently, optionally having one to four heteroatoms selected independently from nitrogen, sulfur and oxygen;

said Ar, Ar¹ and Ar² moieties optionally substituted, on one ring if the moiety is monocyclic, or one or both rings if the moiety is bicyclic, on carbon, nitrogen or sulfur with up to three substituents independently selected from R¹, R² and R³ wherein R¹, R² and R³ are oxo, hydroxy, nitro, halo, $(C_1-C_6)$alkoxy, $(C_1-C_4)$ alkoxy$(C_1-C_4)$alkyl, $(C_1-C_4)$ alkoxycarbonyl, $(C_1-C_7)$ alkyl, $(C_3-C_7)$cycloalkyl, $(C_3-C_7)$cycloalkyl$(C_1-C_4)$ alkyl, $(C_3-C_7)$ cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, sulfonamido, $(C_1-C_4)$ alkylsulfonamido, amino, mono-N- or di-N,N—$(C_1-C_4)$alkylamino, carbamoyl, mono-N- or di-N,N—$(C_1-C_4)$alkylcarbamoyl, cyano, thiol, $(C_1-C_6)$alkylthio, $(C_1-C_6)$alkylsulfinyl, $(C_1-C_4)$ alkylsulfonyl or mono-N- or di-N,N—$(C_1-C_4)$ alkylaminosulfinyl;

R¹, R² and R³ are optionally mono-, di- or tri-substituted on carbon independently with halo or hydroxy; and V is a bond or $(C_1-C_3)$alkylene optionally mono-unsaturated and optionally mono- or di- substituted independently with hydroxy or fluoro, with the proviso that when K is $(C_2-C_4)$alkylene and M is Ar and Ar is cyclopent-1-yl, cyclohex-1-yl, cyclohept-1-yl or cyclooct-1-yl then said $(C_5-C_8)$ cycloalkyl substituents are not substituted at the one position with hydroxy;

or (ii):

B is N;

A is $(C_1-C_6)$alkanoyl, or $(C_3-C_7)$cycloalkyl$(C_1-C_6)$ alkanoyl, said A moieties optionally mono-, di- or tri-substituted independently on carbon with hydroxy or halo;

Q is

—$(C_2-C_6)$alkylene-W—$(C_1-C_3)$alkylene-,

—$(C_4-C_8)$alkylene-, said —$(C_4-C_8)$alkylene-optionally substituted with up to four substituents independently selected from fluoro or $(C_1-C_4)$alkyl, —X—$(C_2-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, —$(C_0-C_4)$alkylene-X-W—$(C_1-C_3)$alkylene-, —$(C_2-C_5)$alkylene-W-X-W—$(C_1-C_3)$alkylene-, wherein the two occurrences of W are independent of each other, —$(C_1-C_4)$alkylene-ethenylene—$(C_1-C_4)$alkylene-, —$(C_1-C_4)$alkylene-ethenylene—$(C_0-C_2)$alkylene-X—$(C_0-C_5)$alkylene-, —$(C_1-C_4)$alkylene-ethenylene—$(C_0-C_2)$alkylene-X-W—$(C_1-C_3)$alkylene-, —($C_1$-$C_4$)alkylene-ethynylene—($C_1$-$C_4$)alkylene-, or
—($C_1$-$C_4$)alkylene-ethynylene-X—($C_0$-$C_3$)alkylene-;

W is oxy, thio, sulfino, sulfonyl, aminosulfonyl-, -mono-N—($C_1$-$C_4$) alkyleneaminosulfonyl-, sulfonylamino, N—($C_1$-$C_4$)alkylenesulfonylamino, carboxamido, N—($C_1$-$C_4$)alkylenecarboxamido, carboxamidooxy, N—($C_1$-$C_4$) alkylenecarboxamidooxy, carbamoyl, -mono-N—($C_1$-$C_4$)alkylenecarbamoyl, carbamoyloxy, or -mono-N—($C_1$-$C_4$)alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, or di- substituted independently with halo, ($C_1$-$C_3$)alkyl, trifluoromethyl, trifluoromethyloxy, difluoromethyloxy, hydroxyl, ($C_1$-$C_4$)alkoxy, or carbamoyl;

Z is carboxyl, ($C_1$-$C_6$)alkoxycarbonyl, tetrazolyl, 1,2,4-oxadiazolyl, 5-oxo-1,2,4-oxadiazolyl, ($C_1$-$C_4$) alkylsulfonylcarbamoyl or phenylsulfonylcarbamoyl;

K is ($C_1$-$C_8$)alkylene, thio($C_1$-$C_4$)alkylene or oxy($C_1$-$C_4$)alkylene, said ($C_1$-$C_8$) alkylene optionally mono-unsaturated and wherein K is optionally mono-, di- or tri-substituted independently with fluoro, methyl or chloro;

M is —Ar, —$Ar^1$—V—$Ar^2$, —$Ar^1$—S—$Ar^2$, —$Ar^1$—O—$Ar^2$, —$Ar^1$—S—($C_1$-$C_3$)—$Ar^2$—, —$Ar^1$—($C_1$-$C_3$)—S—$Ar^2$— or —$Ar^1$—($C_1$-$C_3$)—S—($C_1$-$C_3$)—$Ar^2$ wherein Ar, $Ar^1$ and $Ar^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, $Ar^1$ and $Ar^2$ moieties optionally substituted, on one ring if the moiety is monocyclic, or one or both rings if the moiety is bicyclic, on carbon, nitrogen or sulfur with up to three substituents independently selected from $R^1$, $R^2$ and $R^3$ wherein $R^1$, $R^2$ and $R^3$ are oxo, H, hydroxy, nitro, halo, ($C_1$-$C_6$)alkoxy, ($C_1$-$C_4$) alkoxy($C_1$-$C_4$)alkyl, ($C_1$-$C_4$)alkoxycarbonyl, ($C_1$-$C_7$) alkyl, ($C_3$-$C_7$)cycloalkyl, ($C_3$-$C_7$)cycloalkyl($C_1$-$C_4$) alkyl, ($C_3$-$C_7$)cycloalkyl($C_1$-$C_4$)alkanoyl, formyl, ($C_1$-$C_8$)alkanoyl, ($C_1$-$C_6$)alkanoyl($C_1$-$C_6$)alkyl, ($C_1$-$C_4$)alkanoylamino, ($C_1$-$C_4$)alkoxycarbonylamino, sulfonamido, ($C_1$-$C_4$) alkylsulfonamido, amino, mono-N- or di-N,N—($C_1$-$C_4$)alkylamino, carbamoyl, mono-N- or di-N,N—($C_1$-$C_4$)alkylcarbamoyl, cyano, thiol, ($C_1$-$C_6$)alkylthio, ($C_1$-$C_6$)alkylsulfinyl, ($C_1$-$C_4$) alkylsulfonyl or mono-N- or di-N,N—($C_1$-$C_4$) alkylaminosulfinyl;

$R^1$, $R^2$ and $R^3$ are optionally mono-, di- or tri-substituted independently on carbon with halo or hydroxy; and V is a bond or ($C_1$-$C_3$)alkylene optionally mono-unsaturated and optionally mono- or di- substituted independently with hydroxy or fluoro with the proviso that when K is ($C_2$-$C_4$)alkylene and M is Ar and Ar is cyclopent-1-yl, cyclohex-1-yl, cyclohept-1-yl or cycloct-1-yl then said ($C_5$-$C_8$) cycloalkyl substituents are not substituted at the one position with hydroxy and with the proviso that 6-[(3-phenyl-propyl)-(2-propyl-pentanoyl)-amino]-hexanoic acid and its ethyl ester are not included.

Yet another aspect of this invention is directed to a pharmaceutical composition comprising:

a therapeutically effective amount of a compound of Formula IA or a pharmaceutically acceptable salt or prodrug thereof and a therapeutically effective amount of 2-(4-methoxy-phenyl)-3-[4-(2-piperidin-1-yl-ethoxy)-phenoxy]-benzo[b]thiophen-6- or a pharmaceutically acceptable salt thereof or 3-[4-(1,2-diphenyl-but-1-enyl)-phenyl]-acrylic acid or a pharamceutically acceptable salt thereof.

Yet another aspect of this invention is directed to a method for treating a mammal having a condition which presents with low bone mass comprising administering to said mammal a therapeutically effective amount of a compound of Formula IA or a pharmaceutically acceptable salt or prodrug thereof and a therapeutically effective amount of 2-(4-methoxy-phenyl)-3-[4-(2-piperidin-1-yl-ethoxy)-phenoxy]-benzo[b]thiophen-6-ol or a pharmaceutically acceptable salt thereof or 3-[4-(1,2-diphenyl-but-1-enyl)-phenyl]-acrylic acid or a pharamceutically acceptable salt thereof.

Yet another aspect of this invention is directed to a kit comprising a therapeutically effective amount of a compound of Formula IA or a pharmaceutically acceptable salt or prodrug thereof and a pharmaceutically acceptable carrier in a first unit dosage form;

a therapeutically effective amount of 2-(4-methoxy-phenyl)-3-[4-(2-piperidin-1-yl-ethoxy)-phenoxy]-benzo[b]thiophen-6-ol or a pharmaceutically acceptable salt thereof or 3-[4-(1,2-diphenyl-but-1-enyl)-phenyl]-acrylic acid or a pharamceutically acceptable salt thereof and a pharmaceutically acceptable carrier in a second unit dosage form; and container means for containing said first and second dosage forms.

Yet another aspect of this invention is directed to a method for treating a mammal in need of kidney regeneration comprising administering to said mammal a therapeutically effective amount of a compound of Formula 1A or a pharmaceutically acceptable salt or prodrug thereof.

Yet another aspect of this invention is directed to a method for treating a mammal having a condition which presents with low bone mass comprising administering to said mammal a therapeutically effective amount of a compound of Formula IA or a pharmaceutically acceptable salt or prodrug thereof.

Yet another aspect of this invention is directed to a pharmaceutical composition which comprises a therapeutically effective amount of a compound of Formula IA or a pharmaceutically acceptable salt or prodrug thereof and a pharmaceutically acceptable carrier.

Yet another aspect of this invention is directed to a method for lowering intraocular pressure in a mammal comprising administering a therapeutically effective amount of a compound of Formula IA or a pharamceutically acceptable salt or prodrug thereof to a mammal in need.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, osteotomy and childhood idiopathic bone loss. The "condition(s) which presents with low bone mass" also includes long term complications of osteoporosis such as curvature of the spine, loss of height and prosthetic surgery.

The phrase "condition which presents with low bone mass" also refers to a mammal known to have a significantly higher than average chance of developing such diseases as are described above including osteoporosis (e.g., post-menopausal women, men over the age of 60).

Other bone mass augmenting or enhancing uses include increasing the bone fracture healing rate, enhancing the rate of successful bone grafts, bone healing following facial reconstruction or maxillary reconstruction or mandibular reconstruction, prosthetic ingrowth, vertebral synostosis or long bone extension.

Those skilled in the art will recognize that the term bone mass actually refers to bone mass per unit area which is sometimes (although not strictly correctly) referred to as bone mineral density. The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to substituents wherein the Z moiety is independently carboxyl and the free hydrogen is replaced by $(C_1-C_4)$alkyl, $(C_2-C_7)$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as b-dimethylaminoethyl), carbamoyl—$(C_1-C_2)$alkyl, N,N-di$(C_1-C_2)$alkylcarbamoyl—$(C_1-C_2)$alkyl and piperidino-, pyrrolidino- or morpholino$(C_2-C_3)$alkyl.

Exemplary five to six membered aromatic rings optionally having one or two heteroatoms selected independently from oxygen, nitrogen and sulfur (i.e., X rings) are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to four heteroatoms selected independently from oxygen, sulfur and nitrogen (i.e., Ar, $Ar^1$ and $A^2$) are cyclopentyl, cyclohexyl, cycloheptyl, cyclooctyl and phenyl. Further exemplary five membered rings are furyl, thienyl, 2H-pyrrolyl, 3H-pyrrolyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 1,2,3,4-oxatriazolyl, 1,2,3,5-oxatrizaolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-trizainyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings are azepinyl, oxepinyl, thiepinyl and 1,2,4-diazepinyl.

Further exemplary eight membered rings are cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen are indolizinyl, indolyl, isoindolyl, 3H-indolyl, 1H-isoindolyl, indolinyl, cyclopenta(b) pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, 4Hquinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompases the particular example) are methylene, ethylene, propylene, butylene, pentylene, hexylene, heptylene).

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N—$(C_1-C_x)$ alkyl . . . refers to the $(C_1-C_x)$alkyl moiety taken independently when it is di-N,N—$(C_1-C_x)$alkyl . . . (x refers to integers).

Unless otherwise stated the "M" moieties defined above are optionally substituted (e.g., the mere listing of a substituent such as $R^1$ in a subgenus or dependent claim does not mean that M is always substituted with the $R^1$ moiety unless it is stated that the M moiety is substituted with $R^1$).

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

DTT means dithiothreitol. DMSO means dimethyl sulfoxide. EDTA means ethylenediamine tetraacetic acid.

The methods and compounds of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

DETAILED DESCRIPTION OF THE INVENTION

In the DETAILED DESCRIPTION OF THE INVENTION reference to "Formula I" is to be interpreted as reference to "Formula I or Formula IA" in order to encompass the subject matter added in this continuation-in-part.

In general the compounds of this invention can be made by processes which include processes known in the chemical arts, particularly in light of the description contained herein.

Certain processes for the manufacture of the compounds of this invention are provided as further features of the invention and are illustrated by the following reaction schemes. Other processes may be described in the experimental section.

Some substituents (e.g., carboxyl) may best be prepared through conversion of another functional group (for carboxyl examples are hydroxyl or carboxaldehyde) at a point later in the synthetic sequence.

In general, the Formula I compounds wherein B is nitrogen can be prepared by sequential alkylation of sulfonamide or amide with two appropriate alkyl halides or alkylsulfonates; or reductive amination of an amine containing the necessary acidic functionality (suitably protected) with an aldehyde followed by reaction with an acylating agent or a sulfonyl chloride followed by hydrolysis.

Generally, the compounds of Formula I (wherein B is N (nitrogen) and A, K, M and Q are as described in the Summary) can be prepared according to the methods described in SCHEMES 1 and 2 below. In general, the sequences involve sequential alkylation of the appropriate formula 1 sulfonamide or amide with two appropriate alkyl halides or alkylsulfonates. It is noted that SCHEMES 1 and 2 merely differ in the order of addition of the two alkylating agents. The alkylation order is typically chosen depending on the reactivity of the electrophilic side-chain. In order to reduce the amount of dialkylation which occurs in the first alkylation step, the less reactive electrophilic side-chain is typically introduced first. One of the alkylating agents typically contains a carboxylic acid or acid isostere suitably masked with an appropriate protecting group. In SCHEMES 1 and 2, the formula 3 acid precursor is a carboxylic ester where R represents either a straight chain lower alkyl, preferably methyl or ethyl, or a tert-butyl or phenyl group. Other acid isosteres can be employed by appropriately modifying these SCHEMES using methods known to those skilled in the art (see SCHEME 6 which describes a tetrazol preparation for an example). Typical alkylating agents are primary, secondary, benzylic or allylic and are preferably alkyl bromides or alkyl iodides.

The formula 1 sulfonamide or amide is converted to its anion with a strong base such as sodium hydride, lithium diisopropylamide, lithium bis(trimethylsilyl)amide, potassium bis(trimethylsilyl)amide, potassium tert-butoxide, etc. in an aprotic solvent such as dimethylformamide, tetrahydrofuran (THF) or dimethylformamide/benzene at a temperature of about −78° C. to about 100° C. The resulting anion is alkylated with the appropriate formula 2 or 3 alkyl halide or alkyl sulfonate (wherein X' is the halide or sulfonate) at a temperature of about 0° C. to about 100° C. to yield the corresponding alkylated formula 4 or 5 compound. In some cases, varying amounts of a side-product resulting from dialkylation of the amide or sulfonamide are obtained and can be removed using chromatographic techniques, preferably by flash chromatography (W. C. Still, M. Kahn, A. Mitra, J. Org. Chem. 43, 2923, 1978). The formula 4 or 5 compounds are converted to the anion again using a suitable base such as sodium hydride, lithium bis(trimethylsilyl)amide, lithium diisopropylamide, potassium bis(trimethylsilyl)amide, potassium tert-butoxide, or potassium carbonate in an aprotic solvent such as dimethylformamide, THF, dimethylformamide/benzene, or acetone at a temperature of about -78° C. to about 100° C., Alkylation (as described above) with the appropriate second alkyl halide or alkyl sulfonate (formula 3 or 2 compound) provides the corresponding formula 6 ester. The formula 6 ester is hydrolyzed to the corresponding Formula I acid (in cases where R represents methyl or ethyl) with a dilute aqueous basic solution (preferably sodium or potassium hydroxide in aqueous methanol or ethanol), lithium hydroxide in aqueous alcoholic solvent, aqueous tetrahydrofuran at a temperature of about 0° C. to about 80° C., or by using methods described in "Protecting Groups in Organic Synthesis," Second Edition, T. W. Greene and P. G. M. Wuts, John Wiley and Sons, Inc., 1991.

SCHEME 1

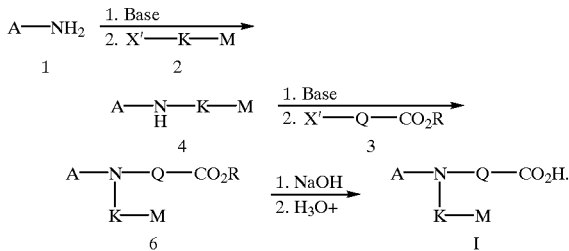

SCHEME 2

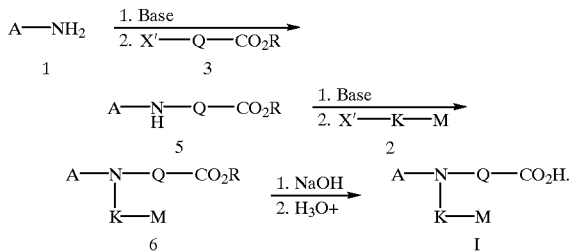

Formula I compounds (e.g., formula 13 or 14 compounds wherein B is N and A, K, M, Q and Z are as defined in the Summary) can also be prepared from amines (see SCHEMES 34 for examples). Generally, the appropriate amine starting materials (formula 9 and 10 compounds) can be commercially obtained or can be prepared using methods known to those skilled in the art (see "The Chemistry of Amino, Nitroso and Nitro Compounds and their Derivatives," Ed. S. Patai, J. Wiley, New York, 1982). For example, according to SCHEMES 3 and 4, the amine starting materials may be prepared from the corresponding formula 7 or 8 nitriles. Nitriles are either available from commercial sources or can be prepared using methods known to those skilled in the art (see Rappaport, "The Chemistry of the Cyano Group," Interscience, New York, 1970 or Patai and Rappaport, "The Chemistry of Functional Groups," pt. 2, Wiley, New York, 1983). The formula 7 or 8 nitrile is reduced with a reducing agent such as borane-tetrahydrofuran complex, borane-methyl sulfide complex, lithium aluminum hydride, or hydrogenation in the presence of Raney nickel or a platinum or palladium catalyst in a protic solvent such as methanol or ethanol at a temperature of about 0° C. to about 50° C. The resulting formula 9 or 10 amine is converted to either the formula 11 or 12 sulfonamide or amide by treatment (acylation) with an acid chloride or sulfonyl chloride in the presence of a weak base such as triethylamine, pyridine, or 4-methylmorpholine in an aprotic solvent such as methylene chloride or diethyl ether at a temperature of about –20° C. to about 50° C. Alternatively, coupling of amines of formulas 9 or 10 with carboxylic acids are conveniently carried out in an inert solvent such as dichloromethane or N,N-dimethylformamide (DMF) by a coupling reagent such as 1-(3-dimethylaminopropyl)-3-ethylcarbodiimide hydrochloride (EDC) or 1,3-dicyclohexylcarbodiimide (DCC) in the presence of 1-hydroxybenzotriazole hydrate (HOBT) to generate compounds of formula 11 or 12. In the case where the amine is present as the hydrochloride salt, it is preferable to add one equivalent of a suitable base such as triethylamine to the reaction mixture. Alternatively, the coupling can be effected with a coupling reagent such as benzotriazol-1-yloxy-tris(dimethylamino)-phosphonium hexafluorophosphate (BOP) in an inert solvent such as methanol. Such coupling reactions are generally conducted at temperatures of about –30° C. to about 80° C., preferably 0° C. to about 25° C. For a discussion of other conditions used for coupling peptides see Houben-Weyl, Vol. XV, part 11, E. Wunsch, Ed., George Theime Verlag, 1974, Stuttgart. Alkylation and if desired, deprotection, of the formula 11 or 12 compound as described in SCHEMES 1 and 2 affords the corresponding acid formula 13 and 14 compound.

The formula 9 and 10 amines may also be prepared via reduction of formula 15 and 16 amides. The reduction can be achieved using reagents such as a borane-tetrahydrofuran complex, a borane-methyl sulfide complex, or diisobutylaluminum hydride in an aprotic solvent such as tetrahydrofuran or diethyl ether at a temperature of about –78° C. to about 60° C.

The formula 9 and 10 amines can also be obtained from the corresponding nitro precursors by reduction of the nitro group using reducing reagents such as zinc/HCl, hydrogenation in the presence of Raney nickel, palladium, or platinum catalysts, and other reagents as described by P. N. Rylander in "Hydrogenation Methods," Academic Press, New York, 1985.

SCHEME 3

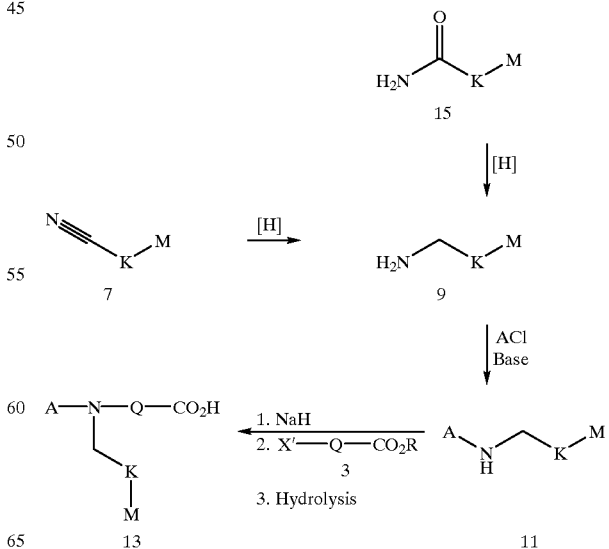

SCHEME 4

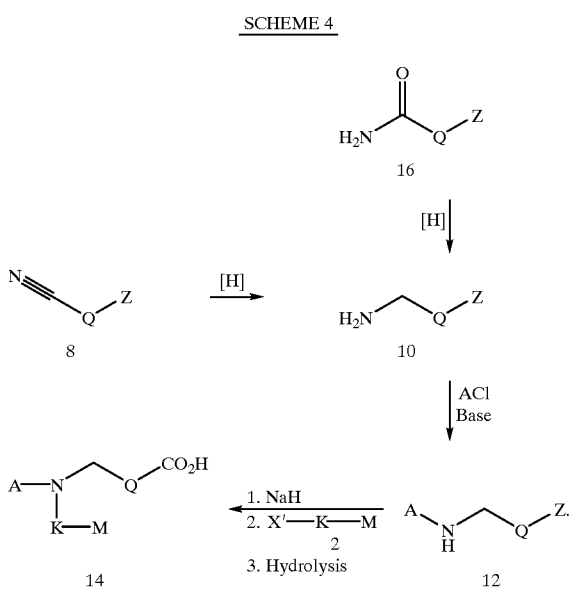

The description of, and preparation of other amines and alkylating agents useful for the above syntheses are described below in the section entitled PREPARATIONS.

An alternative to the alkylation chemistry described above for the preparation of Formula I compounds (wherein B is N and A, K, M and Q are as described in the Summary) involves reductive amination of an amine containing the necessary acidic functionality (suitably protected) with an aldehyde and is shown in SCHEME 5. Alternatively, the aldehyde may contain the acidic functionality for coupling with an amine.

The reductive amination is typically carried out with a reducing agent such as sodium cyanoborohydride or sodium triacetoxyborohydride preferably at a pH of between 6 and 8. The reaction is normally performed in a protic solvent such as methanol or ethanol at temperatures of about −78° C. to about 40° C. (for a leading reference see A. Abdel-Magid, C. Maryanoff, K. Carson, Tetrahedron Lett. 39, 31, 5595–5598, 1990). Other conditions involve the use of titanium isopropoxide and sodium cyanoborohydride (R.J. Mattson et al, J. Org. Chem. 1990, 55, 2552–4) or preformation of the imine under dehydrating conditions followed by reduction. The resulting formula 42, 42A amine, is transformed to the desired sulfonamide or amide by coupling with an acid chloride, sulfonyl chloride, or carboxylic acid as described in SCHEMES 3 and 4. If desired, hydrolysis provides the corresponding acid.

SCHEME 5

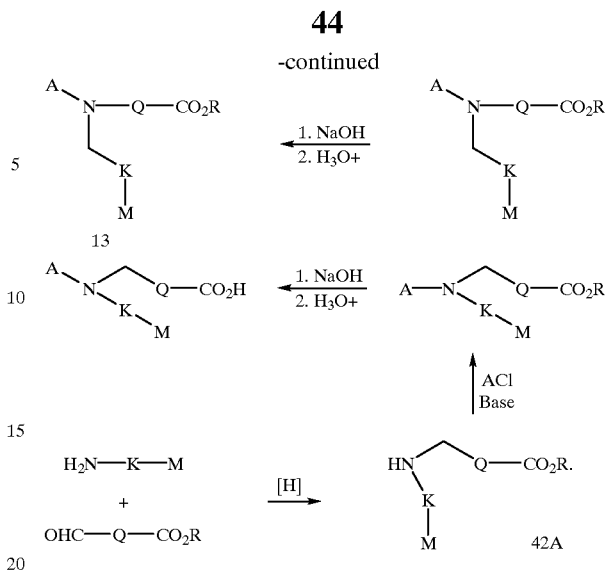

The description of and use of aldehydes useful in the above SCHEME 5 may be found in the PREPARATIONS section.

Alternatively, another method of preparing certain Formula I compounds (i.e., formula 60 tetrazoles wherein B is N and A, K, M, and Q are as described above) is described in SCHEME 6. The starting formula 4 sulfonamide or amide is alkylated with the appropriate alkyl halide or sulfonate (wherein X' is halide or sulfonate), preferable a primary, secondary, benzylic, or allylic alkyl bromide, iodide, or sulfonate, which contains a nitrile to provide formula 59 compounds. The alkylation is achieved by treatment of the formula 59 compound with a base such as sodium hydride, lithium bis(trimethylsilyl)amide, potassium bis(trimethylsilyl)amide, potassium tert-butoxide, or potassium carbonate in an aprotic solvent such as dimethylformamide, dimethylformamide/benzene, or acetone. Alkylation occurs at a temperature of about −78° C. to about 100° C. Preferred conditions for converting the resulting nitrile to the formula 60 tetrazole, involve treatment with dibutyltin oxide and trimethylsilylazide, in toluene at reflux (S. J. Wittenberger and B.G. Donner, J. Org. Chem. 1993, 58, 4139-4141, 1993). For a review of alternative preparations of tetrazoles see R. N. Butler, Tetrazoles, In Comprehensive Heterocyclic Chemistry; Potts, K. T. Ed.; Pergamon Press: Oxford, 1984, Vol. 5, pp 791–838.

SCHEME 6

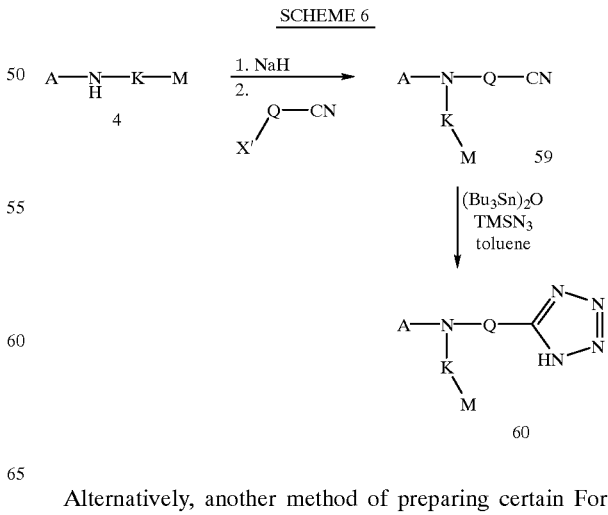

Alternatively, another method of preparing certain Formula I compounds (wherein B is N and A, Q and M are as described in the Summary) is described in SCHEME 7. Formula 46 esters can be prepared using the procedures described earlier (see SCHEMES 1 and 2). Subsequent Heck coupling of this intermediate to an arylhalide (preferably an aryl bromide or aryl iodide), an aryl triflate, or a ring system which contains a vinyl bromide, iodide, or triflate is accomplished with a palladium catalyst, such as palladium acetate or tetrakis(triphenylphosphine)palladium(0) in the presence of a trialkylamine, such as triethylamine. In some cases, a triarylphosphine may be added to the reaction. The reaction is typically performed in an aprotic solvent such as dimethylformamide or acetonitrile at a temperature of about 0° C. to about 150° C. (see R.F. Heck in Comp. Org. Syn., Vol. 4, Ch. 4.3, p. 833 or Daves and Hallberg, Chem. Rev. 1989, 89, 1433). If desired formula 47 compounds can be hydrolyzed to the corresponding acid. Alternatively, the formula 47 compounds can be hydrogenated and, if desired, further hydrolyzed to the corresponding formula 49 acid. Preferred conditions for hydrogenation involve the use of a palladium or platinum catalyst in an alcoholic solvent such as ethanol or methanol at a temperature of about 0° C. to about 50° C. In cases where M represents a partially saturated ring system, hydrogenation will generate a saturated ring system.

SCHEME 7

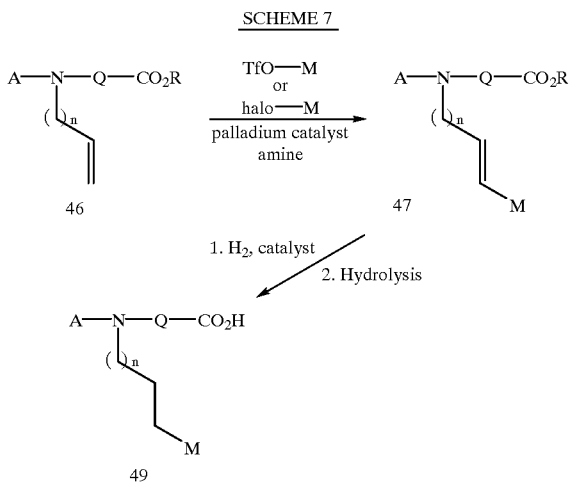

Alternatively, another method of preparing certain Formula I compounds (wherein B is N and A, Q, K and M are as described in the Summary and R is as described for SCHEMES 1 and 2) is described in SCHEME 8. Formula 51 compounds can be prepared as described in SCHEMES 1 and 2 by alkylation of formula 5 compounds with an electrophile of formula 2 which contains the appropriate functionality on the ring M, for subsequent conversion to an aldehyde. For example, electrophiles of formula 2 (SCHEME 2) could contain a protected alcohol on the ring, M, which, after alkylation, can be deprotected and oxidized to the aldehyde, using reagents known to those skilled in the art, to generate formula 51 compounds. An alternative method is to alkylate with an electrophile of formula 2 where M contains a vinyl group. After alkylation, oxidative cleavage of the double bond provides the desired formula 51 aldehyde. The oxidative cleavage can be accomplished by transforming the double bond to the 1,2-diol with catalytic osmium tetroxide and N-methylmorpholine followed by oxidative cleavage to the aldehyde using sodium periodate. Alternatively, oxidative cleavage via ozonolysis followed by reduction using reagents such as methyl sulfide, triphenylphosphine, zinc/acetic acid, or thiourea, will generate the desired formula 51 aldehyde. Addition of LMetal where LMetal represents any organometallic reagent such as an organolithium or Grignard reagent in an aprotic solvent such as diethyl ether or tetrahydrofuran at a temperature of about −78° C. to about 80° C., followed by hydrolysis of the ester as described above, provides the desired formula 50 compound.

SCHEME 8

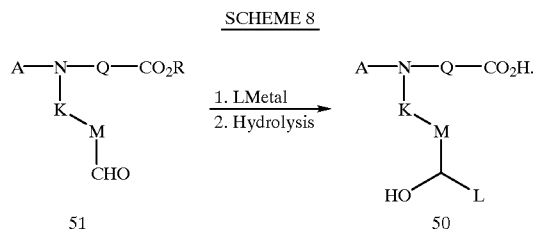

Alternatively, another method of preparing certain Formula I compounds (wherein B is N and A, K, and Q are as described in the Summary) is described in SCHEME 9. The appropriate formula 5 sulfonamide or amide is alkylated using the conditions described in SCHEMES 1 and 2 with an electrophile which contains an aromatic bromide or iodide or a ring system which contains a vinyl bromide or iodide ($Ar_1$) to provide formula 53 compounds. Suzuki-type coupling of the formula 53 compound with an aryl boronic add ($Ar_2$) provides formula 53a compounds (for a review of the Suzuki reaction see A. R. Martin and Y. Yang in Acta Chem. Scand. 1993, 47, 221). The coupling reaction is achieved using about two equivalents of a base, such as sodium carbonate, potassium carbonate, sodium hydroxide, thallium hydroxide, potassium phosphate, or sodium methoxide, in the presence of a palladium catalyst, such as tetrakis (triphenylphosphine)palladium(0), palladium acetate, palladium chloride, tris(dibenzylideneacetone)dipalladium(0) or [1,4-bis(diphenylphosphine)butane]palladium(0). The reaction may be run in aqueous alcoholic solvents (methanol or ethanol), aqueous tetrahydrofuran, aqueous acetone, aqueous glycol dimethyl ether, or aqueous benzene at temperatures ranging from about 0° C. to about 120° C. When $Ar_1$ represents a partially saturated ring, if appropriate, reduction of the ring to provide a saturated ring system may be performed at this point. Conditions to accomplish this transformation involve hydrogenation in the presence of a catalyst such as palladium or platinum in an alcoholic solvent (ethanol or methanol) and/or ethyl acetate. Ester hydrolysis of formula 53a compounds, if desired, provides the corresponding acid. The resulting acids may contain functional groups on either of the ring systems ($Ar_1$ or $Ar_2$) which can be modified using methods known to those skilled in the art. Examples of such modifications are shown in SCHEME 10.

SCHEME 9

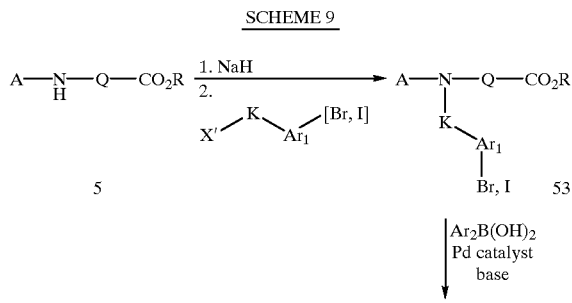

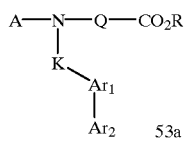

53a

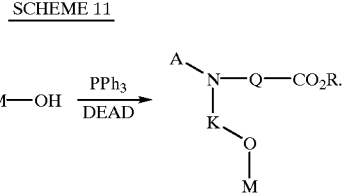

SCHEME 11

Formula 54 compounds which contain an aldehyde functional group can be prepared using methods described in SCHEMES 8 and 9. According to SCHEME 10, treatment of the formula 54 compound with an appropriate organometallic reagent (LMetal), such as an organolithium or Grignard reagent, in an aprotic solvent such as diethyl ether or tetrahydrofuran at a temperature of about −78° C. to about 80° C., followed by hydrolysis of the ester, provides formula 56 compounds (wherein B is N and A, Q and K are as described in the Summary and $Ar_1$ and $Ar_2$ are as described in SCHEME 9). Alternatively, reduction of the aldehyde followed by hydrolysis provides formula 55 compounds.

SCHEME 10

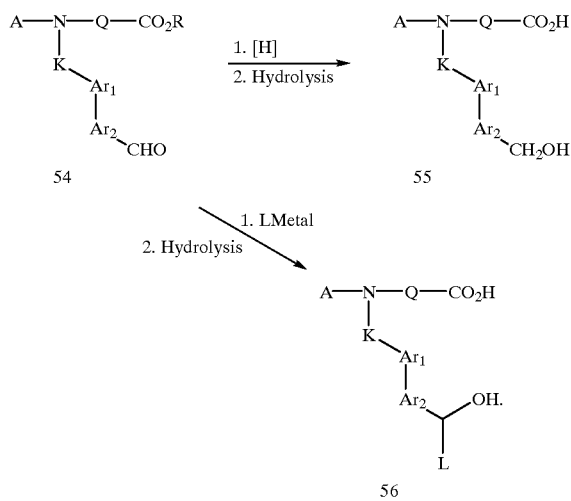

Alternatively, another method of preparing certain Formula I compounds (i.e., formula 57 compounds wherein B is N and A, K, and Q are as described in the Summary and R is as described in SCHEMES 1 and 2 and accordingly the corresponding acids) is described in SCHEME 11. The formula 58 starting alcohol can be prepared using the methods described in SCHEMES 1 and 2. Intermediate 58 is coupled with a variety of aryl alcohols (M represents an aromatic ring) using Mitsonobu conditions (for a review see O. Mitsonobu, Synthesis, 1, 1981). Typically the coupling is achieved by addition of a coupling agent such as triphenylphosphine and diethyl azodicarboxylate (DEAD) or diisopropyl azodicarboxylate in inert solvents such as methylene chloride or tetrahydrofuran at a temperature of about 0° C. to about 80° C. If desired, subsequent hydrolysis yields the corresponding acid.

Alternatively, another method of preparing certain Formula I compounds (i.e., formula 106 compounds wherein B is N and A, K, and M are as described in the Summary and R is as described in SCHEMES 1 and 2 and accordingly, the corresponding acids) is described in SCHEME 12. A formula 102 compound is added to a formula 105 compound (wherein the X is an aromatic ring such as a benzene ring or a thiophene ring) in the presence of a Lewis acid such as titanium tetrachloride or a mineral acid such as hydrochloric acid. If desired the formula 106 ester can be converted to the corresponding acid by hydrolysis or deprotection.

SCHEME 12

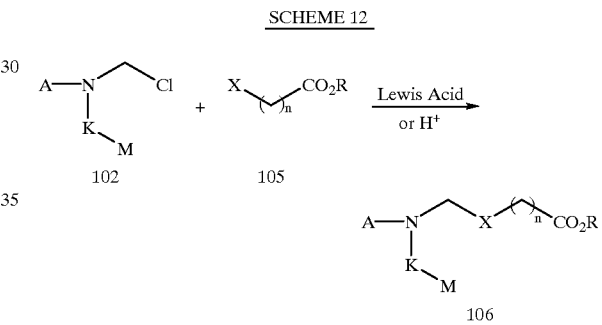

Alternatively, another method of preparing certain Formula I compounds (i.e., formula 107 or 108 compounds wherein B is N and A, and Q are as described in the Summary and accordingly, the corresponding acids) is described in SCHEME 13. Formula 104 chloromethyl compounds are treated with the appropriate substituted aromatic ring system, M, such as 4-ethoxybenzene or thiophene in the presence of a Lewis acid such as titanium tetrachloride or a mineral acid such as hydrochloric acid in an aprotic solvent such as chloroform at a temperature of about 0° C. to about 80° C. to yield the formula 107 compound which may subsequently be hydrolyzed or deprotected as described above to yield the corresponding acid. Alternatively, formula 104 chloromethyl compounds can be treated with a Lewis acid such as titanium tetrachloride and an appropriately substituted vinyl silane in an aprotic solvent such as methylene chloride at a temperature of about −50° C. to about 50° C. to give formula 108 compounds which may subsequently be hydrolyzed or deprotected as described above to yield the corresponding acid. If desired, reduction of the double bond can be accomplished using conditions described in SCHEME 7.

SCHEME 13

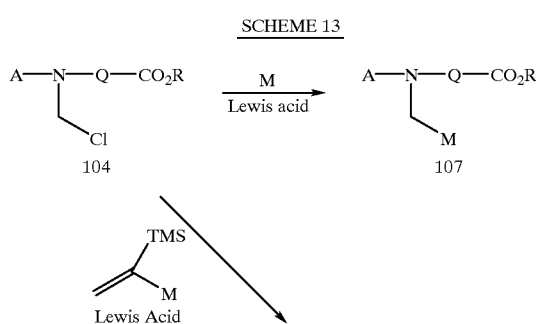

Alternatively, another method of preparing certain Formula I compounds (i.e., formula 109 compounds, wherein B is N and A, Q, R and M are as described above, and accordingly, the corresponding acids) is described in SCHEME 14. Formula 104 chloromethyl compounds are treated with a Lewis acid such as titanium tetrachloride and an appropriately substituted allyl silane in an aprotic solvent such as chloroform at a temperature of about 0° C. to about 80° C. to give formula 109 compounds which may subsequently be hydrolyzed or deprotected as described above.

SCHEME 14

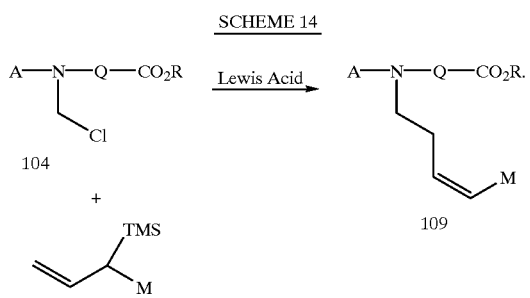

Alternatively, another method of preparing certain Formula I compounds (i.e., formula 112 compounds, wherein B is N and A, Q, R and M are as described above, and accordingly, the corresponding acids) is described in SCHEME 15. Formula 104 chloromethyl compounds are treated with a formula 111 sulfinic acid in the presence of a base such as triethylamine in an aprotic solvent such as chloroform at a temperature of about −30° C. to about 50° C. to give formula 112 compounds which may subsequently be hydrolyzed or deprotected as described above to yield the corresponding acid.

SCHEME 15

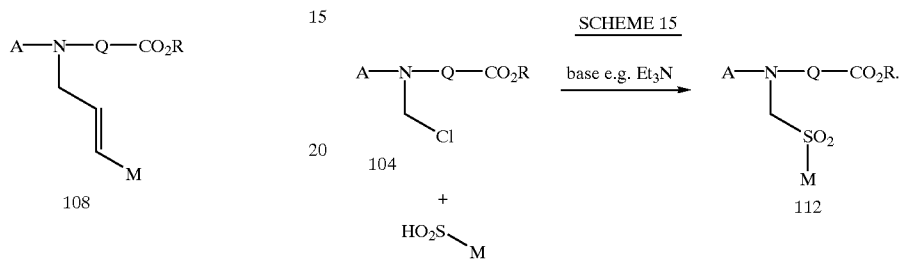

Formula I compounds (wherein B is C(H) and Q, M and K are as described in the Summary, $R^4$ is a small chain alkyl group, and $R_1$ represents the alkyl groups on A as described in the Summary) can be prepared according to SCHEME 16. Formula 113 beta-ketoesters are alkylated sequentially with formula 114 compounds followed by alkylation of formula 116 compounds to give formula 117 compounds (J. Med. Chem. 26, 1993, p335–41). Alkylations can be carried out in a suitable solvent such as DMF, THF, ether, or benzene using an appropriate base such as sodium hydride, LDA, or potassium carbonate at a temperature of about −78° C. to about 80° C. The resulting formula 117 disubstituted keto esters are hydrolyzed and decarboxylated to give the corresponding formula 118 compound by using an aqueous base such as sodium hydroxide to hydrolyze the ester, followed by an acidic quench such as aqueous hydrochloric acid to effect decarboxylation.

SCHEME 16

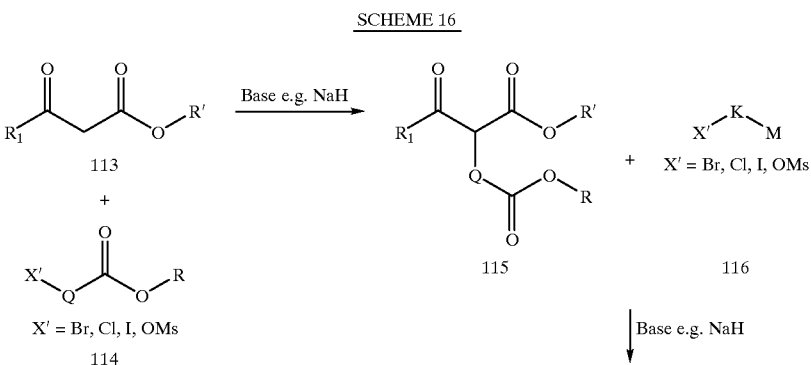

-continued

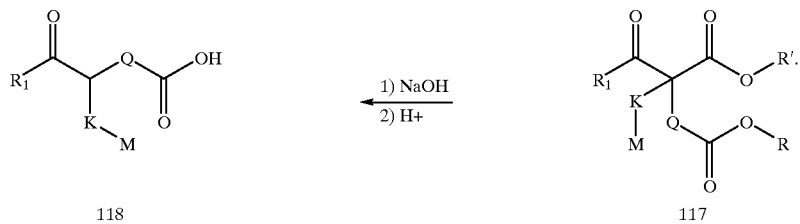

Alternatively, Formula I compounds (wherein B is C(H) and Q, M and K are as described in the Summary, R' is as described above, and $R_1$ represents the alkyl groups on A as described in the Summary) may be prepared according to SCHEME 17. Sequential alkylation of a malonate derivative of formula 119 provides the formula 121 dialkylated species.

which after hydrolysis of the terminal ester provide the keto-acid compounds of formula 118.

Alternatively formula 118 compounds can be prepared using methods described previously (e.g. see SCHEMES 7, 8, 9, 10, and 11) where one or both of the side chains are further functionalized after attachment.

SCHEME 17

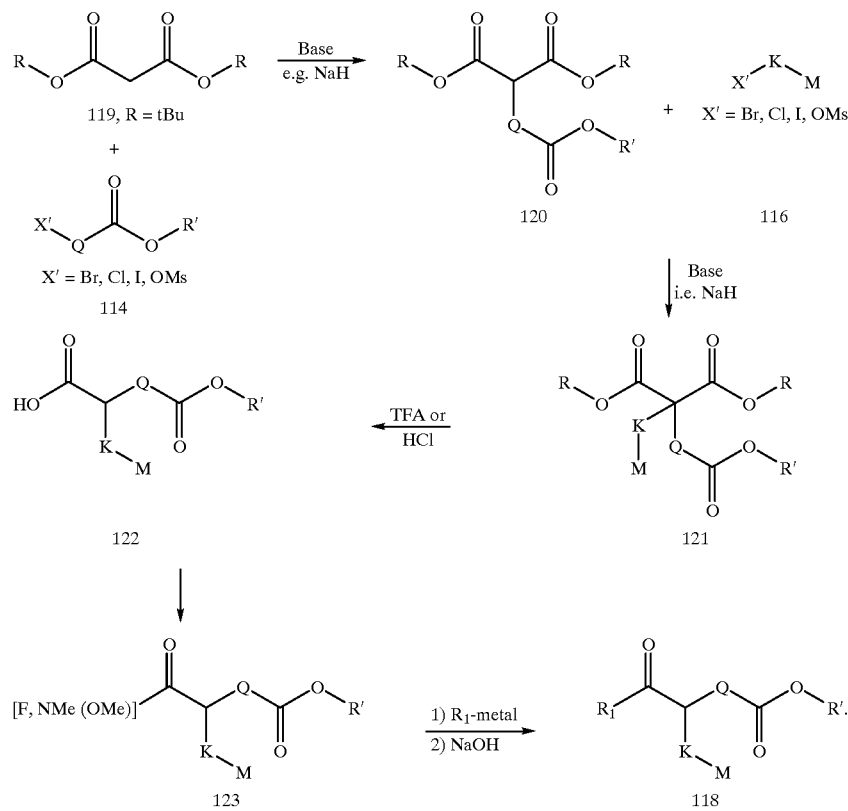

Deprotection of the ester group by treatment with a strong acid such as TFA or HCl in ethanol at a temperature of about −20° C. to about 50° C. leads to the formula 122 decarboxylated product. Conversion of the acid to an acid chloride using thionyl chloride or oxalyl chloride in an aprotic solvent at a temperature of about −78° C. to about 50° C. or to a Weinreb amide using methoxymethyl amine in the presence of a suitable coupling agent such as DCC or DEC in an aprotic solvent at a temperature of about −30° C. to about 50° C. provides formula 123 compounds. Formula 123 are suitable substrates for addition of various organometallic species (e.g., grignard reagents, organo-cadmium reagents)

PREPARATIONS

Amines, Amides and Sulfonamides

Certain amides or sulfonamides described by formulas 21, 22, and 23 (wherein W and Z are as described in the Summary and X and M are aromatic or saturated ring systems may be prepared according to SCHEME 18. Formula 25, 26 and 27 alkynyl amides or sulfonamides are prepared by coupling a formula 24 alkynyl sulfonamide or amide to an aromatic or vinyl halide, preferably an aromatic or vinyl bromide or iodide (wherein W and Z are as defined above and where X and M represent an aromatic ring or a partially saturated ring system). The coupling is typically accomplished in the presence of copper iodide, a palladium catalyst, such as palladium chloride, bis(triphenylphosphine)palladium dichloride, or tetrakis(triphenylphosphine)palladium(0), and an amine such as triethylamine, diisopropylamine, or butylamine in an aprotic solvent such as acetonitrile at a temperature of about 0° C. to about 100° C. The resulting formula 25, 26 and 27 alkynes can be converted to the corresponding formula 21, 22 or 23 alkanes, via hydrogenation in the presence of a palladium or platinum catalyst and in solvents such as methanol, ethanol, and/or ethyl acetate at a temperature of about 0° C. to about 50° C. Alternatively, one can convert the alkyne to the cis-alkene using the Lindlar catalyst (Pd—$CaCO_3$—PbO). In the case where M represents a partially saturated ring system, hydrogenation will convert M to a fully saturated ring system. Alkylation and deprotection as described in SCHEMES 1 and 2 affords the corresponding Formula I compounds.

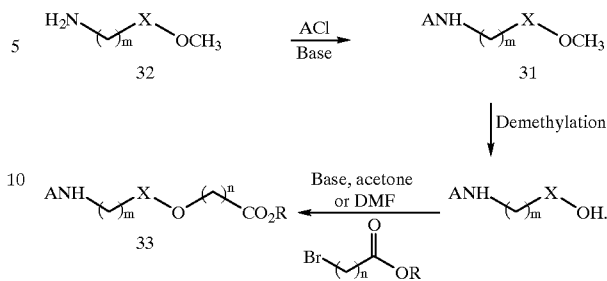

Alkylating Agents

Numerous methods exist for the synthesis of the desired alkylating agents used in the above procedures and are

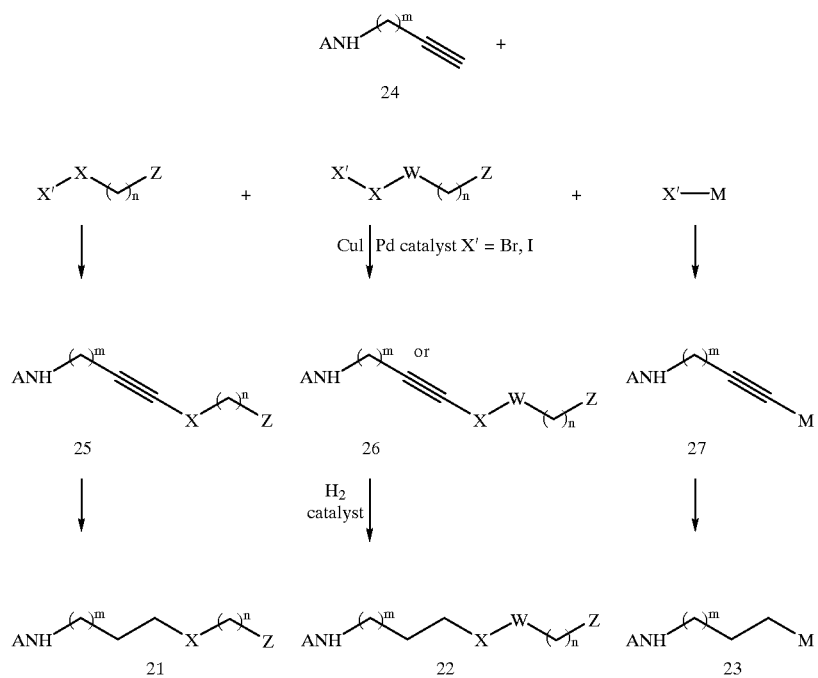

According to SCHEME 19 formula 33 compounds (wherein A and X are as described in the Summary) can be prepared from a suitable formula 32 amine (e.g., methoxyarylalkylamine). Formula 32 amines are commercially available or can be prepared by methods known to those skilled in the art (for example, see SCHEME 4) and are converted to formula 31 sulfonamides or amides using methods, for example, described in SCHEME 3 and 4. The resulting formula 31 aromatic methyl ether is deprotected with reagents such as boron tribromide, pyridinium hydrochloride, hydrogen bromide/acetic acid, or other reagents as described in Protecting Groups in Organic Synthesis, Second Edition, T. W. Greene and P. G. M. Wuts, John Wiley and Sons, Inc., 1991. Alkylation with a bromoalkylester using a mild base such as potassium carbonate in an aprotic solvent such as dimethylformamide or acetone at a temperature of about 0° C. to about 100° C. generates the desired formula 33 amide or sulfonamide.

known to those skilled in the art (see "The Chemistry of the Carbon-Halogen Bond," Ed. S. Patai, J. Wiley, New York, 1973 and "The Chemistry of Halides, Pseudo-Halides, and Azides," Eds. S. Patai and Z. Rappaport, J. Wiley, New York, 1983). Some examples are shown in SCHEMES 20–26. As shown in SCHEME 20, tolyl or allylic substrates can be converted via halogenation to benzylic or allylic bromides (wherein M, X, W and Z are as described in the Summary). This reaction is typically performed with N-bromosuccinimide (NBS) in the presence of a radical initiator such as AIBN or a peroxide, preferably benzoyl peroxide. Alternatively, the reaction can be initiated with light. The reaction is done in an inert solvent such as carbon tetrachloride or chloroform at a temperature of about 50° C. to about 100° C.

SCHEME 20

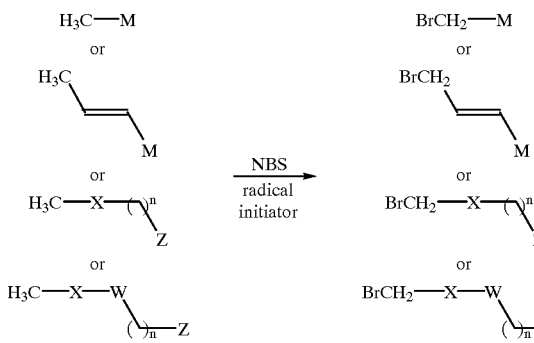

SCHEME 21 demonstrates the synthesis of alkylating agents useful for preparing Formula I compounds where M represents a biaryl or aryl cyclic group. Suzuki-type coupling of an aryl iodide or bromide or a ring system containing a vinyl bromide or iodide ($Ar_2$) with a methylaryl boronic acid ($Ar_1$) using the conditions described in SCHEME 9 provides formula 34 compounds. In the case where a vinyl bromide or iodide is used, formula 34 compounds can be reduced to generate a fully saturated ring. The reduction is accomplished by hydrogenation in the presence of palladium or platinum catalysts typically in protic solvents (methanol or ethanol), tetrahydrofuran, or ethyl acetate. Halogenation of the methyl group using reagents and conditions as described in SCHEME 20 provides formula 35 alkylating agents.

SCHEME 21

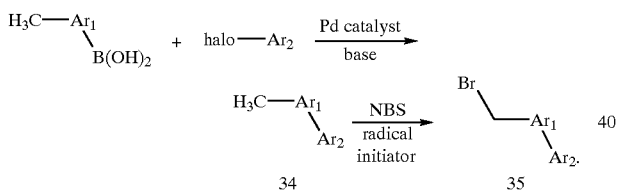

Another common method for accessing alkyl halides is by halogenation of an alcohol or an alcohol derivative. Alcohols are obtained from commercial sources or can be prepared using methods known to those skilled in the art. For example, in SCHEME 22, a carboxylic acid or ester is reduced to the alcohol using reagents such as sodium borohydride, lithium aluminum hydride, borane-tetrahydrofuran complex, borane-methyl sulfide complex, etc. The corresponding alkyl chlorides are typically prepared from the alcohols with reagents such as hydrogen chloride, thionyl chloride, phosphorous pentachloride, phosphorous oxychloride, or triphenylphosphine/carbon tetrachloride. For the preparation of alkyl bromides, the alcohol is commonly treated with reagents such as hydrogen bromide, phosphorous tribromide, triphenylphosphine/bromine, or carbonyldiimidazole/allyl bromide (Kamijo, T., Harada, H., Iizuka, K. Chem. Pharm. Bull. 1983, 38, 4189). To access alkyl iodides, one typically reacts the alcohol with reagents such as triphenylphosphine/iodine/imidazole or hydogen iodide. Alkyl chlorides can be converted to the more reactive alkyl bromides or alkyl iodides by treatment with an inorganic salt such as sodium bromide, lithium bromide, sodium iodide, or potassium iodide in solvents such as acetone or methyl ethyl ketone. Alkyl sulfonates can also be used as electrophiles or can be converted to alkyl halides. Sulfonates are prepared from the alcohol using a mild base such as triethylamine or pyridine and a sulfonyl chloride in an inert solvent such a methylene chloride or diethyl ether. Conversion to the halide is accomplished by treatment with an inorganic halide (sodium iodide, sodium bromide, potassium iodide, potassium bromide, lithium chloride, lithium bromide, etc) or a tetrabutylammonium halide.

SCHEME 22

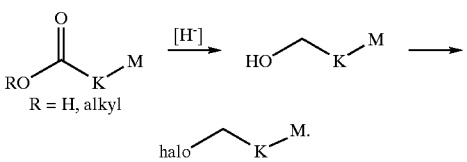

Cinnamic acids or esters are commonly available from commercial sources and can by converted to formula 37 or 38 alkylating agents as follows (see SCHEME 23). The cinnamic acid or ester derivatives are reduced by hydrogenation in the presence of palladium or platinum catalysts typically in protic solvents (e.g., methanol or ethanol), tetrahydrofuran, or ethyl acetate. Reduction and conversion to the alkyl halide or sulfonate as described in SCHEME 22 provides formula 38. Where appropriate, the cinnamic acids or esters are converted directly to formula 39 alcohols by treatment with reagents such as lithium aluminum hydride in inert solvents such as tetrahydrofuran and diethyl ether. Alternatively, the cinnamic acid or ester can be reduced to the formula 40 allylic alcohol using reagents such as lithium aluminum hydride/aluminum chloride, diisobutylaluminum hydride, or lithium borohydride. Conversion to the allylic halide or sulfonate as described in SCHEME 22 provides formula 37 reagents.

SCHEME 23

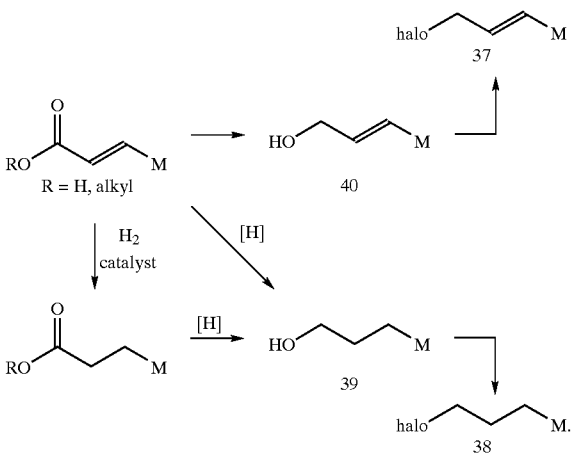

The preparation of formula 41 alkylating agents (wherein W and M are as described in the Summary above) are described in SCHEME 24. Formula 42 compounds are alkylated with a variety of bases the choice of which is dependent on the nature of W and M. Some preferred bases are sodium hydroxide, sodium hydride, lithium diisopropylamide, lithium bis(trimethylsilyl)amide, potassium bis(trimethylsilyl)amide and potassium tert-butoxide, etc. Treatment of the resulting anion with a variety of dialkylhalides generates the desired formula 41 alkylating agents. For the preparation of compounds where W represents an oxygen and M is an aromatic ring, the preferred conditions involve formation of the alkoxide anion with sodium hydroxide followed by addition of a dihaloalkane, e.g. dibromoalkane. The reaction is normally performed in water at about 75° C. to about 125° C.

SCHEME 24

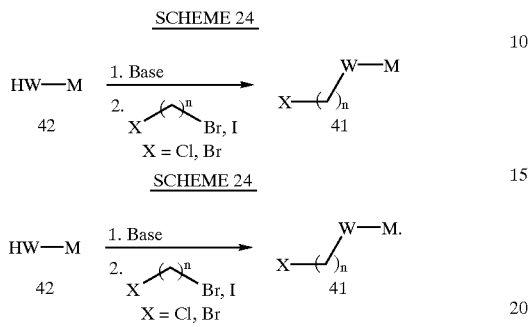

Aldehydes useful for the chemistry described in SCHEME 5 are available from commercial sources or can be prepared from available intermediates using methods known to those skilled in the art. SCHEME 25 demonstrates an exemplary method used to prepare formula 43 hydroxy aldehydes (where M in SCHEME 5 contains a hydroxy substituted alkyl group). Treatment of a dialdehyde, where one of the aldehydes is protected as a formula 44 acetal (wherein the OR groups are conventional substituents used in an acetal protecting group), with an organometallic reagent (LMetal), preferably an organolithium or Grignard reagent, in an inert solvent such as tetrahydrofuran or diethyl ether, provides formula 45 compounds. Subsequent acetal hydrolysis under mildly acidic conditions, e.g. dilute hydrogen chloride, Amberlyst-15 resin, silica gel, or other reagents as described in "Protecting Groups in Organic Synthesis," Second Edition, T. W. Greene and P. G. M. Wuts, John Wiley and Sons, Inc., 1991 provides the desired formula 43 hydroxy aldehydes.

SCHEME 25

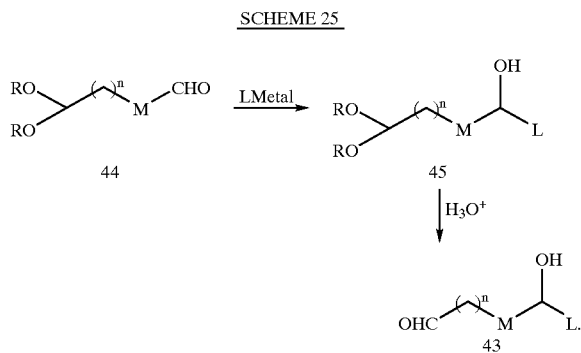

Chloromethyl Intermediates

Intermediate chloromethyl compounds can be prepared as described in SCHEMES 26 and 27. In general, the appropriate formula 101 or 103 sulfonamide or carboxamide is treated with a formaldehyde equivalent such as paraformaldehyde in an inert organic solvent such as methylene chloride or chloroform with a suitable catalyst such as HCl, zinc chloride or trimethylsilyl chloride at temperatures ranging from about 0° C. to about 60° C. to give the formula 102 and 104 chloromethyl derivatives, respectively.

SCHEME 26

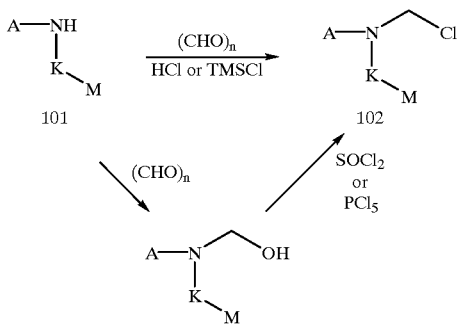

SCHEME 27

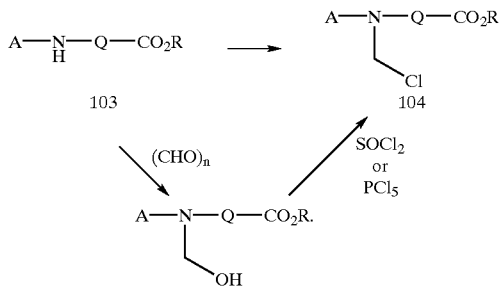

Those skilled in the art will recognize that anti-resorptive agents (for example progestins polyphosphonates, bisphosphonate(s), estrogen agonists/antagonists, estrogen, estrogen/progestin combinations, Premarin, estrone, estriol or 17α- or 17β-ethynyl estradiol) may be used in conjunction with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, granted Aug. 8, 1972, the disclosures of which are incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3-3-dimethyl-3-amino-1-hydroxy-1,1-diphosphonic acid, phenyl amino methane diphosphonic acid, N,N-dimethylamino methane diphosphonic acid, N(2-hyroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art according to standard assays including estrogen receptor binding assays, standard bone histomorphometric and densitometer methods, (Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

A preferred estrogen agonist/antagonist is droloxifene: (phenol, 3-[1-[4[2-(dimethylamino)ethoxy]phenyl]-2-phenyl-1-butenyl]-, (E)-) and associated compounds which are disclosed in U.S. Pat. No. 5,047,431 (the disclosure of which is hereby incorporated by reference).

Another preferred estrogen agonist/antagonist is tamoxifen: (ethanamine,2-[-4-(1,2-diphenyl-1-butenyl)phenoxy]-N,N-dimethyl, (Z)-2-, 2-hydroxy-1,2,3-propanetricarboxylate(1:1)) and associated compounds which are disclosed in U.S. Pat. No. 4,536,516 (the disclosure of which is hereby incorporated by reference).

Another related compound is 4-hydroxy tamoxifen which is disclosed in U.S. Pat. No. 4,623,660 (the disclosure of which is hereby incorporated by reference).

A preferred estrogen agonist/antagonist is raloxifene: (methanone, [6-hydroxy-2-(4-hydroxyphenyl)benzo[b]thien-3-yl][4-[2-(1-piperidinyl)ethoxy]phenyl]-hydrochloride) which is disclosed in U.S. Pat. No. 4,418,068 (the disclosure of which is hereby incorporated by reference).

Another preferred estrogen agonist/antagonist is toremifene: (ethanamine, 2-[4-(4-chloro-1,2-diphenyl-1-butenyl)phenoxy]-N,N-dimethyl-, (Z)-, 2-hydroxy-1,2,3-propanetricarboxylate (1:1) which is disclosed in U.S. Pat. No. 4,996,225 (the disclosure of which is hereby incorporated by reference).

Another preferred estrogen agonist/antagonist is centchroman: 1-[2-[[4-(-methoxy-2,2, dimethyl-3-phenyl-chroman-4-yl)-phenoxy]-ethyl]-pyrrolidine, which is disclosed in U.S. Pat. No. 3,822,287 (the disclosure of which is hereby incorporated by reference). Also preferred is levormeloxifene.

Another preferred estrogen agonist/antagonist is idoxifene: pyrrolidine, 1-[-[4-[[1-(4-iodophenyl)-2-phenyl-1-butenyl]phenoxy]ethyl] which is disclosed in U.S. Pat. No. 4,839,155 (the disclosure of which is hereby incorporated by reference).

Another preferred estrogen agonist/antagonist is 6-(4-hydroxy-phenyl)-5-[4-(2-piperidin-1-yl-ethoxy)-benzyl]-naphthalen -2-ol which is disclosed in U.S. Pat. No. 5,484,795 the disclosure of which is hereby incorporated by reference.

Another preferred estrogen agonist/antagonist is {4-[2-(2-aza-bicyclo[2.2.1] hept-2-yl)-ethoxy]-phenyl}-[6-hydroxy-2-(4-hydroxy-phenyl)-benzo[b]thiophen-3-yl]-methanone which is disclosed, along with methods of preparation, in PCT publication no. WO 95/10513 assigned to Pfizer Inc.

Another preferred estrogen agoinist/antagonist is GW5638: 3-[4-(1,2-diphenyl-but-1-enyl)-phenyl]-acrylic acid; see Wilson, T. M. and coworkers in Endrocrinology 1997, 138, 9, 3901–3911.

Other preferred estrogen agonist/antagonists include compounds as described in commonly assigned U.S. Pat. No. 5,552,412 the disclosure of which is hereby incorporated by reference. Especially preferred compunds described therein are:

Cis-6-(4-fluoro-phenyl)-5-[4-(2-piperidin-1-yl-ethoxy)-phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;

Cis-6-phenyl-5-[4-(2-pyrrolidin-1-yl-ethoxy)-phenyl]-5,6,7,8-tetrahydro-naphthalene-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis-6-(4-hydroxyphenyl)-5-[4-(2-piperidin-1-yl-ethoxy)-phenyl]-5,6,7,8-tetrahydro-naphthalene-2-ol; and 1-(4'-Pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is hereby incorporated by reference). U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents (bone mass augmenting agents) may be used in conjunction with the compounds of this invention. A bone mass augmenting agent is a compound that augments bone mass to a level which is above the bone fracture threshold (as detailed in the World Health Organization Study World Health Organization, "Assessment of Fracture Risk and its Application to Screening for Postmenopausal Osteoporosis (1994). Report of a WHO Study Group. World Health Organization Technical Series 843").

Any prostaglandin, or prostaglandin agonist/antagonist may be used as the second compound of this invention (this would include utilizing two different compounds of Formula I of this inventon). Those skilled in the art will recognize that IGF-1, with or without IGF binding protein 3, sodium fluoride, parathyroid hormone (PTH), active fragments of parathyroid hormone, growth hormone or growth hormone secretagogues may also be used. The following paragraphs describe exemplary second compounds of this invention in greater detail.

Any prostaglandin may be used as the second compound of this invention. The term prostaglandin refers to compounds which are analogs of the natural prostaglandins $PGD_1$, $PGD_2$, $PGE_2$, $PGE_1$ and $PGF_2$ which are useful in the treatment of osteoporosis. These compounds bind to the prostaglandin receptors. Such binding is readily determined by those skilled in the art according to standard assays (e.g., An S. et al., Cloning and Expression of the $EP_2$ Subtype of Human Receptors for Prostaglandin $E_2$, Biochemical and Biophysical Research Communications, 1993, 197(1):263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position.

A variety of prostaglandins are described and referenced below, however, other prostaglandins will be known to those skilled in the art. Exemplary prostaglandins are disclosed in U.S. Pat. Nos. 4,171,331 and 3,927,197 (the disclosures of which are hereby incorporated by reference).

Norrdin et al., *The Role of Prostaglandins in Bone In Vivo*, (Prostaglandins Leukotriene Essential Fatty Acids 41, 139–150, 1990) is a review of bone anabolic prostaglandins. Jee and Ma, The In Vivo Anabolic Actions of Prostaglandins in Bone. (Bone, 21: 297–304) is a recent review of prostaglandins' bone anabolic action.

Any prostaglandin agonist/antagonist may be used as the second compound of this invention. The term prostaglandin agonist/antagonist refers to compounds which bind to prostaglandin receptors (e.g., J. W. Regan et al., Cloning of a Novel Human Prostaglandin Receptor with Characteristics of the Pharmacologically Defined $EP_2$ Subtype, Molecular Pharmacology, 46: 213–220, 1994.) and mimic the action of prostaglandin in vivo (e.g., stimulate bone formation and increase bone mass and strength). Such actions are readily determined by those skilled in the art according to standard assays (Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below, however, other prostaglandin agonists/antagonists will be known to those skilled in the art. Exemplary prostaglandin agonists/antagonists are disclosed as follows.

Commonly assigned U.S. Pat. No. 3,932,389 (the disclosure of which is hereby incorporated by reference) discloses 2-descarboxy-2-(tetrazol-5-yl)-11-desoxy-15-substituted-omega-pentanorprostaglandins useful for bone formation activity.

Commonly assigned U.S. Pat. No. 4,018,892 (the disclosure of which is hereby incorporated by reference) discloses 16-aryl-13,14-dihydro-$PGE_2$ p-biphenyl esters useful for bone formation activity.

Commonly assigned U.S. Pat. No. 4,219,483 (the disclosure of which is hereby incorporated by reference) discloses 2,3,6-substituted4-pyrones useful for bone formation activity.

Commonly assigned U.S. Pat. No. 4,132,847 (the disclosure of which is hereby incorporated by reference) discloses 2,3,6-substituted-4-pyrones useful for bone formation activity.

U.S. Pat. No. 4,000,309 (the disclosure of which is hereby incorporated by reference) discloses 16-aryl-13,14-dihydro-$PGE_2$ p-biphenyl esters useful for bone formation activity.

U.S. Pat. No. 3,982,016 (the disclosure of which is hereby incorporated by reference) discloses 16-aryl-13,14-dihydro-$PGE_2$ p-biphenyl esters useful for bone formation activity.

U.S. Pat. No. 4,621,100 (the disclosure of which is hereby incorporated by reference) discloses substituted cyclopentanes useful for bone formation activity.

U.S. Pat. No. 5,216,183 (the disclosure of which is hereby incorporated by reference) discloses cyclopentanones useful for bone formation activity.

Sodium fluoride may be used as the second compound of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478, the disclosure of which is hereby incorporated by reference. The activity of sodium fluoride is readily determined by those skilled in the art according to biological protocols (e.g., see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296).

Any parathyroid hormone (PTH) may be used as the second compound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogues of parathyroid related peptides see WO 94/01460. Such functional activity is readily determined by those skilled in the art according to standard assays (e.g., see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50-62; Wahner H. W. and Fogelman I., The Evaluation of Osteoporosis: Dual Energy X-Ray Absorptiometry in Clinical Practice., Martin Dunitz Ltd., London 1994, pages 1-296). A variety of these compounds are described and referenced below, however, other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1–34 Treatment of Osteoporosis with Added Hormone Replacement Therapy: Biochemical, Kinetic and Histological Responses" Osteoporosis Int. 1 :162-170.

Any growth hormone or growth hormone secretagogue may be used as the second compound of this invention. The term growth hormone secretagogue refers to compounds which stimulate the release of growth hormone or mimic the action of growth hormone (e.g., increase bone formation leading to increased bone mass). Such actions are readily determined by those skilled in the art according to standard assays. A variety of these compounds are included in the following published PCT patent applications: WO 95/14666; WO 95/13069; WO 94/19367; WO 94/13696; and WO 95/34311. However, other growth hormone or growth hormone secretagogues will be known to those skilled in the art.

In particular a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

Other preferred growth hormone secretagogues include

2-Amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide or its L-tartaric acid salt;

2-Amino-N-{1-(R)-benzyloxymethyl-2-[3a-(R)-(4-fluoro-benzyl)-2-methyl-3-oxo-2,3,3a,4,6,7-hexahydro-pyrazolo[4,3-c]pyridin-5-yl]-2-oxo-ethyl}isobutyramide; and 2-Amino-N-[2-(3a-(R)-benzyl-3-oxo-2,3,3a,4,6,7-hexahydro-pyrazolo[4,3-c]pyridin-5-yl)-1-(R) benzyloxymethyl-2-oxo-ethyl]isobutyramide.

2-Amino-N-{1-(2,4-difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide Some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The starting materials and reagents for the above described compounds, are also readily available or can be easily synthesized by those skilled in the art using conventional methods of organic synthesis. For example, many of the compounds used therein, are related to, or are derived from compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

Many of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The compounds of this invention are all adapted to therapeutic use as agents that stimulate bone formation and increase bone mass in mammals, particularly humans. Since bone formation is closely related to the development of osteoporosis and bone related disorders, these compounds, by virtue of their action on bone, prevent, arrest and/or regress osteoporosis.

The utility of the compounds of the present invention as medical agents in the treatment of conditions which present with low bone mass (e.g., osteoporosis) in mammals (e.g. humans, particularly the female) is demonstrated by the activity of the compounds of this invention in conventional assays, including the in vivo assay, a receptor binding assay, the Cyclic AMP assay and the Fracture healing assay (all of which are described below). The in vivo assay (with appropriate modifications within the skill in the art) may be used to determine the activity of other anabolic agents as well as the prostaglandin agonists of this invention. The estrogen agonist/antagonist protocol may be used to determine the activity of estrogen agonists/antagonists in particular and also other anti-resorptive agents (with appropriate modifications within the skill in the art). The combination and sequential treatment protocol described below is useful for demonstrating the utility of the combinations of the anabolic agents (e.g., the compounds of this invention) and anti-resorptive agents (e.g., estrogen agonists/antagonists) described herein. Such assays also provide a means whereby the activities of the compounds of this invention (or the other anabolic agents and anti-resorptive agents described herein) can be compared to each other and with the activities of other known compounds. The results of these comparisons are useful for determining dosage levels in mammals, including humans, for the treatment of such diseases.

Anabolic Agent In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with prostaglandin agonists at different doses (such as 1, 3, or 10 mg/kg/day) for 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vit.$D_3$. All rats are given subcutaneous injections of 10 mg/kg calcein on days 12 and 2 before sacrifice. The rats are sacrificed. The following endpoints are determined:

Femoral Bone Mineral Measurements:

The right femur from each rat is removed at autopsy and scanned using dual energy x-ray absorptiometry (DXA, QDR 1000/W, Hologic Inc., Waltham, Mass.) equipped with "Regional High Resolution Scan" software (Hologic Inc., Waltham, MA). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses:

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using Reichert-Jung Polycut S microtome. The 4 $\mu$m sections are stained with modified Masson's Trichrome stain while the 10 $\mu$m sections remained unstained. One 4 $\mu$m and one 10 $\mu$m sections from each rat are used for cancellous bone histomorphometry.

Cross sections of tibial shaft at 10 $\mu$m thickness are cut using Reichert-Jung Polycut S microtome. These sections are using for cortical bone histomorphometric analysis.

Cancellous Bone Histomorphometry:

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I) Measurements and Calculations Related to Trabecular Bone Volume and Structure:

(1) Total metaphyseal area (TV, mm$^2$): metaphyseal area between 1.2 and 3.6 mm distal to the growth plate-epiphyseal junction. (2) Trabecular bone area (BV, mm$^2$): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, $\mu$m): (2000/1.199)×(BV/BS). (7) Trabecular bone separation (TBS, $\mu$m): (2000×1.199)×(TV−BV).

II) Measurements and Calculations Related to Bone Resorption:

(1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and Calculations Related to Bone Formation and Turnover:

(1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, $\mu$m): average distance between two calcein labels. (4) Percent mineralizing perimeter (PMS, %): (SLS/2+DLS)/BS×100. (5) Mineral apposition rate (MAR, $\mu$m/day): ILW/label interval. (6) Bone formation rate/surface ref. (BFR/BS, $\mu$m$^2$/d/$\mu$m): (SLS/2+DLS)×MAR/BS. (7) Bone turnover rate (BTR, %/y): (SLS/2+DLS)×MAR/BV×100.

Cortical Bone Histomorphometry:

A Bioquant OS/2 histomorphometry system (R&M biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area−marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter×100], mineral apposition rate (interlabeled width/intervals), and bone formation rate [mineral apposition rate×[(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD are used to compare the differences between groups.

Determination of cAMP Elevation in 293-S Cell Lines Stably Overexpressing Recombinant Human EP2 and EP4 Receptors.

cDNAs representing the complete open reading frames of the human EP2 and EP4 receptors are generated by reverse transcriptase polymerase chain reaction using oligonucleotide primers based on published sequences (1, 2) and RNA from primary human kidney cells (EP2) or primary human lung cells (EP4) as templates. cDNAs are cloned into the multiple cloning site of pcDNA3 (Invitrogen) and used to transfect 293-S human embryonic kidney cells via calcium phosphate co-precipitation. G418-resistant colonies are expanded and tested for specific [3-H]PGE2 binding. Transfectants demonstrating high levels of specific [3-H]PGE2 binding are further characterized by scatchard analysis to determine Bmax and Kds for PGE2. The lines selected for compound screening have approximately 338,400 receptors per cell and a Kd=12 nM for PGE2 (EP2), and approximately 256,400 receptors per cell and a Kd=2.9 nM for PGE2 (EP4). Constituitive expression of both receptors in parental 293-S cells is negligible. Cells are maintained in RPMI supplemented with fetal bovine serum (10% final) and G418 (700 ug/ml final).

cAMP responses in the 293-S/EP2 and 293-S/EP4 lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37° C., 5% CO$_2$, 95% relative humdity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000×g for 5 minutes, and cleared lysates are transferred to fresh tubes. cAMP concentrations are determined using a commercially available cAMP radioimmunoassay kit (NEK-033, NEN/DuPont) after diluting cleared lysates 1:10 in cAMP RIA assay buffer. Typically, one treats cells with 6–8 concentrations of the compound to be tested in 1 log increments. EC50 calculations are performed on a Hewlett Packard 32Sill hand-held calculator using linear regression analysis on the linear portion of the dose response curves.

REFERENCES

1. Regan, J. W. Bailey, T. J. Pepperl, D. J. Pierce, K. L. Bogardus, A. M. Donello, J. E. Fairbairn, C. E. Kedzie, K. M. Woodward, D. F. and Gil, D. W. 1994 Cloning of a Novel Human Prostaglandin Receptor with Characteristics of the Pharmaclogically Defined $EP_2$ Subtype. Mol. Pharmacology 46:213–220.
2. Bastien, L., Sawyer, N., Grygorczyk, R., Mefters, K., and Adam, M. 1994 Cloning, Functional Expression, and Characterization of the Human Prostaglandin E2 Receptor EP2 Subtype. J. Biol. Chem. Vol 269, 16:11873–11877.

Assay for Binding to Prostaglandin E2 Receptors

Membrane Preparation:

All operations are performed at 4° C. Transfected cells expressing prostaglandin E2 type 1 receptors (EP1), type 2 (EP2), type 3 (EP3) or type 4 (EP4) receptors are harvested and suspended to 2 million cells per ml in Buffer A [50 mM Tris-HCl (pH 7.4), 10 mM $MgCl_2$, 1 mM EDTA, 1 mM Pefabloc peptide, (Sigma, St. Louis, Mo.), 10 uM Phosporamidon peptide, (Sigma, St. Louis, Mo.), 1 uM Pepstatin A peptide, (Sigma, St. Louis, Mo.), 10 uM Elastatinal peptide, (Sigma, St. Louis, Mo.), 100 uM Antipain peptide, (Sigma, St. Louis, Mo.)]. These are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg protein per ml, protein concentration being determined according to the method of Bradford [Bradford, M., Anal. Biochem., 72, 248 (1976)]. Resuspended membranes are then stored frozen at −80° C. until use.

Binding Assay:

Frozen membranes prepared as above are thawed and diluted to 1 mg protein per ml in Buffer A. One volume of membrane preparation is combined with 0.05 volume test compound or buffer and one volume of 3 nM 3H-prostaglandin E2 (#TRK 431, Amersham, Arlington Heights, Ill.) in Buffer A. The mixture (205 μL total volume) is incubated for 1 hour at 25° C. The membranes are then recovered by filtration through type GF/C glass fiber filters (#1205–401, Wallac, Gaithersburg, Md.) using a Tomtec harvester (Model Mach II/96, Tomtec, Orange, Conn.). The membranes with bound 3H-prostaglandin E2 are trapped by the filter, the buffer and unbound 3H-prostaglandin E2 pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of 3H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound 3H-prostaglandin E2.

Fracture Healing Assays Assay for Effects on Fracture Healing After Systemic Administration Fracture Technique:

Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and animals with fractures outside the specified diaphyseal area or with displaced nails are excluded. The remaining animals are divided randomly into the following groups with 10–12 animals per each subgroup for testing the fracture healing. The first group receives daily gavage of vehicle (water: 100% Ethnanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and autopsied by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringer's solution (+4° C., pH 7.4) for radiographs and biomechanical testing which is performed.

Histological Analysis:

The methods for histologic analysis of fractured bone have been previously published by Mosekilde and Bak (The Effects of Growth Hormone on Fracture Healing in Rats: A Histological Description. Bone, 14:19–27, 1993). Briefly, the fracture side is sawed 8 mm to each side of the fracture line, embedded undecalcified in methymethacrylate, and cut frontals sections on a Reichert-Jung Polycut microtome in 8 μm thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap-measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis:

The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique:

female or male beagle dogs at approximately 2 years of age are used in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). The wire is pulled through the fracture site to ensure complete anatomical disruption of the bone. Thereafter, local delivery of prostaglandin agonists to the fracture site is achieved by slow release of compound delivered by slow release pellets or Alzet minipumps for 10, 15, or 20 weeks.

Histological Analysis:

The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74–70, 1996) and Mosekilde and Bak (The Effects of Growth Hormone on Fracture Healing in Rats: A Histological Description. Bone, 14:19–27, 1993). Briefly, the fracture side is sawed 3 cm to each side of the fracture line, embedded undecalcified in methymethacrylate, and cut on a Reichert-Jung Polycut microtome in 8 $\mu$m thick of frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap-measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis:

The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Estrogen Agonist/Antagonist Protocol

Estrogen agonist/antagonists are a class of compounds which inhibits bone turnover and prevents estrogen-deficiency induced bone loss. The ovariectomized rat bone loss model has been widely used as a model of postmenopausal bone loss. Using this model, one can test the efficacy of the estrogen agonist/antagonist compounds in preventing bone loss and inhibiting bone resorption.

Sprague-Dawley female rats (Charles River, Wilmington, Mass.) at different ages (such as 5 months of age) are used in these studies. The rats are singly housed in 20 cm×32 cm×20 cm cages during the experimental period. All rats are allowed free access to water and a pelleted commercial diet (Agway ProLab 3000, Agway County Food, Inc., Syracuse, N.Y.) containing 0.97% calcium, 0.85% phosphorus, and 1.05 IU/g of Vit.$D_3$ A group of rats (8 to 10) are sham-operated and treated p.o. with vehicle (10% ethanol and 90% saline, 1 ml/day), while the remaining rats are bilaterally ovariectomized (OVX) and treated with either vehicle (p.o.), 17$\beta$-estradiol (Sigma, E-8876, $E_2$, 30 $\mu$g/kg, daily subcutaneous injection), or estrogen agonist/antagonists (such as droloxifene at 5, 10, or 20 mg/kg, daily p.o.) for a certain period (such as 4 weeks). All rats are given subcutaneous injections of 10 mg/kg calcein (fluorochrome bone marker) 12 and 2 days before being sacrificed in order to examine the dynamic changes in bone tissue. After 4 weeks of treatment, the rats are sacrificed and autopsied. The following endpoints are determined:

Body Weight Gain:

body weight at autopsy minus body weight at surgery.

Uterine Weight and Histology:

The uterus is removed from each rat during autopsy, and weighed immediately. Thereafter, the uterus is processed for histologic measurements such as uterine cross-sectional tissue area, stromal thickness, and luminal epithelial thickness.

Total Serum Cholesterol:

Blood is obtained by cardiac puncture and allowed to clot at 4° C., and then centrifuged at 2,000 g for 10 min. Serum samples are analyzed for total serum cholesterol using a high performance cholesterol calorimetric assay (Boehringer Mannheim Biochemicals, Indianapolis, Ind.).

Femoral Bone Mineral Measurements:

The right femur from each rat is removed at autopsy and scanned using dual energy x-ray absorptiometry (DEXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) is determined Proximal Tibial Metaphyseal Cancellous Bone Histomorphometric Analyses:

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 $\mu$m thickness are cut using Reichert-Jung Polycut S microtome. One 4 $\mu$m and one 10 $\mu$m sections from each rat are used for cancellous bone histomorphometry. The 4 $\mu$m sections are stained with modified Masson's Trichrome stain while the 10 $\mu$m sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region is omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and Calculations Related to Trabecular Bone Volume and Structure:
1. Total metaphyseal area (TV, $mm^2$): metaphyseal area between 1.2 and 3.6 mm distal to the growth plate-epiphyseal junction.
2. Trabecular bone area (BV, $mm^2$): total area of trabeculae within TV.
3. Trabecular bone perimeter (BS, mm): the length of total perimeter of trabeculae.
4. Trabecular bone volume (BV/TV, %): BV/TV×100.
5. Trabecular bone number (TBN, #/mm): 1.199/2×BS/TV.
6. Trabecular bone thickness (TBT, μm): (2000/1.199)×(BV/BS).
7. Trabecular bone separation (TBS, μm): (2000×1.199)×(TV−BV).

II. Measurements and Calculations Related to Bone Resorption:
1. Osteoclast number (OCN, #): total number of osteoclast within total metaphyseal area.
2. Osteoclast perimeter (OCP, mm): length of trabecular perimeter covered by osteoclast.
3. Osteoclast number/mm (OCN/mm, #/mm): OCN/BS.
4. Percent osteoclast perimeter (%OCP, %): OCP/BS×100.

III. Measurements and Calculations Related to Bone Formation and Turnover:
1. Single-calcein labeled perimeter (SLS, mm): total length of trabecular perimeter labeled with one calcein label.
2. Double-calcein labeled perimeter (DLS, mm): total length of trabecular perimeter labeled with two calcein labels.
3. Inter-labeled width (ILW, μm): average distance between two calcein labels.
4. Percent mineralizing perimeter (PMS, %): (SLS/2+DLS)/BS×100.
5. Mineral apposition rate (MAR, μm/day): ILW/label interval.
6. Bone formation rate/surface ref. (BFR/BS, $μm^2/d/μm$): (SLS/2 +DLS)×MAR/BS.
7. Bone turnover rate (BTR, %/y): (SLS/2+DLS)×MAR/BV×100.

Statistics

Statistics are calculated using StatView 4.0 packages (Abacus Concepts, Inc., Berkeley, Calif.). The analysis of variance (ANOVA) test followed by Fisher's PLSD is used to compare the differences between groups.

Combination and Sequential Treatment Protocol

The following protocols can of course be varied by those skilled in the art. For example, intact male or female rats, sex hormone deficient male (orchidectomy) or female (ovariectomy) rats may be used. In addition, male or female rats at different ages (such as 12 months of age) can be used in the studies. The rats can be either intact or castrated (ovariectomized or orchidectomized), and administered with anabolic agents such as the compounds of this invention at different doses (such as 1, 3 or 6 mg/kg/day) for a certain period (such as two weeks to two months), and followed by administration of an anti-resorptive agent such as droloxifene at different doses (such as 1,5,10 mg/kg/day) for a certain period (such as two weeks to two months), or a combination treatment with both anabolic agent and anti-resorptive agent at different doses for a certain period (such as two weeks to two months). In the castrated rats, treatment can be started at the next day after surgery (for the purpose of preventing bone loss) or at the time bone loss has already occurred (for the purpose of restoring bone mass).

The rats are sacrificed under ketamine anesthesia. The following endpoints are determined:

Femoral Bone Mineral Measurements:

The right femur from each rat is removed at autopsy and scanned using dual energy x-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Lumbar Vertebral Bone Mineral Measurements:

Dual energy x-ray absorptiometry (QDR 1000NV, Hologic, Inc., Waltham, Mass.) equipped with a "Regional High Resolution Scan" software (Hologic, Inc., Waltham, Mass.) is used to determined the bone area, bone mineral content (BMC), and bone mineral density (BMD) of whole lumbar spine and each of the six lumbar vertebrae (LV1–6) in the anesthetized rats. The rats are anesthetized by injection (i.p.) of 1 ml/kg of a mixture of ketamine/rompun (ratio of 4 to 3), and then placed on the rat platform. The scan field sized is 6×1.9 cm, resolution is 0.0254×0.0127 cm, and scan speed is 7.25 mm/sec. The whole lumbar spine scan image is obtained and analyzed. Bone area (BA), and bone mineral content (BMC) is determined, and bone mineral density is calculated (MBC divided by BA) for the whole lumbar spine and each of the six lumbar vertebrae (LV1–6).

Proximal Tibial Metaphyseal Cancellous Bone Histomorphometric Analyses:

The right tibia is removed at autopsy, dissected free of muscle, and cut into three parts. The proximal tibia is fixed in 70% ethanol, dehydrated in graded concentrations of ethanol, defatted in acetone, then embedded in methyl methacrylate (Eastman Organic Chemicals, Rochester, N.Y.). Frontal sections of proximal tibial metaphyses at 4 and 10 μm thickness is cut using Reichert-Jung Polycut S microtome. One 4 μm and one 10 μm sections from each rat is used for cancellous bone histomorphometry. The 4 μm sections is stained with modified Masson's Trichrome stain while the 10 μm sections remained unstained.

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 μm sections are used to determine indices related to bone volume, bone structure, and bone resorption, while the 10 μm sections are used to determine indices related to bone formation and bone turnover.

I. Measurements and Calculations Related to Trabecular Bone Volume and Structure:
1. Total metaphyseal area (TV, mm$^2$): metaphyseal area between 1.2 and 3.6 mm distal to the growth plate-epiphyseal junction.
2. Trabecular bone area (BV, mm$^2$): total area of trabeculae within TV.
3. Trabecular bone perimeter (BS, mm): the length of total perimeter of trabeculae.
4. Trabecular bone volume (BV/TV, %): BV/TV×100.
5. Trabecular bone number (TBN, #/mm): 1.199/2×BS/TV.
6. Trabecular bone thickness (TBT, μm): (2000/1.199)× (BV/BS).
7. Trabecular bone separation (TBS, μm): (2000×1.199)× (TV−BV).

II. Measurements and Calculations Related to Bone Resorption:
1. Osteoclast number (OCN, #): total number of osteoclast within total metaphyseal area.
2. Osteoclast perimeter (OCP, mm): length of trabecular perimeter covered by osteoclast.
3. Osteoclast number/mm (OCN/mm, #/mm): OCN/BS.
4. Percent osteoclast perimeter (%OCP, %): OCP/BS× 100.

III. Measurements and Calculations Related to Bone Formation and Turnover:
1. Single-calcein labeled perimeter (SLS, mm): total length of trabecular perimeter labeled with one calcein label.
2. Double-calcein labeled perimeter (DLS, mm): total length of trabecular perimeter labeled with two calcein labels.
3. Inter-labeled width (ILW, μm): average distance between two calcein labels.
4. Percent mineralizing perimeter (PMS, %): (SLS/2+ DLS)/BS×100.
5. Mineral apposition rate (MAR, μm/day): ILW/label interval.
6. Bone formation rate/surface ref. (BFR/BS, μm$^2$/d/μm): (SLS/2+DLS)×MAR/BS.
7. Bone turnover rate (BTR, %/y): (SLS/2+DLS)×MAR/ BV×100.

Statistics

Statistics can be calculated using StatView 4.0 packages (Abacus Concepts, Inc., Berkeley, Calif.). The analysis of variance (ANOVA) test followed by Fisher's PLSD can be used to compare the differences between groups.

Use of a Prostaglandin receptor agonist in Kidney Regeneration.

The role of a prostaglandin agonist in kidney regeneration was investigated by the ability of PGE$_2$ or a prostaglandin agonist to induce the expression of Bone Morphogenetic Protein 7 (BMP-7) in wild type 293S cells and in 293S cells transfected with the EP$_2$ receptor.

Methods: 293S and EP2 293S cells were grown in Dulbecco's Modified Egale medium (DMEM, Gibco, BRL; Gaithersburg, Md.). One day prior to treatment with PGE$_2$ or a prostaglandin agonist, cells were plated at a density of 1.5×10$^6$ cells/10 cm dish. The next day the cell monolayer was washed once with OptiMEM (Gibco, BRL) followed by the addition of 10 mL OptiMEM/dish in the presence and absense of vehicle (DMSO), PGE2 (10$^{-6}$M) or prostaglandin agonist (10$^{-6}$M). Cells were harvested and RNA extracted at 8, 16 and 24 hours. Northern blot analysis of total (20 mg/lane) was carried out by probing the blots with $^{32}$P-labeled BMP-7 probe. The blots were normalized for RNA loading by hybridization with $^{32}$P-labeled 18s ribosomal RNA probe. It was observed that both PGE$_2$ and the prostaglandin agonist in a time dependent manner induce the expression of BMP-7 in the EP$_2$ 293S cells but not in the parental cell line. Given the known role of BMP-7 in kidney regeneration and the ability of a prostaglandin agonist to induce BMP-7 expression in 293S kidney cells in a time and receptor specific manner indicates a role for a prostaglandin agonist in kidney regeneration.

Administration of the compounds of this invention can be via any method which delivers a compound of this invention systemically and/or locally (e.g., at the site of the bone fracture, osteotomy, or orthopedic surgery). These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

The compounds are used for the treatment and promotion of healing of bone fractures and osteotomies by the local application (e.g., to the sites of bone fractures or osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier such as bone-wax, demineralized bone powder, polymeric bone cements, bone sealants etc. Alternatively, local application can be achieved by applying a solution or dispersion of the compound in a suitable carrier onto the surface of, or incorporating it into solid or semi-solid implants conventionally used in orthopedic surgery, such as dacron-mesh, Gore-tex®, gel-foam and kiel bone, or prostheses.

The compounds of this invention may also be applied locally to the site of the fracture or osteotomy in a suitable carrier in combination with one or more of the anabolic agents or bone anti-resorptive agents described above.

The two different compounds of this invention can be co-administered simultaneously or sequentially in any order, or a single pharmaceutical composition comprising a Formula I compound as described above and a second compound as described above in a pharmaceutically acceptable carrier can be administered.

For example, the bone anabolic agent can be used alone or in combination with an anti-resorptive agent for one week to three years, followed by an anti-resorptive agent alone for three months to three years, with optional repeat of the full treatment cycle. Alternatively, for example, the bone anabolic agent can be used alone or in combination with an anti-resorptive agent for three months to three years, followed by an anti-resorptive agent alone for the remainder of the patient's life. For example, in one preferred mode of administration a Formula I compound as described above may be administered once daily and a second compound as described above (e.g., estrogen agonist/antagonist) may be administered daily in single or multiple doses. Alternatively, for example, in another preferred mode of administration the two compounds may be administered sequentially wherein the Formula I compound as described above may be administered once daily for a period of time sufficient to augment bone mass to a level which is above the bone fracture threshold (World Health Organization Study "Assessment of Fracture Risk and its Application to Screening for Postmenopausal Osteoporosis (1994). Report of a World Health Organization Study Group. World Health Organization Technical Series 843") followed by administration of a second compound, as described above (e.g., estrogen agonist/antagonist), daily in single or multiple doses. It is preferred that the first compound as described above is administered once daily in a rapid delivery form such as oral delivery (e.g., sustained release delivery form is preferably avoided).

In any event the amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment (e.g., bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

In general an amount of a compound of this invention is used that is sufficient to augment bone mass to a level which is above the bone fracture threshold (as detailed in the World Health Organization Study previously cited herein).

In general an effective dosage for the anabolic agents described above is in the range of 0.001 to 100 mg/kg/day, preferably 0.01 to 50 mg/kg/day.

The following paragraphs provide preferred dosage ranges for various anti-resorptive agents.

The amount of the anti-resorptive agent to be used is determined by its activity as a bone loss inhibiting agent. This activity is determined by means of an individual compound's pharmacokinetics and its minimal maximal effective dose in inhibition of bone loss using a protocol such as described above (e.g., ESTROGEN AGONIST/ANTAGONIST PROTOCOL).

In general, an effective dosage for an anti-resorptive agent is about 0.001 mg/kg/day to about 20 mg/kg/day.

In general, an effective dosage for progestins is about 0.1 to 10 mg per day; the preferred dose is about 0.25 to 5 mg per day.

In general, an effective dosage for polyphosphonates is determined by its potency as a bone resorption inhibiting agent according to standard assays.

Ranges for the daily administration of some polyphosphonates are about 0.001 mg/kg/day to about 20 mg/kg/day.

In general an effective dosage for the treatment of this invention, for example the bone resorption treatment of this invention, for the estrogen agonists/antagonists of this invention is in the range of 0.01 to 200 mg/kg/day, preferably 0.5 to 100 mg/kg/day.

In particular, an effective dosage for droloxifene is in the range of 0.1 to 40 mg/kg/day, preferably 0.1 to 5 mg/kg/day.

In particular, an effective dosage for raloxifene is in the range of 0.1 to 100 mg/kg/day, preferably 0.1 to 10 mg/kg/day.

In particular, an effective dosage for tamoxifen is in the range of 0.1 to 100 mg/kg/day, preferably 0.1 to 5 mg/kg/day.

In particular, an effective dosage for
Cis-6-(4-fluoro-phenyl)-5-[4-(2-piperidin-1-yl-ethoxy)-phenyl]-5,6,7,8-tetrahydro-naphthalene-2-ol;

(−)-Cis-6-phenyl-5-[4-(2-pyrrolidin-1-yl-ethoxy)-phenyl]-5,6,7,8-tetrahydro-naphthalene-2-ol;
Cis-6-phenyl-5-[4-(2-pyrrolidin-1-yl-ethoxy)-phenyl]-5,6,7,8-tetrahydro-naphthalene-2-ol;
Cis-1-[6'-pyrrolodinoethoxy-3'-pyridyl]-2-phenyl-6-hydroxy-1,2,3,4-tetrahydrohaphthalene;
1-(4'-Pyrrolidinoethoxyphenyl)-2-(4"-fluorophenyl)-6-hydroxy-1,2,3,4-tetrahydroisoquinoline;
Cis-6-(4-hydroxyphenyl)-5-[4-(2-piperidin-1-yl-ethoxy)-phenyl]-5,6,7,8-tetrahydro-naphthalene-2-ol; or
1-(4'-Pyrrolidinolethoxyphenyl)-2-phenyl-6-hydroxy-1,2,3,4-tetrahydroisoquinoline
is in the range of 0.0001 to 100 mg/kg/day, preferably 0.001 to 10 mg/kg/day.

In particular, an effective dosage for 4-hydroxy tamoxifen is in the range of 0.0001 to 100 mg/kg/day, preferably 0.001 to 10 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, e.g., a bone disorder.

Since the present invention has an aspect that relates to the augmentation and maintenance of bone mass by treatment with a combination of active ingredients which may be administered separately, the invention also relates to combining separate pharmaceutical compositions in kit form. The kit comprises two separate pharmaceutical compositions: a compound of Formula I and a second compound as described above. The kit comprises container means for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also a daily dose of Formula I compound can consist of one tablet or capsule while a daily dose of the second compound can consist of several tablets or capsules and vice versa. The memory aid should reflect this.

In another specific embodiment of the invention a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

| Formulation 4: Suspensions | |
|---|---|
| Ingredient | Quantity (mg/5 ml) |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient are passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

| Formulation 5: Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.
Suppositories are prepared as follows:

| Formulation 6: Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.
An intravenous formulation is prepared as follows:

| Formulation 7: Intravenous Solution | |
|---|---|
| Ingredient | Quantity |
| Active ingredient | 20 mg |
| Isotonic saline | 1,000 mL |

The solution of the above ingredients is intravenously administered to a patient at a rate of about 1 mL per minute.
The active ingredient above may also be a combination of agents.

General Experimental Procedures

NMR spectra were recorded on a Varian XL-300 (Varian Co., Palo Alto, Calif.) a Bruker AM-300 spectrometer at about 23° C. at 300 MHz for proton and 75.4 mHz for carbon (Bruker Co., Billerica, Mass.) or a Varian Unity 400 at 400 Mhz for proton nuclei. Chemical shifts are expressed in parts per million downfield from trimethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization (APCI) mass spectra were obtained on a Fisons Platform II Spectrometer. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Column chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatron (model 7924T, Harrison Research) Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 45° C. Reactions conducted at "0–20° C." or "0–25° C." were conducted with initial cooling of the vessel in an insulated ice bath which was allowed to warm to room temperature over several hours. The abbreviation "min" and "h" stand for "minutes" and "hours" respectively.

EXAMPLE 1

7-[(4-Butyl-benzyl)-methanesulfonyl-amino]-heptanoic acid

Step A: Alkylation

Ethyl 7-[(4-Butyl-benzyl)-methanesulfonyl-amino]-heptanoate.

A solution of ethyl-7-methanesulfonyl-amino-heptanoate (250 mg, 1.0 mmol) in DMF (2 mL) was added dropwise to NaH (48 mg, 1.19 mmol, 60% in oil) in DMF at 0° C. After stirring for 45 minutes at room temperature, 1-bromomethyl-4-butyl-benzene (271 mg, 1.19 mmol) was added dropwise. The reaction was stirred for 2 h and the DMF was removed in vacuo. The residue was diluted with $CH_2Cl_2$ and the organic solution was sequentially washed with 1N HCl (1×), water (2×), and brine (1×). The organic solution was dried over $MgSO_4$, filtered, and concentrated in vacuo. The product was purified via radial chromatography (15% EtOAc/hexanes to 40% EtOAc/hexanes) to afford the title compound of Step A (379 mg). $^1H$ NMR (400 MHz, $CDCl_3$) δ 7.12–7.30 (m, 4H), 4.35 (s, 2H), 4.12 (q, 2H), 3.10–3.19 (m, 2H), 2.80 (s, 3H), 2.60 (t, 2H), 2.25 (t, 2H), 1.46-1.62 (m, 7H), 1.18–1.39 (m, 6H), 0.92 (t, 3H); MS 415 (M+18).

Step B: Ester Hydrolysis
7-[(4-Butyi-benzyl)-methanesulfonyl-aminol-heptanoic Acid.

To a solution of the title compound of Step A (379 mg, 0.95 mmol) in MeOH (6 mL) was added NaOH (1.0 mL, 5N). The reaction was stirred at room temperature for 24 h and was acidified with aqueous HCl (1N). The MeOH was removed in vacuo and the residue was dissolved in $CH_2Cl_2$. The organic solution was washed sequentially with HCl (1N, 1×), water (2×), and brine (1×). The organic solution was dried with $MgSO_4$, filtered, and concentrated in vacuo. Purification by radial chromatography ($CH_2Cl_2$ to 6% MeOH/$CH_2Cl_2$) provided the title compound (356 mg). $^1$H NMR (400 MHz, CDCl$_3$) δ 7.30–7.12 (m, 4H), 4.35 (s, 2H), 3.10–3.19 (m, 2H), 2.80 (s, 3H), 2.60 (t, 2H), 2.31 (t, 2H), 1.48–1.65 (m, 7H), 1.20–1.40 (m, 6H). 0.97 (t, 3H); MS 387 (M+18).

EXAMPLES 2–44

Examples 2–44 were prepared from the appropriate starting materials using the Methods described in SCHEMES 1 and 2 and in an analogous manner to Example 1 with variations in reaction temperature and time in Step A as noted.

EXAMPLE 2

(3-{[(4-Butyl-benzyl)-methanesulfonyl-amino]-methyl}-phenyl)-acetic acid $^1$H NMR (400 MHz, CDCl$_3$) δ 7.32–7.14 (m, 5H), 4.32 (s, 2H), 4.29 (s, 2H), 3.66 (s, 2H), 2.76 (s, 3H), 2.60 (t, 2H), 1.59 (m, 2H), 1.34 (m, 2H), 0.93 (t, 3H); MS 388 (M+)

EXAMPLE 3

7-{[2-(3,5-Dichloro-phenoxy)-ethyl]-methanesulfonyl-amino}-heptanoic acid

Step A: Reaction time of 24 h at room temperature. $^1$HNMR (400 MHz, CDCl$_3$) δ 7.00 (m, 1H), 6.80 (m, 2H), 4.12 (t, 2H), 3.60 (t, 2H), 3.26 (t, 2H), 2.90 (s, 3H), 2.37 (t, 2H), 1.65 (m, 4H), 1.39 (m, 4H); MS 412 (M+).

EXAMPLE 4

4-(2-{[3-(3,5-Dichloro-phenyl)-allyl]-methanesulfonyl-amino}-ethyl)-benzoic acid $^1$H NMR (400 MHz, CDCl$_3$) δ 8.02 (d, 2H), 7.30 (d, 2H), 7.20 (s, 1H), 7.19 (s, 2H), 6.39 (d, 1H), 6.08 (m, 1H), 3.94 (m, 2H), 3.50 (t, 2H), 3.00 (t, 2H), 2.78 (s, 3H).

EXAMPLE 5

7-[Methanesulfonyl-(4-trifluoromethyl-benzyl)-amino]-heptanoic acid $^1$H NMR (400 MHz, CDCl$_3$) δ 7.60 (d, 2H), 7.48 (d, 2H), 4.41 (s, 2H), 3.16 (t, 2H), 2.87 (s, 3H), 2.29 (t, 2H), 1.40–1.61 (m, 4H), 1.13–1.33 (m, 4H).

EXAMPLE 6

Trans-7-[Methanesulfonyl-(3-phenyl-allyl)-amino]-heptanoic acid

Step A: Reaction time of 24 h at 90° C. $^1$H NMR (400 MHz, CDCl$_3$) δ 7.2–7.4 (m, 5H), 6.59 (d, 1H), 6.12–6.21 (m, 1H), 4.0 (d, 2H), 3.21 (t, 2H), 2.32 (t, 2H), 1.55-1.70 (m, 4H), 1.27–1.40 (m, 4H); MS 338.1 (M−1).

EXAMPLE 7

Trans-(4-{[3-(3,5-Dichloro-phenyl)-allyl]-methanesulfonyl-amino}-butoxy)-acetic acid Step A: Reaction time of 2 h at 100° C. $^1$H NMR (400 MHz, CDCl$_3$) δ 7.37 (m, 2H), 7.23 (m, 1H), 6.42–6.52 (m, 1H), 6.15–6.28 (m, 1H), 3.96 (m, 4H), 3.52 (m, 2H), 3.23 (m, 2H), 2.86 (s, 3H), 1.55–1.72 (m, 4H); MS 411.5 (M+1).

EXAMPLE 8

7-{[4-(1-Hydroxy-hexyl)-benzyl]-methanesulfonyl-amino]-heptanoic acid

Step A: Reaction time of 24 h at 90° C. Mp 68–70° C.; $^1$H NMR (400 MHz, CDCl$_3$) δ 7.20–7.38 (m, 4H), 4.62–4.66 (m, 1H), 4.34 (s, 2H), 3.10–3.18 (m, 2H), 2.94 (s, 1H), 2.83 (s, 3H), 2.17–2.39 (m, 3H), 1.10–1.83 (m, 16H), 0.80–0.90 (m, 3H).

EXAMPLE 9

7-[Methanesulfonyl-(2'-trifluoromethyl-biphenyl4-ylmethyl)-amino]-heptanoic acid Step A: Reaction time of 24 h at room temperature. $^1$H NMR (CDCl$_3$ 400 MHz) δ 7.75–7.23 (m, 8H), 4.46 (s, 2H), 3.21 (t, 2H), 2.84 (s, 3H), 2.34 (t, 2H), 1.57 (m, 4H), 1.28 (m, 4H).

EXAMPLE 10

7-[(2',6'-Dichloro-biphenyl4-ylmethyl)-methanesulfonyl-amino]-heptanoic acid

Step A: Reaction time of 24 h at room temperature. $^1$H NMR (CDCl$_3$ 400 MHz) δ 7.60–7.20 (m, 7H), 4.41 (s, 2H), 3.21 (t, 2H), 2.82 (s, 3H), 2.30 (t, 2H), 1.56 (m, 4H), 1.27 (m, 4H); MS 458 (M+).

EXAMPLE 11

7-[Methanesulfonyl-(2-phenoxy-ethyl)-amino]-heptanoic acid $^1$H NMR (400 MHz, CDCl$_3$) δ 7.25–7.36 (m, 2H), 6.85–7.03 (m, 3H), 4.11 (t, 2H), 3.62 (t, 2H), 3.27 (t, 2H), 2.91 (s, 3H), 2.34 (t, 2H), 1.72–1.54 (m, 4H), 1.45–1.25 (m, 4H).

EXAMPLE 12

7-[(Methylsulfonyl)[[4-(2-pyridinyl)phenyl]methyl]amino]-heptanoic acid hydrochloride salt Step A: Reaction time of 45 minutes at room temperature. $^1$H NMR (400 MHz, CDCl$_3$) δ 8.72 (bs, 1H), 7.64–7.95 (m, 4H), 7.48 (d, 2H), 7.21–7.32 (m, 1H), 4.40 (s, 2H), 3.14 (t, 2H), 2.85 (s, 3H), 2.15–2.35 (m, 2H), 1.40–1.60 (m, 4H), 1.08–1.30 (m, 4H).

EXAMPLE 13

7-[Methanesulfonyl-(5-phenyl-pentyl)-amino]-heptanoic acid

Step A: Reaction time of 2 h at room temperature and 18 h at 70° C. $^1$H NMR (400 MHz, CDCl$_3$) δ 7.28–7.14 (m, 5H), 3.12 (m, 4H), 2.78 (s, 3H), 2.60 (t, 2H), 2.34 (t, 2H), 1.62 (m, 8H), 1.32 (m, 6H).

EXAMPLE 14

7-{[2-(2,4-Dichloro-phenoxy)-ethyl]-methanesulfonyl-amino}-heptanoic acid

Step A: Reaction time of 20 h at 65° C. $^1$H NMR (400 MHz, CDCl$_3$) δ 7.33 (d, 1H), 7.16 (dd, 1H), 6.83 (d, 1H), 4.13 (t, 2H), 3.62 (t, 2H), 3.31 (t, 2H), 2.94 (s, 3H), 2.31 (m, 2H), 1.61 (m, 4H), 1.33 (m, 4H).

EXAMPLE 15

Trans-[3-({[3-(3,5-Dichloro-phenyl)-allyl]-methanesulfonyl-amino}-methyl)-phenyl]-acetic acid $^1$H NMR (400 MHz, CDCl$_3$) δ 7.32–7.13 (m, 7H), 6.33 (d, 1H), 6.09 (m, 1H), 4.38 (s, 2H), 3.91 (d, 2H), 3.61 (s, 2H), 2.89 (s, 3H).

EXAMPLE 16

7-{[3-(3,5-Dichloro-phenyl)-propyl]-methanesulfonyl-amino}-heptanoic acid

Step A: Reaction time of 60° C. for 72 h. H NMR (400 MHz, CDCl$_3$) δ 7.25 (s, 1H), 7.19 (s, 2H), 3.15 (m, 4H), 2.81 (s, 3H), 2.60 (t, 2H), 2.34 (t, 2H), 1.89 (m, 2H), 1.60 (m, 4H), 1.32 (m, 4H).

EXAMPLE 17

[3-({[3-(3-Chloro-phenyl)-propyl]-methanesulfonyl-amino}-methyl)-phenyl]-acetic acid Step A: Reaction time of 24 h at room temperature. $^1$H NMR (400 MHz, CDCl$_3$) δ 7.31–6.91 (m, 8H), 4.34 (s, 2H), 3.64 (s, 2H), 3.18 (t, 2H), 2.81 (s, 3H), 2.49 (t, 2H), 1.78 (m, 2H); MS 413 (M+18).

EXAMPLE 18

7-[(2-lndan-2-yl-ethyl)-methanesulfonyl-amino]-heptanoic acid

Step A: Reaction time of 4 h at room temperature. $^1$H NMR (400 MHz, CDCl$_3$) δ 7.13 (m, 4H), 3.24 (t, 2H), 3.17 (t, 2H), 3.08 (m, 2H), 2.83 (s, 3H), 2.62 (m, 2H), 2.48 (m, 1H), 2.35 (t, 2H), 1.81 (m, 2H), 1.62 (m, 4H), 1.37 (m, 4H).

EXAMPLE 19

7-[Methanesulfonyl-(4-phenyl-butyl)-amino]-heptanoic acid

Step A: Reaction time of 72 h at 60° C. $^1$H NMR (400 MHz, CDCl$_3$) δ 7.26 (m, 2H), 7.17 (m, 3H), 3.16 (t, 2H), 3.10 (t, 2H), 2.78 (s, 3H), 2.63 (t, 2H), 2.34 (t, 2H), 1.70–1.51 (m, 8H), 1.32 (m, 4H).

EXAMPLE 20

[3-({[2-(3,5-Dichloro-phenoxy)-ethyl]-methanesulfonyl-amino}-methyl)-phenyl]- acetic acid Step A: Reaction time of 24 h at room temperature. $^1$H NMR (400 MHz, CDCl$_3$) δ 7.27 (m, 5H), 4.48 (s, 2H), 3.97 (t, 2H), 3.64 (s, 2H), 3.57 (t, 2H), 2.92 (s, 3H).

EXAMPLE 21

4-(4-{[3-(3-Chloro-phenyl)-propyl]-methanesulfonyl-amino}-phenyl)-butyric acid

Step A: Reaction time of 1 h at room temperature. $^1$H NMR (400 MHz, CDCl$_3$) δ 7.32–6.97 (m, 8H), 3.67 (t, 2H), 2.85 (s, 3H), 2.68 (t, 2H), 2.63 (t, 2H), 2.40 (t, 2H), 1.97 (m, 2H), 1.77 (m, 2H).

EXAMPLE 22

[2-(2-[3-(3-Chloro-phenyl)-propyl]-methanesulfonyl-amino}-ethyl)-phenoxy]-acetic acid Step A: Reaction time of 1 h at room temperature. $^1$H NMR (400 MHz, CDCl$_3$) δ 7.29–6.71 (m, 8H), 4.64 (s, 2H), 3.44 (t, 2H), 3.23 (m, 2H), 2.95 (t, 2H), 2.71 (s, 3H), 2.58 (t, 2H), 1.89 (m, 2H).

EXAMPLE 23

[3-({Methanesulfonyl-[3-(3-trifluoromethyl-phenyl)-propyl]-amino}methyl)-phenyl]-acetic acid Step A: Reaction time of 24 h at room temperature. $^1$H NMR (CDCl$_3$ 400 MHz) δ 7.42–7.21 (m, 4H), 4.34 (s, 2H), 3.62 (s, 2H), 3.22 (t, 2H), 2.81 (s, 3H), 2.56 (t, 2H), 1.79 (m, 2H); MS 447 (M+18).

EXAMPLE 24

{4-[(4-Butyl-benzyl)-methanesulfonyl-amino]-butoxy}-acetic acid

Step A: Reaction time of 2 h at 100° C. $^1$H NMR (400 MHz, CDCl$_3$) δ 7.23 (m, 2H), 7.14 (m, 2H), 4.34 (s, 2H), 4.03 (s, 2H), 3.48 (t, 2H), 3.19 (t, 2H), 2.79 (s, 3H), 2.59 (t, 2H), 1.57 (m, 6H), 1.32 (m, 2H), 0.91 (t, 3H); MS 370 (M−1).

EXAMPLE 25

5-(3-{[3-(3-Chloro-phenyl)-propyl]-methanesulfonyl-amino}-propyl)-thiophene-2-carboxylic acid Step A: Reaction time of 5 h at 100° C. $^1$H NMR (400 MHz, CDCl$_3$) δ 7.71 (m, 1H), 7.24–7.15 (m, 3H), 7.03 (m, 1H), 6.83 (m, 1H), 3.19 (m, 4H), 2.89 (t, 2H), 2.81 (s, 3H), 2.61 (t, 2H), 1.94 (m, 4H).

EXAMPLE 26

7-{[5-(1-Hydroxy-hexyl)-thiophen-2-ylmethyl]-methanesulfonyl-amino}-heptanoic acid $^1$HNMR (400 MHz, CDCl$_3$) δ 6.87 (d, 1H), 6.81 (d, 1H), 4.86 (t, 1H), 4.53 (s, 2H), 3.20 (t, 2H), 2.76 (s, 3H), 2.33 (t, 2H), 1.79 (m, 2H), 1.22–1.68 (m, 14H), 0.82-0.92 (m, 3H).

EXAMPLE 27

5-{3-[(4-Butyl-benzyl)-methanesulfonyl-amino]-propyl}-thiophene-2-carboxylic acid Step A: Reaction time of 4 h at 100° C. $^1$HNMR (400 MHz, CDCl$_3$) δ 7.65 (s, 1H), 7.20 (m, 4H), 6.68 (s, 1H), 4.33 (s, 2H), 3.22 (m, 2H), 2.81 (m, 5H), 2.59 (m, 2H), 1.84 (m, 2H), 1.57 (m, 2H), 1.33 (m, 2H), 0.91 (m, 3H); MS 408 (M−1).

EXAMPLE 28

Trans-7-{[3-(3,5-Difluoro-phenyl)-allyl]-methanesulfonyl-amino}-heptanoic acid $^1$HNMR (400 MHz, CDCl$_3$) δ 6.87 (m, 2H), 6.70 (m, 1H), 6.50 (d, 1H), 6.14-6.25 (m, 1H), 3.98 (d, 2H), 3.20 (t, 2H), 2.85 (s, 3H), 2.32 (t, 2H), 1.61 (m, 4H), 1.35 (m, 4H).

EXAMPLE 29

7-{[3-(3-Chloro-phenyl)-propyl]-methanesulfonyl-amino}-heptanoic acid

Step A: Reaction time of 24 h at room temperature. $^1$HNMR (400 MHz, CDCl$_3$) δ 7.04–7.30 (m, 4H), 3.15 (m, 4H), 2.80 (s, 3H), 2.62 (t, 2H), 2.35 (t, 2H), 1.90 (m, 2H), 1.50–1.67 (m, 4H), 1.25–1.40 (m, 4H).

EXAMPLE 30

Trans-5-(3-{[3-(3,5-Dichloro-phenyl)-allyl]-methanesulfonyl-amino}-propyl)-thiophene-2-carboxylic acid Step A: Reaction time of 4 h at 100° C. $^1$HNMR (400 MHz, CD$_3$OD) δ 7.15-7.46 (m, 4H), 6.79 (s, 1H), 6.55 (d, 1H), 6.35 (m, 1H), 3.99 (d, 2H), 3.29 (m, 2H), 2.91 (m, 5H), 1.99 (m, 2H); MS 447.7 (M−1).

EXAMPLE 31

7-[(4-isobutyl-benzyl)-methanesulfonyl-amino]-heptanoic acid

Step A: Reaction time of 72 h at room temperature. $^1$HNMR (400 MHz, CDCl$_3$) δ 7.24 (d, 2H), 7.12 (d, 2H), 4.32 (s, 2H), 3.12 (t, 2H), 2.79 (s, 3H), 2.45 (d, 2H), 2.30 (t, 2H), 1.85 (m, 1H), 1.45–1.62 (m, 4H), 1.16–1.32 (m, 4H), 0.90 (d, 6H).

EXAMPLE 32

7-{[3-(2-Chloro-phenyl)-propyl]-methanesulfonyl-amino}-heptanoic acid

Step A: Reaction time of 24 h at room temperature. $^1$HNMR (400 MHz, CDCl$_3$) δ 7.10–7.39 (m, 4H), 3.22 (t, 2H), 3.10 (t, 2H), 2.82 (s, 3H), 2.73 (t, 2H), 2.35 (t, 2H), 1.86–2.00 (m, 2H), 1.52–1.70 (m, 4H), 1.28–1.45 (m, 4H); MS 376 (M+1).

EXAMPLE 33

7-[(2'-Chloro-biphenyl4-ylmethyl)-methanesulfonyl-amino]-heptanoic acid

Step A: Reaction time of 24 h at room temperature. $^1$HNMR (400 MHz, CDCl$_3$) δ 7.21–7.50 (m, 8H), 4.44 (s, 2H), 3.15–3.26 (m, 2H), 2.86 (s, 3H), 2.27–2.38 (m, 2H), 1.48–1.68 (m, 5H), 1.20–1.38 (m, 4H).

EXAMPLE 34

7-[(4-Benzyl-benzyl)-methanesulfonyl-amino]-heptanoic acid $^1$HNMR (400 MHz, CDCl$_3$) δ 7.13–7.30 (m, 9H), 4.32 (s, 2H), 3.98 (s, 2H), 3.12 (t, 2H), 2.90 (s, 3H), 2.30 (t, 2H), 2.45–2.60 (m, 4H), 1.16–1.32 (m, 4H).

EXAMPLE 35

Trans-[3-({[3-(3,5-Dichloro-phenyl)-allyl]-methanesulfonyl-amino}-methyl)-phenoxy]-acetic acid Step A: Reaction time of 4 h at 100° C. $^1$HNMR (400 MHz, CDCl$_3$) δ 7.30–7.22 (m, 3H), 7.14 (m, 1H), 6.98–6.82 (m, 3H), 6.34 (d, 1H), 6.09 (m, 1H), 4.66 (s, 2H), 4.38 (s, 2H), 3.93 (d, 2H), 2.89 (s, 3H); MS 443.8 (M−1).

EXAMPLE 36

(4-{[(4-Butyl-benzyl)-methanesulfonyl-amino]-methyl}-phenoxy)-acetic acid

Step A: Reaction time of 4 h at 100° C. $^1$HNMR (400 MHz, CDCl$_3$) δ 7.29–7.13 (m, 5H), 6.98–6.82 (m, 3H), 4.65 (s, 2H), 4.29 (s, 4H), 2.76 (s, 3H), 2.58 (t, 2H), 1.57 (m, 2H), 1.33 (m, 2H), 0.91 (t, 3H); MS 405 (M+).

EXAMPLE 37

3-(2-{[2-(3,5-Dichloro-phenoxy)-ethyl]-methanesulfonyl-amino}-ethoxy)-benzoic acid Step A: Reaction time of 4 h at 100° C. $^1$HNMR (400 MHz, CD$_3$OD) δ 7.60 (d, 1H), 7.51 (s, 1H), 7.34 (t, 1H), 7.11 (m, 1H), 6.95 (m, 1H), 6.83 (s, 1H), 4.20 (m, 4H), 3.73 (m, 4H), 3.01 (s, 3H); MS 447.8 (M−1).

EXAMPLE 38

7-{[2-(3-Chloro-phenoxy)-ethyl]-methanesulfonyl-amino}-heptanoic acid

Step A: Reaction time of 24 h at 65° C. $^1$HNMR (400 MHz, CDCl$_3$) δ 7.19 (m, 1H), 6.94 (m, 1H), 6.86 (m, 1H), 6.76 (m, 1H), 4.09 (t, 2H), 3.59 (t, 2H), 3.25 (t, 2H), 2.89 (s, 3H), 2.33 (t, 2H), 1.63 (m, 4H), 1.35 (m, 4H); MS 395 (M+18).

EXAMPLE 39

7-[(2'-Cyano-biphenyl-4-ylmethyl)-methanesulfonyl-amino]-heptanoic acid

Step A: Reaction time of 6 h at 90° C. HNMR (400 MHz, CDCl$_3$) δ 7.75 (d, 1H), 7.65 (t, 1H), 7.40–7.60 (m, 6H), 4.20 (s, 2H), 3.20 (t, 2H), 2.85 (s, 3H), 2.25 (t, 2H), 1.55 (m, 4H), 1.25 (m, 4H); MS 414 (M+1).

EXAMPLE 40

5-(3-{[2-(3,5-Dimethyl-phenoxy)-ethyl]-methanesulfonyl-amino}-propyl)-thiophene-2-carboxylic acid Step A: Reaction time of 72 h at room temperature. $^1$HNMR (400 MHz, CDCl$_3$) δ 7.69 (d, 1H), 6.84 (d, 1H), 6.62 (s, 1H), 6.46 (s, 2H), 4.08 (t, 2H), 3.62 (t, 2H), 3.35 (t, 2H), 2.92 (m, 5H), 2.27 (s, 6H), 2.07 (m, 2H); MS 411 (M+).

EXAMPLE 41

5-(3-{[2-(3,5-Dimethoxy-phenoxy)-ethyl]-methanesulfonyl-amino}-propyl)-thiophene-2-carboxylic acid Step A: Reaction time of 24 h at room temperature. $^1$HNMR (400 MHz, CDCl$_3$) δ 7.69 (d, 1H), 6.84 (d, 1H), 6.09 (m, 1H), 6.01 (m, 2H), 4.08 (t, 2H), 3.74 (s, 6H), 3.61 (t, 2H), 3.34 (t, 2H), 2.93 (t, 2H), 2.90 (s, 3H), 2.07 (m, 2H); MS 444 (M+1).

EXAMPLE 42

5-(3-{[2-(3,5-Dichloro-phenoxy)-ethyl]-methanesulfonyl-amino}-propyl)-thiophene-2-carboxylic acid Step A: Reaction time of 5 h at 100° C. HNMR (400 MHz, CDCl$_3$) δ 7.70 (d, I H), 6.97 (m, 1H), 6.84 (d, 1H), 7.22 (d, 2H), 4.08 (t, 2H), 3.59 (t, 2H), 3.33 (t, 2H), 2.92 (t, 2H), 2.89 (s, 3H), 2.06 (m, 2H); MS 452 (M+1).

EXAMPLE 43

[3-({[3-(3-Chloro-phenyl)-propyl]-methanesulfonyl-amino}-methyl)-phenoxy]-acetic acid Step A: Reaction time of 5 h at 100° C. $^1$HNMR (400 MHz, CDCl$_3$) δ 7.30–6.85 (m, 8H), 4.66 (s, 2H), 4.32 (s, 2H), 3.18 (t, 2H), 2.82 (s, 3H), 2.49 (t, 2H), 1.76 (m, 2H); MS 412 (M+).

EXAMPLE 44

[3-({f[2-(3,5-Dichloro-phenoxy)-ethyl]-methanesulfonyl-amino}-methyl)-phenoxy]-acetic acid Step A: Reaction time of 5 h at 100° C. $^1$HNMR (400 MHz, CD$_3$OD) δ 7.24 (t, 1H), 6.98 (m, 3H), 6.84 (m, 1H), 6.78 (d, 2H), 4.60 (s, 2H), 4.44 (s, 2H), 3.99 (t, 2H), 3.57 (t, 2H), 2.98 (s, 3H); MS 448 (M+).

EXAMPLE 45

Trans-7-{[3-(3-Hydroxy-phenyl)-allyl]-methanesulfonyl-amino}-heptanoic acid

Step A: Heck Coupling

Trans-Ethyl-7-{[3-(3-Hydroxy-phenyl)-allyl]-methanesulfonyl-amino}-heptanoate

To a solution of 7-(allyl-methanesulfonyl-amino)-heptanoic acid ethyl ester (250 mg, 0.86 mmol), 1-acetyloxy-3-iodo-benzene (225 mg, 0.86 mmol), and triethylamine (139 mL, 1 mmol) in DMF (3 mL) was added palladium acetate (25 mg). The reaction was heated to 80° C. under nitrogen for 24 h. The mixture was cooled to room temperature and aqueous sodium thiosulfate and CH$_2$Cl$_2$ were added. The aqueous solution was extracted with CH$_2$Cl$_2$ (2×) and the combined organic layers were washed with water (1×) and brine (1×). The organic solution was dried with MgSO$_4$, filtered, and concentrated in vacuo. The product was purified by radial chromatography (hexanes to 25% EtOAc/hexanes) to afford the title compound of Step A (95 mg). $^1$H NMR (CDCl$_3$ 400 MHz) δ 6.88–7.34 (m, 4H), 6.53–6.60 (m, 1H), 6.13–6.20 (m, 1H), 4.10 (q, 2H), 3.95 (d, 2H), 3.17–3.21 (m, 2H), 2.85 (s, 3H), 2.24-2.31 (m, 2H), 2.31 (s, 3H), 1.56–1.62 (m, 4H), 1.27–1.33 (m, 4H), 1.23 (t, 3H).

Step B: Ester Hydrolysis

Trans-7-{[3-(3-Hydroxy-phenyl)-allyl]-methanesulfonyl-amino]-heptanoic acid.

In an analogous manner to the procedure described in Step B of Example 1, the title compound of Step A was hydrolyzed to provide the title compound (53 mg). $^1$H NMR (400 MHz, CDCl$_3$) δ 7.14–7.25 (m, 1H), 6.81–6.89 (m, 2H), 6.74–6.77 (m, 1H), 6.50 (d, 1H), 6.08–6.15 (m, 1H), 3.95 (d, 2H), 3.16–3.20 (m, 2H), 2.85 (s, 3H), 2.26–2.33 (m, 2H), 1.50–1.65 (m, 4H), 1.20–1.38 (m, 4H); MS 353.9 (M−1).

EXAMPLES 46–50

Examples 46–50 were prepared from the appropriate starting materials in an analogous manner to Example 45.

EXAMPLE 46

Trans-7-{[3-(2-Hydroxy-phenyl)-allyl]-methanesulfonyl-amino}-heptanoic acid $^1$H NMR (400 MHz, CDCl$_3$) δ 6.49 (d, 1H), 6.12 (m, 1H), 3.94 (d, 2H), 3.18 (t, 2H), 2.85 (s, 3H) 2.31 (t, 2H), 1.58 (m, 4H), 1.32 (m, 4H); MS 353.9 (M−1).

EXAMPLE 47

Trans-7-{[3-(3-Hydroxymethyl-phenyl)-allyl]-methanesulfonyl-amino}-heptanoic acid $^1$H NMR (400 MHz, CDCl$_3$) δ 7.19–7.41 (m, 4H), 6.58 (d, 1H), 6.13–6.25 (m, 1H), 4.70 (s, 2H), 3.92–4.02 (m, 2H), 3.15–3.25 (m, 2H), 2.85 (s, 3H), 2.29 (t, 2H), 1.52–1.68 (m, 4H), 1.18–1.39 (m, 4H); MS 368 (M−1).

EXAMPLE 48

Trans-7-{[3-(3,5-Dichloro-phenyl)-allyl]-methanesulfonyl-amino}heptanoic acid $^1$H NMR (400 MHz, CDCl$_3$) δ 7.25 (m, 3H), 4.80 (d, 1H). 6.15–6.28 (m, 1H), 3.98 (m, 2H), 3.22 (t, 2H), 2.87 (s, 3H), 2.35 (m, 2H), 1.48–1.72 (m, 4H), 1.19–1.42 (m, 4H).

EXAMPLE 49

Trans-7-{[3-(3,5-Bis-trifluoromethyl-phenyl)-allyl]-methanesulfonyl-amino}-heptanoic acid $^1$H NMR (400 MHz, CDCl$_3$) δ 7.77 (m, 3H), 6.66 (m, 1H), 6.36 (m, 1H), 4.02 (d, 2H), 3.24 (t, 2H), 2.89 (s, 3H), 2.33 (t, 2H), 1.62 (m, 4H), 1.35 (m, 4H).

EXAMPLE 50

Trans-7-[Methanesulfonyl-(4-phenyl-but-3-enyl)-amino]-heptanoic acid $^1$H NMR (400 MHz, CDCl$_3$) δ 7.23 (m, 5H), 6.46 (d, 1H), 6.13 (m, 1H), 3.31 (t, 2H), 3.19 (t, 2H), 2.83 (s, 3H), 2.52 (m, 2H), 2.34 (m, 2H), 1.62 (m, 4H), 1.35 (m, 4H); MS 353 (M+).

EXAMPLE 51

7-{[3-(3,5-Bis-trifluoromethyl-phenyl)-propyl]-methanesulfonyl-amino}-heptanoic acid Hydrogenation A solution of trans-7-{[3-(3,5-bis-trifluoromethyl-phenyl)-allyl]-methanesulfonyl-amino}-heptanoic acid (210 mg, 0.44 mmol) in MeOH (10 mL) was added to 10% Pd/carbon (200 mg). The mixture was placed on a Parr hydrogenator at 50 psi and was hydrogenated for 20 h. The reaction was filtered through Celite with the aid of MeOH and the solvent was removed in vacuo. Purification by radial chromatography (2 mm rotary plate, 20:80:0.1 v/v/v EtOAc/hexanes/AcOH) provided the title compound (190 mg). $^1$H NMR (CDCl$_3$ 400 MHz) δ 7.69 (s, 1H), 7.63 (s, 2H), 3.20 (t, 2H), 3.14 (t, 2H), 2.81 (m, 5H), 2.28 (m, 2H), 1.94 (m, 2H), 1.32 (m, 4H); MS 495 (M+18).

EXAMPLES 52–54

Examples 52–54 were prepared from the appropriate starting materials in an analogous manner to Example 51.

EXAMPLE 52

7-[Methanesulfonyl-(3-phenyl-propyl)-amino]-heptanoic acid $^1$H NMR (400 MHz, CDCl$_3$) δ 7.10–7.30 (m, 5H), 3.18 (t, 2H), 3.13 (t, 2H), 2.80 (s, 3H), 2.63 (t, 2H), 2.34 (t, 2H), 1.92 (m, 2H), 1.48–2.72 (m, 4H), 1.09–1.42 (m, 4H).

EXAMPLE 53

7-[Methanesulfonyl-(3-m-tolyl-propyl)-amino]-heptanoic acid $^1$H NMR (400 MHz, CDCl$_3$) δ 6.94–7.21 (m, 4H), 3.18 (t, 2H), 3.13 (t, 2H), 2.80 (s, 3H), 2.59 (t, 2H), 2.34 (t, 2H), 2.32 (s, 3H), 2.85–2.97 (m, 2H), 2.50–2.68 (m, 5H), 1.23–1.40 (m, 5H).

EXAMPLE 54

7-{[3-(3,5-Difluoro-phenyl)-propyl]-
methanesulfonyl-amino}-heptanoic acid $^1$HNMR (400 MHz, CDCl$_3$) δ 6.60–6.78 (m, 3H), 3.12 (m, 4H), 2.82 (s, 3H), 2.64 (t, 2H), 2.37 (t, 2H), 1.92 (m, 2H), 1.50–1.70 (m, 4H), 1.18–1.42 (m, 4H).

EXAMPLE 55

7-{[-(1-Hydroxy-3-phenyl-propyl)-benzyl]-
methanesulfonyl-amino}-heptanoic acid

Step A: Grignard Reaction

Ethyl-7-{[4-(1-Hydroxy-3-phenyl-propyl)-benzyl]-
methanesulfonyl-amino}-heptanoate.

A solution of ethyl 7-[(4-formyl-benzyl)-methanesulfonyl-amino]-heptanoate (200 mg, 0.54 mmol) in CH$_2$Cl$_2$ (2.5 mL) was cooled to 0° C. Phenethylmagnesium chloride (0.6 mL, 1M in THF, 0.6 mmol) was added dropwise and the reaction mixture was stirred at room temperature for 24 h. Water and HCl (1N) were added and the aqueous solution was extracted with CH$_2$Cl$_2$. The organic solution was washed with water (1×) followed by brine (1×), dried over MgSO$_4$, filtered, and concentrated in vacuo. The product was purified by flash chromatography (10% EtOAc/hex to 40% EtOAc/hex) to afford the title compound of Step A (40 mg). $^1$H NMR (400 MHz, CDCl$_3$) δ 7.95 (d, 1H), 7.45 (d, 1H), 7.13–7.40 (m, 7H), 4.654.73 (m, 1H), 4.32–4.46 (m, 2H), 4.11 (q, 2H), 3.25–3.35 (m, 1H), 3.00-3.22 (m, 2H), 2.83 (s, 3H), 2.60–2.81 (m, 1H), 1.96–2.34 (m, 4H), 1.15–1.70 (m, 12H); MS 493 (M+18).

Step B: Ester Hydrolysis

7-{[4-(1-Hydroxy-3-phenyl-propyl)-benzyl]-
methanesulfonyl-amino}-heptanoic. acid In an analogous manner to the procedure described in Step B of Example 1, the title compound of Step A was hydrolyzed to afford the title compound (11 mg). $^1$H NMR (400 MHz, CDCl$_3$) δ 7.93 (d, 1H), 7.48 (d, 1H), 7.15–7.38 (m, 7H), 4.31–4.50 (m, 2H), 3.02–3.35 (m, 4H), 2.83 (s, 3H), 2.60–2.80 (m, 1H), 1.96–2.33 (m, 4H), 1.12–1.61 (m, 8H).

EXAMPLES 56–58

Examples 56–58 were prepared from the appropriate starting materials in an analogous manner to Example 55.

EXAMPLE 56

7-{[4-(1-Hydroxy-pentyl)-benzyl]-methanesulfonyl-
amino}-heptanoic acid $^1$H NMR (400 MHz, CDCl$_3$) δ 7.35–7.25 (m, 4H), 4.66 (t, 1H), 4.34 (s, 2H), 3.15 (t, 2H), 2.82 (s, 3H), 2.25 (t, 2H), 1.85–1.61 (m, 2H), 1.55–1.12 (m, 13H), 0.90-0.82 (m, 3H); MS 417 (399+18).

EXAMPLE 57

7-{[4-(1-Hydroxy-2-phenyl-ethyl)-benzyl]-
methanesulfonyl-amino}-heptanoic acid $^1$H NMR (400 MHz, CDCl$_3$) δ 7.15–7.35 (m, 9H), 4.854.97 (m, 1H), 4.35 (s, 2H), 3.15 (t, 2H), 2.98–3.05 (m, 2H), 2.82 (s, 3H), 2.28 (t, 2H), 1.40–1.60 (m, 4H), 1.14–1.32 (m, 4H); MS 451 (M+18).

EXAMPLE 58

7-{(2'-(1-Hydroxy-hexyl)-biphenyl4-ylmethyl]-
methanesulfonyl -amino}- heptanoic acid $^1$H NMR (CDCl$_3$ 400 MHz) δ 7.55–7.62 (m, 1H). 7.15–7.45 (m, 7H), 4.74 (t, 1H), 4.41 (s, 2H), 3.12–3.28 (m, 2H), 2.88 (s, 3H), 2.30 (t, 3H), 1.43–1.75 (m, 6H), 1.05–1.32 (m, 11H), 0.80 (t, 3H); MS 507 (M+18).

EXAMPLE 59

Trans-N-[3-(3,5-Dichloro-phenyl)-allyl]-N-[6-(1H-
tetrazol-5-yl)-hexyl]-methanesulfonamide

Step A: Alkylation

Trans-N-(6-Cyano-hexyl)-N-[3-(3,5-dichloro-
phenyl)-allyl]-methanesulfonamide

In an analogous manner to the procedure described in Step A of Example 1, trans-N-[3-(3,5-dichloro-phenyl)-allyl]-methanesulfonamide (500 mg, 2.45 mmol) was alkylated with 7-bromoheptanenitrile (781 mg, 2.94 mmol) at room temperature over 24 h to provide the title compound of Step A (760 mg). $^1$H NMR (CDCl$_3$ 400 MHz) δ 7.26 (m, 3H), 6.49 (d, 1H), 6.22 (m, 1H), 3.98 (m, 2H), 3.22 (t, 2H), 2.88 (s, 3H), 2.36 (t, 2H), 1.68–1.35 (m, 8H).

Step B: Tetrazole Formation

Trans-N-[3-(3,5-Dichloro-phenyl)-allyl]-N-[6-(1H-
tetrazol-5-yl)-hexyl]-methanesulfonamide Trimethylsilylazide (0.136 mL, 1.026 mmol) and dibutyltinoxide (38 mg, 0.15 mmol) were added to a solution of trans-N-(6-cyano-hexyl)-N-[3-(3,5-dichlorophenyl)-allyl]-methanesulfonamide (59A) (199 mg, 0.52 mmol) in toluene (4 mL). The reaction was heated at reflux overnight. The reaction was diluted with CH$_2$Cl$_2$ and the organic solution was washed sequentially with HCl (1N, 1×), water (1×), and brine (1×). The organic solution was dried over MgSO$_4$, filtered, and concentrated in vacuo. The product was purified via radial chromatography (CH$_2$Cl$_2$ to 5% MeOH/CH$_2$Cl$_2$) to afford the title compound (120 mg). $^1$H NMR (CDCl$_3$ 400 MHz) δ 7.26 (m, 3H), 6.50 (d, 1H), 6.22 (m, 1H), 4.00 (m, 2H), 3.23 (t, 2H), 3.02 (t, 2H), 2.90 (s, 3H), 1.83 (t, 2H), 1.62 (t, 2H), 1.38 (m, 4H); MS 132 (M+).

EXAMPLES 60–61

Examples 60–61 were prepared from the appropriate starting materials in an analogous manner to Example 59.

EXAMPLE 60

N-(4-Butyl-benzyl)-N-[6-(2H-tetrazol-5-yl)-hexyl]-
methanesulfonamide $^1$H NMR (CDCl$_3$ 400 MHz) δ 7.26–7.17 (m, 4H), 4.36 (s, 2H), 3.17 (t, 2H), 3.00 (t, 2H), 2.81 (s, 3H), 2.59 (t, 2H), 1.88 (t, 2H), 1.54 (m, 6H), 1.15 (m, 4H), 0.93 (t, 3H); MS 394 (M+1).

EXAMPLE 61

N-[2-(3,5-Dichloro-phenoxy)-ethyl]-N-[6-(1H-
tetrazol-5-yl)-hexyl]-methanesulfonamide $^1$H NMR (CDCl$_3$ 400 MHz) δ 6.99 (m, 1H), 6.78 (m, 2H), 4.10 (t, 2H), 3.61 (t, 2H), 3.25 (t, 2H), 3.02 (t, 2H), 2.96 (s, 3H), 1.84 (m, 2H), 1.64 (m, 2H), 1.40 (m, 4H); MS 436 (M+).

EXAMPLE 62

7-[(2'-Hydroxymethyl-biphenyl4-ylmethyl)-methanesulfonyl-amino]-heptanoic acid Step A: Reduction Ethyl 7-[(2'-hydroxymethyl-biphenyl4-ylmethyl)-methanesulfonyl-amino]-heptanoate Sodium borohydride (37 mg, 0.95 mmol) was added to a solution of ethyl 7-{[2'-(1-formyl)-biphenyl-4-ylmethyl]}-heptanoate (415 mg, 0.95 mmol) in MeOH (4 mL) at −78° C. The reaction was stirred at −20° C. for 1.5 h and water was added. The reaction was diluted with $CH_2Cl_2$ and the organic solution was washed with water (1x) and brine (1x). The organic solution was dried over $MgSO_4$, filtered, and concentrated in vacuo. The product was purified by flash chromatography (10% EtOAc/hexanes to 50% EtOAc/hexanes) to afford the title compound of Step A (397 mg). $^1$H NMR (400 MHz, $CDCl_3$) δ 7.55–7.62 (m, 1H), 7.23–7.45 (m, 7H), 4.62 (s, 2H), 4.42 (s, 2H), 4.09 (q, 2H), 3.20 (t, 2H), 2.89 (s, 3H), 2.26 (t, 2H), 1.19–1.70 (m, 1H); MS 465 (M+18).

Step B: Hydrolysis

7-[(2'-Hydroxmethyl-biphenyl-4-ylmethyl)-methanesulfonyl-amino]-heptanoic acid

In an analogous manner to the procedure described in Step B of Example 1, the title compound of Step A was hydrolyzed to afford the title compound (300 mg). $^1$H NMR (400 MHz, $CDCl_3$) δ 7.51–7.59 (m, 1H), 7.22–7.43 (m, 7H), 4.60 (s, 2H), 4.42 (s, 2H), 3.20 (t, 2H), 2.90 (s, 3H), 2.30 (t, 2H), 1.45–1.62 (m, 4H), 1.20–1.30 (m, 4H); MS 437 (M+18).

EXAMPLE 63

7-(Biphenyl-4-ylmethyl-methanesulfonyl-amino)-heptanoic acid

Step A: Suzuki Coupling

Ethyl 7-(Biphenyl4-ylmethyl-methanesulfonyl-amino)-heptanoate

Tetrakis(triphenylphosphine)palladium(0) (102 mg, 0.09 mmol), aqueous $Na_2CO_3$ (0.9 mL, 1M), and phenyl boronic Acid (216 mg, 1.77 mmol) were added to a solution of ethyl 7-{[4-iodobenzyl]-methanesulfonyl-amino}-heptanoate (415 mg, 0.89 mmol) in toluene (37 mL) and EtOH (7 mL). The reaction mixture was heated at reflux for 3 h. The solution was diluted with EtOAc and was washed with water (2x) followed by brine (1x). The organic solution was dried over $MgSO_4$, filtered, and concentrated in vacuo. Purification by radial chromatography (10% EtOAc/hexanes to 30% EtOAC/hexanes) provided the title compound of Step A (298 mg). $^1$H NMR (400 MHz, $CDCl_3$) δ 7.62–7.30 (m, 4H), 4.41 (s, 2H), 4.12 (q, 2H), 3.20 (t, 2H), 2.82 (s, 3H), 2.23 (t, 3H), 1.58 (m, 4H), 1.35 (m, 7H); MS 418.3 (M+).

Step B: Hydrolysis 7-(Biphenyl-4-ylmethyl-methanesulfonyl-amino)-heptanoic acid

In an analogous manner to the procedure described in Step B of Example 1, the title compound of Step A (298 mg, 0.71 mmol) was hydrolyzed to afford the title compound (200 mg). $^1$H NMR (400 MHz, $CDCl_3$) δ 7.62–7.30 (m, 9H), 4.42 (s, 2H), 3.20 (t, 2H), 2.87 (s, 3H), 2.30 (t, 2H), 1.58 (m, 4H); MS 407 (M+18).

EXAMPLE 64

7-[(2'-Formyl-biphenyl-4-ylmethyl)-methanesulfonyl-amino]-heptanoic acid

Step A: Suzuki Coupling

Ethyl 7-{[2'-(1-formyl)-biphenyl4-ylmethyl]}-heptanoate

Tetrakis(triphenyl-phosphine)palladium(0) (85 mg, 0.07 mmol), $Na_2CO_3$ (0.8 mL, 1 M) and 2-formylbenzene boronic Acid were added to a solution of ethyl 7-{[4-iodobenzyl]-methanesulfonyl-amino}-heptanoate (345 mg, 0.74 mmol) in toluene (30 mL) and EtOH (6 mL). After refluxing for 3 h, the solution was diluted with EtOAc and was washed with water (2x), followed by brine (1x). The organic solution was dried over $MgSO_4$, filtered, and concentrated in vacuo. The product was purified via radial chromatotography to afford ethyl 7-{[2'-(1-formyl)-biphenyl4-ylmethyl]}-heptanoate (320 mg). $^1$H NMR (400 MHz, $CDCl_3$) δ 9.95 (s, 1H), 8.05 (d, 1H), 7.35–7.70 (m, 7H), 4.46 (s, 2H), 4.10 (q, 2H), 3.19–3.28 (m, 2H), 2.90 (s, 3H), 2.28 (t, 2H), 1.50–1.62 (m, 5H), 1.20–1.35 (m, 6H); MS 463 (M+18).

Step B: Hydrolysis

7-[(2'-Formyl-biphenyl-4-ylmethyl)-methanesulfonyl-amino]-heptanoic acid

In an analogous manner to the procedure described in Step B of Example 1, ethyl 7-{[2'-(1-formyl)-biphenyl4-ylmethyl]}-heptanoate (75 mg, 0.172 mmol) was hydrolyzed to afford the title compound (55 mg). $^1$H NMR (400 MHz, $CDCl_3$) δ 9.93 (s, 1H), 8.04 (d, 1H), 7.63 (m, 1H), 7.52–7.37 (m, 6H), 4.43 (s, 2H), 3.22 (t, 2H), 2.91 (s, 3H), 2.32 (t, 2H), 1.56 (m, 4H), 1.30 (m, 4H).

EXAMPLE 65

7-{[4-(3-Hydroxymethyl-thiophen-2-yl)-benzyl]-methanesulfonyl-amino}-heptanoic acid Step A: Suzuki Coupling Ethyl 7-{[4-(3-formyl-thiophen-2-yl)-benzyl]-methanesulfonyl-amino}-heptanoate Tetrakis(triphenylphosphine)palladium(0) (91 mg, 0.08 mmol), $Na_2CO_3$ (0.87 mL, 1M) and 5-formyl-2-thiopheneboronic Acid (247 mg, 1.58 mmol) were added to a solution of ethyl 7-{[4-iodobenzyl]-methanesulfonyl-amino}-heptanoate (371 mg, 0.79 mmol) in toluene (33 mL) and EtOH (6.5 mL). The reaction mixture was heated at reflux for 3 h. The solution was diluted with EtOAc and the organic solution was washed with water (2x followed by brine (1x). The organic solution was dried over $MgSO_4$, filtered, and concentrated in vacuo. The product was purified via radial chromatography (25% EtOAc/hexanes to 50% EtOAc/hexanes) to afford the title compound of Step A (75 mg). $^1$H NMR (400 MHz, $CDCl_3$) δ 9.89 (s, 1H), 7.44–7.60 (m, 5H), 7.21–7.31 (m, 1H), 4.45 (s, 2H), 4.10 (q, 2H), 3.20 (t, 2H), 2.90 (s, 3H), 2.25 (t, 3H), 1.58 (m, 4H), 1.35 (m, 7H); MS 452 (M+).

Step B: Reduction

Ethyl 7-{[4-(3-Hydroxymethyl-thiophen-2-yl)-benzyl]-methanesulfonyl-aminoheptanoate Sodium borohydride (6.0 mg, 0.16 mmol) was added to a solution of the title compound of Step A (70 mg, 0.16 mmol) in MeOH (1 mL) at −78° C. The reaction was stirred at −20° C. for 2 h and water was added. The mixture was diluted with $CH_2Cl_2$ and the organic solution was washed with water (1×) and brine (1×). The organic solution was dried over $MgSO_4$, filtered, and concentrated in vacuo to afford 65B (62 mg) which was used without further purification. $^1H$ NMR (400 MHz, $CDCl_3$) δ 7.15-7.52 (m, 6H), 4.68 (s, 2H), 4.40 (s, 2H), 4.09 (q, 2H), 3.19 (t, 2H), 2.86 (s, 3H), 2.24 (t, 2H), 1.82 (bs, 1H), 1.18–1.60 (m, 11H).

Step C: Hydrolysis

7-{[4-(3-Hydroxymethyl-thiophen-2-yl)-benzyl]-methanesulfonyl-amino}-heptanoic acid In an analogous manner to the procedure described in Step B of Example 1, the title compound of Step B (60 mg, 0.13 mmol) was hydrolyzed to afford the title compound (29 mg). $^1H$ NMR (400 MHz, $CDCl_3$) δ 7.15–7.52 (m, 7H), 4.68 (s, 2H), 4.40 (s, 2H), 3.19 (t, 2H), 2.88 (s, 3H), 2.30 (t, 2H), 1.52 (m, 4H), 1.33 (m, 4H); MS 443 (M+18).

EXAMPLE 66

7-[(4-Hexanoyl-benzyl)-methanesulfonyl-amino]-heptanoic acid

A solution of 7-{[4-(1-hydroxy-hexyl)-benzyl]-methanesulfonyl-amino}-heptanoic Acid (88 mg, 0.21 mmol) and Dess-Martin reagent (145 mg, 0.34 mmol) in $CH_2Cl_2$ (2 mL) was stirred at room temperature for 72 h. Sodium thiosulfate solution was added and the reaction mixture was stirred until all solids were dissolved. The aqueous layer was extracted with $CH_2Cl_2$ (2×), and the organic solution was dried over $MgSO_4$, filtered, and concentrated in vacuo. Purification by radial chromatography ($CH_2Cl_2$ to 5% $MeOH/CH_2Cl_2$) provided the title compound (93.6 mg). $^1H$ NMR (400 MHz, $CDCl_3$) δ 7.92 (d, 2H), 7.43 (d, 2H), 4.40 (s, 2H), 3.15 (t, 2H), 2.95 (t, 2H), 2.85 (s, 3H), 2.28 (t, 2H), 1.71 (m, 2H), 1.50 (m, 4H), 1.15–1.40 (m, 8H), 0.85–0.95 (m, 3H).

EXAMPLE 67

(4-{2-[(4-Butyl-benzyl)-methanesulfonyl-amino]-ethyl}-phenyl)-acetic acid

Step A: Alkylation

(4-{2-[(4-Buty-benzyl)-methanesulfonyl-amino]-ethyl}-phenyl)-acetic Acid Methyl Ester A mixture of [4-[2-methanesulfonylamino-ethyl]-phenyl]-acetic Acid methyl ester (38 mg, 0.14 mmol), 1-bromomethyl-4-butylbenzene (35 mg, 0.15 mmol), $K_2CO_3$ (25 mg, 0.182 mmol) and acetonitrile was heated at reflux for 1 h. Aqueous HCl (2 mL, 1N) and EtOAc (30 mL) were added to the reaction. The organic solution was dried with $MgSO_4$, filtered, and concentrated in vacuo. The product was purified by flash chromatography (30% EtOAc/hexanes) to afford the title compound of Step A. $^1H$ NMR (400 MHz, $CDCl_3$) δ 7.28–7.05 (m, 8H), 4.37 (s, 2H), 3.65 (s, 3H), 3.58 (s, 2H), 3.26 (t, 2H), 2.77 (t, 2H), 2.69 (s, 3H), 2.60 (t, 2H), 1.59 (m, 2H), 1.37 (m, 2H), 0.94 (t, 3H).

Step B: Hydrolysis

(4-{2-[(4-Butyl-benzyl)-methanesulfonyl-amino]-ethyl}-phenyl)-acetic acid

In an analogous manner to Step B of Example 1, the title compound of Step A was hydrolyzed to provide the title compound. $^1H$ NMR (400 MHz, $CDCl_3$) 7.15 (m, 8H), 4.35 (s, 2H), 3.66 (s, 2H), 3.35 (t, 2H), 2.75 (t, 2H), 2.65 (s, 3H), 2.59 (m, 2H), 1.58 (m, 2H), 1.34 (m, 2H), 0.91 (t, 3H).

EXAMPLE 68

7-[[4-(1-Hydroxy-hexyl)-benzyl]-(propane-1-sulfonyl)-amino]-heptanoic acid

Step A: Reductive Amination

7-Methyl-{[4-(1-hydroxy-hexyl)-benzyl]-amino}-heptanoate

A solution of 7-aminoheptanoic methyl ester hydrochloride (1.57 g, 8.02 mmol), 4-(1-hydroxy-hexyl)-benzaldehyde (1.98 g, 9.63 mmol), sodium acetate (1.32 g, 16.05 mmol) and $NaBH_3CN$ (605 mg, 9.63 mmol) in MeOH (50 mL) was stirred at room temperature for 24 h. The reaction mixture was concentrated in vacuo and was diluted with EtOAc. The solution was washed sequentially with $NaHCO_3$ (1×), water (1×), and brine (1×). The organic solution was dried over $MgSO_4$, filtered, and concentrated in vacuo. The product was purified by flash chromatography (1% $MeOH/CHCl_3$ to 5% $MeOH/CHCl_3$) to afford 7-methyl-{([4-(1-hydroxy-hexyl)-benzyl]-amino}- heptanoate (1.28 g).

Step B: Amide Formation

7-[[4-(1-Hydroxy-hexyl)-benzyl]-(propane-1-sulfonyl)-amino]-heptanoic Acid Methyl Ester A solution of 7-methyl-{[4-(1-hydroxy-hexyl)-benzyl]-amino}-heptanoate (82.2 mg, 0.235 mmol), 1-propanesulfonyl chloride (29.1 μL, 0.259 mmol) and 4-methylmorpholine (28.5 μL, 0.259 mmol) in $CH_2Cl_2$ (10 mL) was stirred at room temperature for 24 h. Additional 1-propanesulfonyl chloride (14.5 μL) and 4-methylmorpholine (14.3 μL) were added, and the reaction was stirred for 5 days. The organic solution was washed consecutively with 5.5% HCl, water, aqueous $NaHCO_3$, and brine. The organic solution was dried ($MgSO_4$), filtered, and concentrated to yield 7-[[4-(1-hydroxy-hexyl)-benzyl]-(propane-1-sulfonyl)-amino]-heptanoic Acid methyl ester which was used in the next step without further purification.

Step C: Hydrolysis

7-[[4-(1-Hydroxy-hexyl)-benzyl]-(propane-1-sulfonyl)-amino]-heptanoic acid

In an analogous manner to the procedure described in Step B of Example 1, 7-[[4-(1-hydroxy-hexyl)-benzyl]-(propane-1-sulfonyl)-amino]-heptanoic Acid methyl ester was hydrolyzed at room temperature over 24 h to afford the title compound (43 mg) as an oil. $^1H$ NMR (400 MHz, $CDCl_3$) δ 7.35–7.22 (d, 2H), 7.11–7.00 (d, 2H), 4.61 (q, 1H), 4.50 (s, 2H), 3.31 (t, 2H), 2.40–2.20 (m, 4H), 2.81–1.43 (m, 1OH), 1.41–1.22 (m, 8H), 1.31–0.81 (m, 6H); MS 440 (M−1).

EXAMPLE 69

Example 69 was prepared from the appropriate starting materials in an analogous manner to Example 68.

EXAMPLE 69

7-[Methanesulfonyl-(4-phenyl-thiophen-2-ylmethyl)-amino]-heptanoic acid $^1$H NMR (400 MHz, CDCl$_3$) δ 7.55 (d, 1H), 7.40–7.20 (m, 6H), 4.65 (s, 2H), 3.20 (t, 2H), 3.02 (s, 3H), 2.25 (t, 2H), 1.60 (m, 4H), 1.25 (m, 4H); MS 394 (M−1).

EXAMPLE 70

7-{[4-(1-Hydroxy-hexyl)-benzyl]-propionyl-amino}-heptanoic acid

Step A: Amide Formation

7-Methyl-{[4-(1-hydroxy-hexyl)-benzyl]-propionyl-amino}-heptanoate

A solution of 7-methyl-{[4-(1-hydroxy-hexyl)-benzyl]-amino}-heptanoate (314 mg, 0.90 mmol), propionic acid, (73.02 mg, 0.99 mmol), and DCC (203.6 mg, 0.99 mmol) in CH$_2$Cl$_2$ (20 mL) was stirred at room temperature for 24 h. The solids were removed via filtration and the filtrate was concentrated in vacuo. EtOAc was added to the residue and the insolubles were removed by filtration. The organic solution was washed consecutively with aqueous HCl (5.5%, 1×), water (1×), aqueous NaHCO$_3$ (1×), and brine (1×). The organic solution was dried (MgSO$_4$), filtered, and concentrated to afford 7-methyl-{[4-(1-hydroxy-hexyl)-benzyl]-propionyl-amino}-heptanoate (403 mg) as an oil which was used without further purification.

Step B: Hydrolysis

7-{[4-(1-Hydroxy-hexyl)-benzyl]-propionyl-amino}-heptanoic acid

In an analogous manner to the procedure described in Step B of Example 1, 7-methyl-{[4-(1-hydroxy-hexyl)-benzyl]-propionyl-amino}-heptanoate (365 mg, 0.90 mmol) was hydrolyzed at room temperature over 24 h to afford the title compound (254 mg) as an oil. $^1$H NMR (300 MHz, CDCl$_3$) δ 7.33–7.11 (m, 4H), 4.43–4.66 (m, 3H), 3.33 (t, 1H), 3.17 (t, 1H), 2.25–2.47 (m, 4H), 1.02–1.87 (m, 19H), 0.86 (m, 3H); MS 391.4 (M+).

EXAMPLES 71–72

Examples 71–72 were prepared from the appropriate starting materials in an analogous manner to Example 70.

EXAMPLE 71

7-{Butyryl-[4-(1-hydroxy-hexyl)-benzyl]-amino}-heptanoic acid $^1$H NMR (300 MHz, CDCl$_3$) δ 7.32–7.21 (d, 2H), 7.15–7.02 (d, 2H), 4.60 (q, 1H), 4.40 (s, 2H), 3.22 (t, 2H), 2.70 (t, 2H), 2.41–2.20 (t, 2H), 1.85–1.55 (m, 10H), 1.45–1.22 (m, 8H), 1.01–0.85 (m, 6H); MS 404 (M−1).

EXAMPLE 72

7-[(4-Butyl-benzyl)-propionyl-amino]-heptanoic acid $^1$H NMR (300 MHz, CDCl$_3$) δ 7.32–7.21 (d, 2H), 7.10–7.00 (d, 2H), 4.50 (s, 2H), 3.30 (t, 2H), 2.50 (m, 2H), 2.32 (m, 4H), 1.50 (m, 4H), 1.22 (m, 8H), 1.20 (t, 3H), 0.95 (t, 3H); MS 348 (M+).

EXAMPLE 73

7-[Methanesulfonyl-(4-phenethyl-benzyl)-amino]-heptanoic acid

Step A: Alkylation

Trans-7-[Methanesulfonyl-(4-styryl-benzyl)-amino]-heptanoic Acid Ethyl Ester

In an analogous manner to the procedure described in Step A of Example 1, ethyl-7-amino-heptanoate (502 mg, 2 mmol) was alkylated with trans-4-chloromethylstilbene (502.7 mg, 2.2 mmol) at room temperature over 24 h to provide trans-7-[methanesulfonyl-(4-styryl-benzyl)-amino]-heptanoic Acid ethyl ester (0.90 g). $^1$H NMR (400 MHz, CDCl$_3$) δ 7.50 (m, 4H), 7.40–7.20 (m, 5H), 7.10 (m, 2H), 4.36 (s, 2H), 4.09 (q, 2H), 3.15 (t, 2H), 2.81 (s, 3H), 2.22 (t, 2H), 1.54 (m, 4H), 1.15–1.32 (m, 7H).

Step B: Hydrogenation

7-[Methanesulfonyl-(4-phenethyl-benzyl)-amino]-heptanoic Acid Ethyl Ester

A solution of trans-7-[methanesulfonyl-(4-styryl-benzyl)-amino]-heptanoic acid ethyl ester (0.60 g) in MeOH (5 mL) and EtOAc (50 mL) was added to 10% Pd/carbon (0.2 g). The reaction mixture was placed on a Parr hydrogenator and was hydrogenated for 20 h at 50 psi. The reaction mixture was filtered through celite and concentrated in vacuo to afford 7-[methanesulfonyl-(4-phenethyl-benzyl)-amino]-heptanoic Acid ethyl ester (0.60 g). $^1$H NMR (400 MHz, CDCl$_3$) δ 7.30–7.10 (m, 9H), 4.32 (s, 2H), 4.10 (q, 2H), 3.12 (t, 2H), 2.90 (s, 4H), 2.79 (s, 3H), 2.25 (t, 2H), 1.60-1.45 (m, 4H), 1.30–1.19 (m, 7H).

Step C: Ester Hydrolysis

7-[Methanesulfonyl-(4-phenethyl-benzyl)-amino]-heptanoic acid

In an analogous manner to the procedure described in Step B of Example 1, 7-[methanesulfonyl-(4-phenethyl-benzyl)-amino]-heptanoic Acid ethyl ester (600 mg) was hydrolyzed to afford the title compound. $^1$H NMR (400 MHz, CDCl$_3$) δ 7.30–7.10 (m, 9H), 4.32 (s, 2H), 3.13 (t, 2H), 2.91 (s, 4H), 2.79 (s, 3H), 2.30 (t, 2H), 1.61–1.47 (m, 4H), 1.32–1.18 (m, 4H).

EXAMPLE 74

Trans-4-{2-[Methanesulfonyl-(3-phenyl-allyl)-amino]-ethoxy}-benzoic acid

Step A: Alklation

Trans-4-{2-[Methanesulfonyl-(3-phenyl-allyl)-amino]-ethoxy}-benzoic Acid Methyl Ester To a solution of 4-(2-methanesulfonylamino-ethoxy)-benzoic Acid methyl ester (62 mg, 0.23 mmol) in DMF (10 mL) at 0° C. was added sodium bis(trimethylsilyl)amide (1.0 M in THF, 0.24 mL, 0.24 mmol) dropwise. After 20 minutes, cinnamyl bromide (51 mg, 0.26 mmol) was added and the reaction was stirred at room temperature for 2 h. Aqueous 1N HCl was added and the product was extracted into EtOAc. The organic solution was washed with 1N HCl (3×) followed by brine. The organic solution was dried (Na$_2$SO$_4$), filtered, and concentrated. Radial chromatography (20%

EtOAc in hexanes) provided trans4-{2-[methanesulfonyl-(3-phenyl-allyl)-amino]- ethoxy}-benzoic Acid methyl ester (70 mg). $^1$NMR (400 MHz, CDCl$_3$) δ 7.97 (d, 2H), 7.35–7.23 (m, 5H), 6.88 (d, 2H), 6.58 (d, 1H), 6.18 (m, 1H), 4.20 (t, 2H), 4.12 (d, 2H), 3.88 (s, 3H), 3.68 (t, 2H), 2.95 (s, 3H).

Step B: Hydrolysis

Trans4-{2-[Methanesulfonyl-(3-phenyl-allyl)amino]-ethoxy}-benzoic acid

In an analogous manner to the procedure described in Step B of Example 1, trans4-{2-[methanesulfonyl-(3-phenyl-allyl)-amino]-ethoxy}-benzoic Acid methyl ester (60 mg) was hydrolyzed to provide the title compound (35 mg). $^1$H NMR (300 MHz, CDCl$_3$) δ 8.04 (d, 2H), 7.30 (m, 5H), 6.92 (d, 2H), 6.60 (d, 1H), 6.19 (m, 1H), 4.24 (t, 2H), 4.15 (d, 2H), 3.71 (t, 2H), 2.98 (s, 3H); MS 375 (M+).

PREPARATION A1

N-(4-Butyl-benzyl)-methanesulfonamide

Step A: Nitrile Reduction

4-Butylbenzylamine.

A solution of 4-butylbenzonitrile (3.63 g, 22.8 mmol) in THF (10 mL) was placed in a three-neck round bottom flask equipped with a vigreux column and short-path distillation head. The solution was heated to reflux and BH$_3$-methyl sulfide complex (2.0 M in THF, 15 mL, 30 mmol) was added dropwise over 15 minutes. Methyl sulfide was distilled off from the reaction mixture over 1 h and the solution was cooled to room temperature. Aqueous HCl (6N, 25 mL) was added slowly via an addition funnel and the mixture was heated at reflux for 30 minutes. The reaction was cooled to 0° C. and NaOH (7.0 g) was added portionwise. The aqueous solution was extracted with EtOAc (3x) and the organic solution was dried (MgSO$_4$), filtered, and concentrated. The product (4.01 g) was used in the next step without further purification. $^1$H NMR (400 MHz, CDCl$_3$) δ 7.34 (m, 2H), 7.24 (m, 2H), 4.04 (s, 2H), 2.62 (t, 2H), 1.58 (m, 2H), 1.34 (m, 2H), 0.92 (t, 3H).

Step B: Sulfonamide Formation

To a solution of 4-butylbenzylamine (4.01 g, 24.6 mmol) in CH$_2$Cl$_2$ (75 mL) was added pyridine (4.0 mL, 49 mmol) followed by dropwise addition of methanesulfonyl chloride (2.5 mL, 32.3 mmol). The reaction was stirred at room temperature for 24 h and water was added. The product was extracted into CH$_2$Cl$_2$ (2x) and the organic solution was dried (MgSO$_4$), filtered, and concentrated. Flash chromatography (2:1 to 1:1 hexanes:EtOAc) provided the title compound as a white solid (3.4114 g). $^1$H NMR (400 MHz, CDCl$_3$) δ 7.23 (d, 2H), 7.15 (d, 2H), 4.84 (m, 1H), 4.25 (d, 2H), 2.82 (s, 3H), 2.58 (t, 2H), 1.56 (m, 2H), 1.33 (m, 2H), 0.91 (t, 3H).

In an analogous manner, the following compounds were prepared from the appropriate starting materials using the above general procedure of Preparation A1.

PREPARATION A2

N-[2-(3.5-Dichloro-phenoxy)-ethyl]-methanesulfonamide

PREPARATION A3

N-[2-(3-Chloro-phenoxy)-ethyl]-methanesulfonamide

PREPARATION A4

4-Iodobenzyl-methanesulfonamide

The title compound was prepared from 4-iodobenzylamine in an analogous manner to step B of Preparation A1. $^1$H NMR (400 MHz, CDCl$_3$) δ 7.69 (d, 2H), 7.10 (d, 2H), 4.82 (bs, 1H), 4.28 (d, 2H), 2.87 (s, 3H).

PREPARATION A5

N-[3-(2-Chloro-phenyl)-propyl]-methanesulfonamide

PREPARATION B1

Ethyl 7-{[4-iodobenzyl]-methanesulfonyl-amino}-heptanoate

In an analogous manner to the procedure described in Step A of Example 1, 4-iodobenzyl-methanesulfonamide (2.67 g, 8.59 mmol) was alkylated with ethyl-7-bromoheptanoate (2.00 g, 8.44 mmol) at 50° C. for 2 h and at room temperature for 24 h to provide the title compound (3.61 g). $^1$H NMR (400 MHz, CDCl$_3$) δ 7.68 (d, 2H), 7.12 (d, 2H), 7.31 (s, 2H), 4.12 (q, 2H), 3.13 (t, 2H), 2.83 (s, 3H), 2.27 (t, 2H), 1.42-1.65 (m, 5H), 1.15–1.35 (m, 6H); MS 468 (M+).

In an analogous manner, the following compounds were prepared from the appropriate starting materials using the above general procedure of Preparation B1 with variations in reaction temperature and time as indicated.

PREPARATION B2

7-(Allyl-methanesulfonyl-amino)-heptanoic Acid Ethyl Ester

As described in Preparation B1: 24 h at room temperature. $^1$H NMR (400 MHz, CDCl$_3$) δ 5.71–5.81 (m, 1H), 5.16–5.24 (m, 2H), 4.01–4.10 (m, 2H), 3.70–3.80 (m, 2H), 3.07–3.15 (m, 2H), 2.77 (s, 3H), 2.21 (t, 2H), 1.47–1.58 (m, 4H), 1.22–1.34 (m, 4H), 1.18 (t, 3H).

PREPARATION B3

7-(But-3-enyl-methanesulfonyl-amino)-heptanoic Acid Ethyl Ester

As described in Preparation B1: 90° C. for 24 h.

PREPARATION B4

N-(6-Cyano-hexyl)-methanesulfonamide

As described in Preparation B1: 90° C. for 24 h. $^1$H NMR (400 MHz, CDCl$_3$) δ 4.24 (m, 1H), 3.11 (q, 2H), 2.83 (s, 3H), 2.35 (t, 2H), 1.70–1.37 (m, 8H); MS 222 (M+18).

PREPARATION C1

5-(3-Methanesulfonylamino-propyl)-thiophene-2-carboxylic Acid Methyl Ester

Step A 5-(3-Methanesulfonylamino-prop-1-ynyl)-thiophene-2-carboxylic Acid Methyl Ester.

To a solution of 5-bromo-thiophene-2-carboxylic Acid methyl ester (1.66 g, 8.0 mmol), N-prop-2-ynyl-methanesulfonamide (1.09 g, 8.2 mmol), Et$_3$N (1.7 mL, 12.1 mmol), and CH$_3$CN (30 mL) was added Pd(PPh$_3$)$_4$ (462 mg, 0.4 mmol) followed by CuI (76 mg, 0.4 mmol). The reaction was heated at reflux for 24 h and was cooled to room temperature. The volatiles were removed in vacuo and the residue was purified via flash chromatography (20% EtOAc in hexanes to 33% EtOAc in hexanes) to yield 5-(3-methanesulfonylamino-prop-1-ynyl)-thiophene-2-carboxylic Acid methyl ester as a pale yellow solid (1.1 g). $^1$H NMR (300 MHz, CDCl$_3$) δ 7.64 (d, 1H), 7.14 (d, 1H), 4.60 (m, 1H), 4.22 (d, 2H), 3.88 (s, 3H), 3.10 (s, 3H); MS 274 (M+1).

Step B: Hydrogenation

A solution of 5-(3-methanesulfonylamino-prop-1-ynyl)-thiophene-2-carboxylic Acid methyl ester (3.0 g, 10.9 mmol) in EtOAc (100 mL) and MeOH (50 mL) was hydrogenated with 10% Pd/C (680 mg) at 50 psi for 7 h. The solution was filtered through a pad of Celite with the aid of MeOH and was concentrated in vacuo to provide the title compound as an off-white solid (2.95 g). $^1$H NMR (300 MHz, CDCl$_3$) δ 7.62 (d, 1H), 7.23 (d, 1H), 4.29 (m, 1H), 3.85 (s, 3H), 3.18 (q, 2H), 2.93 (m, 5H), 1.96 (m, 2H).

In an analogous manner, the following compounds were prepared from the appropriate starting materials using the above general procedure of Preparation C1.

PREPARATION C2

N-[3-(3-Chloro-phenyl)-propyl]-methanesulfonamide

PREPARATION C3

N-[3-(3-Trifluoromethyl-phenyl)-propyl]-methanesulfonamide

PREPARATION D1

1-Bromomethyl-4-butyl-benzene

HBr was bubbled into a solution of (4-butyl-phenyl)-methanol (10.0 g, 60.9 mmol) in CH$_2$Cl$_2$ (100 mL) for 15 minutes. The reaction was stirred for an additional 45 minutes and was poured onto ice water. The aqueous solution was extracted with CH$_2$Cl$_2$ (2×) and was dried (MgSO$_4$), filtered, and concentrated to provide the title compound which was used without further purification. $^1$H NMR (400 MHz, CDCl$_3$) δ 7.29 (d, 2H), 7.14 (d, 2H), 4.49 (s, 2H), 2.60 (t, 2H), 1.58 (m, 2H), 1.36 (m, 2H), 0.92 (t, 3H).

In an analogous manner, the following compound was prepared from the appropriate starting materials using the general procedure of Preparation D1.

PREPARATION D2

1-Bromomethyl4-isopropyl-benzene $^1$H NMR (400 MHz, CDCl$_3$) δ 7.31 (d, 2H), 7.19 (d, 2H), 4.49 (s, 2H), 2.90 (m, 1H), 1.24 (d, 6H).

PREPARATION E1

4'-Bromomethyl-2-chloro-biphenyl

Step A: Suzuki Coupling

4'-Methyl-2-chloro-biphenyl.

Tetrakis(triphenylphosphine)palladium(0) (637 mg, 0.551 mmol), Na$_2$CO$_3$ (5 mL, 1M) and 4-methylbenzene boronic Acid (1.5 g, 11.0 mmol) were added to a solution of 2-chloroiodobenzene (1.315 g, 5.514 mmol) in toluene (98 mL) and EtOH (20 mL). The reaction mixture was heated at reflux for 3 h. The cooled solution was diluted with EtOAc, and the organic solution was washed with water (2×) followed by brine (1×). The organic solution was dried over MgSO$_4$, filtered, and concentrated in vacuo. The product was purified by flash chromatography (hexanes to 10% EtOAC/hexanes) to afford 4'-methyl-2-chlorobiphenyl (1.08 g). $^1$H NMR (CDCl$_3$ 400 MHz) δ 7.49–7.21 (m, 8H), 2.39 (s, 3H).

Step B: Benzylic Bromination

A mixture of 4'-methyl-2-chloro-biphenyl (1.08 g, 5.33 mmol), NBS (1.14 g, 6.40 mmol) and AIBN (175 mg, 1.06 mmol) in CCl$_4$ (37 mL) was heated at reflux for 3 h. The reaction mixture was diluted with CH$_2$Cl$_2$ and the organic solution was washed sequentially with aqueous saturated NaHCO$_3$ (2×), water (1×), and brine (1×). The organic solution was dried over MgSO$_4$, filtered, and concentrated in vacuo. The product was purified by flash chromatography (hexanes to 5% EtOAc/hexanes) to afford the title compound (920 mg). $^1$H NMR (CDCl$_3$ 400 MHz) δ 7.63–7.25 (m, 8H), 4.56 (s, 2H).

In an analogous manner, the following compounds were prepared from the appropriate starting materials using the above general procedure of Preparation E1.

PREPARATION E2

4'-Bromomethyl-2-trifluoromethyl-biphenyl

PREPARATION E3

4'-Bromomethyl-2,6-dichloro-biphenyl

PREPARATION F1

(3-Bromomethyl-phenyl)-acetic Acid Methyl Ester.

A solution of m-toly-acetic Acid methyl ester (11.41 g, 69.49 mmol), N-bromosuccinimide (12.59 g, 70.73 mmol), AIBN (100 mg) in CCl$_4$ (200 mL) was heated at reflux for 16 h. The reaction was cooled to room temperature and aqueuos NaHCO$_3$ (satd) was added. The aqueous solution was extracted with CH$_2$Cl$_2$ (2×) and the organic solution was dried (MgSO$_4$), filtered, and concentrated. Purification by flash chromatography (hexanes to 9:1 hexanes:EtOAc) provided the title compound as a clear and colorless liquid (11.99 g). $^1$H NMR (CDCl$_3$ 400 MHz) δ 7.27 (m, 4H), 4.47 (s, 2H), 3.69 (s, 3H), 3.62 (s, 2H).

In an analogous manner, the following compound was prepared from the appropriate starting materials using the above general procedure of Preparation F1).

PREPARATION F2

2-(4-Bromomethyl-phenyl)-pyridine

PREPARATION G1

4-[(1-Acetyloxy)-hexyl]-benzyl bromide

Step A: Grignard Reaction And Protection

4-[(1-Acetyloxy)-hexyl]-toluene.

Pentylmagnesium bromide (2.0 M in Et$_2$O, 25 mL, 50 mmol) was added slowly to p-tolylbenzaldehyde (5.0 mL, 42.4 mmol) in THF (50 mL) at 0° C. The reaction was warmed to room temperature and was stirred for 3 h. Aqueous 1N HCl was added and the aqueous solution was extracted with EtOAc. The organic solution was washed with brine, dried over MgSO$_4$, filtered, and concentrated. The residue was dissolved in pyridine (35 mL) and AC2O (10 mL) was added. The reaction was stirred for 24 h and was diluted with water. The product was extracted into EtOAc (3×) and the organic solution was washed with 1N HCl followed by brine, dried over MgSO$_4$, filtered, and concentrated. The product was purified by flash chromatography (10% EtOAc/hexanes) to afford 4-[(1-acetyloxy)-hexyl]-toluene (2.082 g). $^1$H NMR (400 MHz, CDCl$_3$) δ 7.12–7.28 (m, 4H), 5.69 (t, 1H), 2.33 (s, 3H), 2.04 (s,3H), 1.88 (m, 1H), 1.74 (m, 1H), 1.27 (m, 6H), 0.86 (m, 3H); MS 252 (M+18).

Step B: Benzylic Bromination

A mixture of 4-[(1-acetyloxy)-hexyl]-toluene (2.082 g, 8.89 mmol), NBS (1.58 g, 8.89 mmol), and catalytic AIBN in CCl$_4$ (30 mL) was heated at reflux for 2 h. The reaction was cooled and was washed with aqueous NaHCO$_3$ (satd), dried over MgSO$_4$, filtered, and concentrated. The product was purified by flash chromatography (5% EtOAc/hexanes) to afford the title compound (2.67 g). $^1$H NMR (400 MHz, CDCl$_3$) δ 7.34–7.40 (m, 4H), 5.70 (t, 1H), 4.47 (s, 2H), 2.06 (s, 3H), 1.86 (m, 1H), 1.73 (m, 1H), 1.27 (m, 6H), 0.85 (m, 3H).

In an analogous manner, the following compound was prepared from the appropriate starting materials using the above general procedure of Preparation G1.

PREPARATION G2

Acetic Acid 1-(5-bromomethyl-thiophen-2-yl)-hexyl Ester

PREPARATION H1

Trans-1-(3-Bromo-propenyl)-3,5-dichloro-benzene

Step A: Grignard Reacton 1-(3,5-Dichloro-phenyl)-prop-2-en-1-ol.

A solution of 3,5-dichlorobenzaldehyde (7.5 g, 43 mmol) in THF (75 mL) was cooled to 0° C. and vinylmagnesium bromide (1M in THF, 48 mL, 48 mmol) was added dropwise. The reaction was warmed to room temperature and was stirred overnight. Aqueous HCl (1N) and EtOAc were added. The aqueous solution was extracted with EtOAc and the organic solution was dried (MgSO$_4$), filtered, and concentrated. The residue was used in the next step without further purification.

Step B: Bromination

The residue prepared in Step A was dissolved in Et$_2$O and HBr gas was slowly bubbled into the solution for about 15 minutes. The reaction was stirred at room temperature for 24 h and water and EtOAc were added. The aqueous solution was extracted with EtOAc and the organic solution was dried (MgSO$_4$), filtered, and concentrated. Purification by flash chromatography (hexanes) provided the title compound (6.91 g). $^1$H NMR (400 MHz, CDCl$_3$) δ 7.24 (s, 3H), 6.53 (d, 1H), 6.40 (m, 1H), 4.10 (m, 2H).

In an analogous manner, the following compound was prepared from the appropriate starting materials using the above general procedure of Preparation H1.

PREPARATION H2

Trans-1-(3-Bromo-propenyl)-3,5-difluoro-benzene $^1$H NMR (400 MHz, CDCl$_3$) δ 6.83–6.95 (m, 2H), 6.65–6.75 (m, 1H), 6.55 (d, 1H), 6.34–6.45 (m, 1H), 4.10 (d, 2H).

PREPARATION I1

4-isobutylbenzylbromide

Step A: Reduction (4-Isobutyl-phenyl)-methanol.

A solution of lithium aluminum hydride (30 mL, 1M in THF, 30 mmol) was added dropwise to a solution of 4-isobutylbenzoic acid (5.34 g, 30 mmol) in THF (50 mL) at 0° C. The ice bath was removed and the reaction was stirred at room temperature for 1 h. The reaction was carefully poured onto a mixture of ice and aqueous HCl (10 mL, 6N). The product was extracted into EtOAc and the organic solution was dried (MgSO$_4$), filtered, and concentrated to obtain (4-isobutyl-phenyl)-methanol which was used in the next step without further purification. $^1$H NMR (400 MHz, CDCl$_3$) δ 7.26 (d, 2H), 7.13 (d, 2H), 4.65 (s, 2H), 2.46 (d, 2H), 1.85 (m, 1H), 0.89 (d, 6H).

Step B: Bromination

HBr gas was bubbled through a solution of (4-isobutyl-phenyl)-methanol (5 g, 28 mmol) in Et$_2$O (50 mL) for 10–15 minutes. The reaction was stirred for 1 h and was poured onto ice (100 g). Et$_2$O was added and the organic solution was washed with brine (2×). The organic solution was dried (MgSO$_4$), filtered, and concentrated to provide the title compound (6 g). $^1$H NMR (400 MHz, CDCl$_3$) δ 7.28 (d, 2H), 7.10 (d, 2H), 4.49 (s, 2H), 2.45 (d, 2H), 1.84 (m, 1H), 0.89 (d, 6H).

In an analogous manner, the following compound was prepared from the appropriate starting materials using the above general procedure of Preparation I1.

PREPARATION I2

1-(Bromomethyl)-4-(phenylmethyl)-benzene

PREPARATION J1

7-[(4-Formyl-benzyl)-methanesulfonyl-amino]-heptanoic acid

Step A

1-Bromomethyl-4-vinyl-benzene.

Bromine (16.4 g, 103 mmol) was slowly added to a solution of triphenylphosphine (28.87 g, 110.1 mmol) in CH$_2$Cl$_2$ (260 mL) at 0° C. After 10 minutes, 4-vinylbenzyl alcohol (12.5 g, 93.3 mmol) was added and the reaction mixture was stirred at 0° C. for 2 h. The reaction mixture was washed with water (1×) followed by brine (1×). The organic solution was dried over MgSO$_4$, filtered, and concentrated in vacuo. The product was triturated with petroleum ether (3×), and the ethereal solution was concentrated in vacuo. The residue was purified by flash chromatography (hexanes) to afford 4-vinyl-benzyl bromide (6.23 g). $^1$H NMR (400 MHz, CDCl$_3$) δ 7.32–7.45 (m, 4H), 6.72 (dd, 1H), 5.77 (d, 1H), 5.28 (d, 1H), 4.50 (s, 2H).

Step B: Alkylation

Ethyl-7-[(4-vinyl-benzyl)-methanesulfonyl-amino]-heptanoate.

According to the procedure described in Preparation B1, ethyl-7-methanesulfonyl-amino-heptanoate (2.30 g, 9.02 mmol) was alkylated with 4-vinylbenzyl bromide (1.77 g, 9.02 mmol) over 3 h at room temperature to provide, after flash chromatography chromatography (10% EtOAc/hexanes to 50% EtOAc/hexanes), ethyl-7-[(4-vinylbenzyl)-methanesulfonyl-amino]-heptanoate (2.21 g). $^1$H NMR (400 MHz, CDCl$_3$) δ 7.23–7.45 (m, 4H), 6.72 (dd, 1H), 5.76 (d, 1H), 5.28 (d, 1H), 4.38 (s, 2H), 4.12 (q, 2H), 3.14 (t, 2H), 2.83 (s, 3H), 2.24 (t, 2H), 1.15–1.64 (m, 11H); MS 385 (M+18).

Step C: Oxidation

A solution of ethyl-7-[(4-vinyl-benzyl)-methanesulfonyl-amino]-heptanoate (2.2 g, 6.0 mmol) in dioxane (45 mL) was added to a solution of N-methylmorpholine N-oxide (1.47 g, 12.5 mmol) in water (45 mL). Osmium tetroxide (4.6 mL, 2.5 wt % in 2-methyl-2-propanol) was added and the mixture was stirred at room temperature for 1 h. The reaction was quenched with 1N HCl (50 mL) and the aqueous solution was extracted with CH$_2$Cl$_2$. The organic layer was washed with water (1×) followed by brine (1×), dried over MgSO$_4$, filtered, and concentrated in vacuo. The residue was dissolved in 35% aqueous THF (100 mL) and NaIO$_4$ (1.41 g, 6.59 mmol) was added. The mixture was stirred at room temperature for 2 h and was diluted with EtOAc and water. The organic solution was washed with water (1×) followed by brine (1×), dried over MgSO$_4$, filtered, and concentrated in vacuo to afford the title compound (1.9 g) which was used without further purification. $^1$H NMR (400 MHz, CDCl$_3$) δ 10.0 (s, 1H), 7.82–7.90 (d, 1H), 7.50–7.59 (d, 2H), 5.30 (s, 2H), 4.45 (s, 2H), 4.05–4.18 (m, 2H), 3.12–3.22 (m, 2H), 2.86 (s, 3H), 2.19–2.30 (m, 2H), 1.42–1.62 (m, 6H), 1.18–1.30 (m, 3H); MS 387 (M+18).

PREPARATION K1

(4-Methanesulfonylamino-butoxy)-acetic Acid Ethyl Ester

Step A: Alkylation (4-Bromo-butoxy)-acetic Acid Ethyl Ester.

A solution of ethyl glycolate (4.6 g, 44 mmol) in DMF (50 mL) was cooled to 0° C. and sodium bis(trimethylsilyl)amide (1.0 M in THF, 53 mL, 53 mmol) was slowly added. The reaction was stirred for 15 minutes and 1,4-dibromobutane (5.6 mL, 48.4 mmol) was added. The reaction was warmed to room temperature and was stirred for 24 h. Et$_2$O was added, and the organic solution was washed consecutively with HCl (1N, 3×), water (3×), and brine (1×). The organic solution was dried (Na$_2$SO$_4$), filtered, and concentrated. Attempted vacuum distillation removed a majority of the impurities and provided a mixture of product and 1,4-dibromobutane (3.539 g). Flash chromatography (9:1 hexanes:EtOAc) of this material provided (4-bromo-butoxy)-acetic Acid ethyl ester (1.862 g). $^1$H NMR (400 MHz, CDCl$_3$) δ 4.19 (q, 2H), 4.04 (s, 2H), 3.54 (t, 2H), 3.45 (t, 2H), 1.97 (m, 2H), 1.75 (m, 2H), 1.26 (t, 3H); MS 239.1 (M+).

Step B: Alkylation

To a mixture of NaH (60% in oil, 167 mg, 4.18 mmol) and DMF (10 mL) was added a solution of methanesulfonamide (398 mg, 4.18 mmol) in DMF (5 mL). The mixture was heated at 100° C. for 1.5 h and was cooled to room temperature. A solution of (4-bromo-butoxy)-acetic Acid ethyl ester (1.000 g, 4.182 mmol) in DMF (10 mL) was added and the reaction was heated at 100° C. for 21 h. Water was added to the cooled reaction mixture and the aqueous solution was acidified to pH=2 with concentrated HCl. The aqueous solution was extracted with EtOAc (4×) and the organic solution was dried (MgSO$_4$), filtered, and concentrated. The product was purified by flash chromatography (60% EtOAc/hexanes) to afford the title compound (181 mg). $^1$H NMR (400 MHz, CDCl$_3$) δ 4.90 (m, 1H), 4.20 (q, 2H), 4.04 (s, 2H), 3.54 (m, 2H), 3.16 (m, 2H), 2.93 (s, 2H), 1.69 (m, 4H), 1.26 (t, 3H); MS 254.1 (M+1).

PREPARATION L1

1-(2-Bromo-ethoxy)-3,5-dichloro-benzene

To a solution of NaOH (2.45 g, 61.3 mmol) in water (20 mL) was added 3,5-dichlorophenol (5 g, 30.7 mmol). The solution was heated at reflux for 1 h and was cooled to room temperature. Dibromoethane (11.52 g, 61.3 mmol) was added and the reaction was heated at reflux for 24 h. The cooled solution was diluted with EtOAc and the organic solution was washed sequentially with HCl (1N, 1×), water (1×), and brine (1×). The organic solution was dried (MgSO$_4$), filtered, and concentrated. Purification by flash chromatography (hexanes to 5% EtOAc in hexanes ) provided the title compound (3.79 g). $^1$H NMR (400 MHz, CDCl$_3$) δ 6.98 (m, 1H), 6.82 (m, 2H), 4.25 (t, 2H), 3.61 (t, 2H).

In an analogous manner, the following compounds were prepared from the appropriate starting materials using the above general procedure of Preparation L1.

PREPARATION L2

1-(2-Bromo-ethoxy)-3,5-dimethyl-benzene

PREPARATION L3

1-(2-Bromo-ethoxy)-3,5-dimethoxy-benzene

PREPARATION M1

4-(1-Hydroxy-hexyl)-benzaldehyde

A solution of 4-diethoxymethyl-benzaldehyde (0.300 mL, 1.51 mmol) in THF (3 mL) was cooled to 0° C. Pentylmagnesium bromide (3.0 mL, 2.0 M in THF, 6 mmol) was added dropwise. The reaction was stirred at 0° C. for 1 h and was warmed to room temperature. Aqueous NH$_4$Cl (satd) was added and the aqueous solution was extracted with EtOAc. The organic solution was washed with brine, dried (MgSO$_4$), filtered, and concentrated. The residue was dissolved in 10% aqueous acetone (50 mL) and wet Amberlyst-15 resin (1.5 g) was added. The mixture was stirred for 24 h and the resin was filtered off through Celite. The solution was concentrated in vacuo. Purification via flash chromatography (4:1 hexanes:EtOAc) provided the title compound (1.15 g). $^1$H NMR (400 MHz, CDCl$_3$) δ 9.99 (s, 1H), 7.86 (d, 2H), 7.51 (d, 2H), 4.77 (m, 1H), 1.89 (m, 1H), 1.74 (m, 2H), 1.48–1.28 (m, 6H), 0.87 (m, 3H).

PREPARATION N1

1-(3-Bromo-propyl)-3-chloro-benzene

Step A: Reduction 3-(3-Chloro-phenyl)-propan-1-ol.

A slurry of lithium aluminum hydride (2.08 g, 54.7 mmol) in THF (100 mL) was cooled to −78° C. A solution of 3-chlorocinnamic acid (5.00 g, 27.4 mmol) in THF (25 mL)

was added dropwise. The cold bath was removed and the mixture was warmed to room temperature. After 6 h, the reaction was quenched by addition of sodium sulfate decahydrate and the mixture was stirred overnight. The solids were removed by filtration with the aid of EtOAc and the organic solution was washed with brine, dried over $MgSO_4$, filtered, and concentrated in vacuo to yield 3-(3-chloro-phenyl)-propan-1-ol (5.17 g) as an oil. $^1H$ NMR (400 MHz, $CDCl_3$) δ 7.30–7.07 (m, 4H), 5.06 (bs, 1H), 3.67 (m, 2H), 2.69 (m, 2H), 1.89 (m, 2H).

Step B: Bromination

A solution of 3-(3-chloro-phenyl)-propan-1-ol (12.54 g, 73.6 mmol) and N,N'-carbonyl diimidazole (13.12 g, 81 mmol) in $CH_3CN$ was stirred at room temperature for 1 h. Allyl bromide (53.43 g, 442 mmol) was added and the reaction was heated at reflux for 24 h. The reaction was cooled to room temperature and brine and EtOAc were added. The aqueous solution was extracted with EtOAc and the organic solution was dried ($MgSO_4$), filtered, and concentrated. Flash chromatography provided the title compound in about 85% yield. $^1H$ NMR (400 MHz, $CDCl_3$) δ 7.30-7.09 (m, 4H), 3.38 (t, 2H), 2.76 (t, 2H), 2.15 (t, 2H).

PREPARATION O1

2-Indanyl-ethyl Bromide

Step A: Reduction

2-Indanylethanol.

Lithium aluminum hydride (1M in $Et_2O$, 14 mL, 14 mmol) was slowly added to a solution of 2-indanylacetic Acid (2.5 g, 14 mmol) in $Et_2O$. The reaction mixture was heated at reflux for 2 h and was cooled to room temperature. Water and EtOAc were added and the organic solution was washed with water (2×) and brine (1×), dried over $MgSO_4$, filtered, and concentrated to afford 2-indanylethanol (2.1 g) which was used in the next step without further purification. $^1H$ NMR (400 MHz, $CDCl_3$) δ 7.08–7.24 (m, 4H), 3.75 (t, 2H), 3.07 (m, 2H), 2.61 (m, 3H), 1.80 (m, 2H); MS 180 (M+18).

Step B: Bromination 2-indanyl-ethyl Bromide.

N,N-Carbonyl diimidazole (2.0 g, 12.3 mmol) was added to a solution of 2-indanylethanol (2.0 g, 12.3 mmol) in acetonitrile. The reaction mixture was stirred at room temperature for 1 h and allyl bromide (8.93 g, 73.8 mmol) was added. The reaction mixture was heated to 70° C. for 24 h and was poured onto water. The aqueous solution was extracted with $Et_2O$ and the organic solution was washed with water (1×) followed by brine (1×). The organic solution was dried over $MgSO_4$, filtered, and concentrated to afford the title compound (2.54 g). $^1H$ NMR (400 MHz, $CDCl_3$) δ 7.10–7.25 (m, 4H), 3.48 (t, 2H), 3.11 (m, 2H), 2.63 (m, 3H), 2.07 (m, 2H).

PREPARATION P1

Trans-3-[(3.5-Dichloro-phenyl)-allyl]-methanesulfonamide

A mixture of methanesulfonamide (3.27 g, 34.4 mmol), trans-(3,5-dichlorophenyl)-allyl bromide (1.83 g, 6.88 mmol), $K_2CO_3$ (0.95 g, 6.88 mmol) and $CH_3CN$ was heated to 55° C. for 24 h. The reaction mixture was poured onto EtOAc and 1N HCl. The organic solution was washed several times with 1N HCl, dried over $MgSO_4$, filtered, and concentrated. The product was purified by flash chromatography (30% EtOAc/hexanes to 40% EtOAc/hexanes) to afford the title compound (1.40 g). $^1H$ NMR (400 MHz, $CDCl_3$) δ 7.24 (m, 3H), 6.50 (d, 1H), 6.25 (m, 1H), 4.45 (m, 1H), 3.94 (m, 2H), 3.00 (s, 3H).

PREPARATION Q1

(4-Methanesulfonylamino-phenyl)-butyric Acid Ethyl Ester

Step A: Esterification 4-(4-Amino-phenyl)-butyric Acid Ethyl Ester.

Catalytic sulfuric Acid was added to a solution of 4-(4-aminophenyl) butyric Acid (6.0 g, 33.48 mmol) in EtOH. The reaction mixture was stirred at room temperature for 24 h. HCl (5 mL, 6N) was added and the reaction mixture was heated at reflux for 24 h. The reaction mixture was concentrated in vacuo and $CH_2Cl_2$ and water were added. The pH was adjusted to 7.0 with aqueous $NaHCO_3$ (satd). The organic solution was washed with water (1×) and brine (1×), dried over $MgSO_4$, filtered, and concentrated to afford 4-(4-aminophenyl)-butyric Acid ethyl ester (1.53 g). H NMR (400 MHz, $CDCl_3$) δ 6.95 (d, 2H), 6.61 (d, 2H), 4.10 (q, 2H), 3.66 (bs, 2H), 2.53 (t, 2H), 2.29 (t, 2H), 1.88 (m, 2H), 1.24 (t, 3H).

Step B: Sulfonamide Formation

Pyridine (0.87 mL, 10.9 mmol) was added to a solution of 4-(4-amino-phenyl)-butyric Acid ethyl ester (1.50 g, 7.25 mmol) in $CH_2Cl_2$. The reaction mixture was cooled to 0° C. and methanesulfonyl chloride (913 mg, 7.97 mmol) was added. The reaction was stirred at 0° C. for 1 h and at room temperature for 2 h. The mixture was poured into water and $CH_2Cl_2$ was added. The pH was adjusted to 1.0 using 1N HCl. The organic solution was washed water (1×) and brine (1×), dried over $MgSO_4$, filtered, and concentrated in vacuo. The product crystallized on standing to afford the title compound (2.03 g). $^1H$ NMR (400 MHz, $CDCl_3$) δ 7.09–7.32 (m, 4H), 4.12 (q, 2H), 2.97 (s, 3H), 2.60 (t, 2H), 2.30 (t, 2H), 1.91 (m, 2H), 1.24 (t, 3H).

PREPARATION R1

[2-(2-Methanesulfonylamino-ethyl)-phenoxy]-acetic Acid Ethyl Ester

Step A: Sulfonamide Formation

N-[2-(2-Methoxy-phenyl)-ethyl]-methanesulfonamide.

Pyridine (12.0 mL, 150 mmol) was added to a solution of 2-methoxyphenethylamine (15.1 g, 100 mmol) in $CH_2Cl_2$ (100 mL). The reaction was cooled to 0° C. and methanesulfonyl chloride (12.6 g, 110 mmol) was added. The reaction was stirred at 0° C. for 0.5 h and at room temperature for 2 h. Water was added and the aqueous layer was extracted with $CH_2Cl_2$ (2×). The organic solution was washed water (1×) and brine (1×), dried over $MgSO_4$, filtered and concentrated to afford N-[2-(2-methoxy-phenyl)-ethyl]-methanesulfonamide (18.5 g).

Step B: Demethylation

N-[2-(2-Hydroxy-phenyl)-ethyl]-methanesulfonamide.

Boron tribromide (1.0 M in $CH_2Cl_2$, 80.8 mL, 80.8 mmol) was added to a solution of N-[2-(2-methoxy-phenyl)-ethyl]- methanesulfonamide (18.5 g, 80.8 mmol) in $CH_2Cl_2$ (200 mL). The reaction was stirred at room temperature for 2 h and was poured onto water (200 mL). The aqueous layer was extracted with $CH_2Cl_2$ (2×) and the organic solution was washed with water (1×) and aqueous $NaHCO_3$ (satd, 1×). The organic solution was dried over $MgSO_4$, filtered, and concentrated to afford N-[2-(2-hydroxy-phenyl)-ethyl]-methanesulfonamide (16.8 9). $^1H$ NMR (400 MHz, $CDCl_3$) δ 7.11 (m, 2H), 6.86 (m, 1H), 6.80 (m, 1H), 4.79 (m, 1H), 3.39 (t, 2H), 2.88 (t, 2H), 2.77 (s, 3H).

Step C: Alkylation

A mixture of N-[2-(2-hydroxy-phenyl)-ethyl]-methanesulfonamide (4.3 g, 20 mmol), NaI (1.2 g, 8.0 mmol), $K_2CO_3$ (6.07 g, 44 mmol), ethyl bromoacetate (3.34 g, 20 mmol), and DMF (70 mL) was stirred at room temperature for 24 h. The reaction was poured into water and the aqueous solution was extracted with $CH_2Cl_2$. The organic solution was washed with water (1×) followed by brine (1×). The organic solution was dried ($MgSO_4$), filtered, and concentrated. Flash chromatography (hexanes to 7:3 hexanes:EtOAc) provided the title compound (800 mg). $^1H$ NMR (400 MHz, $CDCl_3$) δ 7.18 (m, 2H), 6.93 (t, 1H), 6.71 (d, 1H), 4.97 (m, 1H), 4.65 (s, 2H), 4.24 (q, 2H), 3.42 (m, 2H), 2.94 (t, 2H), 2.75 (s, 3H), 1.27 (t, 3H); MS 319 (M+18).

PREPARATION S1

1-(3,5-Dichlorophenyl)-propyl Bromide

Step A 3-(3,5-Dichlorophenyl)-acrylic acid.

A mixture of 3,5-dichlorobenzaldehyde (15.0 g, 85.7 mmol), malonic Acid (12.5 g, 120.2 mmol), and piperidine (5 mL) was heated at 100° C. for 2 h and at 150° C. for 1 h. The reaction was poured onto 3N HCl (200 mL) and the precipitate was removed via filtration. The product was purified by recrystallization (100 mL hot EtOH) to afford 3-(3,5-dichlorophenyl)-acrylic Acid (11.5 g). $^1H$ NMR (250 MHz, DMSO-$d_6$) δ 12.6 (bs, 1H), 7.83 (m, 2H), 7.64–7.51 (m, 2H), 6,72 (d, 1H).

Step B: Hydrogenation 3-(3,5-Dichlorophenyl)-propionic acid.

To a solution of 10% Pd/C (1.5 g) in THF (200 mL) was added 3-(3,5-dichlorophenyl)-acrylic Acid (11.5 g). The reaction was hydrogenated on a Parr shaker at 50 psi for 3 h. The catalyst was removed by filtration through celite and the organic solution was concentrated in vacuo to afford 3-(3,5-dichlorophenyl)-propionic Acid (11.3 g). $^1H$ NMR (400 MHz, $CDCl_3$) δ 7.00–7.35 (m, 3H), 2.89 (t, 2H), 2.66 (t, 2H).

Step C: Reduction 3-(3,5-Dichlorophenyl)-propanol.

$LiAlH_4$ (1M in $Et_2O$, 10 mL, 10 mmol) was slowly added to a solution of 3-(3,5-dichlorophenyl)-propionic Acid (2.19 g, 10 mmol) in $Et_2O$ (50 mL). The reaction was heated at reflux for 2 h. The reaction was cooled to room temperature and 2N NaOH (1 mL) and aqueous $NH_4Cl$ (satd., 3 mL) as carefully added. The solution was filtered through Celite and the filtrate was dried over $MgSO_4$, filtered, and concentrated. The product was purified by flash chromatography (25% EtOAc/hexanes) to afford 3-(3,5-dichlorophenyl)-propanol (640 mg). $^1H$ NMR (400 MHz, $CDCl_3$) δ 7.17 (m, 1H), 7.07 (m, 2H), 3.64 (m, 2H), 2.65 (t, 2H), 1.84 (m, 2H).

Step D: Bromination

Triphenylphosphine (315 mg, 1.20 mmol) was added to a solution of 3-(3,5-dichlorophenyl)-propanol (200 mg, 0.98 mmol) in $CH_2Cl_2$ (20 mL). The reaction mixture was cooled to 0° C. and bromine (207 mg, 1.30 mmol) was added dropwise. The reaction was stirred at 0° C. for 1 h and was warmed to room temperature. The reaction was poured into water and the aqueous solution was extracted with $CH_2Cl_2$. The organic solution was washed with brine, dried over $MgSO_4$, filtered, and concentrated in vacuo. The product was purified by flash chromatography (hexanes) to afford the title compound (134 mg). $^1H$ NMR (400 MHz, $CDCl_3$) δ 7.21 (m, 1H), 7.08 (m, 2H), 3.37 (t, 2H), 2.74 (t, 2H), 2.13 (m, 2H).

PREPARATION T1

4-(2-Methanesulfonylamino-ethoxy)-benzoic Acid Methyl Ester

Step A: Deprotection 4-(2-Amino-ethoxy)-benzoic Acid Methyl Ester Hydrochloride Salt.

To a solution of 4-[2-(2,2-dimethyl-propionylamino)-ethoxy]-benzoic Acid methyl ester (350 mg) in EtOH (6 mL) at 0° C. was added concentrated HCl (3 mL). The solution was warmed to room temperature and was concentrated in vacuo to provide the hydrochloride salt of 4-(2-amino-ethoxy)-benzoic Acid methyl ester (266 mg) as a white solid which was used in the next step without further purification.

Step B: Sulfonamide Formation

Methanesulfonyl chloride (144 mg, 1.27 mmol) was added to a solution of 4-(2-amino-ethoxy)-benzoic Acid methyl ester (266 mg, 1.15 mmol) and pyridine (255 mg, 2.52 mmol) in $CH_2Cl_2$ (10 mL) at 0° C. The solution was warmed to room temperature and was stirred for 24 h. EtOAc was added and the organic solution was washed with HCl (1N, 2×) followed by brine. The organic solution was dried ($Na_2SO_4$), filtered, and concentrated to yield the title compound as a white solid (240 mg). $^1H$ NMR (400 MHz, $CDCl_3$) δ 7.99 (dd, 2H), 6.90 (dd, 2H), 4.77 (m, 1H), 4.15 (t, 2H), 3.88 (s, 3H), 3.58 (m, 2H), 3.02 (s, 3H); MS 274 (M+1).

PREPARATION U1

7-(4-Butyl-phenylamino)-heptanoic Acid Methyl Ester

Following the procedure described in Step A of Example 68, reductive amination of 4-butyl-benzaldehyde (1.50 g, 9.26 mmol) with 7-aminoheptanoic methyl ester hydrochloride (1.51 g, 7.72 mmol) provided the title compound (955 mg). 1H NMR (300 MHz, $CDCl_3$) δ 7.29 (d, 2H), 7.16 (d, 2H), 3.85 (s, 2H), 3.67 (s, 3H), 3.54 (m, 1H), 2.70 (t, 2H), 2.59 (t, 2H), 2.29 (t, 2H), 1.60 (m, 6H), 1.32 (m, 6H), 0.92 (t, 3H); MS 306 (M+1).

PREPARATION V1

[3-(Methanesulfonylamino-methyl)-phenoxy]-acetic acid

Step A: Sulfonamide Formation

N-(3-Methoxy-benzyl)-methanesulfonamide.

Methanesulfonyl chloride (4.170 g, 36.4 mmol) was added to a solution of 3-methoxybenzylamine (5.000 g, 36.4 mmol) and triethylamine (3.946 g, 39.0 mmol) in THF (100 mL) at room temperature. The mixture was stirred for 18 h and the insolubles were removed by filtration. The organic solution was concentrated to a yellow oil which was purified by flash chromatography (6:4 hexanes:EtOAc to 1:1 hexanes:EtOAc) to yield N-(3-methoxybenzyl)-methanesulfonamide (7.431 g). $^1$H NMR (400 MHz, CDCl$_3$) δ 7.26 (m, 1H), 6.92–6.82 (m, 3H), 4.62 (m, 1H), 4.28 (d, 2H), 3.80 (s, 3H), 2.87 (s, 3H); MS 214 (M-1).

Step B: Demethylation

N-(3-Hydroxy-benzyl)-methanesulfonamide.

A solution of BBr$_3$ (1.0 M in CH$_2$Cl$_2$, 111 mL, 111 mmol) was slowly added to a solution of N-(3-methoxy-benzyl)-methanesulfonamide (12.000 g, 55.7 mmol) in CH$_2$Cl$_2$ (200 mL) at 0° C. The reaction was warmed to room temperature and was stirred for 4 h. Methanol (100 mL) was cautiously added and the solution was concentrated in vacuo. Flash chromatography (1:1 hexanes:EtOAc) provided N-(3-hydroxy-benzyl)-methanesulfonamide (11.50 g). $^1$H NMR (400 MHz, CDCl$_3$) δ 7.20 (m, 1H), 6.84 (m, 2H), 6.77 (m, 1H), 4.83 (bs, 1H), 4.24 (s, 2H), 2.86 (s, 3H); MS 201 (M+).

Step C: Alkylation

A mixture of N-(3-hydroxy-benzyl)-methanesulfonamide (6.000 g, 29.82 mmol), methyl bromoacetate (4.562 g, 29.82 mmol), K$_2$CO$_3$ (4.121 g, 29.82 mmol), and acetone (250 mL) was stirred at room temperature for 68 h. The solids were removed by filtration and the solution was concentrated in vacuo. Purification by flash chromatography (1:1 hexanes:EtOAc) provided the title compound (5.637 g). $^1$H NMR (400 MHz, CDCl$_3$) δ 7.25 (m, 1H), 6.96 (m, 1H), 6.89 (s, 1H), 6.82 (m, 1H), 4.63 (m, 3H), 4.28 (m, 2H), 3.80 (s, 3H), 2.86 (s, 3H); MS 274 (M+1).

It should be understood that the invention is not limited to the particular embodiments described herein, but that various changes and modifications may be made without departing from the spirit and scope of this novel concept as defined by the following claims.

PREPARATION W1

[3-(Methanesulfonylamino-methyl)-phenyl]-acetic Acid Ethyl Ester

Step A: Ester Formation (3-Bromo-phenyl)-acetic Acid Ethyl Ester.

To a solution of 3-bromophenylacetic Acid (10.0 g, 46.5 mmol) in CH$_3$CN (150 mL) was added K$_2$CO3 (7.39 g, 53.5 mmol) followed by ethyl iodide (5.6 mL, 70.0 mmol). The mixture was heated at reflux for 2.5 h and was cooled to room temperature. The volatiles were removed in vacuo and water was added. The aqueous solution was extracted with EtOAc (3×) and the combined organic extracts were washed with brine. The organic solution was dried (MgSO$_4$), filtered, and concentrated to provide (3-bromo-phenyl)-acetic Acid ethyl ester (9.30 g) as an oil. $^1$H NMR (400 MHz, CDCl$_3$) δ 7.43 (s, 1H), 7.38 (m, 1H), 7.21–7.16 (m, 2H), 4.14 (q, 2H), 3.56 (s, 2H), 1.24 (t, 3H).

Step B: Nitrile Formation (3-Cyano-phenyl)-acetic Acid Ethyl Ester.

A mixture of (3-bromo-phenyl)-acetic Acid ethyl ester (9.15 g, 37.6 mmol), copper cyanide (5.06 g, 56.5 mmol), and 1-methyl-2-pyrrolidinone (80 mL) was placed into an oil bath heated at 120° C. behind a protective shield. The reaction was heated to 200° C. for 1 h and additional copper cyanide (spatula tip) was added. After heating for an additional 0.5 h, the reaction was cooled to room temperature. The reaction was diluted with EtOAc and the organic solution was washed with water/ammonium hydroxide solution (2:1 v/v) until the aqueous solution was no longer blue. The organic solution was washed with brine, dried (MgSO$_4$), filtered, and concentrated. Flash chromatography (9:1 hexanes:EtOAc) provided (3-cyano-phenyl)-acetic Acid ethyl ester (6.31 g) as a clear oil which solidified on standing. $^1$H NMR (400 MHz, CDCl$_3$) δ 7.57–7.50 (m, 3H), 7.42 (m, 1H), 4.15 (q, 2H), 3.63 (s, 2H), 1.24 (t, 3H).

Step C: Nitrile Reduction (3-Aminomethyl-phenyl)-acetic Acid Ethyl Ester Hydrochloride.

A solution of (3-cyano-phenyl)-acetic Acid ethyl ester (6.3 g, 33.29 mmol) in EtOH (50 mL) was added to a mixture of 10% Pd/C (1.26 g) in EtOH (50 mL) under Nitrogen. Additional EtOH (150 mL) was added followed by a solution of HCl in dioxane (4 M, 11.4 mL, 45.6 mmol). The mixture was hydrogenated on a Parr shaker at 45 psi for 20 h and the catalyst was removed by filtration through celite. The solution was concentrated to afford (3-aminomethyl-phenyl)-acetic Acid ethyl ester as the hydrochloride salt (7.31 g). $^1$H NMR (400 MHz, CD$_3$OD) δ 7.42–7.32 (m, 4H), 4.12 (q, 2H), 4.09 (s, 2H), 3.68 (s, 2H), 1.23 (t, 3H).

Step D: Sulfonamide Formation

[3-(Methanesulfonylamino-methyl)-phenyl]-acetic Acid Ethyl Ester.

Methanesulfonyl chloride (2.6 mL, 34 mmol) was slowly added to a solution of (3-aminomethyl-phenyl)-acetic Acid ethyl ester hydrochloride (7.31 g, 34 mmol) and triethylamine (9.8 mL, 70 mmol) in CH$_2$Cl$_2$ (100 mL) at 0° C. The mixture was stirred for 1 h and 1N aqueous HCl solution was added. The aqueous solution was extracted with CH$_2$Cl$_2$ (3×) and the combined organic extracts were washed with brine. The organic solution was dried over MgSO$_4$, filtered, and concentrated. Purification by flash chromatography (1:1 hexanes:EtOAc) provided the title sulfonamide (8.56 g) as a clear and colorless oil. $^1$H NMR (400 MHz, CDCl$_3$) δ 7.34–7.21 (m, 4H), 4.70 (broad, 1H), 4.29 (d, 2H), 4.12 (q, 2H), 3.60 (s, 2H), 2.86 (s, 3H), 1.24 (t, 3H).

ADDITIONAL GENERAL EXPERIMENTAL PROCEDURES

Medium pressure chromatography was performed on a Flash 40 Biotage System (Biotage Inc., Dyax Corp., Charlottesville, Va.).

EXAMPLES 75–110

Examples 75–110 were prepared in an analogous manner to Example 1 starting with the appropriate alkylating agents and sulfonamides in the alkylation Step A followed by ester hydrolysis in Step B with variations in reaction temperature and time in Step A as noted.

EXAMPLE 75

5-{3-[(6-Chloro-quinolin-2-ylmethyl)-methanesulfonyl-amino]-propyl}-thiophene-2-carboxylic acid Step A: Reaction time of 2 h at room temperature and 24 h at 75° C. $^1$H NMR (400 MHz, CDCl$_3$) δ 8.01 (d, 1H), 7.80

(d, 1H), 7.70 (s, 1H), 7.52–7.54 (m, 2H), 7.35 (d, 1H), 6.50 (d, 1H), 4.54 (s, 2H), 4.02 (bs, 1H), 3.19–3.24 (m, 2H), 2.89 (s, 2H), 2.62 (t, 2H), 1.72 (t, 2H); MS 453 (M+14).

EXAMPLE 76

5-(3-{[2-(3,5-Bis-trifluoromethyl-phenoxy)-ethyl]-methanesulfonyl-amino}-propyl)-thiophene-2-carboxylic acid Step A: Reaction time of 24 h at room temperature. $^1$H NMR (400 MHz, CDCl$_3$) δ 7.69 (d, 1H), 7.48 (s, 1H), 7.25 (s, 2H), 6.84 (d, 1H), 4.22 (t, 2H), 3.63 (t, 2H), 3.36 (t, 2H), 2.91–2.96 (m, 5H), 2.10 (t, 2H); MS 519 (M+1).

EXAMPLE 77

5-(3-{Methanesulfonyl-[2-(3-methoxy-phenoxy)-ethyl]-amino}-propyl)-thiophene-2-carboxylic acid Step A: Reaction time of 30 min at room temperature. $^1$H NMR (400 MHz, CDCl$_3$) δ 7.70 (d, 1H), 7.15–7.19 (m, 1H), 6.84 (d, 1H), 6.51–6.54 (m, 1H), 6.39–6.47 (m, 2H), 4.10 (t, 2H), 3.77 (s, 3H), 3.62 (t, 2H), 3.35 (t, 2H), 2.91–2.97 (m, 5H), 2.07 (t, 2H); MS 412 (M–1).

EXAMPLE 78

7-{[3-(3-Chloro-5-methoxy-phenoxy)-propyl]-methanesulfonyl-amino}-heptanoic acid Step A: Reaction time of 24 h at room temperature. $^1$H NMR (400 MHz, CDCl$_3$) δ 6.48–6.51 (m, 2H), 6.32 (s, 1H), 3.97 (t, 2H), 3.76 (s, 3H), 3.33 (t, 2H), 3.16 (t, 2H), 2.82 (s, 3H), 2.33 (t, 2H), 2.07 (t, 2H), 1.60–1.61 (m, 4H), 1.31–1.33 (m, 4H); MS 420 (M–1).

EXAMPLE 79

5-(3-{[3-(3-Chloro-5-methoxy-phenoxy)-propyl]-methanesulfonyl-amino}-propyl)-thiophene-2-carboxylic acid Step A: Reaction time of 24 h at room temperature. $^1$H NMR (400 MHz, CDCl$_3$) δ 7.69 (d, 1H), 6.81 (d, 1H), 6.47–6.50 (m, 2H), 6.30–6.31 (m, 1H), 3.97 (t, 2H), 3.75 (s, 3H), 3.36 (t, 2H), 3.24 (t, 2H), 2.90 (t, 2H), 2.83 (s, 2H), 1.98–2.11 (m, 4H); MS 460 (M–1).

EXAMPLE 80

5-(3-[3-(3,5-Dichloro-phenoxy)-propyl]-methanesulfonyl-amino}-propyl)-thiophene-2-carboxylic acid Step A: Reaction time of 24 h at room temperature. $^1$H NMR (400 MHz, CDCl$_3$) δ 7.69 (d, 1H), 6.94 (t, 1H), 6.82 (d, 1H), 6.76 (s, 2H), 3.99 (t, 2H), 3.35 (t, 2H), 3.24 (t, 2H), 2.90 (t, 2H), 2.84 (s, 3H), 1.98–2.12 (m, 4H); MS 466 (M–1).

EXAMPLE 81

5-(3-[2-(3-Ethyl-phenoxy)-ethyl]-methanesulfonyl-amino}-propyl)-thiophene-2-carboxylic acid Step A: Reaction time of 24 h at room temperature. $^1$H NMR (400 MHz, CDCl$_3$) δ 7.70 (d, 1H), 7.19 (t, 1H), 6.81–6.85 (m, 2H), 6.65–6.68 (m, 2H), 4.11 (t, 2H), 3.64 (t, 2H), 3.36 (t, 2H), 2.91–2.95 (m, 2H), 2.92 (s, 3H), 2.60 (q, 2H), 2.06–2.12 (m, 2H), 1.19–1.25 (m, 3H); MS 410 (M$^+$–1).

EXAMPLE 82

5-(3-{[2-(3-Isopropyl-phenoxy)-ethyl]-methanesulfonyl-amino}-propyl)-thiophene-2-carboxylic acid Step A: Reaction time of 24 h at room temperature. $^1$H NMR (400 MHz, CDCl$_3$) δ 7.70 (d, 1H), 7.20 (t, 1H), 6.84–6.86 (m, 2H), 6.65–6.71 (m, 2H), 4.11 (t, 2H), 3.64 (t, 2H), 3.37 (t, 2H), 2.92–2.95 (m, 2H), 2.92 (s, 3H), 2.82–2.89 (m, 1H), 2.08 (t, 2H), 1.22 (d, 6H); MS 424 (M$^+$–1).

EXAMPLE 83

5-(3-[Methanesulfonyl-[2-(3-trifluoromethyl-phenoxy)-ethyl]-amino}-propyl)-hiophene-2-carboxylic acid Step A: Reaction time of 24 h at room temperature. $^1$H NMR (400 MHz, CDCl$_3$) δ 7.68 (d, 1H), 7.37 (t, 1H), 7.21–7.23 (m, 1H), 7.05 (s, 1H), 7.00 (d, 1H), 6.82 (d, 1H), 4.14 (t, 2H), 3.62 (t, 2H), 3.34 (t, 2H), 2.92 (t, 2H), 2.90 (s, 3H), 2.07 (t, 2H); MS 450 (M$^+$–1).

EXAMPLE 84

2-(3-{[2-(3,5-Dichloro-phenoxy)-ethyl]-methanesulfonyl-amino}-propyl)-thiazole4-carboxylic acid Step A: Reaction time of 5 h at 100° C. $^1$H NMR (400 MHz, CDCl$_3$) δ 8.20 (s, 1H), 6.98 (s, 1H), 6.89 (s, 2H), 4.16 (t, 2H), 3.62 (t, 2H), 3.37 (t, 2H), 3.08 (t, 2H), 2.93 (s, 3H), 2.15 (t, 2H); MS 452 (M$^+$–1).

EXAMPLE 85

5-{3-[Methanesulfonyl-(3-phenyl-propyl)-amino]-propyl}-thiophene-2-carboxylic acid Step A: Reaction time of 5 h at 100° C. $^1$H NMR (400 MHz, CDCl$_3$) δ 7.57 (d, 1H), 7.22–7.26 (m, 2H), 7.12–7.18 (m, 3H), 6.86 (d, 1H), 3.16–3.22 (m, 4H), 2.87 (t, 2H), 2.83 (s, 3H), 2.61 (t, 2H), 1.84–1.97 (m, 4H); MS 380 (M$^+$–1).

EXAMPLE 86

7-{[3-(3,5-Dichloro-phenoxy)-propyl]-methanesulfonyl-amino}-heptanoic acid

Step A: Reaction time of 24 h at room temperature. $^1$H NMR (400 MHz, CDCl$_3$) δ 7.70 (d, 1H), 7.19–7.23 (m, 1H), 6.84 (d, 1H), 6.61–6.70 (m, 2H), 6.56 (d, 1H), 4.10 (t, 2H), 3.62 (t, 2H), 3.34 (t, 2H), 2.90 (s, 3H), 2.86–2.95 (m, 2H), 2.07 (t, 2H); MS 401 (M$^+$–1).

EXAMPLE 87

5-(3-{Methanesulfonyl-[2-(3-fluoro-phenoxy)-ethyl]-amino}-propyl)-thiophene-2-carboxylic acid Step A: Reaction time of 24 h at room temperature. $^1$H NMR (400 MHz, CDCl$_3$) δ 7.70 (d, 1H), 7.19–7.23 (m, 1H), 6.84 (d, 1H), 6.61–6.70 (m, 2H), 6.56 (d, 1H), 4.10 (t, 2H), 3.62 (t, 2H), 3.34 (t, 2H), 2.90 (s, 3H), 2.86–2.95 (m, 2H), 2.07 (t, 2H); MS 400 (M$^+$–1).

EXAMPLE 88

5-(3-{Methanesulfonyl-[3-(3-methoxy-phenyl)-propyl]-amino}-propyl)-thiophene-2-carboxylic acid Step A: Reaction time of 2 h at room temperature. $^1$H NMR (400 MHz, CDCl$_3$) δ 7.71 (d, 1H), 7.20 (t, 1H), 6.83 (d, 1H), 6.71–6.78 (m, 3H), 3.78 (s, 3H), 3.17–3.22 (m, 4H), 2.89 (t, 2H), 2.81 (s, 3H), 2.61 (t, 2H), 1.88–2.01 (m, 4H); MS 411 (M+).

EXAMPLE 89

5-[3-(Benzofuran-2-ylmethyl-methanesulfonyl-amino)-propyl]-thiophene-2-carboxylic acid Step A: Reaction time of 2 h at room temperature. $^1$H NMR (400 MHz, CDCl$_3$) δ7 7.68 (d, 1H), 7.54 (d, 1H), 7.42 (d, 1H), 7.22–7.32 (m, 2H), 6.82 (d, 1H), 6.68 (s, 1H), 4.58 (s, 2H, 3.32 (t, 2H), 2.92 (t, 2H), 2.86 (s, 3H), 2.01–2.08 (m, 2H); MS 393 (M+).

EXAMPLE 90

5-(3-{[2-(3-Chloro-5-methoxy-phenoxy)-ethyl]-methanesulfonyl-amino}-propyl)-thiophene-2-carboxylic acid Step A: Reaction time of 24 h at room temperature. $^1$H NMR (400 MHz, CDCl$_3$) δ 7.71 (d, 1H), 6.84 (d, 1H), 6.53 (s, 1H), 6.44 (s, 1H), 6.28 (s, 1H), 4.08 (t, 2H), 3.75 (s, 3H), 3.60 (t, 2H), 3.34 (t, 2H), 2.90–2.95 (m, 3H), 2.07 (t, 2H); MS 448 (M+).

EXAMPLE 91

5-(3-{[2-(3-Ethoxy-phenoxy)-ethyl]-methanesulfonyl-amino}-propyl)-thiophene-2-carboxylic acid Step A: Reaction time of 24 h at room temperature. $^1$H NMR (400 MHz, CDCl$_3$) δ 7.69 (d, 1H), 7.16 (t, 1H), 6.83 (d, 1H), 6.50–6.53 (m, 1H), 6.39–6.44 (m, 1H), 4.10 (t, 2H), 3.98 (q, 2H), 3.62 (t, 2H), 3.35 (t, 2H), 2.86–2.94 (m, 5H), 2.04–2.11 (m, 2H), 1.39 (t, 3H); MS 428 (M+).

EXAMPLE 92

(4-{[2-(3,5-Dichloro-phenoxy)-ethyl]-methanesulfonyl-amino}-butoxy)-acetic acid

Step A: Reaction time of 2 h at room temperature. $^1$H NMR (400 MHz, CDCl$_3$) δ 6.96 (s, 1H), 6.77 (s, 2H), 4.10 (s, 4H), 3.56–3.60 (m, 4H), 3.30 (t, 2H), 2.89 (s, 3H), 1.73-1.80 (m, 2H), 1.63–1.69 (m, 2H); MS 415 (M+1).

EXAMPLE 93

(3-{[(4-Butoxy-benzyl)-methanesulfonyl-amino]-methyl}-phenyl)-acetic acid

Step A: Reaction time of 2 h at room temperature and 3 h at 70° C. $^1$H NMR (400 MHz, CDCl$_3$) δ 7.28–7.33 (m, 1H), 7.17–7.25 (m, 5H), 6.85 (d, 2H), 4.29 (s, 2H), 4.24 (s, 2H), 3.94 (t, 2H), 3.64 (s, 3H), 2.73 (s, 3H), 1.72–1.79 (m, 2H), 1.44–1.53 (m, 2H), 0.97 (t, 3H); MS 423 (M+18).

EXAMPLE 94

7-[(4-Butoxy-benzyl)-methanesulfonyl-amino]-heptanoic acid

Step A: Reaction time of 2 h at room temperature. $^1$H NMR (400 MHz, CDCl$_3$) δ 7.23 (d, 2H), 6.85 (d, 2H), 4.29 (s, 2H), 3.94 (t, 2H), 3.11 (t, 2H), 2.77 (s, 3H), 2.29 (t, 2H), 1.75 (m, 2H), 1.58–1.43 (m, 6H), 1.24 (m, 4H), 0.96 (t, 3H); MS 403 (M+18).

EXAMPLE 95

7-[(6-Chloro-quinolin-2-ylmethyl)-methanesulfonyl-amino]-heptanoic acid

Step A: Reaction time of 2 h at room temperature. $^1$H NMR (400 MHz, CDCl$_3$) δ 8.13 (d, 1H), 8.03 (d, 1H), 7.81 (s, 1H), 7.67 (m, 2H), 4.72 (s, 2H), 3.26 (t, 2H), 2.99 (s, 3H), 2.25 (t, 2H), 1.52 (m, 4H), 1.22 (m, 4H); MS 417 (M+18).

EXAMPLE 96

{3-[(Benzofuran-2-ylmethyl-methanesulfonyl-amino)-methyl]-phenyl}-acetic acid

Step A: Reaction time of 2 h at room temperature. $^1$H NMR (400 MHz, CDCl$_3$) δ 7.52–7.19 (m, 8H), 4.42 (s, 2H), 4.37 (s, 2H), 3.63 (s, 2H), 2.91 (s, 3H).

EXAMPLE 97

(3-{[(4-Ethyl-benzyl)-methanesulfonyl-amino]-methyl}-phenyl)-acetic acid

Step A: (3-{[(4-Ethyl-benzyl)-methanesulfonyl-amino]-methyl}-phenyl)-acetic acid Methyl Ester.

Reaction time of 24 h at room temperature. $^1$H NMR (400 MHz, CDCl$_3$) δ 7.29–7.33 (m, 1H), 7.16–7.25 (m, 7H), 4.30 (d, 4H), 3.69 (s, 3H), 3.62 (s, 2H), 2.76 (s, 3H), 2.64 (q, 2H), 1.54 (t, 3H); MS 376 (M$^+$+1).

Step B: (3-{[f(4-Ethyl-benzyl)-methanesulfonyl-amino]-methyl}-phenyl)-acetic acid.

$^1$H NMR (400 MHz, CDCl$_3$) δ 7.30–7.34 (m, 1H), 7.15–7.25 (m, 7H), 4.29 (d, 4H), 3.65 (s, 2H), 2.75 (s, 3H), 2.63 (q, 2H), 1.20–1.24 (m, 3H).

EXAMPLE 98

(3-{[Methanesulfonyl-(4-propyl-benzyl)-amino]-methyl}-phenyl)-acetic acid

Step A: (3-{[Methanesulfonyl-(4-propyl-benzyl)-amino]-methyl}-phenyl)-acetic acid Methyl Ester.

Reaction time of 24 h at room temperature. MS 408 (M$^+$+18).

Step B: (3-{[Methanesulfonyl-(4-propyl-benzyl)-amino]-methyl}-phenyl)-acetic acid
MS 374 (M$^+$−1).

EXAMPLE 99

(3-{[(4-Benzyl-benzyl)-methanesulfonyl-amino]-methyl}-phenyl)-acetic acid

Step A: (3-{[(4-Benzyl-benzyl)-methanesulfonyl-amino]-methyl}-phenyl)-acetic acid Methyl Ester.

Reaction time of 24 h at room temperature. $^1$H NMR (400 MHz, CDCl$_3$) δ 7.14–7.29 (m, 13H), 4.28 (d, 4H), 3.95 (s, 2H), 3.67 (s, 3H), 3.59 (s, 2H), 2.75 (s, 3H); MS 456 (M$^+$+18).

Step B: (3-{[(4-Benzyl-benzyl)-methanesulfonyl-amino]-methyl}-phenyl)-acetic acid.

$^1$H NMR (400 MHz, CDCl$_3$) δ 7.12–7.29 (m, 13H), 4.27 (d, 4H), 3.94 (s, 2H), 3.61 (s, 2H), 3.73 (s, 3H); MS 422 (M$^+$−1).

EXAMPLE 100

(3-{[(4-Butyl-benzyl)-(propane-1-sulfonyl)-amino]-methyl}-phenyl)-acetic acid

Step A: (3-{[(4-Butyl-benzyl)-(propane-1-sulfonyl)-amino]-methyl}-phenyl)-acetic acid Methyl Ester.

$^1$H NMR (400 MHz, CDCl$_3$) δ 4.30 (d, 4H), 3.69 (s, 3H), 3.61 (s, 2H), 2.82–2.86 (m, 2H), 2.59 (t, 2H), 1.78–1.84 (m, 2H), 1.58 (t, 2H).

Step B: (3-{[(4-Butyl-benzyl)-(propane-1-sulfonyl)-amino-methyl}-phenyl)-acetic acid.

$^1$H NMR (400 MHz, CDCl$_3$) δ 7.12–7.32 (m, 8H), 4.30 (d, 4H), 3.64 (s, 2H), 2.81–2.90 (m, 2H), 2.59 (t, 2H), 1.74–1.83 (m, 2H), 1.54–1.61 (m, 2H), 1.31–1.40 (m, 2H), 0.87-0.97 (m, 6H); MS 416 (M$^+$−1).

EXAMPLE 101

7-{Methanesulfonyl-[3-(5-methyl-thiophen-2-yl)-propyl]-amino}-heptanoic acid

Step A: 7-{Methanesulfonyl-[3-(5-methyl-thiophen-2-yl)-propyl]-amino}-heptanoic Acid Methyl Ester.

Reaction time of 1 h at 60° C. $^1$H NMR (400 MHz, CDCl$_3$) δ 6.55 (d, 2H), 3.66 (s, 2H), 3.12–3.21 (m, 4H), 2.80

(s, 3H), 2.76–2.80 (m, 2H), 2.42 (s, 3H), 2.30 (t, 2H), 1.89–1.97 (m, 2H), 1.53–1.65 (m, 4H), 1.31–1.36 (m, 4H); MS 376 (M$^+$+1), 393 (M$^+$+18).

Step B: 7-{Methanesulfonyl-[3-(5-methyl-thiophen-2-yl)-propyl]-amino}-heptanoic acid.

$^1$H NMR (400 MHz, CDCl$_3$) δ 6.53–6.57 (m, 2H), 3.12–3.21 (m, 4H), 2.80 (s, 3H), 2.78 (t, 2H), 2.42 (s, 3H), 2.34 (t, 2H), 1.89–1.97 (m, 2H), 1.54–1.66 (m, 4H), 1.30–1.40 (m, 4H); MS 379 (M$^+$+18).

EXAMPLE 102

5-{3-[(3-Furan-2-yl-propyl)-methanesulfonyl-amino]-propyl}-thiophene-2-carboxylic acid Step A: 5-{3-[(3-Furan-2-propyl)-methanesulfonyl-amino]-propyl}-thiophee-2-carboxylic Acid Methyl Ester.

Reaction time of 2 h at room temperature. $^1$H NMR (400 MHz, CDCl$_3$) δ 7.62 (d, 1H), 7.29 (d, $_1$H), 6.80 (d, 1H), 6.26–6.28 (m, 1H), 6.00 (d, 1H), 3.85 (s, 3H), 3.18–3.23 (m, 4H), 2.88 (t, 2H), 2.81 (s, 3H), 2.66 (t, 2H), 1.90-2.03 (m, 4H).

Step B: 5-{3-[(3-Furan-2-yl-propyl)-methanesulfonyl-amino]-propyl}-thiophene-2-carboxylic acid.

$^1$H NMR (400 MHz, CDCl$_3$) δ 7.71 (d, 1H), 7.29 (d, 1H), 6.84 (d, 1H), 6.26–6.28 (m, 1H), 6.00–6.01 (m, 1H), 3.22 (q, 4H), 2.90 (t, 2H), 2.82 (s, 3H), 2.67 (t, 2H), 1.88–2.03 (m, 4H); MS 370 (M$^+$−1).

EXAMPLE 103

7-{Methanesulfonyl-[3-(3-methoxyphenyl)-propyl]-amino}-heptanoic acid

Step A: 7-{Methanesulfonyl-[3-(3-methoxyphenyl)-propyl]-amino}-heptanoic acid Methyl Ester.

Reaction time of 2 h at room temperature. $^1$H NMR (400 MHz, CDCl$_3$) δ 7.18–7.22 (m, 1H), 6.75–6.78 (m, 2H), 6.73 (s, 1H), 3.79 (s, 3H), 3.66 (s, 3H), 3.11-3.20 (m, 4H), 2.80 (s, 3H), 2.61 (t, 2H), 2.29 (t, 2H), 1.88–1.95 (m, 2H), 1.52–1.64 (m, 4H), 1.28–1.32 (m, 4H).

Step B: 7-{Methanesulfonyl-[3-(3-methoxyphenyl)-propyl]-amino}-heptanoic acid.

$^1$H NMR (400 MHz, CDCl$_3$) δ 7.18–7.22 (m, 1H), 6.75–6.78 (m, 2H), 6.73 (s, 1H), 3.79 (s, 3H), 3.11–3.20 (m, 4H), 2.80 (s, 3H), 2.61 (t, 2H), 2.34 (t, 2H), 1.89–1.95 (m, 2H), 1.53–1.66 (m, 4H), 1.29–1.36 (m, 4H).

EXAMPLE 104

[3-({[4-(1-Hydroxy-hexyl)-benzyl]-methanesulfonyl-amino}-methyl)-phenyl]-acetic acid Step A: [3-({[4-(1-Hydroxy-hexyl)-benzyl]-methanesulfonyl-amino}-methyl)-phenyl]-acetic Acid Ethyl Ester.

Reaction time of 2 h at room temperature. $^1$H NMR (400 MHz, CDCl$_3$) δ 7.17–7.31 (m, 8H), 5.70 (t, 1H), 4.31 (s, 4H), 4.12–4.17 (m, 4H), 3.60 (s, 2H), 2.76 (s, 3H), 2.06 (s, 3H), 1.83–1.88 (m, 1H), 1.57–1.75 (m, 1H), 1.20–1.27 (m, 9H), 0.85 (t, 3H); MS 525 (M$^+$+18).

Step B: [3-({[4-(1-Hydroxy-hexyl)-benzyl]-methanesulfonyl-amino}-methyl)-phenyl]-acetic acid.

$^1$H NMR (400 MHz, CDCl$_3$) δ 7.13–7.28 (m, 7H), 7.02 (s, 1H), 4.61 (t, 1H), 4.29 (d, 4H), 3.53 (s, 2H), 2.79 (s, 3H), 1.60–1.77 (m, 2H), 1.18–1.36 (m, 6H), 0.83 (t, 3H); MS 432 (M$^+$−1).

EXAMPLE 105

5-(3-{[2-(3-Chloro-phenoxy)-ethyl]-methanesulfonyl-amino}-propyl)-thiophene-2-carboxylic acid Step A: 5-(3-{[2-(3-Chloro-phenoxy)-ethyl]-methanesulfonyl-amino}-propyl)-thiophene-2-carboxylic Acid Methyl Ester.

Reaction time of 18 h at 60° C. $^1$H NMR (400 MHz, CDCl$_3$) δ 7.60–7.62 (m, 1H), 7.15–7.20 (m, 1H), 6.93–6.95 (m, 1H), 6.79-6.80 (m, 2H), 6.71–6.73 (m, 1H), 4.09 (t, 2H), 3.84 (s, 3H), 3.60 (t, 2H), 3.32 (t, 2H), 2.89 (s, 3H), 2.86–2.94 (m, 2H), 2.01–2.08 (m, 2H).

Step B: 5-(3-{[2-(3-Chloro-phenoxy)-ethyl]-methanesulfonyl-amino}-propyl)-thiophene-2-carboxylic acid.

$^1$H NMR (400 MHz, CDCl$_3$) δ 7.67 (d, 1H), 7.11–7.22 (m, 1H), 6.91–6.93 (m, 1H), 6.81 (s, 2H), 6.69–6.72 (m, 1H), 4.07 (t, 2H), 3.59 (t, 2H), 3.31 (t, 2H), 2.88 (s, 3H), 2.78–2.91 (m, 2H), 2.01–2.05 (m, 2H).

EXAMPLE 106

2-{3-[Methanesulfonyl-(3-phenyl-propyl)-amino]-propyl}-thiazole4 carboxylic acid Step A: 2-{3-[Methanesulfonyl-(3-phenyl-propyl)-amino]-propyl}-thiazole-4 Carboxylic Acid Ethyl Ester.

Reaction time of 5 h at 100° C. $^1$H NMR (400 MHz, CDCl$_3$) δ 8.03 (s, 1H), 7.23–7.27 (m, 2H), 7.13–7.18 (m, 3H), 4.38 (q, 2H), 3.18–3.25 (m, 4H), 3.06 (t, 2H), 2.79 (s, 3H), 2.61 (t, 2H), 2.05–2.13 (m, 2H), 1.86–1.94 (m, 2H), 1.37 (t, 3H); MS 411 (M$^+$+1).

Step B: 2-{3-[Methanesulfonyl-(3-phenyl-propyl)-amino]-propyl}-thiazole-4 Carboxylic acid.

$^1$H NMR (400 MHz, CDCl$_3$) δ 8.20 (s, 1H), 7.10–7.24 (m, 5H), 3.17–3.28 (m, 4H), 3.04 (t, 2H), 2.83 (s, 3H), 2.61 (t, 2H), 2.02–2.09 (m, 2H), 1.85–1.92 (m, 2H); MS 381 (M$^+$−1).

EXAMPLE 107

2-(3-{[8-(3-Chloro-phenyl)-propyl]-methanesulfonyl-amino}-propyl)-thiazole4-carboxylic acid Step A: 2-(3-{[3-(3-Chloro-phenyl)-propyl]-methanesulfonyl-amino}-propyl)-thiazole-4-carboxylic Acid Ethyl Ester.

Reaction time of 5 h at 100° C. $^1$H NMR (400 MHz, CDCl$_3$) δ 8.06 (s, 1H), 7.16–7.23 (m, 3H), 7.05 (d, 1H), 4.40 (q, 2H), 3.09 (t, 2H), 3.19–3.28 (m, 4H), 2.83 (s, 3H), 2.62 (t, 2H), 2.08–2.17 (m, 2H), 1.87–1.95 (m, 2H), 1.39 (t, 3H); MS 445 (MH$^+$).

Step B: 2-(3-{[3-(3-Chloro-phenyl)-propyl]-methanesulfonyl-amino}-propyl)-thiazole4-carboxylic acid.

$^1$H NMR (400 MHz, CDCl$_3$) δ 8.22 (s, 1H), 7.21–7.25 (m, 2H), 7.12-7.16 (m, 2H), 3.20–3.30 (m, 4H), 3.07 (t, 2H), 2.86 (s, 3H), 2.63 (t, 2H), 2.05–2.12 (m, 2H), 1.86–1.94 (m, 2H); MS 415 (M$^+$−1).

EXAMPLE 108

2-{3-[(4-Butyl-benzyl)-methanesulfonyl-amino]-propyl}-thiazole-4-carboxylic acid Step A: 2-{3-(4-Butyl-benzyl)-methanesulfonyl-amino]-propyl}-thiazole-4-carboxylic Acid Ethyl Ester.

Reaction time of 5 h at 100° C. $^1$H NMR (400 MHz, CDCl$_3$) δ 8.00 (s, 1H), 7.21 (d, 2H), 7.11 (d, 2H), 4.38 (q, 2H), 4.33 (s, 2H), 3.23 (t, 2H), 2.96 (t, 2H), 2.78 (s, 3H), 2.56 (t, 2H), 1.96–2.03 (m, 2H), 1.50–1.58 (m, 2H), 1.37 (t, 3H), 1.26-1.33 (m, 2H), 0.89 (t, 3H); MS 439 (M+1).

Step B: 2-{3-[(4-Butyl-benzyl)-methanesulfonyl-amino]-propyl}-thiazole4-carboxylic acid.

$^1$H NMR (400 MHz, CDCl$_3$) δ 8.15 (s, 1H), 7.25 (d, 2H), 7.12 (d, 2H), 4.32 (s, 2H), 3.22–3.28 (m, 2H), 2.88–2.91 (m, 2H), 2.88 (s, 3H), 2.57 (t, 2H), 1.87 (m, 2H), 1.54 (m, 2H), 1.27–1.32 (m, 2H), 0.90 (t, 3H); MS 409 (M−1).

EXAMPLE 109

(5-{[(4-Isobutyl-benzyl)-methanesulfonyl-amino]-methyl}-thiophen-2-yl)-acetic acid Step A: (5-{[(4-Isobutyl-benzyl)-methanesulfonyl-amino]-methyl}-thiophen-2-yl)-acetic Acid Methyl Ester.

Reaction time of 24 h at room temperature.

Step B: (5-{[(4-Isobutyl-benzyl)-methanesulfonyl-amino]-methyl}-thiophen-2-yl)-acetic acid.

$^1$H NMR (400 MHz, CDCl$_3$) δ 6.80–7.32 (m, 6H), 4.40 (s, 2H), 3.80 (s, 2H), 2.75 (s, 3H), 1.80 (m, 2H), 0.85 (d, 6H); MS 394 (M–1).

EXAMPLE 110

2-{3-[(4-Butyl-benzyl)-methanesulfonyl-amino]-propy}-thiazole-4-carboxylic acid

Step A: 2-{3-[(4-Butyl-benzyl)-methanesulfonyl-amino]-propyl}-thiazole-4-carboxylic Acid Ethyl Ester.

Reaction time of 5 h at 100° C. H NMR (400 MHz, CDCl$_3$) δ 8.00 (s, 1H), 7.21 (d, 2H), 7.11 (d, 2H), 4.38 (q, 2H), 4.33 (s, 2H), 3.23 (t, 2H), 2.96 (t, 2H), 2.78 (s, 3H), 2.56 (t, 2H), 1.96–2.03 (m, 2H), 1.50–1.58 (m, 2H), 1.37 (t, 3H), 1.26-1.33 (m, 2H), 0.89 (t, 3H); MS 439 (M$^+$+1).

Step B: 2-{3-[(4-Butyl-benzyl)-methanesulfonyl-amino]-propyl}-thiazole-4-carboxylic acid.

$^1$H NMR (400 MHz, CDCl$_3$) δ 8.15 (s, 1H), 7.25 (d, 2H), 7.12 (d, 2H), 4.32 (s, 2H), 3.22–3.28 (m, 2H), 2.88–2.91 (m, 2H), 2.88 (s, 3H), 2.57 (t, 2H), 1.87 (m, 2H), 1.54 (m, 2H), 1.27–1.32 (m, 2H), 0.90 (t, 3H); MS 409 (M$^+$–1).

EXAMPLE 111

7-{[2-(3,5-Dichloro-phenoxy)-ethyl]-methanesulfonyl-amino}-heptanoic acid

Step A: 2-[2-(3,5-Dichloro-phenoxy)-ethyl]-isoindole-1,3-dione.

A solution of 1-(2-bromo-ethoxy)-3,5-dichloro-benzene (2.41 g, 8.93 mmol) and potassium phthalimide (2.00 g, 10.64 mmol) in DMF (7.6 mL) was heated at 85° C. for 1 h. The reaction was cooled to room temperature and chloroform was added. The organic solution was washed with 0.2 N aqueous NaOH followed by water. The organic solution was dried (Na$_2$SO$_4$), filtered, and concentrated. The residue was suspended in Et$_2$O and the solid was collected by filtration to provide the title compound (2.21 g). $^1$HNMR (400 MHz, CDCl$_3$) δ 7.82 (m, 2H), 7.77 (m, 2H), 6.89 (m, 1H), 6.88 (m, 2H), 4.16 (t, 2H), 4.05 (t, 2H); MS 336 (M+).

Step B: 2-(3,5-Dichloro-phenoxy)-ethylamine.

A solution of 2-[2-(3,5-dichloro-phenoxy)-ethyl]-isoindole-1,3-dione (1.29 g, 3.84 mmol) and hydrazine hydrate (202 mg, 4.05 mmol) in MeOH (16 mL) was heated at reflux for 2 h. The mixture was cooled to room temperature and Et$_2$O was added. The suspension was shaken with 40% aqueous potassium hydroxide. The aqueous solution was extracted with Et$_2$O (3×) and the combined organic layers were dried (K$_2$CO$_3$), filtered, and concentrated to provide the title compound (870 mg). $^1$HNMR (400 MHz, CDCl$_3$) δ 6.95 (m, 1H), 6.80 (m, 2H), 3.95 (m, 2H), 3.07 (t, 2H), 1.70 (bs, 2H).

Step C: N-[2-(3,5-Dichloro-phenoxy)-ethyl]-methanesulfonamide.

The title compound was prepared from 2-(3,5-dichloro-phenoxy)-ethylamine, Et$_3$N, and methanesulfonyl chloride using the procedure described in Step 2 of Preparation A1. Recrystallization from EtOH provided the title compound. $^1$HNMR (400 MHz, CDCl$_3$) δ 6.93 (m, 1H), 6.74 (m, 2H), 5.09 (m, 1H), 4.01 (t, 2H), 3.47 (q, 2H), 2.96 (s, 3H).

Step D: 7-{[2-(3,5-Dichloro-phenoxy)-ethyl]-methanesulfonyl-amino}-heptanoic acid Ethyl Ester.

A solution of NaH (60% in oil, 338 mg, 8.45 mmol) in DMF (23 mL) was cooled to 0° C. followed by addition of N-[2-(3,5-dichloro-phenoxy)-ethyl]-methanesulfonamide (2.0 g, 7.04 mmol). The reaction was stirred at room temperature for 0.5 h and was cooled to 0° C. followed by addition of ethyl 7-bromoheptanoate (2.0 g, 8.45 mmol). The reaction was heated at 65° C. for 3 h and was cooled to room temperature. EtOAc was added and the organic solution was washed consecutively with 1N HCl, water, and brine. The organic solution was dried (MgSO$_4$), filtered, and concentrated. Purification by flash chromatography (4:1 hexanes:EtOAc) provided the title compound (2.84 g). $^1$HNMR (400 MHz, CDCl$_3$) δ 6.95 (m, 1H), 6.75 (m, 2H), 4.06 (m, 5H), 3.56 (t, 2H), 3.22 (t, 2H), 2.86 (s, 3H), 2.26 (t, 2H), 1.60 (m, 4H), 1.32 (m, 4H), 1.22 (t, 3H).

Step E: 7-{[2-(3.5-Dichloro-phenoxy)-ethyl]-methanesulfonyl-amino}-heptanoic acid.

The title compound was prepared from 7-{[2-(3,5-dichloro-phenoxy)-ethyl]-methanesulfonyl-amino}-heptanoic Acid ethyl ester using the procedure described in Step B of Example 1 with 2N NaOH. Purification by flash chromatography (1% MeOH in CH$_2$Cl$_2$) provided the title acid. $^1$HNMR (400 MHz, CDCl$_3$) δ 6.95 (m, 1H), 6.75 (m, 2H), 4.07 (t, 2H), 3.56 (t, 2H), 3.23 (t, 2H), 2.86 (s, 3H), 2.33 (t, 2H), 1.61 (m, 4H), 1.33 (m, 4H); MS 411 (M–1).

Example numbers 112–122 are not used in this specification

EXAMPLES 123–137

Examples 123–137 were prepared in an analogous manner to Example 1 starting with the appropriate alkylating agents and sulfonamides in the alkylation Step A followed by ester hydrolysis in Step B with variations in reaction temperature and time in Step A as noted.

EXAMPLE 123

[5-({[3-(3-Chloro-phenyl)-propyl]-methanesulfonyl-amino}-methyl)-thiophen-2-yl]-acetic acid Step A: [5-({[3-(3-Chloro-phenyl)-propyl]-methanesulfonyl-amino}-methyl)-thiophen-2-yl]-acetic Acid Methyl Ester.

Reaction time of 24 h at room temperature.

Step B: [5-({[3-(3-Chloro-phenyl)-propyl]-methanesulfonyl-amino}-methyl)-thiophen-2-yl]-acetic acid.

$^1$H NMR (400 MHz, CDCl$_3$) δ 7.06–7.36 (M, 4H), 6.86 (m, 2H), 4.40 (s, 2H), 3.80 (s, 2H), 2.90 (s, 3H), 3.00 (t, 2H, J=7.0), 2.40 (t, 2H, J=7.0), 1.70 (m, 2H); MS 399 (M–1).

EXAMPLE 124

[5-({[2-(3,5-Dichloro-phenoxy)-ethyl]-methanesulfonyl-amino}-methyl)-thiophen-2-yl]-acetic acid Step A: [5-({[2-(3,5-Dichloro-phenoxy)-ethyl]-methanesulfonyl-amino}-methyl)-thiophen-2-yl]-acetic Acid Methyl Ester.

Reaction time of 24 h at room temperature.

Step B: [5-({[2-(3,5-Dichloro-phenoxy)-ethyl]-methanesulfonyl-amino}-methyl)-thiophen-2-yl]-acetic acid.

$^1$H NMR (400 MHz, CDCl$_3$) δ 6.60–7.60 (m, 5H), 4.60 (s, 2H), 4.10 (m, 2H), 3.80 (s, 2H), 3.60 (m, 2H), 2.90 (s, 3H); MS 436 (M–1), 438 (M+1).

EXAMPLE 125

(5-{[(4-Butyl-benzyl)-methanesulfonyl-amino]-methyl}-thiophen-2-yl)-acetic acid

Step A: (5-{[4-Butyl-benzyl)-methanesulfonyl-amino]-methyl}-thiophen-2-yl)-acetic Acid Methyl Ester.

Reaction time of 24 h at room temperature.

Step B: (5-{[(4-Butyl-benzyl)-methanesulfonyl-amino]-methyl}-thiophen-2-yl)-acetic acid.

$^1$H NMR (400 MHz, CDCl$_3$) δ 7.00–7.30 (m, 4H), 6.80 (d, 1H, J=4.0), 6.70 (d, 1H, J=4.0), 4.40 (s, 2H), 4.30 (s, 2H), 3.80 (s, 2H), 2.90 (s, 3H), 2.60 (m, 2H), 1.60 (m, 2H), 1.30 (m, 2H), 0.90 (t, 3H, J=7.0); MS 394 (M−1).

EXAMPLE 126

5-(3-{[2-(3,5-Dichloro-phenoxy)-ethyl]-methanesulfonyl-amino}-propyl)-furan-2-carboxylic acid Step A: 5-(3-{[2-(3,5-Dichloro-phenoxy)-ethyl]-methanesulfonyl-amino}-propyl)-furan-2-carboxylic Acid Methyl Ester.

Reaction time of 72 h at room temperature; MS 450 (M+1).

Step B: 5-(3-{[2-(3,5-Dichloro-phenoxy)-ethyl]-methanesulfonyl-amino}-propyl)-furan-2-carboxylic acid.

$^1$H NMR (400 MHz, CDCl$_3$) δ 6.80–7.70 (m, 5H), 6.19 (d, 1H, J=3.8), 4.20 (t, 2H, J=7.0), 3.80 (m, 2H), 3.25–3.40 (m, 4H), 2.95 (s, 3H), 2.65 (m, 2H), 1.80–2.00 (m, 2H); MS 435 (M−1), 436 (M+1).

EXAMPLE 127

Trans-5-(3-{[3-(3,5-Dichloro-phenyl)-allyl]-methanesulfonyl-amino}-propyl)-furan-2-carboxylic acid Step A: Trans-5-(3-{[3-(3,5-Dichloro-phenyl)-allyl]-methanesulfonyl-amino}-propyl)-furan-2-carboxylic Acid Methyl Ester.

Reaction time of 72 h at room temperature; MS 446 (M+).

Step B: Trans-5-(3-{[3-(3,5-Dichloro-phenyl)-allyl]-methanesulfonyl-amino}-propyl)-furan-2-carboxylic acid.

$^1$H NMR (400 MHz, CDCl$_3$) δ 7.00–7.50 (m, 4H), 6.00–6.60 (m, 3H), 4.00 (d, 2H, J=5.0), 3.20 (m, 2H), 2.60–2.70 (m, 2H), 1.70–2.00 (m, 2H); MS 430 (M−1), 432 (M+1).

EXAMPLE 128

3-(2-{[2-(3,5-Dichloro-phenoxy)-ethyl]-methanesulfonyl-amino}-ethyl)-benzoic acid Step A: 3-(2-{[2-(3,5-Dichloro-phenoxy)-ethyl]-methanesulfonyl-amino}-ethyl)-benzoic Acid Methyl Ester.

Reaction time of 2 h at room temperature; MS 446 (M+).

Step B: 3-(2-{[2-(3,5-Dichloro-phenoxy)-ethyl]-methanesulfonyl-amino}-ethyl)-benzoic acid.

$^1$H NMR (400 MHz, CDCl$_3$) δ 6.80–7.90 (m, 7H), 4.20 (t, 2H, J=6.7), 3.20–3.30 (m, 4H), 2.85 (s, 3H), 2.30 (t, 2H, J=6.8); MS 431 (M−1).

EXAMPLE 129

[3-(3-{[3-(3-Chloro-phenyl)-propyl]-methanesulfonyl-amino}-propyl)-phenyl]-acetic acid Step A: [3-(3-{[3-(3-Chloro-phenyl)-propyl]-methanesulfonyl-amino}-propyl)-phenyl]-acetic Acid Methyl Ester.

Reaction time of 2 h at room temperature. $^1$H NMR (400 MHz, CDCl$_3$) δ 7.03–7.29 (m, 8H), 3.68 (s, 3H), 3.59 (s, 2H), 3.15–3.20 (m, 4H), 2.80 (s, 3H), 2.58–2.64 (m, 4H), 1.84–1.94 (m, 4H).

Step B: [3-(3-{[3-(3-Chloro-phenyl)-propyl]-methanesulfonyl-amino}-propyl)-phenyl]-acetic acid.

$^1$H NMR (400 MHz, CDCl$_3$) δ 7.02–7.29 (m, 8H), 3.61 (s, 2H), 3.14–3.19 (m, 4H), 2.78 (s, 3H), 2.57–2.80 (m, 4H), 1.82–1.93 (m, 4H).

EXAMPLE 130

5-{3-[(3-Benzo[1,3]dioxol-5-yl-propyl)-methanesulfonyl-amino]-propyl}-thiophene-2-carboxylic acid Step A: 5-{3-[(3-Benzo[1,3]dioxol-5-yl-propyl)-methanesulfonyl-amino]-propyl}-thiophene-2-carboxylic Acid Methyl Ester.

Reaction time of 2 h at room temperature. $^1$H NMR (400 MHz, CDCl$_3$) δ 7.61 (d, 1H), 6.79 (d, 1H), 6.58–6.72 (m, 3H), 5.91 (s, 2H), 3.85 (s, 3H), 3.14–3.21 (m, 4H), 2.87 (t, 2H), 2.80 (s, 3H), 2.55 (t, 2H), 1.82–1.99 (m, 4H).

Step B: 5-{3-[(3-Benzo[1.3]dioxol-5-yl-propyl)-methanesulfonyl-amino]-propyl}-thiophene-2-carboxylic acid.

$^1$H NMR (400 MHz, CDCl$_3$) δ 7.70 (d, 1H), 6.83 (d, 1H), 6.59–6.73 (m, 3H), 5.91 (s, 2H), 3.15–3.22 (m, 4H), 2.89 (t, 2H), 2.81 (s, 3H), 2.55 (t, 2H), 1.83–2.01 (m, 4H); MS 424 (M−1).

EXAMPLE 131

(3-{[(4-Isobutyl-benzyl)-methanesulfonyl-amino]-methyl}-phenyl)-acetic acid

Step A: (3-{[(4-Isobutyl-benzyl)-methanesulfonyl-amino]-methyl}-phenyl)-acetic acid Methyl Ester.

Reaction time of 2 h at room temperature. $^1$H NMR (400 MHz, CDCl$_3$) δ 7.20–7.32 (m, 6H), 7.11 (d, 2H), 4.30 (d, 4H), 3.69 (s, 3H), 3.62 (s, 3H), 3.62 (s, 3H), 2.75 (s, 3H), 2.46 (s, 2H), 1.81–1.88 (m, 1H), 0.88 (d, 6H); MS 404 (M+1), 426 (M+23).

Step B: (3-{[(4-Isobutyl-benzyl)-methanesulfonyl-amino]-methyl}-phenyl)-acetic acid.

$^1$H NMR (400 MHz, CDCl$_3$) δ 7.18–7.31 (m, 6H), 7.10 (d, 2H), 4.29 (d, 4H), 3.63 (s, 2H), 2.73 (s, 3H), 2.45 (d, 2H), 1.80–1.87 (m, 1H), 0.88 (d, 6H).

EXAMPLE 132

7-[(4-Isopropyl-benzyl)-methanesulfonyl-amino]-heptanoic acid

Step A: 7-[(4-Isopropyl-benzyl)-methanesulfonyl-amino]-heptanoic Acid Ethyl Ester.

Reaction time of 24 h at room temperature. $^1$H NMR (400 MHz, CDCl$_3$) δ 7.20–7.30 (m, 4H), 4.35 (s, 2H), 4.10 (q, 2H), 3.15 (t, 2H), 2.85–2.95 (m, 1H), 2.80 (s, 3H), 2.25 (t, 2H), 1.48–1.62 (m, 4H), 1.18–1.32 (m, 13H); MS 384 (M+1).

Step B: 7-[(4-Isopropyl-benzyl)-methanesulfonyl-amino]-heptanoic acid.
MS 356 (M+1).

EXAMPLE 133

7-{[2-(3,5-Difluoro-phenoxy)-ethyl]-methanesulfonyl-amino}-heptanoic acid

Step A: 7-{[2-(3,5-Difluoro-phenoxy)-ethyl]-methanesulfonyl-amino}-heptanoic acid Methyl Ester.

Reaction time of 24 h at 50° C. $^1$H NMR (400 MHz, CDCl$_3$) δ 6.39–6.45 (m, 3H), 4.08 (t, 2H), 3.65 (s, 2H), 3.58

(t, 2H), 3.23–3.27 (m, 2H), 2.88 (s, 3H), 2.30 (t, 2H), 1.57–1.65 (m, 5H), 1.33–1.35 (m, 4H); MS 394 (M+1).
Step B: 7-{[2-(3,5-Difluoro-phenoxy)-ethyl]-methanesulfonyl-amino}-heptanoic acid.
$^1$H NMR (400 MHz, CDCl$_3$) δ 6.39–6.45 (m, 3H), 4.08 (t, 2H), 3.58 (t, 2H), 3.25 (t, 2H), 2.35 (t, 2H), 1.64 (m, 5H), 1.24–1.37 (m, 4H); MS 380 (M−1).

EXAMPLE 134

7-{[2-(3,5-Dimethyl-phenoxy)-ethyl]-methanesulfonyl-amino}-heptanoic acid

Step A: 7-{[2-(3,5-Dimethyl-phenoxy)-ethyl]-methanesulfonyl-amino}-heptanoic acid Methyl Ester.

Reaction time of 24 h at 50° C. $^1$H NMR (400 MHz, CDCl$_3$) δ 6.61 (s, 1H), 6.49 (s, 2H), 4.06–4.14 (m, 2H), 3.65 (s, 3H), 3.61 (t, 2H), 3.26 (t, 2H), 2.90 (s, 3H), 2.27–2.33 (m, 8H), 1.55–1.63 (m, 4H), 1.25 (bs, 4H); MS 385 (M+1).
Step B: 7-{[2-(3,5-Dimethyl-phenoxy)-ethyl]-methanesulfonyl-amino}-heptanoic acid.
$^1$H NMR (400 MHz, CDCl$_3$) δ 6.61 (s, 1H), 6.49 (s, 2H), 4.06–4.07 (m, 2H), 3.59–3.61 (m, 2H), 3.27 (t, 2H), 2.91 (s, 3H), 2.34 (t, 2H), 2.27 (s, 6H), 1.63–1.65 (m, 4H), 1.36 (bs, 4H); MS 370 (M−1).

EXAMPLE 135

(2-{3-[(4-Butyl-benzyl)-methanesulfonyl-amino]-propyl}-phenyl)-acetic acid

Step A: (2-{3-[(4-Butyl-benzyl)-methanesulfonyl-amino]-propyl}-phenyl)-acetic acid Methyl Ester.
$^1$H NMR (400 MHz, CDCl$_3$) δ 7.11–7.23 (m, 7H), 6.99–7.01 (m, 1H), 4.31 (s, 2H), 3.63 (s, 3H), 3.54 (s, 2H), 3.19 (t, 2H), 2.78 (s, 3H), 2.49–2.59 (m, 4H), 1.72–1.80 (m, 2H), 1.54–1.59 (m, 2H), 1.27–1.36 (m, 2H), 0.89 (t, 3H); MS 432 (M+1).
Step B: (2-{3-[(4-Butyl-benzyl)-methanesulfonyl-amino]-propyl}-phenyl)-acetic acid.
$^1$H NMR (400 MHz, CDCl$_3$) δ 7.13–7.27 (m, 7H), 7.02 (d, 1H), 4.32 (s, 2H), 3.59 (s, 2H), 3.21 (t, 2H), 2.79 (s, 3H), 2.50–2.61 (m, 4H), 1.73–1.81 (m, 2H), 1.54–1.62 (m, 2H), 1.29–1.38 (m, 2H), 0.92 (t, 3H); MS 416 (M−1).

EXAMPLE 136

5-(3-{[2-(Benzo[1,3]dioxol-5-yloxy)-ethyl]-methanesulfonyl-amino}-propyl)-thiophene-2-carboxylic acid Step A: 5-(3-{[2-(Benzo[1,3]dioxol-5-yloxy)-ethyl]-methanesulfonyl-amino}-propyl)-thiophene-2-carboxylic Acid Methyl Ester.

Reaction time of 24 h at room temperature. $^1$H NMR (400 MHz, CDCl$_3$) δ 7.61 (d, 1H), 6.80 (d, 1H), 6.67–6.70 (m, 1H), 6.41 (d, 1H), 6.24–6.27 (m, 1H), 5.91 (s, 2H), 4.03 (t, 2H), 3.85 (s, 3H), 3.59 (t, 2H), 3.33 (t, 2H), 2.89 (s, 3H), 2.88–2.92 (m, 2H), 2.01–2.08 (m, 2H); MS 442 (M+1).
Step B: 5-(3-{[2-(Benzo[1,3]dioxol-5-yloxy)-ethyl]-methanesulfonyl-amino}-propyl)-thiophene-2-carboxylic acid.
$^1$H NMR (400 MHz, CDCl$_3$) δ 7.69 (d, 1H), 6.84 (d, 1H), 6.68 (d, 1H), 6.40 (s, 1H), 6.24–6.27 (m, 1H), 5.91 (s, 2H), 4.03 (t, 2H), 3.60 (t, 2H), 3.34 (t, 2H), 2.90 (s, 3H), 2.90–2.94 (m, 2H), 2.02–2.10 (m, 2H); MS 426 (M−1).

EXAMPLE 137

[3-({[2-(3-Chloro-phenoxy)-ethyl]-methanesulfonyl-amino}-methyl)-phenyl]-acetic acid Step A: [3-({[2-(3-Chloro-phenoxy)-ethyl]-methanesulfonyl-amino}-methyl)-phenyl]-acetic Acid Methyl Ester.
$^1$H NMR (400 MHz, CDCl$_3$) δ 7.15–7.33 (m, 5H), 6.93–6.95 (m, 1H), 6.80–6.81 (m, 1H), 6.69–6.71 (m, 1H), 4.49 (s, 2H), 3.96–4.02 (m, 2H), 3.67 (s, 2H), 3.54–3.67 (m, 4H), 2.94 (s, 3H).
Step B: [3-({[2-(3-Chloro-phenoxy)-ethyl]-methanesulfonyl-amino}-methyl)-phenyl]-acetic acid.
$^1$H NMR (400 MHz, CDCl$_3$) δ 7.13–7.33 (m, 5H), 6.91 (d, 1H), 6.78 (s, 1H), 6.66–6.69 (m, 1H), 4.48 (s, 2H), 3.98 (t, 2H), 3.62 (s, 2H), 3.56 (t, 2H), 2.92 (s, 3H).

EXAMPLE 138

[3-(2-{[3-(3-Chloro-phenyl)-propyl]-methanesulfonyl-amino}-ethyl)-phenyl]-acetic acid Step A: Alkylation

[3-(2-{[3-(3-Chloro-phenyl)-propyl]-methanesulfonyl-amino}-ethyl)-phenyl]-acetic acid Tert-butyl Ester.

Step A was performed with the appropriate starting materials in an analagous manner to Step A of Example 1 with a reaction time of 24 h at room temperature; MS 466 (M+).

Step B: Ester Hydrolysis

[3-(2-{[3-(3-Chloro-phenyl)-propyl]-methanesulfonyl-amino}-ethyl)-phenyl]-acetic acid.

A solution of [3-(2-{[3-(3-chloro-phenyl)-propyl]-methanesulfonyl-amino}-ethyl)-phenyl]-acetic Acid tert-butyl ester (170 mg, 0.36 mmol) in HCl/dioxane (5 mL) was stirred for 48 h at room temperature. The reaction was concentrated and the residue was taken up in dilute aqueous NaOH (10 mL, pH=9.3). The aqueous solution was washed with EtOAc (10 mL) and the layers were separated. The aqueous layer after extraction with EtOAc (10 mL) was acidified with dilute aqueous HCl to a pH of 2.5. After extraction of the acidic aqueous layer with EtOAc (10 mL) the organic solution was dried over MgSO$_4$, filtered, and concentrated to afford the title compound as an oil (20 mg). $^1$H NMR (400 MHz, CDCl$_3$) δ 6.90–7.50 (m, 8H), 3.00–3.30 (m, 4H), 2.95 (s, 3H), 2.45–2.85 (m, 4H), 1.80 (m, 2H); MS 408 (M−1).

EXAMPLES 139–140

Examples 139–140 were prepared in an analogous manner to Example 138 starting with the appropriate alkylating agents and sulfonamides in the alkylation Step A followed by ester hydrolysis in Step B with variations in reaction temperature and time in Step A as noted.

EXAMPLE 139

[3-(2-{[2-(3,5-Dichloro-phenoxy)-ethyl]-methanesulfonyl-amino}-ethyl)-phenyl]-acetic acid Step A: [3-(2-{[2-(3,5-Dichloro-phenoxy)-ethyl]-methanesulfonyl-amino}-ethyl)-phenyl]-acetic Acid Tert-butyl Ester.

Reaction time of 4 h at room temperature.
Step B: [3-(2-{[2-(3,5-Dichloro-phenoxy)-ethyl]-methanesulfonyl-amino}-ethyl)-phenyl]-acetic acid.
$^1$H NMR (400 MHz, CDCl$_3$) δ 6.70–7.50 (m, 7H), 4.20 (m, 2H), 3.25 (m, 4H), 2.95 (s, 3H), 2.35–2.65 (m, 2H); MS 445 (M−1).

EXAMPLE 140

5-(3-{[3-(3-Chloro-phenyl)-propyl]-trifluoroacetyl-amino}-propyl)-thiophene-2-carboxylic acid Step A: 5-(3-{[3-(3-Chloro-phenyl)-propyl]-trifluoroacetyl-amino}-propyl)-thiophene-2-carboxylic Acid Tert-butyl Ester.

Reaction time of 24 h at room temperature. MS 508 (M+18).

Step B: 5-(3-{[3-(3-Chloro-phenyl)-propyl]-trifluoroacetyl-amino}-propyl)-thiophene-2-carboxylic acid.

$^1$H NMR (400 MHz, CDCl$_3$) δ 6.60–7.80 (m, 6H), 3.22 (m, 4H), 2.80 (m, 2H), 2.63 (m, 2H), 1.60–2.02 (m, 4H); MS 433 (M−1).

EXAMPLE 141

(3-{[(2,3-Dihydro-benzo[1,4]dioxin-5-ylmethyl)-methanesulfonyl-amino]-methyl}-phenyl)-acetic acid Step A: Reductive Amination (3-{[(2,3-Dihydro-benzo[1,4]dioxin-5-ylmethyl-amino]-methyl}-phenyl)-acetic acid Ethyl Ester.

To a solution of 1,4-benzodioxan-6-carboxyaldehyde (100 mg, 0.609 mmol) and (3-aminomethyl-phenyl)-acetic Acid ethyl ester hydrochloride (148 mg, 0.645 mmol) in MeOH (2.5 mL) was added triethylamine (65 mg, 0.646 mmol). The reaction was stirred for 3 h, was cooled to 0° C., and NaBH$_4$ (37 mg, 0.975 mmol) was added. After stirring at room temperature for 10 minutes, a 1:1 mixture of saturated aqueous NaHCO$_3$:H$_2$O was added. The product was extracted into CH$_2$Cl$_2$ and the organic solution was washed with water followed by brine. The organic solution was dried over MgSO$_4$, filtered, and concentrated to yield the title compound (202 mg). $^1$H NMR (400 MHz, CDCl$_3$) δ 7.14–7.27 (m, 4H), 6.84 (s, 1H), 6.78 (s, 2H), 4.22 (s, 4H), 4.12 (q, 2H), 3.75 (s, 2H), 3.67 (s, 2H), 3.57 (s, 2H); MS 343 (M+1).

Step B: Sulfonamide Formation
(3-{[(2,3-Dihydro-benzo[1,4]dioxin-5-ylmethyl)-methanesulfonyl-amino]-methyl}-phenyl)-acetic Acid Ethyl Ester.

To a soluton of (3-{[(2,3-dihydro-benzo[1,4]dioxin-5-ylmethyl-amino]-methyl}- phenyl)-acetic Acid ethyl ester (200 mg, 0.585 mmol) and triethylamine (71 mg, 0.702 mmol) in CH$_2$Cl$_2$ (10 mL) was added methanesulfonyl chloride (0.05 mL, 0.643 mmol). The reaction was stirred for 16 h and was diluted with CH$_2$Cl$_2$. The organic solution was washed with water followed by brine, dried over MgSO$_4$, filtered, and concentrated. The product was purified by flash chromatography (20% EtOAc in hexanes to 40% EtOAc in hexanes) to provide the title compound (210 mg). $^1$H NMR (400 MHz, CDCl$_3$) δ 7.20–7.31 (m, 4H), 6.75–6.82 (m, 3H), 4.30 (s, 2H), 4.24 (s, 4H), 4.20 (s, 2H), 4.13 (q, 2H), 3.59 (s, 2H), 2.74 (s, 3H), 1.24 (t, 3H); MS 420 (M+), 437 (M+17).

Step C: Ester Hydrolysis
(3-{[(2,3-Dihydro-benzo[1,4]dioxin-5-ylmethyl)-methanesulfonyl-amino]-methyl}-phenyl)-acetic acid.

To a solution of (3-{[(2,3-dihydro-benzo[1,4]dioxin-5-ylmethyl)-methanesulfonyl-amino]-methyl}-phenyl)-acetic Acid ethyl ester (210 mg, 0.5 mmol) in MeOH (3 mL) at 0° C. was added aqueous NaOH (2N, 0.5 mL). The reaction was stirred at room temperature for 16 h and was diluted with 1N HCl. The product was extracted into CH$_2$Cl$_2$ and the organic solution was washed with water followed by brine. The organic solution was dried over MgSO$_4$, filtered, and concentrated to provide the title compound (165 mg). $^1$H NMR (400 MHz, CDCl$_3$) δ 7.19–7.32 (m, 4H), 6.73–6.81 (m, 3H), 4.29 (s, 2H), 4.22 (s, 4H), 4.18 (s, 2H), 3.63 (s, 2H), 2.75 (s, 3H).

EXAMPLES 142–162

Examples 142–162 were prepared in an analogous manner to Example 141 starting with the appropriate aldehyde and amine reagents in Step A followed by formation of the desired sulfonamide in Step B and ester hydrolysis in Step C.

EXAMPLE 142

(3-{[(5-Ethyl-thiophen-2-ylmethyl)-methanesulfonyl-amino]-methyl}-phenyl)-acetic acid Step A: (3-{[(5-Ethyl-thiophen-2-ylmethyl)-amino]-methyl}-phenyl)-acetic Acid Ethyl Ester.

$^1$H NMR (400 MHz, CDCl$_3$) δ 7.15–7.29 (m, 4H), 6.70 (d, 1H), 6.59 (d, 1H), 4.11–4.15 (m, 2H), 3.90 (s, 2H), 3.80 (s, 2H), 3.58 (s, 2H), 2.76–2.82 (m, 2H), 1.84 (bs, 1H), 1.20–1.29 (m, 6H); MS 318 (M$^+$+1).

Step B: (3-{[(5-Ethyl-thiophen-2-ylmethyl)-methanesulfonyl-amino]-methyl}-phenyl)-acetic Acid Ethyl Ester.

$^1$H NMR (400 MHz, CDCl$_3$) δ 7.23–7.35 (m, 4H), 6.77 (d, 1H), 6.63–6.64 (m, 1H), 4.40 (s, 2H), 4.38 (s, 2H), 4.15 (q, 2H), 3.62 (s, 2H), 2.82 (q, 2H), 2.77 (s, 3H), 1.23–1.31 (m, 6H); MS 413 (M$^+$+18).

Step C: (3-{[(5-Ethyl-thiophen-2-ylmethyl)-methanesulfonyl-amino]-methyl}-phenyl)-acetic acid.

$^1$H NMR (400 MHz, CDCl$_3$) δ 7.23–7.33 (m, 4H), 6.74 (s, 1H), 6.61 (s, 1H), 4.38 (s, 2H), 4.36 (s, 2H), 3.66 (s, 2H), 2.80 (q, 2H), 2.75 (s, 3H), 1.25–1.30 (m, 3H); MS 366 (M+−1).

EXAMPLE 143

(3-{[Methanesulfonyl-(5-phenyl-furan-2-ylmethyl)-amino]-methyl}-phenyl)-acetic acid Step A: (3-{[(5-Phenyl-furan-2-ylmethyl)-amino]-methyl}-phenyl)-acetic Acid Methyl Ester.

$^1$H NMR (400 MHz, CDCl$_3$) δ 7.62 (d, 2H), 7.34 (t, 2H), 7.14–7.29 (m, 5H), 6.55 (d, 1H), 6.24 (d, 1H), 3.81 (d, 4H), 3.66 (s, 3H), 3.59 (s, 2H), 1.73 (bs, 1H).

Step B: (3-{[Methanesulfonyl-(5-phenyl-furan-2-ylmethyl)-amino]-methyl}-phenyl)-acetic Acid Methyl Ester.

$^1$H NMR (400 MHz, CDCl$_3$) δ 7.62 (d, 2H), 7.38–7.42 (m, 2H), 7.23–7.38 (m, 5H), 6.60–6.61 (m,1H), 6.34 (d, 1H), 4.37 (d, 4H), 3.69 (s, 3H), 3.63 (s, 2H), 2.89 (s, 3H); MS 436 (M$^+$+23).

Step C: (3-{[Methanesulfonyl-(5-phenyl-furan-2-ylmethyl)-amino]-methyl}-phenyl)-acetic acid.

$^1$H NMR (400 MHz, CDCl$_3$) δ 7.60 (d, 2H), 7.37 (t, 2H), 7.22–7.33 (m, 5H), 6.57 (d, 1H), 6.31 (d, 1H), 4.36 (s, 2H), 4.33 (s, 2H), 3.64 (s, 2H), 2.87 (s, 3H). 398 MS (M$^+$−1).

EXAMPLE 144

(3-{[(3-Hydroxy-4-propoxy-benzyl)-methanesulfonyl-amino]-methyl}-phenyl)-acetic acid Step A: {3-[(3-Hydroxy-4-propoxy-benzylamino)-methyl]-phenyl}-acetic Acid Methyl Ester.

$^1$H NMR (400 MHz, CDCl$_3$) δ 7.24–7.30 (m, 3H), 7.16 (d, 1H), 6.91 (s, 1H), 6.79 (s, 2H), 3.98 (t, 2H), 3.77 (s, 2H), 3.70 (s, 2H), 3.68 (s, 3H), 3.61 (s, 2H), 1.82 (q, 2H), 1.03 (t, 3H); MS 365 (M$^+$+22).

Step B: (3-{[Methanesulfonyl-(3-methanesulfonyloxy4-propoxy-benzyl)-amino]-methyl}- phenyl)-acetic Acid Methyl Ester.

$^1$H NMR (400 MHz, CDCl$_3$) δ 7.31–7.17 (m, 6H), 6.93 (d, 1H), 4.28 (s, 2H), 4.23 (s, 2H), 3.97 (t, 2H), 3.68 (s, 3H), 3.61 (s, 2H), 3.16 (s, 3H), 2.78 (s, 3H), 1.82 (m, 2H), 1.03 (t, 3H).

Step C: (3-{[(3-Hydroxy-4-propoxy-benzyl)-methanesulfonyl-amino]-methyl}-phenyl)-acetic acid.
¹H NMR (400 MHz, CDCl₃) δ 7.34–7.20 (m, 4H), 6.84–6.78 (m, 3H), 4.31 (s, 2H), 4.20 (s, 2H), 3.98 (t, 2H), 3.65 (s, 2H), 2.76 (s, 3H), 1.83 (m, 2H), 1.04 (t, 3H).

EXAMPLE 145

[3-({[2-(4-Chloro-phenylsulfanyl)-ethyl]-methanesulfonyl-amino}-methyl)-phenyl]-acetic acid

MS 414 (M+).

EXAMPLE 146

(3-{[Methanesulfonyl-(4-phenethylsulfanyl-benzyl)-amino]-methyl}phenyl)-acetic acid
Step A: (3-{[(4-Phenethylsulfanyl-benzyl)-amino]-methyl}-phenyl)-acetic Acid Methyl Ester.
¹H NMR (400 MHz, CDCl₃) δ 7.16–7.33 (m, 13H), 3.78 (d, 4H), 3.68 (s, 3H), 3.61 (s, 2H), 3.12–3.16 (m, 2H), 2.89–2.93 (m, 2H); MS 406 (M+1).
Step B: (3-{[Methanesulfonyl-(4-phenethylsulfanyl-benzyl)-amino]-methyl}-phenyl)-acetic Acid Methyl Ester.
¹H NMR (400 MHz, CDCl₃) 67 7.18–7.31 (m, 13H), 4.30 (d, 4H), 3.69 (s, 3H), 3.61 (s, 2H), 3.13–3.19 (m, 2H), 2.84–2.94 (m, 2H), 2.78 (s, 3H); MS 505 (M+22).
Step C: (3-{[Methanesulfonyl-(4-phenethylsulfanyl-benzyl)-amino3-methyl}-phenyl]-acetic acid.
¹H NMR (400 MHz, CDCl₃) δ 7.13–7.29 (m, 13H), 4.27 (d, 4H), 3.61 (s, 2H), 3.12–3.16 (m, 2H), 2.88–2.92 (m, 2H), 2.76 (s, 3H); MS 468 (M−1).

EXAMPLE 147

[3-({[3-(3,5-Dichloro-phenoxy)-benzyl]-methanesulfonyl-amino}-methyl)-phenyl]-acetic acid
Step A: [-{[3-(3,5-Dichloro-phenoxy)-benzyl-amino}-methyl]-phenyl]-acetic acid Methyl Ester.
¹H NMR (400 MHz, CDCl₃) δ 7.21–7.33 (m, 4H), 7.15 (d, 2H), 7.03–7.04 (m, 2H), 6.88–6.90 (m, 1H), 6.84 (s, 2H), 3.78 (d, 4H), 3.66 (s, 3H), 3.59 (s, 2H), 1.82 (bs, 1H).
Step B: [3-({[3-(3,5-Dichloro-phenoxy)-benzyl]-methanesulfonyl-amino}-methyl)-phenyl]-acetic Acid Methyl Ester.
¹H NMR (400 MHz, CDCl₃) δ 6.81–7.17 (m, 11H), 4.31 (d, 4H), 3.65 (s, 3H), 3.58 (s, 2H), 2.80 (s, 3H).
Step C: [3-({[3-(3,5-Dichloro-phenoxy)-benzyl]-methanesulfonyl-amino}-methyl)-phenyl]-acetic acid.
¹H NMR (400 MHz, CDCl₃) δ 7.07–7.35 (m, 8H), 6.92–6.93 (m, 2H), 6.82 (s, 1H), 4.32 (d, 4H), 3.62 (s, 2H), 2.81 (s, 3H).

EXAMPLE 148

(3-{[Methanesulfonyl-(4-pyrimidin-2-yl-benzyl)-amino]-methyl}-phenyl)-acetic acid
Step A: (3-{[(4-Pyrimidin-2-yl-benzyl)-amino]-methyl}-phenyl)-acetic Acid Methyl Ester.
¹H NMR (400 MHz, CDCl₃) δ 8.77 (d, 2H), 8.37 (d, 2H), 7.44 (d, 2H), 7.23–7.29 (m, 3H), 7.14–7.16 (m, 2H), 3.86 (s, 2H), 3.79 (s, 2H), 3.66 (s, 2H), 3.60 (s, 2H); MS 348 (M+1).
Step B: (3-{[Methanesulfonyl-(4-pyrimidin-2-yl-benzyl)-amino]-methyl}-phenyl)-acetic Acid Methyl Ester.
¹H NMR (400 MHz, CDCl₃) δ 8.83 (s, 2H), 8.43 (s, 2H), 7.44–7.49 (m, 2H), 7.23–7.33 (m, 5H), 4.37–4.41 (m, 4H), 3.71 (s, 3H), 3.61–3.68 (m, 2H), 2.82 (s, 3H); MS 426 (M+1).
Step C: (3-{[Methanesulfonyl-(4-pyrimidin-2-yl-benzyl)-amino]-methyl}-phenyl)-acetic acid.
¹H NMR (400 MHz, CDCl₃) δ 8.82 (d, 2H) 8.15 (d, 2H), 7.30 (d, 2H), 7.24–7.27 (m, 3H), 7.15–7.17 (m, 1H), 7.03 (s, 1H), 4.42 (s, 2H), 4.37 (s, 2H), 3.52 (s, 2H), 2.90 (s, 3H).

EXAMPLE 149

(3-{[Methanesulfonyl-(4-thiazol-2-yl-benzyl)-amino]-methyl}-phenyl)-acetic acid
Step A: (3-{[(4-Thiazol-2-yl-benzyl)-amino]-methyl}-phenyl)-acetic Acid Methyl Ester.
¹H NMR (400 MHz, CDCl₃) δ 7.82–7.91 (m, 3H), 7.38–7.40 (m, 2H), 7.22–7.29 (m, 4H), 7.14–7.16 (m, 1H), 3.82 (s, 2H), 3.78 (s, 2H), 3.66 (s, 3H), 3.59 (s, 2H); MS 353 (M+1).
Step B: (3-{[Methanesulfonyl-(4-thiazol-2-yl-benzyl)-amino]-methyl}-phenyl)-acetic Acid Methyl Ester.
¹H NMR (400 MHz, CDCl₃) δ 7.92 (d, 2H), 7.84 (d, 1H), 7.17–7.37 (m, 7H), 4.33 (d, 4H), 3.67 (s, 3H), 3.59 (s, 2H), 2.80 (s, 3H); MS 431 (M+1).
Step C: (3-{[Methanesulfonyl-(4-thiazol-2-yl-benzyl)-amino]-methyl}-phenyl)-acetic acid.
¹H NMR (400 MHz, CDCl₃) δ 6.98–7.85 (m, 10H), 4.30–4.40 (d, 4H), 3.45 (s, 2H), 2.82 (s, 3H); MS 415 (M−1).

EXAMPLE 150

(3-{[(4-Benzyl-3-hydroxy-benzyl)-methanesulfonyl-amino]-methyl}-phenyl)-acetic acid
Step A: (3-{[(4-Benzyl-3-hydroxy-benzyl)-amino]-methyl}-phenyl)-acetic Acid Methyl Ester.
¹H NMR (400 MHz, CDCl₃) δ 7.24–7.43 (m, 11H), 7.16 (d, 1H), 6.93 (d, 2H), 3.78 (s, 2H), 3.74 (s, 2H), 3.68 (s, 3H), 3.61 (s, 2H); MS 376 (M+1).
Step B: (3-{[(4-Benzyl-3-hydroxy-benzyl)-methanesulfonyl-amino]-methyl}-phenyl)-acetic Acid Methyl Ester.
¹H NMR (400 MHz, CDCl₃) δ 7.20–7.43 (m, 12H), 6.94 (d, 2H), 4.30 (s, 2H), 4.26 (s, 2H), 3.69 (s, 3H), 3.62 (s, 2H), 2.75 (s, 3H); MS 475 (M+22).
Step C: (3-{[(4-Benzyl-3-hydroxy-benzyl)-methanesulfonyl-amino]-methyl}-phenyl)-acetic acid.
¹H NMR (400 MHz, CDCl₃) δ 7.20–7.43 (m, 12H), 6.93 (d, 2H), 4.29 (s, 2H), 4.25 (s, 2H), 3.64 (s, 2H), 2.74 (s, 3H); MS 438 (M−1).

EXAMPLE 151

(3-{[Methanesulfonyl-(4-pyrazin-2-yl-benzyl)-amino]-methyl}-phenyl)-acetic acid
Step A: (3-{[(4-Pyrazin-2-yl-benzyl)-amino]-methyl}-phenyl)-acetic Acid Methyl Ester.
¹H NMR (400 MHz, CDCl₃) δ 9.00 (s, 1H), 8.60 (s, 1H), 7.96–7.98 (m, 2H), 7.46–7.48 (m, 2H), 7.11–7.30 (m, 4H), 3.77–3.88 (m, 4H), 3.58–3.69 (m, 5H); MS 348 (M+1).
Step B: (3-{[Methanesulfonyl-(4-pyrazin-2-yl-benzyl)-amino]-methyl}-phenyl)-acetic Acid Methyl Ester.
¹H NMR (400 MHz, CDCl₃) δ 9.03 (s, 1H), 8.63–8.64 (m, 1H), 8.52 (d, 1H), 8.00 (d, 2H), 7.46 (d, 2H), 7.21–7.34 (m, 4H), 4.41 (s, 2H), 4.36 (s, 2H), 3.70 (s, 3H), 3.62 (s, 2H), 2.83 (s, 3H); MS 426 (M+1).
Step C: (3-{[Methanesulfonyl-(4-pyrazin-2-yl-benzyl)-amino]-methyl}-phenyl)-acetic acid.
¹H NMR (400 MHz, CDCl₃) δ 8.96 (s, 1H), 8.61–8.62 (m, 1H), 8.56–8.57 (m, 1H), 7.78 (d, 2H), 7.34 (d, 2H), 7.16–7.30 (m, 3H), 7.05 (s, 1H), 4.42 (s, 2H), 4.38 (s, 2H), 3.52 (s, 2H), 2.91 (s, 3H); MS 410 (M−1).

EXAMPLE 152

(3-{[Methanesulfonyl-(4-phenoxy-benzyl)-amino]-methyl}-phenyl)-acetic acid

Step A: (3-{[(4-Phenoxy-benzyl)-amino]-methyl}-phenyl)-acetic Acid Methyl Ester.
$^1$H NMR (400 MHz, CDCl$_3$) δ 7.20–7.34 (m, 7H), 7.17–7.19 (m, 2H), 7.06–7.11 (m, 2H), 6.96–7.00 (m, 4H), 3.79 (d, 4H), 3.69 (s, 3H), 3.63 (s, 2H); MS 362 (M+1).

Step B: (3-{[Methanesulfonyl-(4-phenoxy-benzyl)-amino]-methyl}-phenyl)-acetic acid Methyl Ester.
$^1$H NMR (400 MHz, CDCl$_3$) δ 7.20–7.37 (m, 9H), 7.12 (t, 1H), 6.95–7.01 (m, 3H), 4.32 (d, 4H), 3.69 (s, 3H), 3.62 (s, 2H), 2.79 (s, 3H); 457 (M+18).

Step C: (3-{[Methanesulfonyl-(4-phenoxy-benzyl)-amino]-methyl}-phenyl)-acetic acid.
$^1$H NMR (400 MHz, CDCl$_3$) δ 7.22–7.36 (m, 9H), 7.12 (t, 1H), 6.94–7.01 (m, 3H), 4.32 (d, 4H), 3.65 (s, 2H), 2.79 (s, 3H); MS 424 (M−1).

EXAMPLE 153

[3-({Methanesulfonyl-[4-(4-methyl-[1,2,3]triazol-1-yl)-benzyl]-amino}-methyl)-phenyl]-acetic acid Step A: [3-({[4-(4-Methyl-[1,2,3]triazol-1-yl)-benzyl]-amino}-methyl)-phenyl]-acetic Acid Methyl Ester.
$^1$H NMR (400 MHz, CDCl$_3$) δ 7.55 (d, 2H), 7.33 (d, 2H), 7.16–7.30 (m, 4H), 3.84 (t, 2H), 3.77 (s, 4H), 3.68 (s, 3H), 3.61 (s, 2H), 2.59 (t, 2H), 2.31 (bs, 1H), 2.14 (t, 2H); MS 353 (MH+).

Step B: [3-({Methanesulfonyl-[4-(4-methyl-[1,2,3triazol-1-yl)-benzyl]-amino}-methyl)-phenyl]-acetic Acid Methyl Ester.
$^1$H NMR (400 MHz, CDCl$_3$) δ 7.61 (d, 2H), 7.20-7.33 (m, 6H), 4.30 (s, 4H), 3.86 (t, 2H), 3.69 (s, 3H), 3.62 (s, 2H), 2.77 (s, 3H), 2.61 (t, 2H), 2.17 (t, 2H).

Step C: [3-({Methanesulfonyl-[4-(4-methyl-[1,2,3]triazol-1-yl)-benzy]-amino}-methyl)-phenyl]-acetic acid.
$^1$H NMR (400 MHz, CDCl$_3$) δ 7.43 (d, 2H), 7.14–7.31 (m, 5H), 7.05 (s, 1H), 4.28 (d, 4H), 3.82 (t, 2H), 3.50 (s, 2H), 2.82 (s, 3H), 2.60 (t, 2H), 2.13 (t, 2H).

EXAMPLE 154

[3-({Methanesulfonyl-[4-(2-oxo-pyrrolidin-1-yl)-benzyl]-amino}-methyl)-phenyl]-acetic acid Step A: [3-({[4-(2-Oxo-pyrrolidin-1-yl)-benzyl]-amino}-methyl)-phenyl]-acetic acid Methyl Ester.
$^1$H NMR (400 MHz, CDCl$_3$) δ 7.63–7.68 (m, 1H), 7.52–7.58 (m, 2H), 7.41–7.47 (m, 2H), 7.17–7.36 (m, 4H), 3.90 (s, 2H), 3.83 (s, 2H), 3.69 (s, 3H), 3.63 (s, 2H), 2.34 (s, 3H); MS 351 (MH+).

Step B: [3-({Methanesulfonyl-[4-(2-oxo-pyrrolidin-1-yl)-benzyl]-amino}-methyl)-phenyl]-acetic Acid Methyl Ester.
$^1$H NMR (400 MHz, CDCl$_3$) δ 7.57 (s, 1H), 7.41–7.48 (m, 4H), 7.25–7.30 (m, 1H), 7.17–7.20 (m, 3H), 4.36 (s, 2H), 4.14 (s, 2H), 3.68 (s, 3H), 3.61 (s, 2H), 2.86 (s, 3H), 2.33 (s, 3H).

Step C: [3-({Methanesulfonyl-[4-(2-oxo-pyrrolidin-1-yl)-benzyl]-amino}-methyl)-phenyl]-acetic acid.
$^1$H NMR (400 MHz, CDCl$_3$) δ 7.58 (s, 1H), 7.13–7.39 (m, 8H), 4.40 (s, 2H), 4.37 (s, 2H), 3.56 (s, 2H), 2.91 (s, 3H), 2.29 (s, 3H).

EXAMPLE 155

5-{3-[(2,3-Dihydro-benzo[1,4]dioxin-6-ylmethyl)-methanesulfonyl-amino]-propyl}-thiophene-2-carboxylic acid Step A: 5-{3-[(2,3-Dihydro-benzo[1,4]dioxin-6-ylmethyl)-amino]-propyl}-thiophene-2-carboxylic Acid Methyl Ester.
In Step A, triethylamine was replaced by N,N-diisopropylethylamine. MS 348(M+1).

Step B: 5-{3-[(2,3-Dihydro-benzo[1,4]dioxin-6-ylmethyl)-methanesulfonyl-amino]-propyl}-thiophene-2-carboxylic Acid Methyl Ester.
MS 443 (M+18).

Step C: 5-{3-](2,3-Dihydro-benzo[1,4]dioxin-6-ylmethyl)-methanesulfonyl-amino]-propyl}-thiophene-2-carboxylic acid.
$^1$H NMR (400 MHz, CDCl$_3$) δ 7.70 (d, 1H, J=3.8), 6.50–6.80 (m, 4H), 4.40 (s, 2H), 3.23 (m, 2H), 2.80 (m, 2H), 1.70 (m, 2H,); MS 400 (M+1), 398 (M−1).

EXAMPLE 156

(3-{[(4-Ethoxy-benzyl)-methanesulfonyl-amino]-methyl}-phenyl)-acetic acid $^1$H NMR (400 MHz, CDCl$_3$) δ 7.16–7.31 (m, 6H), 6.83 (d, 2H), 4.27 (s, 2H), 4.22 (s, 2H), 3.99 (q, 2H), 3.62 (s, 2H), 2.71 (s, 3H), 1.38 (t, 3H); 376 (M−1).

EXAMPLE 157

(3-{[(4-Dimethylamino-benzyl)-methanesulfonyl-amino]-methyl}-phenyl)-acetic acid $^1$H NMR (400 MHz, CDCl$_3$) δ 7.14–7.37 (m, 6H), 6.66 (d, 2H), 4.27 (s, 2H), 4.19 (s, 2H), 3.61 (s, 2H), 2.91 (s, 6H), 2.69 (s, 3H); 375 (M−1).

EXAMPLE 158

(3-{[(4-Cyclohexyl-benzyl)-methanesulfonyl-amino]-methyl}-phenyl)-acetic acid $^1$H NMR (400 MHz, CDCl$_3$) δ 7.32–7.16 (m, 8H), 4.31 (s, 2H), 4.28 (s, 2H), 3.64 (s, 2H), 2.75 (s, 3H), 2.48 (m, 1H), 1.83 (m, 5H), 1.38 (m, 5H).

EXAMPLE 159

5-{3-[(4-Dimethylamino-benzyl)-methanesulfonyl-amino]-propyl}-thiophene-2-carboxylic acid Step A: 5-[3-(4-Dimethylamino-benzylamino)-propyl]-thiophene-2-carboxylic acid Methyl Ester.
The title compound of Step A was prepared following the procedure described in Step A of Example 141 except triethylamine was replaced with N,N-diisopropylethylamine.

Step B: 5-{3-[(4-Dimethylamino-benzyl)-methanesulfonyl-amino]-propyl}-thiophene-2-carboxylic Acid Methyl Ester. MS 411 (M+1).

Step C: 5-{3-[(4-Dimethylamino-benzyl)-methanesulfonyl-amino]-propyl}-thiophene-2-carboxylic acid.
$^1$H NMR (400 MHz, CDCl$_3$) δ 7.70 (d,1H), 7.15 (d, 2H), 6.72 (m, 3H), 4.43 (s, 2H), 3.22 (m, 2H), 2.95 (s, 6H), 2.85 (m, 2H), 2.80 (s, 3H), 1,82 (m, 2H); MS 395 (M−1).

EXAMPLE 160

(3-{[Methanesulfonyl-(4-pentyl-benzyl)-amino]-methyl}-phenyl)-acetic acid

Step A: {3-[(4-Pentyl-benzylamino)-methyl]-phenyl}-acetic Acid Methyl Ester.
$^1$H NMR (400 MHz, CDCl$_3$) δ 7.29–7.12 (m, 8H), 3.78 (s, 2H), 3.76 (s, 2H), 3.68 (s, 3H), 3.61 (s, 2H), 2.57 (t, 2H), 1.59 (t, 2H), 1.59 (t, 2H), 1.31 (m, 4H), 0.88 (t, 3H); MS 340 (M+1).

Step B: (3-{[Methanesulfonyl-(4-pentyl-benzyl)-amino]-methyl}-phenyl)-acetic acid Methyl Ester.
$^1$H NMR (400 MHz, CDCl$_3$) δ 7.32–7.14 (m, 8H), 4.31 (s, 2H), 4.29 (s, 2H), 3.69 (s, 3H), 3.62 (s, 2H), 2.75 (s, 3H), 2.59 (t, 2H), 1.59 (m, 2H), 1.31 (m, 4H), 0.88 (t, 3H).
Step C: (3-{[Methanesulfonyl-(4-pentyl-benzyl)-amino]-methyl}-phenyl)-acetic acid.
$^1$H NMR (400 MHz, CDCl$_3$) δ 7.34–7.13 (m, 8H), 4.31 (s, 2H), 4.28 (s, 2H), 3.66 (s, 2H), 2.75 (s, 3H), 2.58 (t, 2H), 1.59 (m, 4H), 1.31 (m, 4H), 0.88 (t, 3H); MS 402 (M−1).

EXAMPLE 161

(3-{[(4-Isopropoxy-benzyl)-methanesulfonyl-amino]-methyl}-phenyl)-acetic acid

Step A: {3-[(4-Isopropoxy-benzylamino)-methyl]-phenyl}-acetic Acid Methyl Ester.
$^1$H NMR (400 MHz, CDCl$_3$) δ 7.29–7.15 (m, 6H), 6.84 (d, 2H), 4.52 (m, 1H), 3.78 (s, 2H), 3.72 (s, 2H), 3.68 (s, 3H), 3.61 (s, 2H), 1.32 (d, 6H).
Step B: (3-{[(4-lsopropoxy-benzyl)-methanesulfonyl-amino]-methyl}-phenyl)-acetic Acid Methyl Ester.
$^1$H NMR (400 MHz, CDCl$_3$) δ 7.32–7.19 (m, 6H), 6.84 (d, 2H), 4.53 (m, 1H), 4.30 (s, 2H), 4.25 (s, 2H), 3.69 (s, 3H), 3.66 (s, 2H), 3.62 (s, 2H), 2.75 (s, 3H), 1.32 (d, 6H).
Step C: (3-{[(4-lsopropoxy-benzyl)-methanesulfonyl-amino -methyl}-phenyl)-acetic acid.
$^1$H NMR (400 MHz, CDCl$_3$) δ 7.33–7.17 (m, 6H), 6.83 (d, 2H), 4.52 (m, 1H), 4.29 (s, 2H), 4.24 (s, 2H), 3.65 (s, 2H), 2.74 (s, 3H), 1.32 (d, 6H); MS 390 (M−1).

EXAMPLE 162

(3-{[Methanesulfonyl-(4-pyrimidin-5-yl-benzyl)-amino]-methyl}-phenyl)-acetic acid Step A: {3-[(4-Pyrimidin-5-yl-benzylamino)-methyl]-phenyl}-acetic acid.
$^1$H NMR (400 MHz, CDCl$_3$) δ 9.19 (s, 1H), 8.95 (s, 2H), 7.52 (m, 4H), 7.32–7.15 (m, 4H), 3.88 (s, 2H), 3.82 (s, 2H), 3.69 (s, 3H), 3.63 (s, 2H).
Step B: (3-{[Methanesulfonyl-(4-pyrimidin-5-yl-benzyl)-amino]-methyl}-phenyl)-acetic Acid Methyl Ester.
MS 425 (M+).
Step C: (3-{[Methanesulfonyl-(4-pyrimidin-5-yl-benzyl)-amino]-methyl}-phenyl)-acetic acid.
$^1$H NMR (400 MHz, CDCl$_3$) δ 9.20 (s, 1H), 8.95 (s, 2H), 7.52 (d, 2H), 7.43 (d, 2H), 7.34–7.15 (m, 4H), 4.41 (s, 2H), 4.37 (s, 2H), 3.65 (s, 2H), 2.86 (s, 3H); MS 410 (M−1).

EXAMPLE 163

(3-{[Methanesulfonyl-(4-methyl-benzyl)-amino]-methyl}-phenyl)-acetic acid

Step A: Reductive Amination
(3-{[(4-Methyl-benzyl)-amino]-methyl}-phenyl)-acetic Acid Ethyl Ester.
A solution of 4-methylbenzylamine (0.097 mL, 0.76 mmol) and (3-formyl-phenyl)-acetic Acid ethyl ester (138 mg, 0.72 mmol) in MeOH (2 mL) was stirred for 3 h at room temperature. The reaction was cooled to 0° C. and NaBH$_4$ (43 mg, 1.15 mmol) was added. After stirring at room temperature for 10 minutes, a 1:1 mixture of saturated aqueous NaHCO$_3$:H$_2$O was added. The product was extracted into CH$_2$Cl$_2$ (3×) and the organic solution was dried over MgSO$_4$, filtered, and concentrated to yield the title compound (231 mg). $^1$H NMR (400 MHz, CDCl$_3$) δ 7.13–7.30 (m, 8H), 4.14 (q, 2H), 3.83 (d, 4H), 3.78 (s, 2H), 2.34 (s, 3H), 1.25 (t, 3H); MS 298 (M+1).

Step B: Sulfonamide Formation
(3-{[Methanesulfonyl-(4-methyl-benzyl)-amino]-methyl}-phenyl)-acetic Acid Ethyl Ester.
To a solution of (3-{[(4-methyl-benzyl)-amino]-methyl}-phenyl)-acetic Acid ethyl ester (119 mg, 0.401 mmol) and triethylamine (0.61 mL, 0.726 mmol) in CH$_2$Cl$_2$ (2 mL) at 0° C. was added methanesulfonyl chloride (0.031 mL, 0.405 mmol). The reaction was stirred at room temperature for 2.5 h and 1N HCl was added. The product was extracted into CH$_2$Cl$_2$ (3×). The organic solution was dried over MgSO$_4$, filtered, and concentrated in vacuo. The product was purified by medium pressure chromatography (3:1 hexanes:EtOAc) to provide the title compound (101.4 mg). $^1$H NMR (400 MHz, CDCl$_3$) δ 7.13–7.36 (m, 8H), 4.27–4.30 (m, 4H), 4.14 (q, 2H), 3.60 (s, 2H), 2.74 (s, 3H), 2.33 (s, 3H); MS 376 (M+1).

Step C: Ester Hydrolysis
Step C: (3-{[Methanesulfonyl-(4-methyl-benzyl)-amino]-methyl}-phenyl)-acetic acid.
To a solution of (3-{[methanesulfonyl-(4-methyl-benzyl)-amino)-methyl}-phenyl)-acetic Acid ethyl ester (101.4 mg, 0.27 mmol) in MeOH (3 mL) was added aqueous NaOH (2N, 0.4 mL). The reaction was stirred at room temperature for 1 h and was diluted with a 1:1 mixture of 1N HCl and water. The product was extracted into CH$_2$Cl$_2$ (3×) and the organic solution was dried over MgSO$_4$, filtered, and concentrated to provide the title compound (87 mg). $^1$H NMR (400 MHz, CDCl$_3$) δ 7.13–7.34 (m, 8H), 4.28 (d, 4H), 3.65 (s, 2H), 2.75 (s, 3H), 2.33 (s, 2H); MS 346 (M−1).

EXAMPLE 164–170

Examples 164–170 were prepared in an analogous manner to Example 163 starting with the appropriate aldehyde and amine reagents in Step A followed by formation of the desired sulfonamide in Step B and ester hydrolysis in Step C.

EXAMPLE 164

(3-{[(4-tert-Butyl-benzyl)-methanesulfonyl-amino]-methyl}-phenyl)-acetic acid

Step A: {3-[(4-tert-Butyl-benzylamino)-methyl]-phenyl}-acetic Acid Ethyl Ester.
$^1$H NMR (400 MHz, CDCl$_3$) δ 7.32–7.34 (m, 2H), 7.24–7.27 (m, 5H), 7.15–7.16 (m, 1H), 4.13 (q, 2H), 3.77 (d, 4H), 3.59 (s, 2H), 1.30 (s, 9H), 1.21–1.26 (m, 3H); MS 340 (M$^+$+1).
Step B: (3-{[(4-tert-Butyl-benzyl)-methanesulfonyl-amino]-methyl}-phenyl)-acetic acid Ethyl Ester.
$^1$H NMR (400 MHz, CDCl$_3$) δ 7.20–7.37 (m, 8H), 4.30 (d, 4H), 4.14 (q, 2H), 3.60 (s, 2H), 2.76 (s, 3H), 1.31 (s, 9H), 1.25 (t, 3H).
Step C: (3-{[(4-tert-Butyl-benzyl)-methanesulfonyl-amino]-methyl}-phenyl)-acetic acid. $^1$H NMR (400 MHz, CDCl$_3$) δ 7.20–7.36 (m, 8H), 4.31 (s, 2H), 4.28 (s, 2H), 3.64 (s, 2H), 2.75 (s, 3H), 1.30 (s, 9H); MS 388 (M$^+$−1).

EXAMPLE 165

(3-{[(4-tert-Butyl-benzyl)-methanesulfonyl-amino]-methyl}-phenoxy)-acetic acid

Step A: {3-[(4-tert-Butyl-benzylamino)-methyl]-phenoxy}-acetic Acid Methyl Ester.
Step B: (3-{[(4-tert-Butyl-benzyl)-methanesulfonyl-amino]-methyl}-phenoxy)-acetic Acid Methyl Ester.
Step C: (3-{[(4-tert-Butyl-benzyl)-methanesulfonyl-amino]-methyl}-phenoxy)-acetic acid.

¹H NMR (400 MHz, CDCl₃) δ 7.20–7.36 (m, 5H), 6.84–6.95 (m, 3H), 4.66 (s, 2H), 4.30 (s, 4H), 2.77 (s, 3H), 1.30 (s, 9H); MS 404 (M–1).

EXAMPLE 166

(3-{[Methanesulfonyl-(4-trifluoromethoxy-benzyl)-amino]-methyl}-phenyl)-acetic acid Step A: (3-{[(4-Trifluoromethoxy-benzyl)-amino]-methyl}-phenyl)-acetic Acid Ethyl Ester.

¹H NMR (400 MHz, CDCl₃) δ 7.34–7.36 (m, 2H), 7.14–7.16 (m, 3H), 7.21–7.32 (m, 3H), 4.10–4.16 (m, 2H), 3.77 (d, 4H), 3.60 (s, 2H), 1.21–1.25 (m, 3H); MS 368 (M+1).

Step B: (3-{([Methanesulfonyl-(4-trifluoromethoxy-benzyl)-amino]-methyl}-phenyl)-acetic Acid Ethyl Ester.

¹H NMR (400 MHz, CDCl₃) δ 7.15–7.33 (m, 8H), 4.31 (d, 4H), 4.14 (q, 2H), 3.58 (s, 2H), 2.81 (s, 3H), 1.25 (t, 3H); MS 446 (M+1).

Step C: (3-{[Methanesulfonyl-(4-trifluoromethoxy-benzyl)-amino]-methyl}-phenyl)-acetic acid.

¹H NMR (400 MHz, CDCl₃) δ 7.10–7.32 (m, 8H), 4.30 (s, 4H), 3.62 (s, 2H), 2.80 (s, 3H); MS 416 (M–1).

EXAMPLE 167

[3-({[3-(4-Chloro-phenyl)-propyl]-methanesulfonyl-amino}-methyl)-phenyl]-acetic acid Step A: [3-({[3-(4-Chloro-phenyl)-propyl]-amino}-methyl)-phenyl]-acetic Acid Ethyl Ester Step B: [3-({3–4-Chloro-phenyl)-propyl]-methanesulfonyl-amino}-methyl)-phenyl]-acetic Acid Ethyl Ester.

¹H NMR (400 MHz, CDCl₃) δ 7.18–7.31 (m, 6H), 6.95 (d, 2H), 4.34 (s, 2H), 4.11 (q, 2H), 3.59 (s, 2H), 3.13–3.19 (m, 2H), 2.80 (s, 3H), 2.49 (t, 2H), 1.74–1.82 (m, 2H), 1.23 (t, 3H); MS 424 (M+1).

Step C: (3-({[3-(4-Chloro-phenyl)-propyl]-methanesulfonyl-amino}-methyl)-phenyl]-acetic acid.

MS 393.9 (M–1).

EXAMPLE 168

(3-{[Methanesulfonyl-(3-trifluoromethoxy-benyl)-amino]-methyl}-phenyl)-acetic acid Step A: (3-{[(3-Trifluoromethoxy-benzyl)-amino]-methyl}-phenyl)-acetic Acid Ethyl Ester Step B: (3-{[Methanesulfonyl-(3-trifluoromethoxy-benzyl)-amino]-methyl}-phenyl)-acetic Acid Ethyl Ester.

¹H NMR (400 MHz, CDCl₃) δ 7.13–7.40 (m, 8H), 4.33 (d, 4H), 4.14 (q, 2H), 3.59 (s, 2H), 2.82 (s, 3H), 1.25 (t, 3H); MS 446 (MH+).

Step C: (3-{[Methanesulfonyl-(3-trifluoromethoxy-benzyl)-amino]-methyl}-phenyl)-acetic acid.

MS 417 (M–1).

EXAMPLE 169

[3-({[2-(3-Chloro-phenylsulfanyl)-ethyl]-methanesulfonyl-amino}-methyl)-phenyl]-acetic acid ¹H NMR (400 MHz, CDCl₃) δ 6.98–7.37 (m, 8H), 4.32 (s, 2H), 3.60 (s, 2H), 3.28 (m, 2H), 2.81–2.93 (m, 5H); 412 (M–1).

EXAMPLE 170

[3-({[4-(2-Benzo[1,3]dioxol-5-yl-vinyl)-benzyl]-methanesulfonyl-amino}-methyl)-phenyl]-acetic acid

MS 478 (M–1).

EXAMPLE 171

(3-{[Methanesulfonyl-(4-thiazol-2-yl-benzyl)-amino]-methyl}-phenoxy)-acetic acid Step A: Reductive Amination
{3-[(4-Thiazol-2-yl-benzylamino)-methyl]-phenoxy}-acetic Acid Tert-butyl Ester.

A solution of (3-aminomethyl-phenoxy)-acetic Acid tert-butyl ester (0.14 g, 0.59 mmol) and 4-thiazol-2-yl-benzaldehyde (0.105 g, 0.55 mmol) in 2 mL MeOH was stirred at room temperature for 1.5 hours. After cooling to 0° C., NaBH₄ (0.033 g, 0.88 mmol) was added and the reaction was stirred for 10 minutes. The mixture was quenched with aqueous saturated NaHCO₃:H₂O (1:1) and the MeOH was removed in vacuo. The product was extracted into CH₂Cl₂ and the organic solution was dried over MgSO₄, filtered, and concentrated in vacuo to afford a brown oil. The product was purified via flash chromatography on silica gel (614 EtOAc/Hexanes) to afford the title compound of Step A (0.140 g). ¹H NMR (400 MHz, CDCl₃) δ 7.91 (d, 2H), 7.82 (s, 1H), 7.40 (d, 2H), 7.23–7.38 (m, 2H), 6.94 (m, 2H), 6.78 (d, 1H), 4.49 (s, 2H), 3.80 (s, 2H), 3.76 (s, 2H), 1.45 (s, 9H); MS 411 (M+1).

Step B: Sulfonamide Formation
(3-{[Methanesulfonyl-(4-thiazol-2-yl-benzyl)-amino]-methyl}-phenoxy)-acetic Acid Tert-butyl Ester.

A solution of ({3-[(4-thiazol-2-yl-benzylamino)-methyl]-phenoxy}-acetic Acid tert-butyl ester (0.045 g, 0.109 mmol), triethylamine (16.8 mL, 0.120 mmol) and methanesulfonyl chloride (8.6 ml, 0.11 mmol) in 2 mL CH₂Cl₂ was stirred at room temperature for 2 hours. The reaction was quenched with water. The aqueous solution was washed with CH₂Cl₂ and the organic solution was dried over Na₂SO₄, filtered, and concentrated. The product was purified via flash chromatography on silica gel (1/1 EtOAc/Hexanes) to afford the title compound of Step B as a clear oil. ¹H NMR (400 MHz, CDCl₃) δ 7.97 (d, 2H), 7.85 (s, 1H), 7.35 (m, 3H), 7.32 (m, 1H), 6.80–6.90 (m, 3H), 4.48 (s, 2H), 4.36 (s, 2H), 4.29 (s, 2H), 2.79 (s, 3H), 1.47 (s, 9H); MS 489 (M+1).

Step C: Ester Hydrolysis
(3-{[Methanesulfonyl-(4-thiazol-2-yl-benzyl)-amino]-methyl}-phenoxy)-acetic acid.

A solution of (3-{[methanesulfonyl-(4-thiazol-2-yl-benzyl)-amino]-methyl}-phenoxy)-acetic Acid Tert-butyl Ester (0.074 g) in 2 mL CH₂Cl₂ was cooled to 0° C. and 2 mL trifluoroacetic Acid was added. The reaction was stirred at room temperature for 2 hours. The solvent was removed by evaporation azeotroping with CH₂Cl₂ to afford the title compound (40 mg). ¹H NMR (400 MHz, CDCl₃) δ 9.94 (bs, 1H), 8.14 (s, 1H), 7.81 (d, 2H), 7.55 (s, 1H), 7.37 (d, 2H), 7.18 (m, 1H), 6.90 (d, 1H), 6.80 (d, 1H), 6.63 (s, 1H), 4.58 (s, 2H), 4.35 (s, 2H), 4.29 (s, 2H), 2.93 (s, 3H); MS 431 (M–1).

EXAMPLES 172–178

Examples 172–178 were prepared in an analogous manner to Example 171 starting with the appropriate aldehyde and amine reagents in Step A followed by formation of the desired sulfonamide in Step B and ester hydrolysis in Step C.

EXAMPLE 172

(3-{[Methanesulfonyl-(4-pyridin-2-yl-benzyl)-amino]-methyl}-phenoxy)-acetic acid Hydrochloride Salt The TFA salt isolated in Step C was converted to the HCl salt by addition of 2 equivalents of 1N HCl followed by removal of water and drying in vacuo. MS 427 (M+1), 425 (M–1).

EXAMPLE 173

5-{3-[(2-Benzylsulfanyl-ethyl-methanesulfonyl-amino]-propyl}-thiophene-2-carboxylic acid Step A: 5-{3-[(2-Benzylsulfanyl-ethyl-amino]-propyl}-thiophene-2-carboxylic Acid Tert-butyl Ester.

$^1$H NMR (400 MHz, CDCl$_3$) δ 7.52 (d, 1H), 7.19–7.29 (m, 5H), 6.73 (d, 1H), 3.68 (s, 2H), 2.83 (t, 2H), 2.71 (t, 2H), 2.53–2.59 (m, 4H), 1.81 (t, 2H), 1.54 (s, 9H); MS 392 (M+1).

Step B: 5-{3-[(2-Benzylsulfanyl-ethyl)-methanesulfonyl-amino]-propyl}-thiophene-2-carboxylic Acid Tert-butyl Ester.

$^1$H NMR (400 MHz, CDCl$_3$) δ 7.52 (d, 1H), 7.22–7.30 (m, 5H), 6.74 (d, 1H), 3.71 (s, 2H), 3.23 (t, 2H), 3.06–3.15 (m, 2H), 2.77–2.82 (m, 5H), 2.58 (t, 2H), 1.54 (s, 9H); MS 470 (M+1).

Step C: 5-{3-[(2-Benzylsulfanyl-ethyl)-methanesulfonyl-amino]-propyl}-thiophene-2-carboxylic acid.

MS 412 (M−1).

EXAMPLE 174

5-(3-{[2-(Biphenyl-2-yloxy)-ethyl]-methanesulfonyl-amino}-propyl)-thiophene-2-carboxylic acid Step A: 5-(3-{[2-(Biphenyl-2-yloxy)-ethyl]-amino}-propyl)-thiophene-2-carboxylic acid Tert-butyl Ester.

$^1$H NMR (400 MHz, CDCl$_3$) δ 7.49–7.52 (m, 3H), 7.24–7.39 (m, 5H), 6.90–7.20 (m, 2H), 6.69 (d, 1H), 4.08 (t, 2H), 2.89 (t, 2H), 2.74 (t, 2H), 2.57 (t, 2H), 2.22 (bs, 1H), 1.71–1.79 (m, 2H), 1.55 (s, 9H); MS 438 (M+1).

Step B: 5-(3-{[2-(Biphenyl-2-yloxy)-ethyl]-methanesulfonyl-amino}-propyl)-thiophene-2-carboxylic Acid Tert-butyl Ester.

MS 460 (M−56).

Step C: 5-(3-{[2-(Biphenyl-2-yloxy)-ethyl]-methanesulfonyl-amino}-propyl)-thiophene-2-carboxylic acid.

MS 458 (M−1).

EXAMPLE 175

5-(3-{[3-(1H-Indol-3-yl)-propyl]-methanesulfonyl-amino}-propyl)-thiophene-2-carboxylic acid Step A: 5-(3-{[3-(1H-Indol-3-yl)-propyl]-amino}-propyl)-thiophene-2-carboxylic acid Tert-butyl Ester.

$^1$H NMR (400 MHz, CDCl$_3$) δ 8.11 (s, 1H), 7.49–7.57 (m, 2H), 7.32 (d, 1H), 7.07–7.18 (m, 2H), 6.96 (s, 1H), 6.71 (d, 1H), 2.68–2.81 (m, 8H), 1.91–2.06 (m, 4H), 1.54 (s, 9H); MS 399 (M+1).

Step B: 5-(3-{[3-(1H-Indol-3-yl)-propyl]-methanesulfonyl-amino}-propyl)-thiophene-2-carboxylic Acid Tert-butyl Ester.

$^1$H NMR (400 MHz, CDCl$_3$) δ 8.07 (bs, 1H), 7.50–7.55 (m, 2H), 7.34–7.36 (m, 1H), 7.08–7.20 (m, 2H), 6.98–6.99 (m, 1H), 6.70 (d, 1H), 3.66 (s, 2H), 3.15–3.25 (m, 4H), 3.05–3.11 (m, 1H), 2.73–2.85 (m, 6H), 1.88–2.04 (m, 4H), 1.55 (s, 9H); MS 475 (M−1).

Step C: 5-(3-{[3-(1H-Indol-3-yl)-propyl]-methanesulfonyl-amino}-propyl)-thiophene-2-carboxylic acid.

MS 419 (M−1).

EXAMPLE 176

5-{3-[(4-tert-Butyl-benzyl)-methanesulfonyl-amino]-propyl}-thiophene-2-carboxylic acid Step A: 5-{3-[(4-tert-Butyl-benzyl-amino]-propyl}-thiophene-2-carboxylic Acid Tert-butyl Ester.

$^1$H NMR (400 MHz, CDCl$_3$) δ 7.51 (d, 1H), 7.33 (d, 2H), 7.23–7.25 (m, 2H), 6.72 (d, 1H), 3.74 (s, 2H), 2.87 (t, 2H), 2.69 (t, 2H), 1.90 (t, 2H), 1.54 (s, 9H), 1.29 (s, 9H); MS 388 (M+1).

Step B: 5-{3-[(4-tert-Butyl-benzyl)-methanesulfonyl-amino]-propyl}-thiophene-2-carboxylic Acid Tert-butyl Ester.

$^1$H NMR (400 MHz, CDCl$_3$) δ 7.47–7.49 (m, 1H), 7.34-7.36 (m, 2H), 7.23–7.25 (m, 2H), 6.59 (d, 1H), 4.33 (s, 2H), 3.21 (t, 2H), 2.81 (s, 3H), 2.73 (t, 2H), 1.83 (t, 2H), 1.54 (s, 9H), 1.30 (s, 9H); MS 483 (M+18).

Step C: 5-{3-[(4-tert-Butyl-benzyl)-methanesulfonyl-amino]-propyl}-thiophene-2-carboxylic acid.

$^1$H NMR (400 MHz, CDCl$_3$) δ 7.64 (d, 1H), 7.36 (d, 1H), 7.25–7.26 (m, 2H), 6.66 (d, 1H), 4.34 (s, 2H), 3.23 (t, 2H), 2.82 (s, 3H), 2.77 (t, 2H), 1.79–1.87 (m, 2H), 1.30 (s, 9H); MS 408 (M−1).

EXAMPLE 177

5-(3-{[2-(3-Chloro-phenylsulfanyl)-ethyl]-methanesulfonyl-amino}-propyl)-thiophene-2-carboxylic acid Step A: 5-(3-{[2-(3-Chloro-phenylsulfanyl)-ethyl]-amino}-propyl)-thiophene-2-carboxylic Acid Tert-butyl Ester.

$^1$H NMR (400 MHz, CDCl$_3$) δ 7.48–7.53 (m, 1H), 7.12-7.31 (m, 4H), 6.74 (d, 1H), 3.06 (t, 2H), 2.85 (q, 4H), 2.65 (t, 2H), 1.80–1.87 (m, 2H), 1.55 (s, 9H); MS 412 (MH+).

Step B: 5-(3-{[2-(3-Chloro-phenylsulfanyl)-ethyl]-methanesulfonyl-amino}-propyl)-thiophene-2-carboxylic Acid Tert-butyl Ester.

$^1$H NMR (400 MHz, CDCl$_3$) δ 7.52 (d, 1H), 7.14–7.31 (m, 4H), 6.75 (d, 1H), 3.31–3.35 (m, 2H), 3.21 (t, 2H), 3.11–3.15 (m, 2 H), 2.82–2.87 (m, 2H), 2.82 (s, 3H), 1.94 (t, 2H), 1.54 (s, 9H); MS 508 (M+18).

Step C: 5-(3-{[2-(3-Chloro-phenylsulfanyl)-ethyl]-methanesulfonyl-amino}-propyl)-thiophene-2-carboxylic acid.

$^1$H NMR (400 MHz, CDCl$_3$) δ 7.72 (d, 1H), 7.31 (s, 1H), 7.15–7.25 (m, 3H), 6.97 (d, 1H), 3.34–3.42 (m, 2H), 3.24 (t, 2H), 3.14 (t, 2H), 2.91 (t, 2H), 2.85 (s, 3H), 1.93–2.10 (m, 2H); MS 434 (M+1).

EXAMPLE 178

(3-{[Methanesulfonyl-(4-pyridin-3-yl-benzyl)-amino]-methyl}-phenoxy)-acetic acid Step A: {3-[(4-Pyridin-3-yl-benzylamino)-methyl]-phenoxy}-acetic Acid Tert-butyl Ester.

$^1$H NMR (400 MHz, CDCl$_3$) δ 8.81 (bs, 2H), 7.59 (d, 2H), 7.47 (m, 2H), 7.41 (m, 2H), 7.22 (t, 1H), 6.94 (m, 2H), 6.78 (m, 1H), 4.50 (s, 2H), 3.82 (s, 2H), 3.78 (s, 2H), 1.45 (s, 9H); MS 405 (M+1).

Step B: (3-{[Methanesulfonyl-(4-pyridin-3-yl-benzyl)-amino]-methyl}-phenoxy-acetic Acid Tert-butyl Ester.

$^1$H NMR (400 MHz, CDCl$_3$) δ 8.83 (bs, 1H), 8.59 (m, 1H), 7.85 (m, 1H), 7.55 (m, 2H), 7.40 (d, 2H), 7.36 (m, 1H), 7.24 (m, 1H), 6.91 (d, 1H), 6.86 (m, 1H), 6.82 (dd, 1H), 4.49 (s, 2H), 4.39 (s, 2H), 4.32 (s, 2H), 2.81 (s, 3H), 1.48 (s, 9H); MS 483 (M+1).

Step C: (3-{[Methanesulfonyl-(4-pyridin-3-yl-benzyl)-amino]-methyl}-phenoxy)-acetic acid.

MS 425 (M−1).

EXAMPLE 179

5-(3-{[3-(3-Bromo-phenyl)-propyl]-methanesulfonyl-amino}-propyl)-thiophene-2-carboxylic acid Step A: Reductive Amination 5-(3-{[3-(3-Bromo-phenyl)-propyl]-amino}-propyl)-thiophene-2-carboxylic Acid Tert-butyl Ester.

The title compound was prepared from 5-(3-amino-propyl)-thiophene-2-carboxylic Acid tert-butyl ester hydrochloride and 3-(3-bromo-phenyl)-propionaldehyde following the method described in Step A of Example 141. ¹H NMR (400 MHz, CDCl₃) δ 7.50 (d, 1H), 7.28–7.30 (m, 2H), 7.06–7.14 (m, 2H), 6.75 (d, 1H), 2.85 (t, 2H), 2.65–2.78 (m, 4H), 2.60 (t, 2H), 1.92–2.04 (m, 4H), 1.52–1.54 (m, 9H); MS 438 (M+).

Step B: Sulfonamide Formation
5-(3-{[3-(3-Bromo-phenyl)-propyl]-methanesulfonyl-amino}-propyl)-thiophene-2-carboxylic Acid Tert-butyl Ester.

The title compound was prepared from 5-(3-{[3-(3-bromo-phenyl)-propyl]-amino}- propyl)-thiophene-2-carboxylic Acid tert-butyl ester using the method described in Step B of Example 141. ¹H NMR (400 MHz, CDCl₃) δ 7.52 (d, 1H), 7.30–7.32 (m, 2H), 7.07–7.16 (m, 2H), 6.74 (d, 1H), 3.15–3.20 (m, 4H), 2.84 (t, 2H), 2.80 (s, 3H), 2.59 (t, 2H), 1.85–1.98 (m, 4H), 1.54 (s, 9H); MS 533 (M+17).

Step C: Ester Hydrolysis
5-(3-{[3-(3-Bromo-phenyl)-propyl]-methanesulfonyl-amino}-propyl)-thiophene-2-carboxylic acid.

The title compound was prepared from 5-(3-{[3-(3-bromo-phenyl)-propyl]-methanesulfonyl-amino}- propyl)-thiophene-2-carboxylic Acid tert-butyl ester using the method described in Step C of Example 171. ¹H NMR (400 MHz, CDCl₃) δ 7.71 (d, 1H), 7.31–7.33 (m, 2H), 7.08–7.17 (m, 2H), 6.84 (d, 1H), 3.11–3.22 (m, 4H), 2.90 (t, 2H), 2.81 (s, 3H), 2.60 (t, 2H), 1.82–1.99 (m, 4H); MS 458 (M–1).

EXAMPLE 180

Example 180 was prepared in an analogous manner to Example 179 starting with the appropriate aldehyde and amine reagents in Step A followed by formation of the desired sulfonamide in Step B and ester hydrolysis in Step C.

EXAMPLE 180

5-(3-{(Butane-1-sulfonyl)-[3-(3-chloro-phenyl)-propyl]-amino}-propyl)-thiophene-2-carboxylic acid
Step A: 5-(3-{[3-(3-chloro-phenyl)-propyl]-amino}-propyl)-thiophene-2-carboxylic acid Tert-butyl Ester.

The title compound was prepared following the procedure described in Step A of Example 179 except diisopropylethylamine was used in place of triethylamine.
Step B: 5-(3-{(Butane-1-sulfonyl)-[3-(3-chloro-phenyl)-propyl]-amino}-propyl)-thiophene-2-carboxylic Acid Tert-butyl Ester.
MS 531 (M+18).
Step C: 5-(3-{(Butane-1-sulfonyl)-[3-(3-chloro-phenyl)-propyl]-amino}-propyl)-thiophene-2-carboxylic acid.

¹H NMR (400 MHz, CDCl₃) δ 7.72 (d, 1H, J=4.0), 7.00-7.40 (m, 4H), 6.70 (d, IH, J=4.0), 3.25 (m, 4H), 2.82 (m, 2H), 2.60 (m, 2H), 1.60–2.25 (m, 6H), 1.07 (t, 3H, J=7.0); MS 457 (M–1).

EXAMPLE 181

5-{3-[Cyclopropanecarbonyl-(2,3-dihydro-benzo[1,4]dioxin-6-ylmethyl)-amino]-propyl}- thiophene-2-carboxylic acid Step A: Reductive Amination
5-{3-[(2,3-Dihydro-benzo[1,4]dioxin-6-ylmethyl)-amino]-propyl}-thiophene-2-carboxylic Acid Methyl Ester.

Step A was performed in an analogous manner to Step A of Example 163.

Step B: Amide Formation
5-{3-[Cyclopropanecarbonyl-(2,3-dihydro-benzo[1,4]dioxin-6-ylmethyl)-amino]-propyl}- thiophene-2-carboxylic Acid Methyl Ester.

A solution of 5-{3-[(2,3-dihydro-benzo[1,4]dioxin-6-ylmethyl)-amino]-propyl}-thiophene-2-carboxylic Acid methyl ester (0.435 g, 0.125 mmol), DCC (0.0284 g 0.137 mmol) and cyclopropanecarboxylic acid (0.0119 g, 0.137 mmol) in 10 mL CH₂Cl₂ was stirred at room temperature for 16 h. The mixture was filtered and the mother liquor was concentrated in vacuo. The residue was dissolved in 15 mL EtOAc and was filtered. The organic solution was washed with water followed by brine, dried over MgSO₄, filtered, and concentrated in vacuo to afford the title compound of Step B as an oil (53 mg). MS 416 (M+).

Step C: Ester Hydrolysis
5-{3-[Cyclopropanecarbonyl-(2,3-dihydro-benzo[1,4]dioxin-6-ylmethyl)-amino]-propyl}- thiophene-2-carboxylic acid.

Step C was performed in an analogous manner to Step C of Example 141. ¹H NMR (400 MHz, CDCl₃) δ 7.70 (bs, 1H), 6.50–7.00 (m, 4H), 4.50 (s, 2H), 4.20 (bs, 4H), 3.32 (m, 2H), 2.70 (m, 2H), 1.70–1.80 (m, 2H), 1.00-0.70 (m, 4H); MS 402 (M+1), 400 (M–1).

EXAMPLES 182–184

Examples 182–184 were prepared in an analogous manner to Example 181 starting with the appropriate aldehyde and amine reagents in Step A followed by formation of the desired amide in Step B and ester hydrolysis in Step C.

EXAMPLE 182

5-[3-(Benzofuran-2-ylmethyl-cyclopropanecarbonyl-amino)-propyl]-thiophene-2-carboxylic acid ¹H NMR (400 MHz, CDCl₃) δ 7.70 (bs, 1H), 7.00–7.60 (m, 4H), 6.60–6.95 (m, 2H), 4.60 (s, 2H), 3.20 (m, 2H), 2.70 (m, 2H), 1.80 (m, 2H), 1.00–0.70 (m, 4H); MS 384 (M+1), 382 (M–1).

EXAMPLE 183

5-(3-{[3-(3-Chloro-phenyl)-propyl]-propionyl-amino}-propyl)-thiophene-2-carboxylic acid ¹H NMR (400 MHz, CDCl₃) δ 7.74 (d, 1H), 7.30–7.00 (m, 4H), 6.73 (d, 1H), 3.20 (m, 4H), 2.92 (m, 2H), 2.71 (m, 2H), 2.20 (m, 2H), 1.89–1.70 (m, 4H), 1.20 (t, 3H); MS 392 (M–1).

EXAMPLE 184

5-(3-{Acetyl-[3-(3-chloro-phenyl)-propyl]-amino}-propyl)-thiophene-2-carboxylic acid
Step A: 5-(3-{[3-(3-Chloro-phenyl)-propyl]-amino}-propyl)-thiophene-2-carboxylic acid Methyl Ester.
MS 352 (M+1).
Step B: 5-(3-{Acetyl-[3-(3-chloro-phenyl)-propyl]-amino}-propyl)-thiophene-2-carboxylic Acid Methyl Ester.
MS 394 (M+1).
Step C: 5-(3-{Acetyl-[3-(3-chloro-phenyl)-propyl]-amino}-propyl)-thiophene-2-carboxylic acid.

¹H NMR (400 MHz, CDCl₃) δ 7.70 (d, 1H, J=4.0), 7.00–7.60 (m, 4H), 6.80 (d, 1H, J=4.0), 3.25 (m, 4H), 2.82 (m, 2H), 2.60 (m, 2H), 2.20 (s, 3H), 1.60–2.00 (m, 2H); MS 378 (M–1), 380 (M+1).

EXAMPLE 185

5-{3-[(4-Butyl-benzyl)-(propane-1-sulfonyl)-amino]-propyl}-thiophene-2-carboxylic acid Step A: Reductive Amination
5-{3-[(4-Butyl-benzyl)-amino]-propyl}-thiophene-2-carboxylic Acid Methyl Ester.

A mixture of 4-butylbenzaldehyde (250 mg, 1.541 mmol), 5-(3-amino-propyl)-thiophene-2-carboxylic Acid methyl ester hydrochloride (403 mg, 1.695 mmol), and Na$_2$SO$_4$ (2.189 9, 15.41 mmol) in MeOH (10 mL) was heated at reflux for 4.5 h and additional Na$_2$SO$_4$ (2.19 g) was added. The reaction was heated at reflux for 1 h and was cooled to room temperature. The solids were filtered off with the aid of MeOH and the volatiles were removed in vacuo. The residue was dissolved in THF (10 mL) and CH$_2$Cl$_2$ (10 mL) and the solution was cooled to 0° C. Acetic Acid (185 mg, 3.082 mmol) was added followed by sodium triacetoxyborohydride (653 mg, 3.082 mmol) and the reaction was stirred at room temperature for 16 h. The reaction was diluted with EtOAc and the organic solution was washed with aqueous NaHCO$_3$ followed by brine. The organic solution was dried over MgSO$_4$, filtered, and concentrated. Purification by flash chromatography (99:1 CHCl$_3$:MeOH to 97.5:2.5 CHCl$_3$:MeOH) provided the title compound (309 mg). MS 346 (MH+).

Step B: Sulfonamide Formation
5-{3-[(4-Butyl-benzyl)-(propane-1-sulfonyl)-amino]-propyl}-thiophene-2-carboxylic acid Methyl Ester.

The title compound was prepared using the method described in Step B of Example 141 except N-methylmorpholine was used in place of triethylamine.

Step C: Ester Hydrolysis
5-{3-[(4-Butyl-benzyl)-(propane-1-sulfonyl)-amino]-propyl}-thiophene-2-carboxylic acid.

The title compound was prepared using the method described in Step C of Example 141. $^1$H NMR (400 MHz, CDCl$_3$) δ 7.72 (d, 1H, J=4.0), 7.00–7.40 (m, 4H), 6.70 (d, 1H), J=4.0), 3.22 (t, 2H, J=6.8), 2.65 (t, 2H, J=6.8), 1.60–2.25 (m, 6H), 1.02-1.10 (m, 6H); MS 436 (M–1), 438 (P+1).

EXAMPLE 186

(3-{[(Benzo[1,2,5]oxadiazole-4-sulfonyl)-(4-butyl-benzyl)-amino]-methyl}-phenyl)-acetic acid Step A: Sulfonamide Formation
(3-{[(Benzo[1,2,5]oxadiazole-4-sulfonyl)-(4-butyl-benzyl)-amino]-methyl}-phenyl)-acetic Acid Methyl Ester.

Benzofurazan-4-sulfonyl chloride (109 mg, 0.50 mmol) was added to a solution of {3-[(4-butyl-benzylamino)-methyl]-phenyl}-acetic Acid methyl ester (163 mg, 0.50 mmol) and N,N-diisopropylethylamine (65 mg, 0.50 mmol) in 1,2-dichloroethane. The reaction mixture was stirred at room temperature for 20 h. The reaction was diluted with EtOAc and the organic solution was washed with water followed by brine. The organic solution was dried over MgSO$_4$, filtered, and concentrated to afford (3-{[(benzo[1,2,5]oxadiazole-4-sulfonyl)-(4-butyl-benzyl)-amino]-methyl}-phenyl)-acetic acid methyl ester. $^1$H NMR (400 MHz, CDCl$_3$) δ 7.95 (d, 1H), 7.88 (d, 1H), 7.37–7.41 (m, 1H), 7.06–7.10 (m, 2H), 6.90–6.97 (m, 6H), 4.56 (s, 2H), 4.51 (s, 2H), 3.66 (s, 3H), 3.45 (s, 2H), 2.48 (t, 2H), 1.45–1.53 (m, 2H), 1.23-1.32 (m, 2H), 0.89 (t, 3H); MS 508 (M+18).

Step B: Ester Hydrolysis (3-{[(Benzo[ 1,2,5]oxadiazole4-sulfonyl)-(4-butyl-benzyl)-amino]-methyl}-phenyl)-acetic acid.

The title compound was prepared via hydrolysis of (3-{[(benzo[1,2,5]oxadiazole-4-sulfonyl)-(4-butyl-benzyl)-amino]-methyl ester following the procedure described in Step C of Example 138. $^1$H NMR (400 MHz, CDCl$_3$) δ 7.93 (d, 1H), 7.87 (d, 1H), 7.34–7.38 (m, 1H), 7.07–7.09 (m, 2H), 6.90–6.96 (m, 6H), 4.54 (s, 2H), 4.49 (s, 2H), 3.47 (s, 2H), 2.46 (t, 2H), 1.44–1.51 (m, 2H), 1.21–1.31 (m, 2H), 0.88 (t, 3H); MS 492 (M–1).

EXAMPLES 187–188

Examples 187–188 were prepared in an analogous manner to Example 186 via sulfonamide formation from the appropriate amine in Step A followed by ester hydrolysis in Step B.

EXAMPLE 187

(3-{[(4-Butyl-benzyl)-(propane-1-sulfonyl)-amino]-methyl}-phenyl)-acetic acid

Step A: (3-{[(4-Butyl-benzyl)-(propane-1-sulfonyl)-amino]-methyl}-phenyl)-acetic acid Methyl Ester.
$^1$H NMR (400 MHz, CDCl$_3$) δ 4.30 (d, 4H), 3.69 (s, 3H), 3.61 (s, 2H), 2.82–2.86 (m, 2H), 2.59 (t, 2H), 1.78–1.84 (m, 2H), 1.58 (t, 2H).

Step B: (3-{[(4-Butyi-benzyl)-(propane-1-sulfonyl)-amino]-methyl}-phenyl)-acetic acid.
$^1$H NMR (400 MHz, CDCl$_3$) δ 7.12–7.32 (m, 8H), 4.30 (d, 4H), 3.64 (s, 2H), 2.81–2.90 (m, 2H), 2.59 (t, 2H), 1.74–1.83 (m, 2H), 1.54–1.61 (m, 2H), 1.31–1.40 (m, 2H), 0.87-0.97 (m, 6H); MS 416 (M$^+$–1).

EXAMPLE 188

(3-{[(4-Butyl-benzyl)-(thiophene-2-sulfonyl)-amino]-methyl}-phenyl)-acetic acid

Step A: (3-{[(4-Butyl-benzyl)-(thiophene-2-sulfonyl)-amino]-methyl}-phenyl)-acetic Acid Methyl Ester.
$^1$H NMR (400 MHz, CDCl$_3$) δ 7.51–7.57 (m, 2H), 7.12–7.20 (m, 2H), 6.95–7.08 (m, 7H), 4.30 (d, 4H), 3.68 (s, 3H), 3.52 (s, 2H), 2.55 (t, 2H), 1.51–1.58 (m, 2H), 1.27–1.36 (m, 2H), 0.91 (t, 3H); MS 472 (M+1).

Step B: (3-{[(4-Butyl-benzyl)-(thiophene-2-sulfonyl)-amino]-methyl}-phenyl)-acetic acid.
$^1$H NMR (400 MHz, CDCl$_3$) δ 7.50–7.54 (m, 2H), 7.10–7.18 (m, 2H), 6.89–7.05 (m, 7H), 4.27 (d, 4H), 3.52 (s, 2H), 2.52 (t, 2H), 1.48–1.56 (m, 2H), 1.21–1.34 (m, 2H), 0.89 (t, 3H); MS 456 (M–1).

EXAMPLE 189

3-(3-{[3-(3-Chloro-phenyl)-propyl]-methanesulfonyl-amino}-propyl)-benzoic acid

Step A: Sulfonamide Formation
3-(3-{[3-(3-Chloro-phenyl)-propyl]-methanesulfonyl-amino}-propyl)-benzoic acid Methyl Ester.

To a solution of 3-(3-{[3-(3-chloro-phenyl)-propyl]-amino}-propyl)-benzoic Acid methyl ester (50.3 mg, 0.145 mmol) and triethylamine (32.4 mg, 0.32 mmol) in CH$_2$Cl$_2$ (10 mL) was added methanesulfonyl chloride (18.3 mg, 0.16 mmol) at 0° C. The reaction mixture was stirred for 24 h at room temperature and was diluted with CH$_2$Cl$_2$. The organic solution was washed consecutively with aqueous HCl (5.5%, 1×), H$_2$O (1×), NaHCO$_3$ (1×) and brine (1×). The organic solution was dried over MgSO$_4$, filtered, and concentrated to afford the title product of Step A as an oil (71 mg). MS 424 (M+1).

Step B: Ester Hydrolysis
3-(3-{[3-(3-Chloro-phenyl)-propyl]-methanesulfonyl-amino}-propyl)-benzoic acid.

The title compound was prepared via hydrolysis of 3-(3-{[3-(3-chloro-phenyl)-propyl]-methanesulfonyl-amino}- propyl)-benzoic Acid methyl ester following the procedure described in Step C of Example 141. $^1$H NMR (400 MHz, CDCl$_3$) δ 7.00–8.00 (m, 8H), 3.19 (m, 4H), 3.00 (s, 3H), 2.70 (m, 2H), 2.60 (m, 2H), 1.79–2.03 (m, 4H); MS 408 (M–1), 410 (M+1).

EXAMPLES 190–197

Examples 190–197 were prepared in an analogous manner to Example 189 via sulfonamide formation from the appropriate amine in Step A followed ester hydrolysis in Step B.

EXAMPLE 190

5-(3-{[3-(3-Chloro-phenyl)-propyl]-methanesulfonyl-amino}-propyl)-furan-2-carboxylic acid Step A: 5-(3-{[3-(3-Chloro-phenyl)-propyl]-methanesulfonyl-amino}-propyl)-furan-2-carboxylic Acid Methyl Ester.
MS 414 (M+1).
Step B: 5-(3-{[3-(3-Chloro-phenyl)-propyl]-methanesulfonyl-amino}-propyl)-furan-2-carboxylic acid.
$^1$H NMR (400 MHz, CDCl$_3$) δ 6.75–7.50 (m, 5H), 6.20 (d, 1H, J=4), 2.95 (s, 3H), 2.80 (m, 2H), 2.65 (m, 2H), 1.80–2.00 (m, 4H); MS 398 (M–1), 400 (M+1).

EXAMPLE 191

5-(3-{[3-(3-Chloro-phenyl)-propyl]-methanesulfonyl-amino}-propyl)-tetrahydrofuran-2-carboxylic acid Step A: 5-(3-{[3-(3-Chloro-phenyl)-propyl]-methanesulfonyl-amino}-propyl)-tetrahydrofuran-2-carboxylic Acid Methyl Ester.
MS 418 (M+1).
Step B: 5-(3-{[3-(3-Chloro-phenyl)-propyl]-methanesulfonyl-amino}-propyl)-tetrahydrofuran-2-carboxylic acid.
$^1$H NMR (400 MHz, CDCl$_3$) δ 7.00–7.30 (m, 14H), 3.20 (t, 2H, J=6.8), 2.85 (s, 3H), 2.65 (t, 2H, J=6.7), 1.90 (m, 2H); MS 402 (M–1), 404 (M+1).

EXAMPLE 192

5-(3-{[3-(3-Chloro-phenyl)-propyl]-ethanesulfonyl-amino}-propyl)-furan-2-carboxylic acid Step A: 5-(3-{[3-(3-Chloro-phenyl)-propyl]-ethanesulfonyl-amino}-propyl)-furan-2-carboxylic Acid Methyl Ester.
MS 428 (M+1).
Step B: 5-(3-{[3-(3-Chloro-phenyl)-propyl]-ethanesulfonyl-amino}-propyl)-furan-2-carboxylic acid.
$^1$H NMR (400 MHz, CDCl$_3$) δ 6.80–7.70 (m, 5H), 6.21 (d, 1H, J=4), 3.22 (m, 4H), 2.81 (m, 2H), 2.62 (m, 2H), 1.80–2.20 (m, 6H), 1.05 (t, 3H, J=7); MS 412 (M–1), 414 (M+1).

EXAMPLE 193

5-{3-[(4-Butyl-benzyl)-ethanesulfonyl-amino]-propyl}-thiophene-2-carboxylic acid Step A: 5-{3-[(4-Butyl-benzyl)-ethanesulfonyl-amino]-propyl}-thiophene-2-carboxylic Acid Methyl Ester.
MS 457 (M+18).
Step B: 5-{3-[(4-Butyl-benzyl)-ethanesulfonyl-amino]-propyl}-thiophene-2-carboxylic acid.
$^1$H NMR (400 MHz, CDCl$_3$) δ 7.70 (d, 1H, J=3.9), 7.00–7.40 (m, 4H), 6.72 (d, 1H, J=3.8), 3.22 (t, 2H, J=6.9), 2.60 (t, 2H, J=7.0), 1.72–2.30 (m, 6H), 1.03–1.09 (m, 6H); MS 422 (M–1).

EXAMPLE 194

5-(3-{[3-(3-Chloro-phenyl)-propyl]-ethanesulfonyl-amino}-propyl)-thiophene-2-carboxylic acid Step A: 5-(3-{[3-(3-Chloro-phenyl)-propyl]-ethanesulfonyl-amino}-propyl)-thiophene-2- carboxylic Acid Methyl Ester.
MS 461 (M+18).
Step B: 5-(3-{[3-(3-Chloro-phenyl)-propyl]-ethanesulfonyl-amino}-propyl)-thiophene-2-carboxylic acid.
$^1$H NMR (400 MHz, CDCl$_3$) δ 6.62–7.71 (m, 6H), 3.26 (m, 4H), 2.83 (m, 2H), 2.63 (m, 2H), 1.60–2.25 (m, 6H), 1.06 (t, 3H, J=7.0); MS 428 (M–1), 429 (M+1).

EXAMPLE 195

3-(3-{[3-(3-Chloro-phenyl)-propyl]-ethanesulfonyl-amino}-propyl)-benzoic acid

Step A: 3-(3-{[3-(3-Chloro-phenyl)-propyl]-ethanesulfonyl-amino}-propyl)-benzoic acid Methyl Ester.
MS 438 (M+1).
Step B: 3-(3-{[3-(3-Chloro-phenyl)-propyl]-ethanesulfonyl-amino}-propyl)-benzoic acid.
$^1$H NMR (400 MHz, CDCl$_3$) δ 7.00–8.00 (m, 8H), 3.21 (m, 4H), 2.78 (m, 2H), 2.50 (m, 2H), 1.82–2.20 (m, 6H), 1.05 (t, 3H, J=7.0); MS 422 (M–1), 424 (M+1).

EXAMPLE 196

5-{3-[[3-(3-Chloro-phenyl)-propyl]-(propane-1-sulfonyl)-amino]-propyl}-thiophene-2-carboxylic acid Step A: 5-{3-[[3-(3-Chloro-phenyl)-propyl]-(propane-1-sulfonyl)-amino]-propyl}-thiophene-2-carboxylic Acid Methyl Ester.
MS 476 (M+18).
Step B: 5-{3-[[3-(3-Chloro-phenyl)-propyl]-(propane-1-sulfonyl)-amino]-propyl}-thiophene-2-carboxylic acid.
$^1$H NMR (400 MHz, CDCl$_3$) δ 7.70 (d, 1H, J=4.0), 7.00-7.30 (m, 4H), 6.80 (d, 1H, J=4.0), 3.20 (m, 4H), 2.70 (m, 4H), 2.50 (m, 2H), 1.70–2.00 (m, 6H), 1.00 (t, 3H, J=7.0); MS 444 (M+1), 442 (M–1).

EXAMPLE 197

5-{3-[[3-(3-Chloro-phenyl)-propyl]-(3-chloro-propane-1-sulfonyl)-amino]-propyl}-thiophene-2-carboxylic acid Step A: Sulfonamide Formation
5-{3-[[3-(3-Chloro-phenyl)-propyl]-(3-chloro-propane-1-sulfonyl)-amino]-propyl}-thiophene-2-carboxylic Acid Tert-butyl Ester.

The title compound of Step A was prepared from the appropriate starting materials in an analogous manner to the method described in Step A of Example 189.

Step B: Ester Hydrolysis
5-{3-[[3-(3-Chloro-phenyl)-propyl]-(3-chloro-propane-1-sulfonyl)-amino]-propyl}-thiophene-2-carboxylic acid.

The title compound was prepared via hydrolysis of 5-{3-[[3-(3-chloro-phenyl)-propyl]-(3-chloro-propane-1-sulfonyl)-amino]-propyl}-thiophene-2-carboxylic Acid tert-butyl ester in an analogous manner to the method described in Step C of Example 171. $^1$H NMR (400 MHz, CDCl$_3$) δ 6.60–7.72 (m, 6H), 3.19 (m, 4H), 2.79 (m, 2H), 2.60 (m, 2H), 1.60–2.20 (m, 6H); MS 477 (M–1).

EXAMPLE 198

5-(3-{[3-(3-Chloro-phenyl)-propyl]-hydroxyacetyl-amino}-propyl)-thiophene-2-carboxylic acid Step A: Amide Formation
5-(3-{[3-(3-Chloro-phenyl)-propyl]-hydroxyacetyl-amino}-propyl)-thiophene-2-carboxylic Acid Methyl Ester.
A solution of 5-(3-{[3-(3-chloro-phenyl)-propyl]}-propyl)-thiophene-2-carboxylic Acid methyl ester (80.7 mg, 0.23 mmol), acetoxyacetic acid (30 mg, 0.25 mmol) and DCC (52 mg, 025 mmol) in $CH_2Cl_2$ (10 mL) was stirred for 24 h at room temperature. The reaction mixture was filtered and the filtrate was concentrated. The residue was dissolved in EtOAc (15 mL) and was filtered. The filtrate was washed consecutively with HCl (5.5%, 1×), $H_2O$ (1×), $NaHCO_3$ (1×), brine (1×). The organic solution was dried over $MgSO_4$, filtered, and concentrated to afford the product as an oil (90 mg). MS 452 (M+1).

Step B: Ester Hydrolysis 5-(3-{[3-(3-Chloro-phenyl)-propyl]-hydroxyacetyl-amino}-propyl)-thiophene-2-carboxylic acid.

The title compound was prepared via hydrolyis of 5-(3-{[3-(3-chloro-phenyl)-propyl]-hydroxyacetyl-amino}-propyl)-thiophene-2-carboxylic Acid methyl ester in an analogous manner to the method described in Step C of Example 141. $^1$H NMR (400 MHz, $CDCl_3$) δ 6.70–7.80 (m, 6H), 3.24 (m, 4H), 2.81 (m, 2H), 2.60 (m, 2H), 1.20–2.02 (m, 4H); MS 394 (M−1), 396 (M+1).

EXAMPLES 199–205

Examples 199–205 were prepared in an analogous manner to Example 198 via amide formation from the appropriate amine in Step A followed by ester hydrolysis in Step B

EXAMPLE 199

5-(3-{[3-(3-Chloro-phenyl)-propyl]-cyclopropanecarbonyl-amino}-propyl)-thiophene-2-carboxylic acid Step A: 5-(3-{[3-(3-Chloro-phenyl)-propyl]-cyclopropanecarbonyl-amino}-propyl)-thiophene-2-carboxylic Acid Methyl ester.

Step B: 5-(3-{[3-(3-Chloro-phenyl)-propyl]-cyclopropanecarbonyl-amino}-propyl)-thiophene-2-carboxylic acid.

$^1$H NMR (400 MHz, $CDCl_3$) δ 6.60–7.80 (m, 6H), 3.25 (m, 4H), 2.75 (m, 2H), 2.60 (m, 2H), 1.80–2.00 (m, 4H), 0.70–1.00 (m, 4H); MS 404 (M−1), 406 (M+1).

EXAMPLE 200

5-(3-{[3-(3-Chloro-phenyl)-propyl]-cyclobutanecarbonyl-amino}-propyl)-thiophene-2-carboxylic acid Step A: 5-(3-{[3-(3-Chloro-phenyl)-propyl]-cyclobutanecarbonyl-amino}-propyl)-thiophene-2-carboxylic Acid Methyl Ester.

Step B: 5-(3-{[3-(3-Chloro-phenyl)-propyl]-cyclobutanecarbonyl-amino}-propyl)-thiophene-2-carboxylic acid.

$^1$H NMR (400 MHz, $CDCl_3$) δ 6.60–7.70 (m, 6H), 3.22 (m, 4H), 2.86 (m, 2H), 2.66 (m, 2H), 1.66–1.99 (m, 10H); MS 418 (M−1), 420 (M+1).

EXAMPLE 201

5-(3-{[3-(3-Chloro-phenyl)-propyl]-methoxyacetyl-amino}-propyl)-thiophene-2-carboxylic acid Step A: 5-(3-{[3-(3-Chloro-phenyl)-propyl]-methoxyacetyl-amino}-propyl)-thiophene-2-carboxylic acid.

Step B: 5-(3-{[3-(3-Chloro-phenyl)-propyl]-methoxyacetyl-amino}-propyl)-thiophene-2-carboxylic acid.

$^1$H NMR (400 MHz, $CDCl_3$) δ 6.60–7.82 (m, 6H), 3.25 (m, 4H), 3.20 (s, 3H), 2.80 (t, 2H, J=7.0), 2.60 (t, 2H, J=7.0), 1.60–2.00 (m, 4H); MS 408 (M−1), 410 (M+1).

EXAMPLE 202

5-(3-{Butyryl-[3-(3-chloro-phenyl)-propyl]-amino}-propyl)-thiophene-2-carboxylic acid Step A: 5-(3-{Butyryl-[3-(3-chloro-phenyl)-propyl]-amino}-propyl)-thiophene-2-carboxylic Acid Methyl Ester. MS 422 (M+1).

Step B: 5-(3-{Butyryl-[3-(3-chloro-phenyl)-propyl]-amino}-propyl)-thiophene-2-carboxylic acid.

$^1$H NMR (400 MHz, $CDCl_3$) δ 6.66–7.70 (m, 6H), 3.20 (m, 4H), 2.81 (m, 2H), 2.62 (m, 2H), 1.70–2.20 (m, 6H), 1.04 (t, 3H, J=6.7); MS 408 (M+1), 406 (M−1).

EXAMPLE 203

5-(3-{[3-(3-Chloro-phenyl)-propyl]-propionyl-amino}-propyl)-furan-2-carboxylic acid Step A: 5-(3-{[3-(3-Chloro-phenyl)-propyl]-propionyl-amino}-propyl)-furan-2-carboxylic Acid Methyl Ester. MS 392 (M+1).

Step B: 5-(3-{[3-(3-Chloro-phenyl)-propyl]-propionyl-amino}-propyl)-furan-2-carboxylic acid.

$^1$H NMR (400 MHz, $CDCl_3$) δ 6.80–7.70 (m, 5H), 6.21 (d, 1H, J=3.9), 3.20 (m, 4H), 2.83 (m, 2H), 2.60 (m, 2H), 1.80–2.20 (m, 6H), 1.04 (t, 3H, J=6.8); MS 376 (M−1), 378 (M+1).

EXAMPLE 204

5-(3-{[3-(3-Chloro-phenyl)-propyl]-cyclopropanecarbonyl-amino}-propyl)-furan-2-carboxylic acid Step A: 5-(3-{[3-(3-Chloro-phenyl)-propyl]-cyclopropanecarbonyl-amino}-propyl)-furan-2-carboxylic Acid Methyl Ester.

MS 404 (M+1).

Step B: 5-(3-{[3-(3-Chloro-phenyl)-propyl]-cyclopropanecarbonyl-amino}-propyl)-furan-2-carboxylic acid.

$^1$H NMR (400 MHz, $CDCl_3$) δ 6.80–7.40 (m, 5H), 6.19 (d, 1H, J=4.0), 3.25 (m, 4H), 2.81 (m, 2H), 2.60 (m, 2H), 1.60–2.00 (m, 4H); MS 388 (M−1), 390 (M+1).

EXAMPLE 205

5-(3-{Acetyl-[3-(3-chloro-phenyl)-propyl]-amino}-propyl)-furan-2-carboxylic acid Step A: 5-(3-{Acetyl-[3-(3-chloro-phenyl)-propyl]-amino}-propyl)-furan-2-carboxylic Acid Methyl Ester. MS 378 (M+1).

Step B: 5-(3-{Acetyl-[3-(3-chloro-phenyl)-propyl]-amino}-propyl)-furan-2-carboxylic acid.

$^1$H NMR (400 MHz, $CDCl_3$) δ 6.82–7.70 (m, 5H), 6.20 (d, 1H, J=4), 3.20 (m, 4H), 2.80 (m, 2H), 2.60 (m, 2H), 2.10 (s, 3H), 1.60–2.04 (m, 4H); MS 362 (M−1), 364 (M+1).

EXAMPLE 206

5-(3-{[3-(3-Chloro-phenyl)-propyl]-methanesulfonyl-amino}-propyl)-thiophene-2-carboxylic Acid Sodium Salt To a solution of 5-(3-{[3-(3-chloro-phenyl)-propyl]-methanesulfonyl-amino}-propyl)-thiophene-2-carboxylic Acid (7.378 g, 17.74 mmol) in MeOH (325 mL) and water (25 mL) was added $NaHCO_3$ (1.490 g, 17.74 mmol) and the reaction was stirred at room temperature for 3 h. The reaction was concentrated in vacuo and the residue was azeotroped with MeOH (2×50 mL) followed by $CHCl_3$ (2×50 mL) to provide the sodium salt as a white solid (7.661 g). $^1$H NMR (400 MHz, $CD_3OD$) δ 7.35 (d, 1H), 7.28 (m, 2H), 7.14 (m, 2H), 6.73 (d, 1H), 3.23 (m, 4H), 2.83 (s, 3H), 2.82 (m, 2H), 2.62 (t, 2H), 1.94 (m, 2H), 1.88 (m, 2H).

EXAMPLES 207–216

Following the general procedure described for Example 206, the following sodium salts (Examples 207–216) were prepared with variations as noted.

EXAMPLE 207

(3-{[(4-Butyl-benzyl)-methanesulfonyl-amino]-methyl}-phenyl)-acetic Acid sodium salt Following the procedure described for Example 206 the sodium salt was generated. The sodium salt was stirred in 3% EtOH/EtOAc at 45° C. for 20 h, was cooled to room temperature and was filtered to provide a white solid. mp 158° C.; $^1$H NMR (400 MHz, CD$_3$OD) δ 7.26–7.11 (m, 8H), 4.28 (s, 4H), 3.45 (s, 2H), 3.29 (s, 2H), 2.80 (s, 3H), 2.58 (t, 2H), 1.57 (m, 2H), 1.33 (m, 2H), 0.92 (t, 3H).

EXAMPLE 208

[3-({[3-(3,5-Dichloro-phenyl)-allyl]-methanesulfonyl-amino}-methyl)-phenoxy]-acetic Acid Sodium Salt $^1$H NMR (400 MHz, CD$_3$OD) δ 7.29–7.21 (m, 4H), 6.94 (m, 2H), 6.84 (d, 1H), 6.44 (d, 1H), 6.24 (m, 1H), 4.37 (s, 2H), 4.35 (s, 2H), 3.94 (d, 2H), 2.94 (s, 3H).

EXAMPLE 209

[3-({[2-(3,5-Dichloro-phenoxy)-ethyl]-methanesulfonyl-amino}-methyl)-phenoxy]-acetic Acid Sodium Salt $^1$H NMR (400 MHz, CD$_3$OD) δ 7.21 (m, 1H), 6.96 (m, 3H), 6.83 (m, 3H), 4.44 (s, 2H), 4.35 (s, 2H), 4.01 (t, 2H), 3.56 (t, 2H), 2.97 (s, 3H).

EXAMPLE 210

2-(3-{[2-(3,5-Dichloro-phenoxy)-ethyl]-methanesulfonyl-amino}-propyl)-thiazole4-carboxylic Acid Sodium Salt $^1$H NMR (400 MHz, CD$_3$OD) δ 7.82 (bs, 1H), 6.99 (m, 1H), 6.92 (m, 2H), 4.15 (t, 2H), 3.62 (m, 2H), 3.36 (m, 2H), 3.03 (m, 2H), 2.94 (s, 3H), 2.14 (m, 2H).

EXAMPLE 211

N-[2-(3,5-Dichloro-phenoxy)-ethyl]-N-[6-(1H-tetrazol-5-yl)-hexyl]-methanesulfonamide Sodium Salt $^1$H NMR (400 MHz, CD$_3$OD) δ 7.00 (s, 1H), 6.93 (s, 2H), 4.14 (t, 2H), 3.58 (t, 2H), 3.23 (t, 2H), 2.91 (s, 3H), 2.80 (t, 2H), 1.73 (m, 2H), 1.62 (m, 2H), 1.36 (m, 4H).

EXAMPLE 212

7-{[2-(3,5-Dichloro-phenoxy)-ethyl]-methanesulfonyl-amino}-heptanoic Acid Sodium Salt Following the procedure described for Example 206 the sodium salt was generated. The sodium salt was stirred in 2% water in EtOAc at 65° C. for 20 h. The mixture was cooled to room temperature and was filtered to provide a white solid. mp 166° C.; $^1$H NMR (400 MHz, CD$_3$OD) δ 7.00 (s, 1H), 6.94 (s, 2H), 4.14 (t, 2H), 3.59 (t, 2H), 3.29 (t, 2H), 2.92 (s, 3H), 2.14 (t, 2H), 1.60 (m, 4H), 1.35 (m, 4H).

EXAMPLE 213

7-[(4-Butyl-benzyl)-methanesulfonyl-amino]-heptanoic Acid Sodium Salt

Following the procedure described for Example 206 the sodium salt was generated. The sodium salt was stirred in 10% EtOH in EtOAc at 65° C. for 20 h. The mixture was cooled to room temperature and was filtered to provide a white solid. mp 137° C.; $^1$H NMR (400 MHz, CD$_3$OD) δ 7.27 (d, 2H), 7.15 (d, 2H), 4.32 (s, 2H), 3.12 (t, 2H), 2.85 (s, 3H), 2.60 (t, 2H), 2.09 (t, 2H), 1.60–1.20 (m, 12H), 0.92 (t, 3H).

EXAMPLE 214

(3-{[(4-Cyclohexyl-benzyl)-methanesulfonyl-amino]-methyl}-phenyl)-acetic acid Sodium Salt $^1$H NMR (400 MHz, CD$_3$OD) δ 7.33–7.15 (m, 8H), 4.31 (s, 2H), 4.28 (s, 2H), 3.64 (s, 2H), 2.74 (s, 3H), 2.48 (m, 1H), 1.84 (m, 4H), 1.74 (m, 1H), 1.38 (m, 4H), 1.24 (m, 1H).

EXAMPLE 215

(3-{[(4-tert-Butyl-benzyl)-methanesulfonyl-amino]-methyl}-phenoxy)-acetic acid Sodium Salt Following the procedure described for Example 206 the sodium salt was generated. The sodium salt was stirred in 2% water in EtOAc at 65° C. for 20 h. The mixture was cooled to room temperature and was filtered to provide a white solid. mp 184–186° C.; $^1$H NMR (400 MHz, D$_2$O) δ 7.19 (d, 2H), 7.04 (m, 3H), 6.71 (d, 1H), 6.63 (d, 1H), 6.49 (s, 1H), 4.20 (s, 2H), 4.18 (s, 2H), 4.17 (s, 2H), 2.88 (s, 3H), 1.08 (s, 9H).

EXAMPLE 216

5-(3-{[2-(3,5-Dichloro-phenoxy)-ethyl]-methanesulfonyl-amino}-propyl)-thiophene-2-carboxylic Acid Sodium Salt $^1$H NMR (400 MHz, CD$_3$OD) δ 7.34 (d, 1H), 6.99 (t, 1H), 6.90 (d, 2H), 6.72 (d, 1H), 4.12 (t, 2H), 3.60 (t, 2H), 3.31 (t, 2H), 2.92 (s, 3H), 2.83 (t, 2H), 2.00 (m, 2H).

PREPARATIONS C4–C6

Preparations C4–C6 were prepared from the appropriate starting materials in an analogous manner to Preparation C1.

PREPARATION C4

N-[3-(5-Methyl-thiophen-2-yl)-propyl]-methanesulfonamide $^1$H NMR (400 MHz, CDCl$_3$) δ 6.57–6.53 (m, 2H), 4.35 (m, 1H), 3.17 (m, 2H), 2.93 (s, 3H), 2.83 (t, 2H), 2.42 (s, 3H), 1.90 (m, 2H).

PREPARATION C5

[3-(3-Methanesulfonylamino-propyl)-phenyl]-acetic Acid Methyl ester $^1$H NMR (250 MHz, CDCl$_3$) δ 7.30–7.06 (m, 4H), 4.34 (m, 1H), 3.70 (s, 3H), 3.61 (s, 2H), 3.27 (m, 2H), 2.94 (s, 3H), 2.72 (t, 2H), 1.93 (m, 2H).

PREPARATION C6

[2-(3-Methanesulfonylamino-propyl)-phenyl]-acetic Acid Methyl Ester $^1$H NMR (400 MHz, CDCl$_3$) δ 7.24–7.16 (m, 4H), 4.58 (m, 1H), 3.69 (s, 3H), 3.66 (s, 2H), 3.17 (q, 2H), 2.94 (s, 3H), 2.72 (t, 2H), 1.88 (m, 2H).

PREPARATIONS D3-D4

Preparations D3-D4 were prepared from the appropriate starting materials in an analogous manner to Preparation D1.

PREPARATION D3

1-Bromomethyl4-propyl-benzene $^1$H NMR (400 MHz, CDCl$_3$) δ 7.30–7.25 (m, 2H), 7.14 (m, 2H), 4.48 (s, 2H), 2.56 (t, 2H), 1.62 (m, 2H), 0.93 (t, 3H).

PREPARATION D4

1-Bromomethyl-4-ethyl-benzene $^1$H NMR (400 MHz, CDCl$_3$) δ 7.28 (m, 2H), 7.16 (d, 2H), 4.48 (s, 2H), 2.63 (q, 2H), 1.22 (t, 3H).

PREPARATIONS F3-F4

Preparations F3-F4 were prepared from the appropriate starting materials in an analogous manner to Preparation F1.

PREPARATION F3

2-Bromo-methyl-benzofuran

PREPARATION F4

6-Chloro-2-bromomethyl-quinoline

PREPARATIONS L4-L17

Preparations L4-L17 were prepared from the appropriate starting materials in an analogous manner to Preparation L1.

PREPARATION L4

1-(2-Bromo-ethoxy)-3-ethyl-benzene

PREPARATION L5

1-(2-Bromo-ethoxy)-3-isopropyl-benzene

PREPARATION L6

1-(2-Bromo-ethoxy)-3-trifluoromethyl-benzene

PREPARATION L7

1-(2-Bromo-ethoxy)-3,5-difluoro-benzene $^1$H NMR (400 MHz, CDCl$_3$) δ 6.42 (m, 3H), 4.24 (t, 2H), 3.62 (t, 2H).

PREPARATION L8

1-(2-Bromo-ethoxy)-3,5-dichloro-benzene

PREPARATION L9

1-(2-Bromo-ethoxy)-3-fluoro-benzene

PREPARATION L10

1-(2-Bromo-ethoxy)-3-chloro-5-methoxy-benzene

PREPARATION L11

1-(2-Bromo-ethoxy)-3-ethoxy-benzene

PREPARATION L12

1-(2-Bromo-ethoxy)-3-chloro-benzene

PREPARATION L13

5-(2-Bromo-ethoxy)-benzo[1,3]dioxole $^1$H NMR (400 MHz, CDCl$_3$) δ 6.69 (d, 1H), 6.50 (s, 1H), 6.33 (dd, 1H), 5.91 (s, 2H), 4.20 (t, 2H), 3.59 (t, 2H).

PREPARATION L14

1-(2-Bromo-ethoxy)-3,5-bis-trifluoromethyl-benzene

PREPARATION L15

1-(3-Bromo-propoxy)-3-chloro-5-methoxy-benzene

PREPARATION L16

1-(3-Bromo-propoxy)-3,5-dichloro-benzene

PREPARATION L17

1-(2-Bromo-ethoxy)-3-methoxy-benzene

PREPARATION W2

5-(3-Oxo-propyl)-thiophene-2-carboxylic Acid Tert-butyl Ester

Step A: Ester Formation
5-Bromo-thiophene-2-carboxylic Acid Tert-butyl Ester.

To a mixture of anhydrous MgSO$_4$ (11.60 g, 96.4 mmol) in 100 mL CH$_2$Cl$_2$ was added concentrated H$_2$SO$_4$ (1.45 mL, 24.1 mmol) and the mixture was stirred for 15 minutes followed by addition of 5-bromo-thiophene-2-carboxylic Acid (5.0 g, 24.1 mmol). After stirring for 1 minute, tert-butanol (11.6 g, 20 mmol) was added and the reaction was stirred at room temperature for 18 h. The reaction was quenched with saturated NaHCO$_3$. The layers were separated, the aqueous layer was extracted with CH$_2$Cl$_2$, and the combined organic layers were dried over MgSO$_4$. The organic solution was concentrated to give a clear oil which was purified via medium pressure chromatography (3% EtOAc in hexanes) to afford the title compound (4.97 g). $^1$H NMR (400 MHz, CDCl$_3$) δ 7.45 (d, 1H), 7.02 (d, 1H), 1.54 (s, 9H).

Step B: Aldehyde Formation
5-(3-Oxo-propyl)-thiophene-2-carboxylic Acid Tert-butyl Ester.

To a solution of 5-bromo-thiophene-2-carboxylic Acid tert-butyl ester (0.50 g, 1.89 mmol) in 5 mL DMF was added allyl alcohol (0.51 mL, 7.57 mmol) followed by NaHCO$_3$ (0.397 g, 4.72 mmol), tetrabutylammonium chloride (0.525g, 1.89 mmol), and palladium acetate (0.021 g, 0.094 mmol). The reaction was placed in an oil bath heated to 65° C. and was heated to 90° C. for 2 h. The mixture was diluted with EtOAc and 25 mL water and the solids were removed by filtration through Celite. The layers were separated, and the organic solution was washed with water (4×), dried over MgSO$_4$ and concentrated to a dark yellow oil which was purified via medium pressure chromatography (7:1 hexanes:EtOAc) to afford the title compound (0.190 g). $^1$H NMR (400 MHz, CDCl$_3$) δ 9.80 (s, 1H), 7.51 (d, 1H), 6.78 (d, 1H), 3.14 (t, 2H), 2.86 (t, 2H), 1.54 (s, 9H).

PREPARATION X1

3-(2-Methanesulfonylamino-ethyl)-benzoic Acid Methyl Ester

Step A

3-Cyanomethyl-benzoic Acid Methyl Ester.

A mixture of 3-bromomethyl-benzoic acid methyl ester (3.00 g, 13.10 mmol), potassium cyanide (1.02 g, 15.71 mmol) and DMF (25 mL) was heated at 40–45° C. for 45 minutes and was stirred at room temperature for 18 h. The reaction was heated at 40° C. for 24 h, was cooled to room temperature, and additional potassium cyanide (1.02 g, 15.71 mmol) was added. The reaction was heated at 40° C. for 18 h and was cooled to room temperature. Water (25 mL) was added and the product was extracted into EtOAc (3×25 mL). The combined organic layers were washed with 1N LiCl followed by brine, dried over $MgSO_4$, filtered, and concentrated. Flash chromatography (9:1 hexanes:EtOAc to 4:1 hexanes:EtOAc) provided 3-cyanomethyl-benzoic Acid methyl ester (1.36 g). MS 193 (M+18).

Step B
3-(2-Amino-ethyl)-benzoic Acid Methyl Ester.

A solution of 3-cyanomethyl-benzoic Acid methyl ester (1.36 g) in EtOH (25 mL) was saturated with HCl (g) and $PtO_2$ (200 mg) was added. The reaction was hydrogenated on a Parr shaker at 50 psi for 2.5 h. The catalyst was removed via filtration through Celite and the solvent was removed in vacuo. The resulting solid was stirred in $Et_2O$ and the mixture was filtered to yield the title compound as a white solid (1.18 g). MS 180 (M+1).

Step C
3-(2-Methanesulfonylamino-ethyl)-benzoic Acid Methyl Ester.

To a solution of 3-(2-amino-ethyl)-benzoic Acid methyl ester (500 mg) in $CH_2Cl_2$ (35 mL) at 0° C. was added methanesulfonyl chloride (292 mg, 2.55 mmol) and triethylamine (1.6 mL, 11.5 mmol). The reaction was stirred at room temperature for 18 h and was washed consecutively with 5.5% HCl, water, saturated $NaHCO_3$, and brine. The organic solution was dried over $MgSO_4$, filtered, and concentrated to yield the title compound (522 mg) as a white solid. MS 275 (M+18).

PREPARATION Y1

(3-Formyl-phenyl)-acetic Acid Ethyl Ester

Step A

Method A
(3-Cyano-phenyl)-acetic Acid Ethyl Ester.

To a mixture of of (3-bromo-phenyl)-acetic Acid ethyl ester (15.3 g, 62.9 mmol) and 1-methyl-2-pyrrolidinone (125 mL) was added copper (I) cyanide (8.46 g, 94.4 mmol). The reaction mixture was stirred in an oil bath at 190° C. for 1 h. The reaction was cooled to room temperature and was diluted with EtOAc and 2:1 $H_2O/NH_4OH$. The mixture was stirred for 10 minutes and was filtered through Celite. The aqueous layer was washed with EtOAc (2×). The organic solution was washed with 2:1 $H_2O/NH_4OH$ until the aqueous extracts were no longer blue. The organic solution was dried over $MgSO_4$, filtered and concentrated to afford (3-cyano-phenyl)-acetic Acid ethyl ester (11.95 g). $^1$H NMR (400 MHz, $CDCl_3$) δ 7.51–7.58 (m, 3H), 7.43 (t, 1H), 4.16 (q, 2H), 3.63 (s, 2H), 1.25 (t, 3H).

Method B
(3-Cyano-phenyl)-acetic Acid Ethyl Ester.

A mixture of (3-bromo-phenyl)-acetic acid ethyl ester (12.38 g, 54.05 mmol), zinc cyanide (4.33 g, 36.9 mmol), and DMF (150 mL) was deoxygenated with nitrogen and $Pd(PPh_3)_4$ (3.10 g, 2.68 mmol) was added. The mixture was heated in a 90° C. oil bath for 2.5 h and was cooled to room temperature. Aqueous $NH_4OH$ (5%) was added and the product was extracted into $Et_2O$ (3×). The combined organic extracts were washed with 5% $NH_4OH$ followed by brine. The organic solution was dried over $MgSO_4$, filtered and concentrated. Flash chromatography (9:1 hexanes:EtOAc) provided (3-cyano-phenyl)-acetic Acid ethyl ester (9.08 g) as a pale yellow liquid which was identical spectroscopically to that obtained using Method A above.

Step B
(3-Formyl-phenyl)-acetic Acid Ethyl Ester.

To a solution of (3-cyano-phenyl)-acetic Acid ethyl ester (4.8 g, 25.4 mmol) in 75% aqueous formic Acid was added nickel-aluminum alloy (4.6 g). The mixture was heated at reflux (100° C.) for 2.25 h. The reaction mixture was cooled and was filtered through Celite with the aid of boiling EtOH. The filtrate was diluted with $H_2O$ and the product was extracted into $CHCl_3$ (3×). The organic solution was stirred with saturated $NaHCO_3$ solution until a pH of 8 was attained. The organic solution was dried over $MgSO_4$, filtered, and concentrated. The product was purified by flash chromatography (5:1 hexanes/EtOAc) to afford the title compound (3.33 g). $^1$H NMR (400 MHz, $CDCl_3$) δ 7.76–7.79 (m, 2H), 7.47–7.57 (m, 2H), 4.15 (q, 2H), 3.69 (s, 2H), 1.25 (t, 3H); MS 193 (M+1).

PREPARATION Z1

(3-Formyl-phenyl)-acetic Acid Methyl Ester

Step A
(3-Cyano-phenyl)-acetic Acid Methyl Ester.

Nitrogen was bubbled through a mixture of (3-bromo-phenyl)-acetic Acid methyl ester (22.85 g, 99.78 mmol), $Zn(CN)_2$ (7.25 g, 61.75 mmol), and DMF (100 mL) for about 5 minutes followed by addition of tetrakistriphenylphosphine(0) palladium (4.60 g, 3.98 mmol). The mixture was heated for 3 h at 80° C. and was cooled to room temperature. Aqueous 2N $NH_4OH$ was added and the product was extracted into EtOAc (3×). The organic solution was washed with 2N $NH_4OH$ (2×) followed by brine (2×). The organic solution was dried ($MgSO_4$), filtered, and concentrated in vacuo. Purification by flash chromatography (6:1 hexanes:EtOAc) provided the title compound as an oil (15.19 g). $^1$H NMR (400 MHz, $CDCl_3$) δ 7.57–7.41 (m, 4H), 3.706 (s, 3H), 3.703 (s, 2H).

Step B
(3-Formyl-phenyl)-acetic Acid Methyl Ester.

A mixture of (3-cyano-phenyl)-acetic acid methyl ester (1.56 g, 8.91 mmol), aluminum-nickel alloy (1.63 g) and 75% formic acid (25 mL) was heated at reflux for 1.75 h. The mixture was cooled to room temperature and the solids were removed by filtration through Celite with the aid of boiling EtOH. Water was added and the aqueous solution was washed with $CH_2Cl_2$ (3×). Aqueous saturated $NaHCO_3$ was carefully added to the organic solution until the pH was about 8–9. The organic solution was washed with brine, dried over $MgSO_4$, and concentrated. Purification by flash chromatography (5:1 hexanes:EtOAc) provided the title compound as a clear and colorless oil (870 mg). $^1$H NMR (400 MHz, $CDCl_3$) δ 9.98 (s, 1H), 7.77 (m, 2H), 7.55–7.46 (m, 2H), 3.68 (s, 5H).

PREPARATION AA1

2-(3-Methanesulfonylamino-propyl)-thiazole-4-carboxylic Acid Ethyl Ester

Step A
4-Methanesulfonylamino-butyric Acid Ethyl Ester.

Methanesulfonyl chloride (4.10 g, 35.8 mmol) was added to a suspension of ethyl 4-aminobutyrate hydrochloride (6.00 g, 35.8 mmol) and Et₃N (10.8 mL, 77.4 mmol) in THF (230 mL). The resulting suspension was stirred at room temperature for 43 h. The reaction mixture was filtered and the filtrate was concentrated. Flash chromatography (1:1 EtOAc:hexanes to EtOAc) afforded the title compound (7.08 g). $^1$H NMR (400 MHz, CDCl₃) δ 4.51 (s, 1H), 4.12 (q, 2H), 3.18 (q, 2H), 2.94 (s, 3H), 2.40 (t, 2H), 1.85–1.92 (m, 2H), 1.24 (t, 3H); MS 210 (M$^+$+1).

Step B
4-Methanesulfonylamino-butyramide.

A solution of 4-methanesulfonylamino-butyric Acid ethyl ester (7.08 g, 33.8 mmol) in concentrated NH₄OH (200 mL) was stirred at room temperature for 66 h. The reaction mixture was concentrated to afford the title compound as a white solid (6.16 g). The product was used in the next step without further purification. $^1$H NMR (400 MHz, CDCl₃) δ 3.30 (s, 3H), 3.05–3.09 (m, 2H), 2.91 (s, 3H), 2.24–2.30 (m, 2H), 1.80–1.85 (m, 2H); MS 181 (M$^+$+1).

Step C
4-Methanesulfonylamino-thiobutyramide.

A suspension of 4-methanesulfonylamino-butyramide (0.50 g, 2.8 mmol) and Lawesson's reagent (0.56 g, 1.4 mmol) in THF (50 mL) was stirred at room temperature for 45 minutes. During this time all of the solid dissolved. The solution was concentrated and purified by flash chromatography (79:1 EtOAc:MeOH) to afford the title compound (0.41 g); $^1$H NMR (400 MHz, CDCl₃) δ 3.29 (s, 3H), 3.07–3.11 (m, 2H), 2.91 (s, 3H), 2.62–2.66 (m, 2H), 1.93–1.99 (m, 2H); MS 197 (M$^+$+1).

Step D
2-(3-Methanesulfonylamino-propyl)-thiazole4-carboxylic Acid Ethyl Ester.

A solution of 4-methanesulfonylamino-thiobutyramide (0.35 g, 1.8 mmol) and ethyl bromopyruvate (0.37 g, 1.9 mmol) in EtOH (50 mL) was stirred at room temperature for 17 h. Additional ethyl bromopyruvate (0.05 g, 0.26 mmol) was added and the reaction mixture was stirred at room temperature for 5.5 h. The reaction mixture was concentrated and was purified by flash chromatography (79:1 to 19:1 EtOAc:MeOH) to afford the title compound (0.47 g). $^1$H NMR (400 MHz, CDCl₃) δ 8.05 (s, 1H), 4.40 (q, 2H), 3.24 (t, 2H), 3.17 (t, 2H), 2.96 (s, 3H), 2.10 (t, 2H), 1.39 (t, 3H); MS 293 (M$^+$+1).

PREPARATION BB1

N-(4-Butoxy-benzyl)-methanesulfonamide

Step A: Nitrile Reduction
4-Butoxybenzylamine.

To a solution of 4-butoxybenzonitrile (4.6 g, 26.25 mmol) in Et₂O (50 mL) was added lithium aluminum hydride (1.0M in THF, 26.2 mL, 26.2 mmol) dropwise. The reaction was heated at reflux for 1 h and was cooled to room temperature. The reaction was carefully poured into water (50 mL) and was diluted with Et₂O. The solids were removed by filtration through Celite with the aid of Et₂O. The organic solution was washed with water followed by brine, dried (MgSO₄), filtered, and concentrated in vacuo to provide 4-butoxybenzylamine (2.68 g). $^1$H NMR (400 MHz, CDCl₃) δ 7.16 (m, 2H), 6.82 (m, 2H), 3.91 (m, 2H), 3.75 (s, 2H), 1.73 (m, 2H), 1.46 (m, 2H), 1.39 (m, 2H), 0.95 (t, 3H).

Step B: Sulfonamide Formation
N-(4-Butoxy-benzyl)-methanesulfonamide.

The title compound was prepared following the general procedure described in Step 2 of Preparation A1. $^1$H NMR (400 MHz, CDCl₃) δ 7.24 (d, 2H), 6.86 (d, 2H), 4.76 (bs, 1H), 4.23 (m, 2H), 3.94 (m, 2H), 2.83 (s, 3H), 1.75 (m, 2H), 1.47 (m, 2H), 0.96 (t, 3H).

PREPARATION CC1

3-(3-Chloro-phenyl)-propionaldehyde

A solution of 1-chloro-3-iodobenzene (9.63 g, 40.38 mmol), allyl alcohol (5.86 g, 100.96 mmol), sodium bicarbonate (8.48 g, 100.96 mmol), tetrabutylammonium chloride (11.22 g, 40.38 mmol), and Pd(OAc)₂ (317 mg, 1.413 mmol) in 25 mL DMF was stirred at 50° C. for 18 h. The mixture was cooled to room temperature, diluted with water, and the aqueous solution was washed with EtOAc. The organic solution was washed with water followed by brine, dried over MgSO₄, filtered and concentrated in vacuo. The product was purified via flash chromatography on silica gel (9:1 hexanes:EtOAc) to afford the title compound as an oil (5.04 g).

PREPARATION CC2

3-(3-Bromo-phenyl)-propionaldehyde
The title compound was prepared using the method described above for Preparation CC1 with a reaction time of 1 h at 90° C.

PREPARATION DD1

5-(3-Amino-propyl)-thiophene-2-carboxylic Acid Methyl Ester

Step A
5-(3-tert-Butoxycarbonylamino-prop-1-ynyl)-thiophene-2-carboxylic Acid Methyl Ester.

A mixture of prop-2-ynyl-carbamic Acid tert-butyl ester (1.67 g, 0.011 mmol), 5-bromo-thiophene-2-carboxylic Acid methyl ester (2.50 g, 0.011 mmol), tetrakistriphenylphosphine(0) palladium (0.622 g, 0.0538 mmol), CuI (0.102 g, 0.538 mmol) and triethylamine (1.57 mL, 0.011 mmol) in 50 mL acetonitrile under nitrogen was heated at reflux for 16 h. The reaction was cooled to room temperature, diluted with 75 mL EtOAc, washed with 5.5% HCl, water and brine, dried over MgSO₄, filtered and concentrated in vacuo to an oil. The product was purified via flash chromatography (9:1 to 4:1 hexanes:EtOAc) to afford the title compound as an oil (2.06 g). MS 313 (M+18).

Step B
5-(3-tert-Butoxycarbonylamino-propyl)-thiophene-2-carboxylic Acid Methyl Ester.

A mixture of 5-(3-tert-butoxycarbonylamino-prop-1-ynyl)-thiophene-2-carboxylic acid methyl ester (2.06 g) and 10% palladium on carbon (1.03 g) in 50 mL MeOH was hydrogenated on a Parr shaker at 50 psi H₂ for 16 h. The reaction was filtered through Celite with the aid of MeOH and the filtrate was concentrated in vacuo to afford the title compound as a solid (1.93 g). MS 317 (M+18).

Step C
5-(3-Amino-propyl)-thiophene-2-carboxylic Acid Methyl Ester.

A solution of 5-(3-tert-butoxycarbonylamino-propyl)-thiophene-2-carboxylic Acid methyl ester (0.118 g, 0.5 mmol) in 50 mL MeOH was cooled to 0° C. and was saturated with HCl (g). The reaction was stirred at room temperature for 90 minutes. The solution was concentrated to a solid which was partitioned between EtOAc and saturated NaHCO$_3$. The layers were separated, and the organic layer was washed with brine, dried over MgSO$_4$, filtered and concentrated in vacuo to afford the title compound as an oil (399 mg). MS 200 (M+1).

PREPARATION DD2
5-(3-Amino-propyl)-furan-2-carboxylic Acid Methyl Ester Hydrochloride Salt The title compound was prepared from the appropriate starting materials in an analogous manner to Preparation DD1 with the following exceptions. The hydrogenation performed in Step B was carried out for 5.5 h. In Step C, the reaction was stirred for 16 h at room temperature and was concentrated in vacuo to provide the title compound as the hydrochloride salt.

PREPARATION EE1

5-(3-Amino-propyl)-thiophene-2-carboxylic Acid Tert-butyl Ester

Step A
Prop-2-ynyl-carbamic Acid Benzyl Ester

To a solution of propargylamine (6.4 g, 71.2 mmol) in pyridine (100 mL) was added benzylchloroformate (13.37 g, 78.2 mmol) in 100 mL CH$_2$Cl$_2$ over 0.5 h. The reaction was stirred for 16 h and the volatiles were removed in vacuo The residue was dissolved in EtOAc and the organic solution was washed with water (2×). The organic solution was washed with dilute aqueous HCl followed by saturated NaHCO$_3$. The organic solution was dried over MgSO$_4$, filtered, and concentrated in vacuo to provide the title compound (4.43 g).

Step B
5-(3-Benzyloxycarbonylamino-prop-1-ynyl)-thiophene-2-carboxylic Acid Tert-butyl Ester.

The title compound was prepared from the appropriate starting material in an analogous manner to Step A of Preparation DD1.

Step C
5-(3-Amino-propyl)-thiophene-2-carboxylic Acid Tert-butyl Ester Hydrochloride Salt.

To a solution of 5-(3-benzyloxycarbonylamino-prop-1-ynyl)-thiophene-2-carboxylic acid tert-butyl ester (1.0 g, 2.69 mmol) in 15 mL MeOH and 2.69 mL 1N HCl (aq) was added Pd(OH)$_2$ (1 g). The mixture was shaken in a Parr shaker under 45 psi H$_2$ for 16 h. The catalyst was removed by filtration through Celite and additional Pd(OH)$_2$ (1 g) was added. The reaction was shaken at 45 psi H$_2$ for 6 h and the catalyst was removed by filtration through Celite. The solution was concentrated in vacuo. The residue was azeotroped with CCl$_4$ and was triturated with Et$_2$O to provide the title amine (360 mg).

PREPARATION FF1

5-{3-[3-(3-Chloro-phenyl)-propylamino -propyl}-thiophene-2-carboxylic Acid Methyl Ester A solution of 5-(3-amino-propyl)-thiophene-2-carboxylic Acid methyl ester (0.118 g, 0.5 mmol) and diisopropylethylamine (0.071 g, 0.55 mmol) in 10 mL MeOH was stirred at room temperature for 30 minutes and 3-(3-chloro-phenyl)-propionaldehyde (0.093 g, 0.55 mmol) was added. The mixture was stirred for 90 minutes. The reaction was cooled to 0° C., NaBH$_4$ (0.83 mL, 5.98 mmol) was added and the mixture was stirred for 30 minutes. The reaction was quenched with 1:1 NaHCO$_3$:H$_2$O and was washed with CH$_2$Cl$_2$. The CH$_2$Cl$_2$ extracts were washed with brine, dried over MgSO$_4$, filtered, and concentrated in vacuo to afford the title compound as an oil (171 mg). MS 352 (M+1).

PREPARATIONS FF2-FF4
Preparations FF2-FF4 were prepared from the appropriate starting materials in an analogous manner to Preparation FF1.

PREPARATION FF2

5-{3-[3-(3-Chloro-phenyl)-propylamino]-propyl}-thiophene-2-carboxylic Acid Tert-butyl Ester $^1$H NMR (400 MHz, CDCl$_3$) δ 7.51 (d, 1H), 7.25–7.05 (m, 4H), 6.74 (d, 1H), 2.83 (t, 2H), 2.72–2.59 (m, 6H), 1.97–1.82 (m, 4H), 1.53 (s, 9H); MS 394 (M+1).

PREPARATION FF3

5-{3-[3-(3-Chloro-phenyl)-propylamino]-propyl}-furan-2-carboxylic Acid Methyl Ester

MS 336 (M+1).

PREPARATION FF4

5-{3-[3-(3-Chloro-phenyl)-propylamino]-propyl}-tetrahydrofuran-2-carboxylic acid Methyl Ester

MS 340 (M+1).

PREPARATION GG1

3-(3-Chloro-phenyl)-propylamine

Step A
3-(3-Chloro-phenyl)-acrylamide.

A solution of 3-(3-chloro-phenyl)-acrylic Acid (15.0 g, 82.15 mmol) in 50 mL thionyl chloride was heated at reflux for 30 minutes. The excess thionyl chloride was removed via distillation at atmospheric pressure. The residue was azeotroped with benzene in vacuo to give 17.288 g of an orange oil. The oil was dissolved in 25 mL CH$_2$Cl$_2$ and the solution was added slowly to liquid NH$_3$ (20 mL, 80.07 mmol) in CHCl$_3$ (50 mL) at −78° C. The resulting suspension was warmed to room temperature and was concentrated in vacuo to afford the title compound as a gray solid (19.38 g). $^1$H NMR (400 MHz, CD$_3$OD) δ 7.57 (s, 1H), 7.45 (m, 2H), 7.36 (m, 1H), 6.64 (d, 1H); MS 182 (M+1), 180 (M−1).

Step B
3-(3-Chloro-phenyl)-propylamine.

A 1.0M solution of LiAlH$_4$ in THF (6.0 mL, 6.0 mmol) was added dropwise to a suspension of 3-(3-chloro-phenyl)-acrylamide (1.0 g, 5.51 mmol) in 30 mL THF at 0° C. The reaction was warmed to room temperature and was stirred for 5 h. An additional 4 mL of 1 M LiAlH$_4$ was added and the reaction was stirred for 18 h. An addition 2 mL of 1 M LiAlH$_4$ was added and the reaction was stirred for 24 h. The reaction mixture was quenched by dropwise addition of water. The mixture was concentrated in vacuo to remove THF and was diluted with water. The aqueous solution was extracted with EtOAc. The organic solution was washed with water, dried over MgSO$_4$, filtered and concentrated in vacuo. The residue was dissolved in CHCl$_3$ and the organic solution was washed with 1M HCl. The aqueous solution was basified to pH 11 with 1M NaOH and the product was extracted into CHCl$_3$. The organic solution was dried over MgSO$_4$, filtered and concentrated in vacuo to afford the title compound as a yellow oil (0.134 g). $^1$H NMR (400 MHz, CDCl$_3$) δ 7.20–7.22 (m, 3H),7.16 (m, 1H), 2.74 (t, 2H), 2.61 (t, 2H), 1.74 (m, 2H); MS 170 (M+1).

PREPARATION HH1

4-Pyrimidin-2-yl-benzaldehyde

A solution of 2-bromopyrimidine (1.00 g, 6.3 mmol) and tetrakistriphenylphosphine(0) palladium (0.218 g, 0.189 mmol) in ethylene glycol dimethyl ether (30 mL) was stirred at room temperature for 10 minutes. A solution of 4-formylbenzene boronic acid (1.14 g, 7.61 mmol) and sodium bicarbonate (1.58 g, 18.9 mmol) in 15 mL water was added and the reaction was heated at reflux for 18 h. The mixture was diluted with water and CH$_2$Cl$_2$. The layers were separated, and the aqueous solution was washed with CH$_2$Cl$_2$. The combined organic layers were dried over MgSO$_4$, filtered, and concentrated in vacuo. The residue was purified via flash chromatography (10% to 30% hexanes in EtOAc) to afford the title compound (0.979 g). $^1$H NMR (400 MHz, CDCl$_3$) δ 10.11 (s, 1H), 8.83 (s, 2H), 8.82 (s, 1H), 7.98 (s, 2H), 7.23 (s, 2H).

PREPARATION HH2-HH7

Preparations HH2-HH7 were prepared from the appropriate starting materials in an analogous manner to Preparation HH1.

PREPARATION HH2

4-Pyridin-2-yl-benzaldehyde $^1$H NMR (400 MHz, CDCl$_3$) δ 10.09 (s, 1H), 8.72 (s, 1H),8.16 (s, 2H), 7.95 (s, 2H), 7.79 (s, 2H), 7.29 (m, 1H); MS 184 (M+1).

PREPARATION HH3

4-Pyridin-3-yl-benzaldehyde $^1$H NMR (400 MHz, CDCl$_3$) δ 10.04 (s, 1H), 8.88 (s, 1H),8.64 (s, 1H), 7.97 (s, 2H), 7.91 (m, 1H), 7.75 (m, 2H), 7.39 (m, 1H); MS 184 (M+1).

PREPARATION HH4

4-Pyridin-4-yl-benzaldehyde $^1$H NMR (400 MHz, CDCl$_3$) δ 10.03 (s, 1H), 8.70 (s, 2H),7.99 (s, 2H), 7.79 (s, 2H), 7.52 (s, 2H); MS 184 (M+1).

PREPARATION HH5

4-Thiazol-2-yl-benzaldehyde MS 189 (M+).

PREPARATION HH6

4-Pyrimidin-5-yl-benzaldehyde $^1$H NMR (400 MHz, CDCl$_3$) δ 10.03 (s, 1H), 9.26 (s, 1H), 9.00 (s, 2H), 8.03 (m, 2H), 7.76 (m, 2H).

PREPARATION HH7

4-Pyrazin-2-yl-benzaldehyde $^1$H NMR (400 MHz, CDCl$_3$) δ 10.03 (s, 1H), 9.10 (s, 1H), 8.69 (s, 1H), 8.59 (s, 1H), 8.21 (d, 2H), 8.03 (d, 2H).

PREPARATION II1

5-(3-Oxo-propyl)-1H-pyrazole-3-carboxylic Acid Ethyl Ester

Step A 5-(tert-Butyl-dimethyl-silanyloxy)-pentan-2-one.

A solution of 3-acetyl-1-propanol (3.000 g, 29.37 mmol), tert-butyldimethylsilyl chloride (4.522 g, 30.00 mmol), and imidazole (5.004 g, 73.5 mmol) in DMF (40 mL) was heated at 40° C. for 5 h and was stirred at room temperature for 66 h. Water (60 mL) was added and the product was extracted into EtOAc (4×50 mL). The combined organic extracts were washed with water (2×50 mL), dried over MgSO$_4$, filtered, and concentrated. Purification by flash chromatography (hexanes:EtOAc 9:1) provided the title compound (3.722 g). $^1$H NMR (400 MHz, CDCl$_3$) δ 3.59 (t, 2H), 2.49 (t, 2H), 2.13 (s, 3H), 1.76 (m, 2H), 0.86 (s, 9H), 0.02 (s, 6H); MS 217 (M+1).

Step B 7-(tert-Butyl-dimethyl-silanyloxy)-2,4-dioxo-heptanoic Acid ethyl ester.

Diethyl oxalate (4.048 g, 37.7 mmol) was added to solid sodium ethoxide (0.472 g, 69.3 mmol) at 0° C. followed by slow addition of 5-(tert-butyl-dimethyl-silanyloxy)-pentan-2-one (1.500 g, 69.3 mmol). The resulting orange solution was stirred at 0° C. for 10 minutes and at room temperature for 3 h. Purification by flash chromatography (19:1 hexanes:EtOAc to 9:1 EtOAc:MeOH) provided the title compound (1.982 g); MS 317 (M+1).

Step C

5-[3-(tert-Butyl-dimethyl-silanyloxy)-propyl]-1H-pyrazole-3-carboxylic Acid Ethyl Ester.

A solution of 7-(tert-butyl-dimethyl-silanyloxy)-2,4-dioxo-heptanoic Acid ethyl ester (1.627 g, 51.4 mmol) and hydrazine (17 mL, 55 mmol) in EtOH was heated at reflux for 6 h. The reaction was concentrated in vacuo. Purification by flash chromatography (6:4 hexanes:EtOAc) provided the title compound (333 mg). $^1$H NMR (400 MHz, CDCl$_3$) δ 6.64 (s, 1H), 4.37 (q, 2H), 3.67 (t, 2H), 2.85 (t, 2H), 1.88 (m, 2H), 1.38 (t, 3H), 0.88 (s, 9H), 0.05 (s, 6H); MS 313 (M+1).

Step D 5-(3-Hydroxy-propyl)-1H-pyrazole-3-carboxylic Acid Ethyl Ester.

A solution of 5-[3-(tert-butyl-dimethyl-silanyloxy)-propyl]-1H-pyrazole-3-carboxylic Acid ethyl ester (327 mg, 1.05 mmol) and tetrabutylammonium fluoride (288 mg, 1.10 mmol) in THF (50 mL) was stirred at room temperature for 1 h. The reaction mixture was concentrated in vacuo. Flash chromatography (EtOAc to EtOAc:MeOH 19:1) provided the title alcohol (165 mg). $^1$H NMR (400 MHz, CDCl$_3$) δ 6.58 (s, 1H), 4.35 (q, 2H), 3.71 (t, 2H), 2.84 (t, 2H), 1.91 (m, 2H), 1.36 (t, 3H); MS 199 (M+1).

Step E 5-(3-Oxo-propyl)-1H-pyrazole-3-carboxylic Acid Ethyl Ester.

Dimethylsulfoxide (0.14 mL, 1.9 mmol) was slowly added to a solution of oxalyl chloride (0.137 mg, 1.08 mmol) in CH$_2$Cl$_2$ (1 mL) and THF (1 mL) at −78° C. After stirring for 5 minutes, the solution was added dropwise to a solution of 5-(3-hydroxy-propyl)-1H-pyrazole-3-carboxylic Acid ethyl ester (178 mg, 0.898 mmol) in THF (10 mL) at −78° C. The reaction was stirred for 0.5 h and triethylamine (0.64 mL) was added. The suspension was stirred for 40 minutes and was warmed to room temperature. The reaction was diluted with CH$_2$Cl$_2$:hexanes (1:4, 40 mL) and the mixture was washed with 10% aqueous sodium bisulfate (15 mL) followed by water (2×10 mL). The organic solution was dried over MgSO$_4$, filtered, and concentrated to provide the title aldehyde. $^1$H NMR (400 MHz, CDCl$_3$) δ 9.82 (s, 1H), 6.59 (s, 1H), 4.35 (q, 2H), 3.06 (m, 2H), 2.84 (t, 2H), 1.91 (m, 2H), 1.34 (t, 3H); MS 197 (M+1).

PREPARATION JJ1

[5-(Methanesulfonylamino-methyl)-thiophen-2-yl]-acetic Acid Methyl Ester

To a solution of thiophen-2-yl-acetic Acid methyl ester (2 mL, 12.8 mmol) in 1,4-dioxane (10 mL) was added concentrated HCl (0.4 mL, 4.8 mmol) dropwise over 10 minutes. Zinc chloride (78 mg, 0.57 mmol) was added and the reaction was lowered into a pre-heated water bath at 45° C. and was stirred for 15 minutes. HCl (g) was bubbled into the solution for 2–3 minutes. The temperature of the reaction rose to about 60° C. Upon cooling, 37% aqueous formaldehyde (1.24 mL, 16 mmol) was added dropwise and the temperature rose to 70° C. The reaction was cooled to room temperature and methanesulfonamide (1.25 g, 12.8 mmol) was added in portions. The reaction was stirred for 3 h and was poured into EtOAc (60 mL). The organic solution was washed with water and the aqueous solution was washed with EtOAc (60 mL). The combined organic solutions were washed with brine, dried over MgSO$_4$, filtered, and concentrated. Purification by flash chromatography (CHCl$_3$) provided the title compound (69%) as a gold oil. $^1$H NMR (400 MHz, CDCl$_3$) δ 6.85 (d, 1H), 6.70 (d, 1H), 5.20 (m, 1H), 4.40 (s, 2H), 3.80 (s, 2H), 3.70 (s, 3H), 2.80 (s, 3H).

PREPARATION KK1

5-(3-Bromo-propyl)-benzo[1.3]dioxole

Step A
3-Benzo[1,3]dioxol-5-yl-propan-1-ol.

Lithium aluminum hydride (1M in THF, 30 mL, 30 mmol) was added slowly to a solution of 3-benzo[1,3]dioxol-5-yl-propionic acid (5.83 g, 30 mmol) in THF (60 mL) at 0° C. The reaction was warmed to room temperature and was stirred for 2 h. The solution was added in portions to a mixture of ice (200 g) and concentrated HCl (2 mL). The product was extracted into EtOAc. The organic solution was dried over MgSO$_4$, filtered, and concentrated. Purification by flash chromatography (hexanes:EtOAc 6:4) provided the title alcohol (4.51 g). 1H NMR (400 MHz, CDCl$_3$) δ 6.73–6.62 (m, 3H), 5.91 (s, 2H), 3.66 (t, 2H), 2.63 (t, 2H), 1.84 (m, 2H).

Step B
5-(3-Bromo-propyl)-benzo[1,3]dioxole.

Following the procedure described in Step B of Preparation O1, 3-benzo[1,3]dioxol-5-yl-propan-1-ol was converted to the title bromide. $^1$H NMR (400 MHz, CDCl$_3$) δ 6.74–6.63 (m, 3H), 5.92 (s, 2H), 3.37 (t, 2H), 2.69 (t, 2H), 2.11 (m, 2H).

PREPARATION LL1

2-(3-Iodo-propyl)-furan

To a solution of 3-furan-2-yl-propan-1-ol (6.3 g, 50 mmol) in pyridine (40 mL) at −15° C. was added p-toluenesulfonyl chloride (11.4 g, 60 mmol) in portions and the reaction was stirred for 3 h. Water (10×0.5 mL) was added and the mixture was poured into a mixture of concentrated HCl (65 mL) and ice (200 gm). The product was extracted into Et$_2$O and the organic solution was dried over MgSO$_4$, filtered, and concentrated to provide a yellow oil. The oil was added to a mixture of NaI (9 g, 60 mmol) in acetone (70 mL) and the reaction was stirred for 15 h. The insolubles were removed by filtration and the filtrate was concentrated in vacuo. Purification by flash chromatography (hexanes) provided the title compound (7.2 g). $^1$H NMR (400 MHz, CDCl$_3$) δ 7.30 (m, 1H), 6.28 (m, 1H), 6.04 (m, 1H), 3.19 (t, 2H), 2.75 (t, 2H), 2.14 (m, 2H).

PREPARATION MM1

3-(3-Amino-propyl)-benzoic Acid Methyl Ester Hydrochloride Salt

Step A
3-(3-tert-Butoxycarbonylamino-prop-1-ynyl)-benzoic Acid Methyl Ester.

Following the general procedure described in Step A of Preparation C1, prop-2-ynyl-carbamic acid tert-butyl ester was coupled to 3-bromomethylbenzoate to provide the title compound. MS 307 (M+18).

Step B
3-(3-tert-Butoxycarbonylamino-propyl)-benzoic Acid Methyl Ester.

Following the general procedure described in Step B of Preparation C1, 3-(3-tert-butoxycarbonylamino-prop-1-ynyl)-benzoic Acid methyl ester was hydrogenated to provide the title compound. MS 311 (M+18).

Step C
3-(3-Amino-propyl)-benzoic Acid Methyl Ester Hydrochloride Salt.

A solution of 3-(3-tert-butoxycarbonylamino-propyl)-benzoic Acid methyl ester (565 mg) in MeOH (25 mL) was cooled to 0° C. and the solution was saturated with HCl (g). The reaction was stirred at room temperature for 1.5 h and was concentrated in vacuo to provide the title amine (399 mg). MS 194 (M+1).

PREPARATION NN1

[3-(2-Methanesulfonylamino-ethyl)-phenyl]-acetic Acid Tert-butyl Ester

Step A
3-Bromo-phenyl Acetic Acid Tert-butyl Ester.

A mixture of 3-bromo-phenyl acetic acid (5.00 g, 23.24 mmol), tert-butanol (1.89 g, 25.57 mmol), DMAP (3.12 g, 25.57 mmol), and DCC (5.27 g, 25.57 mmol) in CH$_2$Cl$_2$ (150 mL) was stirred for 24 h at room temperature. The reaction was filtered and the filtrate was concentrated in vacuo. The residue was dissolved in EtOAc and the mixture was filtered. The organic solution was washed consecutively with 5.5% HCl, water, saturated NaHCO$_3$, and brine. The organic solution was dried over MgSO$_4$, filtered, and concentrated to provide the title compound (5.64 g).

Step B
{2-[2-(1,3-Dioxo-1,3-dihydro-isoindol-2-yl)-vinyl]-phenyl}-acetic Acid Tert-butyl Ester.

A mixture of 3-bromo-phenyl acetic Acid tert-butyl ester (5.64 g, 20.80 mmol), N-vinyl phthalimide (3.60 g, 20.80 mmol), diisopropylethylamine (3.63 g, 28.08 mmol), palladium acetate (107 mg, 0.478 mmol), and tri-o- tolylphosphine (475 mg, 1.56 mmol) in acetonitrile (10 mL) was stirred at 90° C. for 20 h. The reaction was cooled to room temperature and ice water (50 mL) was added. EtOAc (50 mL) was added and the organic solution was washed with 5.5% HCl followed by brine. The organic solution was dried over $MgSO_4$, filtered, and concentrated. Purification by flash chromatography (hexanes:EtOAc 9:1 to 4:1) provided the title compound (1.95 g). MS 381 (M+18).

Step C
{2-[2-(1,3-Dioxo-1,3-dihydro-isoindol-2-yl)-ethyl]-phenyl}-acetic Acid Tert-butyl Ester.

To a solution of {2-[2-(1,3-dioxo-1,3-dihydro-isoindol-2-yl)-vinyl)-phenyl}acetic acid tert-butyl ester (1.95 g) in THF (50 mL) was added 10% Pd on carbon (1.00 g) and the reaction was hydrogenated on a Parr shaker at 50 psi for 24 h. The catalyst was removed by filtration through Celite with the aid of THF. The volatiles were removed in vacuo to provide the title compound (1.97 g). MS 383 (M+18).

Step D
[2-(2-Amino-ethyl)-phenyl]-acetic Acid Tert-butyl Ester.

A solution of {2-[2-(1,3-dioxo-1,3-dihydro-isoindol-2-yl)-vinyl]-phenyl}-acetic Acid tert-butyl ester (1.97 g) and hydrazine hydrate (1.97 mL) in EtOH (75 mL) was heated at reflux for 90 minutes. The solids were removed by filtration and the filtrate was concentrated in vacuo. The residue was dissolved in EtOAc (50 mL) and the solution was washed with saturated $NaHCO_3$ followed by brine. The organic solution was dried over $MgSO_4$, filtered, and concentrated. Purification by flash chromatography ($CHCl_3$:MeOH 97.5:2.5 to 95:5 to 9:1) provided the title amine (853 mg). MS 236 (M+1).

Step E
[3-(2-Methanesulfonylamino-ethyl)-phenyl]-acetic Acid Tert-butyl Ester.

A mixture of [2-(2-amino-ethyl)-phenyl]-acetic Acid tert-butyl ester (422.5 mg, 1.795 mmol), triethylamine (908 mg, 8.977 mmol), and methanesulfonyl chloride (226.2 mg, 1.975 mmol) in $CH_2Cl_2$ (20 mL) was combined and stirred at 0° C. for 18 h. The organic solution was washed consecutively with dilute HCl, water, saturated $NaHCO_3$, and brine. The organic solution was dried over $MgSO_4$, filtered, and concentrated to provide the title sulfonamide (535 mg). MS 331 (M+18).

PREPARATION OO1
5-(3-Methanesulfonylamino-propyl)-furan-2-carboxylic Acid Methyl Ester To a solution of 5-(3-amino-propyl)-furan-2-carboxylic Acid methyl ester hydrochloride salt (see Preparation DD2) (150 mg, 0.683 mmol), and triethylamine (0.313 mL, 2.25 mmol) in $CH_2Cl_2$ (15 mL) at 0° C. was added methanesulfonyl chloride (86 mg, 0.75 mmol). The reaction was stirred at room temperature for 18 h. The organic solution was washed consecutively with dilute HCl, water, saturated $NaHCO_3$, and brine. The organic solution was dried over $MgSO_4$, filtered, and concentrated to provide the title sulfonamide (156 mg). MS 262 (M+1).

PREPARATION PP1

5-(3-Amino-propyl)-tetrahydrofuran-2-carboxylic Acid Methyl Ester Hydrochloride Salt Step A
5-(3-tert-Butoxycarbonylamino-prop-1-ynyl)-furan-2-carboxylic Acid Methyl Ester.

The title compound was prepared using the method described in Step A of Preparation DD1.

Step B
5-(3-tert-Butoxycarbonylamino-propyl)-tetrahydrofuran-2-carboxylic Acid Methyl Ester and 5-(3-tert-Butoxycarbonylamino-propyl)-furan-2-carboxylic Acid Methyl Ester.

To a solution of 5-(3-tert-butoxycarbonylamino-prop-1-ynyl)-furan-2-carboxylic Acid methyl ester (1.69 g) in MeOH (50 mL) was added 10% palladium on carbon (850 mg) and the mixture was hydrogenated on a Parr shaker at 50 psi for 18 h. The catalyst was removed via filtration through Celite and the volatiles were concentrated in vacuo. Flash chromatography (hexanes:EtOAc 4:1) provided 5-(3-tert-butoxycarbonylaminopropyl)-furan-2-carboxylic Acid methyl ester (422 mg, MS 284 M+) followed by 5-(3-tert-butoxycarbonylamino-propyl)-tetrahydrofuran-2-carboxylic Acid methyl ester (903 mg).

Step C
5-(3-Amino-propyl)-tetrahydrofuran-2-carboxylic Acid Methyl Ester Hydrochloride Salt.

The title compound was prepared from 5-(3-tert-butoxycarbonylamino-propyl)-tetrahydrofuran-2-carboxylic Acid methyl ester following the procedure described in Step C for Preparation DD2.

PREPARATION QQ1

3-(1H-Indol-3-yi)-propylamine
The title reagent can be prepared using the method described by Jackson in J. Am. Chem. Soc., 52, 5029–5033,1930.

PREPARATON RR1

2-(Biphenyl-2-yloxy)-ethylamine
The title reagent can be prepared using the method described in GB 521575.

PREPARATION SS1

2-(3-Chloro-phenylsulfanyl)-ethylamine
The title reagent can be prepared using the method described in Fed. Rep. Ger. Sci. Pharm., 56, 4, 229–234,1988.

PREPARATION TT1

2-(4-Chloro-phenylsulfanyl)-ethylamine
The title reagent can be prepared using the method described in Can. J. Chem., 37, 325–329, 1959.

PREPARATION UU1

3-(4-Chloro-phenyl)-propylamine
The title reagent can be prepared using the method described in J. Med. Chem., 39, 25,4942–4951, 1996.

PREPARATION VV1
4-Phenethylsulfanyl-benzaidehyde
The title reagent can be prepared using the method described in EP 332331.

PREPARATION WW1

4-(2-Oxo-pyrrolidin-1-yl)-benzaldehyde
The title compound can be prepared using the method described by Kukalenko in Chem. Heterocycl. Compd. (Engl. Transl.), 8, 43, 1972.

PREPARATION XX1

4-Cyclohexyl-benzylamine
The title compound can be prepared using the method described by Meglio and coworkers in Farmaco Ed. Sci.; IT; 35, 3, 191–202, 1980.

PREPARATION YY1

3-Hydroxy-4-propoxy-benzaldehyde

The title compound can be prepared using the method described by Beke in Acta Chim. Acad. Sci. Hung., 14, 325–8, 1958.

PREPARATION ZZ1

5-Phenyl-furan-2-carbaldehyde

The title compound can be prepared using the method described by D'Auria and coworkers in Heterocycles, 24, 6,1575–1578,1986.

What is claimed is:
1. A compound having the Formula I

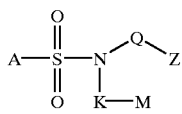

Formula I or a pharmaceutically acceptable salt or prodrug thereof wherein

A is $(C_1-C_6)$alkyl, $(C_3-C_7)$cycloalkyl or $(C_3-C_7)$cycloalkyl$(C_1-C_6)$alkyl, said A moieties optionally mono-, di- or tri-substituted on carbon independently with hydroxy, $(C_1-C_4)$alkyl or halo;

Q is
—$(C_2-C_6)$alkylene-W—$(C_1-C_3)$alkylene-,
—$(C_3-C_8)$alkylene-, said —$(C_3-C_8)$alkylene-being straight chain with the proviso that $(C_3-C_8)$alkylene may be optionally substituted with up to four substituents independently selected from fluoro or $(C_1-C_4)$alkyl,
—X—$(C_1-C_5)$alkylene-,
—$(C_1-C_5)$alkylene-X-,
—$(C_1-C_3)$alkylene-X—$(C_1-C_3)$alkylene-,
—$(C_2-C_4)$alkylene-W-X—$(C_0-C_3)$alkylene-,
—$(C_0-C_4)$alkylene-X-W—$(C_1-C_3)$alkylene-,
—$(C_2-C_5)$alkylene-W-X-W—$(C_1-C_3)$alkylene-, wherein the two occurrences of W are independent of each other,
—$(C_1-C_4)$alkylene-ethenylene—$(C_1-C_4)$alkylene-,
—$(C_1-C_4)$alkylene-ethenylene—$(C_0-C_2)$alkylene-X—$(C_0-C_5)$alkylene-,
—$(C_1-C_4)$alkylene-ethenylene—$(C_0-C_2)$alkylene-X-W—$(C_1-C_3)$alkylene-,
—$(C_1-C_4)$alkylene-ethynylene—$(C_1-C_4)$alkylene-, or
—$(C_1-C_4)$alkylene-ethynylene-X—$(C_0-C_3)$alkylene-;

W is oxy, thio, sulfino, sulfonyl, aminosulfonyl-, -mono-N—$(C_1-C_4)$alkyleneaminosulfonyl-, sulfonylamino, N—$(C_1-C_4)$alkylenesulfonylamino, carboxamido, N—$(C_1-C_4)$alkylenecarboxamido, carboxamidooxy, N—$(C_1-C_4)$alkylenecarboxamidooxy, carbamoyl, -mono-N—$(C_1-C_4)$alkylenecarbamoyl, carbamoyloxy, or -mono-N—$(C_1-C_4)$alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, or di- substituted independently with halo, $(C_1-C_3)$alkyl, trifluoromethyloxy, difluoromethyloxy, hydroxyl, $(C_1-C_4)$alkoxy, or carbamoyl;

Z is carboxyl, $(C_1-C_6)$alkoxycarbonyl, tetrazolyl, 1,2,4-oxadiazolyl, 5-oxo-1,2,4-oxadiazolyl, $(C_1-C_4)$alkylsulfonylcarbamoyl or phenylsulfonylcarbamoyl;

K is a bond, $(C_1-C_8)$alkylene, thio$(C_1-C_4)$alkylene or oxy$(C_1-C_4)$alkylene, said $(C_1-C_8)$alkylene optionally mono-unsaturated and wherein K is optionally mono-, di- or tri-substituted independently with fluoro, methyl or chloro;

M is —Ar, —Ar¹—V—Ar², —Ar¹—S—Ar² or —Ar¹—O—Ar² wherein Ar, Ar¹ and Ar² are each independently a partially saturated, fully saturated or fully unsaturated five to eight membered ring having one to four heteroatoms selected independently from oxygen, sulfur and nitrogen, or, a bicyclic ring consisting of two fused partially saturated, fully saturated or fully unsaturated five or six membered rings, taken independently, having one to four heteroatoms selected independently from nitrogen, sulfur and oxygen;

said Ar, Ar¹ and Ar² moieties optionally substituted, on one ring if the moiety is monocyclic, or one or both rings if the moiety is bicyclic, on carbon with up to three substituents independently selected from R¹, R² and R³ wherein R¹, R² and R³ are hydroxy, nitro, halo, $(C_1-C_6)$alkoxy, $(C_1-C_4)$alkoxy$(C_1-C_4)$alkyl, $(C_1-C_4)$alkoxycarbonyl, $(C_1-C_7)$alkyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, sulfonamido, $(C_1-C_4)$alkylsulfonamido, amino, mono-N- or di-N,N—$(C_1-C_4)$alkylamino, carbamoyl, mono-N- or di-N,N—$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N- or di-N,N—$(C_1-C_4)$alkylaminosulfinyl;

R¹, R² and R³ are optionally mono-, di- or tri-substituted on carbon independently with halo or hydroxy; and V is a bond or $(C_1-C_3)$alkylene optionally mono- or di-substituted independently with hydroxy or fluoro.

2. A compound as recited in claim 1 wherein said A moieties optionally mono-, di-, or tri-substituted on carbon with fluoro;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethoxy;

W is oxy, thio or sulfonyl;

Z is carboxyl, $(C_1-C_4)$alkoxycarbonyl or tetrazolyl;

K is methylene or ethylene;

Ar, Ar¹ and Ar² are each independently thienyl, thiazolyl, pyridyl, pyrimidyl, oxazolyl, furanyl, imidazolyl, isoxazolyl, pyrazinyl or pyrazolyl;

R¹ is halo, $(C_1-C_6)$alkoxy, $(C_1-C_7)$alkyl, $(C_3-C_7)$cycloalkyl, or $(C_3-C_7)$cycloalkyl$(C_1-C_4)$alkyl, said $(C_1-C_6)$alkoxy, $(C_1-C_7)$alkyl, $(C_3-C_7)$cycloalkyl or $(C_3-C_7)$cycloalkyl$(C_1-C_4)$alkyl, optionally mono-, di- or tri-substituted independently with hydroxy, fluoro or chloro; and R² and R³ are chloro, fluoro, methyl, methoxy, difluoromethoxy, trifluoromethoxy or trifluoromethyl.

3. A compound as recited in claim 2 wherein

A is $(C_1-C_3)$alkyl;

Q is
—$(C_2-C_6)$alkylene-W—$(C_1-C_3)$alkylene-,
—$(C_4-C_8)$alkylene-, said —$(C_4-C_8)$alkylene-straight chain optionally substituted with up to four substituents independently selected from fluoro or $(C_1-C_4)$alkyl, —X—(C$_2$–C$_5$)alkylene-,
—(C$_1$–C$_5$)alkylene-X-,
—(C$_1$–C$_3$)alkylene-X—(C$_1$–C$_3$)alkylene-,
—(C$_2$–C$_4$)alkylene-W-X—(C$_0$–C$_3$)alkylene-, or
—(C$_0$–C$_4$)alkylene-X-W—(C$_1$–C$_3$)alkylene-;

M is —Ar$^1$—V—Ar$^2$ or —Ar$^1$—O—Ar$^2$ wherein Ar$^1$ and Ar$^2$ are each independently pyridyl or thienyl;

V is a bond or (C$_1$–C$_2$)alkylene;

R$^1$ is chloro, fluoro, (C$_1$–C$_4$)alkyl or (C$_1$–C$_4$)alkoxy, said (C$_1$–C$_4$)alkyl and (C$_1$–C$_4$)alkoxy optionally mono-, di- or tri-substituted independently with hydroxy or fluoro; and R$^2$ and R$^3$ are each independently chloro or fluoro.

4. A compound as recited in claim 1 wherein

A is (C$_1$–C$_6$)alkyl, (C$_3$–C$_6$)cycloalkyl or (C$_3$–C$_6$)cycloalkyl(C$_1$–C$_6$)alkyl;

X is phenyl, thienyl, or thiazolyl said phenyl, thienyl or thiazolyl optionally mono- or di- substituted independently with fluoro, chloro, trifluoromethyl, methoxy, difluoromethoxy or trifluoromethyloxy;

W is oxy, thio or sulfonyl;

Z is carboxyl, (C$_1$–C$_4$)alkoxycarbonyl or tetrazolyl;

K is (C$_1$–C$_8$)alkylene or oxy(C$_1$–C$_4$)alkylene, said (C$_1$–C$_8$)alkylene optionally mono-unsaturated and wherein K is optionally mono-, di- or tri-substituted independently with methyl, fluoro or chloro;

M is —Ar, said —Ar is thienyl, pyridyl, thiazolyl, oxazolyl, isoxazolyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, imidazolyl, quinolinyl, isoquinolinyl, benzoxazolyl, benzothiazolyl, indolyl, or chromanyl;

R$^1$ is halo, (C$_1$–C$_6$)alkoxy, (C$_1$–C$_7$)alkyl, (C$_3$–C$_7$)cycloalkyl, (C$_1$–C$_7$)alkanoyl or (C$_3$–C$_7$)cycloalkyl(C$_1$–C$_4$)alkyl, said (C$_1$–C$_6$)alkoxy, (C$_1$–C$_7$)alkyl, (C$_3$–C$_7$)cycloalkyl, (C$_1$–C$_7$)alkanoyl or (C$_3$–C$_7$)cycloalkyl(C$_1$–C$_4$)alkyl, optionally mono-, di- or tri-substituted independently with hydroxy, fluoro or chloro; and R$^2$ and R$^3$ are each independently hydroxy, halo, trifluoromethyl, (C$_1$–C$_7$)alkyl, (C$_1$–C$_4$)alkoxy, (C$_1$–C$_5$)alkanoyl, cyano, (C$_3$–C$_7$)cycloalkyl, (C$_3$–C$_7$)cycloalkyl(C$_1$–C$_4$)alkyl, formyl, difluoromethoxy, trifluoromethoxy or carbamoyl.

5. A compound as recited in claim 4 wherein

K is methylene;

A is (C$_1$–C$_3$)alkyl;

M is —Ar and —Ar is thiazolyl, pyridyl, thienyl, oxazolyl, furanyl, wherein —Ar is substituted with at least R$^1$;

R$^1$ is (C$_1$–C$_7$)alkyl or (C$_1$–C$_5$)alkoxy, said (C$_1$–C$_7$)alkyl or (C$_1$–C$_5$)alkoxy optionally mono-, di- or tri-substituted independently with hydroxy or fluoro; and R$^2$ and R$^3$ are each independently chloro, fluoro, methyl, difluoromethoxy, trifluoromethoxy or trifluoromethyl.

6. A compound as recited in claim 5 wherein the compound is

7-{[5-(1-Hydroxy-hexyl)-thiopen-2-ylmethyl]-methanesulfonyl-amino{-heptanoic acid.

7. A compound as recited in claim 5 wherein

Q is —(C$_2$–C$_6$)alkylene-W—(C$_1$–C$_3$)alkylene-; and

W is oxy.

8. A compound as recited in claim 5 wherein

Q is —(C$_3$–C$_8$)alkylene-, said —(C$_3$–C$_8$)alkylene- optionally substituted with from one to four fluorines.

9. A compound as recited in claim 8 wherein

A is methylsulfonyl;

Q is n-hexylene;

Z is carboxyl;

K is methylene; and

M is 5-(1-hydroxy-n-hexylene-1-yl)thien-2-yl.

10. A compound as recited in claim 5 wherein

Q is -X—(C$_1$–C$_5$)alkylene-; and

X is thienyl or phenyl; said phenyl and thienyl optionally mono- or di- substituted independently with fluoro, chloro, trifluoromethyl or methoxy.

11. A compound as recited in claim 5 wherein

Q is —(C$_1$–C$_5$)alkylene-X-; and

X is thienyl or phenyl; said phenyl and thienyl optionally mono- or di- substituted independently with fluoro, chloro, trifluoromethyl or methoxy.

12. A compound as recited in claim 5 wherein

Q is —(C$_1$–C$_3$)alkylene-X—(C$_1$–C$_3$)alkylene-; and

X is thienyl or phenyl; said phenyl and thienyl optionally mono- or di- substituted independently with fluoro, chloro, trifluoromethyl or methoxy.

13. A compound as recited in claim 5 wherein

Q is —(C$_2$–C$_4$)alkylene-W-X—(C$_0$–C$_3$)alkylene-;

X is thienyl or phenyl; said phenyl and thienyl optionally mono- or di- substituted independently with fluoro, chloro, trifluoromethyl or methoxy; and W is oxy.

14. A compound as recited in claim 5 wherein

Q is —(C$_0$–C$_4$)alkylene-X-W—(C$_1$–C$_3$)alkylene-;

X is thienyl or phenyl; said phenyl and thienyl optionally mono- or di- substituted independently with fluoro, chloro, trifluoromethyl or methoxy; and W is oxy.

15. A compound as recited in claim 5 wherein

Q is —(C$_2$–C$_4$)alkylene-W-X-W—(C$_1$–C$_3$)alkylene-;

W is oxy; and

X is thienyl or phenyl; said phenyl and thienyl optionally mono- or di- substituted independently with fluoro, chloro, trifluoromethyl or methoxy.

16. A compound as recited in claim 5 wherein

Q is —(C$_1$–C$_4$)alkylene-ethenylene—(C$_1$–C$_4$)alkylene-; and

M is —Ar and —Ar is thiazolyl, pyridyl or thienyl.

17. A compound as recited in claim 5 wherein

Q is —(C$_1$–C$_4$)alkylene-ethenylene—(C$_0$–C$_2$)alkylene-X—(C$_0$–C$_3$)alkylene-; and X is thienyl or phenyl; said phenyl and thienyl optionally mono- or di- substituted independently with fluoro, chloro, trifluoromethyl or methoxy.

18. A compound as recited in claim 5 wherein

Q is —(C$_1$–C$_3$)alkylene-ethenylene—(C$_0$–C$_2$)alkylene-X—W—(C$_1$–C$_3$)alkylene-;

W is oxy; and

X is thienyl or phenyl; said phenyl and thienyl optionally mono- or di- substituted independently with fluoro, chloro, trifluoromethyl or methoxy.

19. A compound as recited in claim 5 wherein

Q is —(C$_1$–C$_4$)alkylene-ethynylene—(C$_1$–C$_4$)alkylene-.

20. A compound as recited in claim 5 wherein

Q is —$(C_1-C_4)$alkylene-ethynylene-X—$(C_0-C_3)$alkylene-; and

X is thienyl or phenyl; said phenyl and thienyl optionally mono- or di- substituted independently with fluoro, chloro, trifluoromethyl or methoxy.

21. A compound as recited in claim 4 wherein

A is $(C_1-C_3)$alkyl;

K is $(C_1-C_8)$alkylene;

—Ar is thiazolyl, pyridyl, thienyl, benzofuranyl, benzo[1,3]dioxolyl, 2,3-dihydrobenzo[1,4]dioxine, 2,3-dihydrobenzofuranyl, benzimidazolyl, or benzo[b]thiophenyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

22. A compound as recited in claim 21 wherein

Q is —$(C_2-C_6)$alkylene-W—$(C_1-C_3)$alkylene-; and

W is oxy.

23. A compound as recited in claim 21 wherein

Q is —$(C_3-C_8)$alkylene-, said —$(C_3-C_8)$alkylene- optionally substituted with from one to four fluorines.

24. A compound as recited in claim 21 wherein

Q is -X—$(C_1-C_5)$alkylene-; and

X is thienyl or phenyl; said phenyl and thienyl optionally mono- or di- substituted independently with fluoro, chloro, trifluoromethyl or methoxy.

25. A compound as recited in claim 21 wherein

Q is —$(C_1-C_5)$alkylene-X—; and

X is thienyl or phenyl; said phenyl and thienyl optionally mono- or di- substituted independently with fluoro, chloro, trifluoromethyl or methoxy.

26. A compound as recited in claim 21 wherein

Q is —$(C_1-C_3)$alkylene-X—$(C_1-C_3)$alkylene-; and

X is thienyl or phenyl; said phenyl and thienyl optionally mono- or di- substituted independently with fluoro, chloro, trifluoromethyl or methoxy.

27. A compound as recited in claim 21 wherein

Q is —$(C_2-C_4)$alkylene-W-X—$(C_0-C_3)$alkylene-;

X is thienyl or phenyl; said phenyl and thienyl optionally mono- or di- substituted independently with fluoro, chloro, trifluoromethyl or methoxy; and W is oxy.

28. A compound as recited in claim 21 wherein

Q is —$(C_0-C_4)$alkylene-X-W—$(C_1-C_3)$alkylene-;

X is thienyl or phenyl; said phenyl and thienyl optionally mono- or di- substituted independently with fluoro, chloro, trifluoromethyl or methoxy; and W is oxy.

29. A compound as recited in claim 21 wherein

Q is —$(C_2-C_4)$alkylene-W-X-W—$(C_1-C_3)$alkylene-;

W is oxy; and

X is thienyl or phenyl; said phenyl and thienyl optionally mono- or di- substituted independently with fluoro, chloro, trifluoromethyl or methoxy.

30. A compound as recited in claim 21 wherein

Q is —$(C_1-C_4)$alkylene-ethenylene—$(C_1-C_4)$alkylene-; and

M is —Ar and —Ar is thiazolyl, pyridyl or thienyl.

31. A compound as recited in claim 21 wherein

Q is —$(C_1-C_4)$alkylene-ethenylene—$(C_0-C_2)$alkylene-X—$(C_0-C_3)$alkylene-; and X is thienyl or phenyl; said phenyl and thienyl optionally mono- or di- substituted independently with fluoro, chloro, trifluoromethyl or methoxy.

32. A compound as recited in claim 21 wherein

Q is —$(C_1-C_3)$alkylene-ethenylene—$(C_0-C_2)$alkylene-X-W—$(C_1-C_3)$alkylene-;

W is oxy; and

X is thienyl or phenyl; said phenyl and thienyl optionally mono- or di- substituted independently with fluoro, chloro, trifluoromethyl or methoxy.

33. A compound as recited in claim 21 wherein

Q is —$(C_1-C_4)$alkylene-ethynylene—$(C_1-C_4)$alkylene-.

34. A compound as recited in claim 21 wherein

Q is —$(C_1-C_4)$alkylene-ethynylene-X—$(C_0-C_3)$alkylene-; and

X is thienyl or phenyl; said phenyl and thienyl optionally mono- or di- substituted independently with fluoro, chloro, trifluoromethyl or methoxy.

35. A compound as recited in claim 4 wherein

A is $(C_1-C_3)$alkyl;

K is oxy$(C_1-C_4)$alkylene;

—Ar is thienyl, thiazolyl, pyridyl or benzo[1,3]dioxolyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

36. A compound as recited in claim 35 wherein

Q is —$(C_2-C_6)$alkylene-W—$(C_1-C_3)$alkylene-; and w is oxy.

37. A compound as recited in claim 35 wherein

Q is —$(C_3-C_8)$alkylene-, said —$(C_3-C_8)$alkylene- optionally substituted with from one to four fluorines.

38. A compound as recited in claim 35 wherein

Q is -X—$(C_1-C_5)$alkylene-; and

X is thienyl or phenyl; said phenyl and thienyl optionally mono- or di- substituted independently with fluoro, chloro, trifluoromethyl or methoxy.

39. A compound as recited in claim 35 wherein

Q is —$(C_1-C_5)$alkylene-X—; and

X is thienyl or phenyl; said phenyl and thienyl optionally mono- or di- substituted independently with fluoro, chloro, trifluoromethyl or methoxy.

40. A compound as recited in claim 35 wherein

Q is —$(C_1-C_3)$alkylene-X—$(C_1-C_3)$alkylene-; and

X is thienyl or phenyl; said phenyl and thienyl optionally mono- or di- substituted independently with fluoro, chloro, trifluoromethyl or methoxy.

41. A compound as recited in claim 35 wherein

Q is —$(C_2-C_4)$alkylene-W-X—$(C_0-C_3)$alkylene-;

X is thienyl or phenyl; said phenyl and thienyl optionally mono- or di- substituted independently with fluoro, chloro, trifluoromethyl or methoxy; and W is oxy.

42. A compound as recited in claim 35 wherein

Q is —$(C_0-C_4)$alkylene-X-W—$(C_1-C_3)$alkylene-;

X is thienyl or phenyl; said phenyl and thienyl optionally mono- or di- substituted independently with fluoro, chloro, trifluoromethyl or methoxy; and W is oxy.

43. A compound as recited in claim 35 wherein

Q is —$(C_2-C_4)$alkylene-W-X-W—$(C_1-C_3)$alkylene-;

W is oxy; and

X is thienyl or phenyl; said phenyl and thienyl optionally mono- or di- substituted independently with fluoro, chloro, trifluoromethyl or methoxy.

44. A compound as recited in claim 35 wherein
Q is —($C_1$–$C_4$)alkylene-ethenylene—($C_1$–$C_4$)alkylene-; and
M is —Ar and —Ar is thiazolyl, pyridyl or thienyl.

45. A compound as recited in claim 35 wherein Q is —($C_1$–$C_4$)alkylene-ethenylene—($C_0$–$C_2$)alkylene-X—($C_0$–$C_3$)alkylene-; and
X is thienyl or phenyl; said phenyl and thienyl optionally mono- or di- substituted independently with fluoro, chloro, trifluoromethyl or methoxy.

46. A compound as recited in claim 35 wherein
Q is —($C_1$–$C_3$)alkylene-ethenylene—($C_0$–$C_2$)alkylene-X-W—($C_1$–$C_3$)alkylene-;
W is oxy; and
X is thienyl or phenyl; said phenyl and thienyl optionally mono- or di- substituted independently with fluoro, chloro, trifluoromethyl or methoxy.

47. A compound as recited in claim 35 wherein
Q is —($C_1$–$C_4$)alkylene-ethynylene—($C_1$–$C_4$)alkylene-.

48. A compound as recited in claim 35 wherein
Q is —($C_1$–$C_4$)alkylene-ethynylene-X—($C_0$–$C_3$) alkylene-; and
X is thienyl or phenyl; said phenyl and thienyl optionally mono- or di- substituted independently with fluoro, chloro, trifluoromethyl or methoxy.

49. A compound as recited in claim 4 wherein
A is ($C_1$–$C_3$)alkyl;
K is ($C_3$–$C_8$)alkylene, said ($C_3$–$C_8$)alkylene being mono-unsaturated;
—Ar is thienyl, thiazolyl, pyridyl, and
$R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

50. A compound as recited in claim 49 wherein
Q is —($C_2$–$C_6$)alkylene-W—($C_1$–$C_3$)alkylene-; and
W is oxy.

51. A compound as recited in claim 49 wherein
Q is —($C_3$–$C_8$)alkylene-, said —($C_3$–$C_8$)alkylene- optionally substituted with from one to four fluorines.

52. A compound as recited in claim 49 wherein
Q is -X—($C_1$–$C_5$)alkylene-; and
X is thienyl or phenyl; said phenyl and thienyl optionally mono- or di- substituted independently with fluoro, chloro, trifluoromethyl or methoxy.

53. A compound as recited in claim 49 wherein
Q is —($C_1$–$C_5$)alkylene-X-; and
X is thienyl or phenyl; said phenyl and thienyl optionally mono- or di- substituted independently with fluoro, chloro, trifluoromethyl or methoxy.

54. A compound as recited in claim 49 wherein
Q is —($C_1$–$C_3$)alkylene-X—($C_1$–$C_3$)alkylene-; and
X is thienyl or phenyl; said phenyl and thienyl optionally mono- or di- substituted independently with fluoro, chloro, trifluoromethyl or methoxy.

55. A compound as recited in claim 49 wherein
Q is —($C_2$–$C_4$)alkylene-W-X—($C_0$–$C_3$)alkylene-;
X is thienyl or phenyl; said phenyl and thienyl optionally mono- or di- substituted independently with fluoro, chloro, trifluoromethyl or methoxy; and
W is oxy.

56. A compound as recited in claim 49 wherein
Q is —($C_0$–$C_4$)alkylene-X-W—($C_1$–$C_3$)alkylene-;
X is thienyl or phenyl; said phenyl and thienyl optionally mono- or di- substituted independently with fluoro, chloro, trifluoromethyl or methoxy; and
W is oxy.

57. A compound as recited in claim 49 wherein
Q is —($C_2$–$C_4$)alkylene-W-X-W—($C_1$–$C_3$)alkylene-;
W is oxy; and
X is thienyl or phenyl; said phenyl and thienyl optionally mono- or di- substituted independently with fluoro, chloro, trifluoromethyl or methoxy.

58. A compound as recited in claim 49 wherein
Q is —($C_1$–$C_4$)alkylene-ethenylene—($C_1$–$C_4$)alkylene-; and
M is —Ar and —Ar is thiazolyl, pyridyl or thienyl.

59. A compound as recited in claim 49 wherein
Q is —($C_1$–$C_4$)alkylene-ethenylene—($C_0$–$C_2$)alkylene-X—($C_0$–$C_3$)alkylene-; and
X is thienyl or phenyl; said phenyl and thienyl optionally mono- or di- substituted independently with fluoro, chloro, trifluoromethyl or methoxy.

60. A compound as recited in claim 49 wherein
Q is —($C_1$–$C_3$)alkylene-ethenylene—($C_0$–$C_2$)alkylene-X-W—($C_1$–$C_3$)alkylene-;
W is oxy; and
X is thienyl or phenyl; said phenyl and thienyl optionally mono- or di- substituted independently with fluoro, chloro, trifluoromethyl or methoxy.

61. A compound as recited in claim 49 wherein
Q is —($C_1$–$C_4$)alkylene-ethynylene—($C_1$–$C_4$)alkylene-.

62. A compound as recited in claim 49 wherein
Q is —($C_1$–$C_4$)alkylene-ethynylene-X—($C_0$–$C_3$) alkylene-; and
X is thienyl or phenyl; said phenyl and thienyl optionally mono- or di- substituted independently with fluoro, chloro, trifluoromethyl or methoxy.

63. A method for treating a mammal having a condition which presents with low bone mass comprising administering to said mammal a therapeutically effective amount of a compound of claim 1 or a pharmaceutically acceptable salt or prodrug thereof.

64. The method as recited in claim 63 wherein osteoporosis, osteotomy, childhood idiopathic bone loss or bone loss associated with periodontitis is treated.

65. The method as recited in claim 64 wherein osteoporosis is treated in a human.

66. The method as recited in claim 63 wherein glucocorticoid-induced osteoporosis, hyperthyroidism-induced osteoporosis, immobilization-induced osteoporosis, heparin-induced osteoporosis or immunosuppressive-induced osteoporosis is treated.

67. A method for augmenting and maintaining bone mass in a mammal comprising administering to a mammal a therapeutically effective amount of a compound of claim 1 or a pharmaceutically acceptable salt or prodrug thereof.

68. The method as recited in claim 67 wherein bone healing following facial reconstruction, maxillary reconstruction or mandibular reconstruction is treated, vertebral synostosis is induced or long bone extension is enhanced, the healing rate of a bone graft is enhanced or prosthetic ingrowth is enhanced.

69. The method as recited in claim 67 wherein a bone fracture is treated in a human.

70. A pharmaceutical composition which comprises a therapeutically effective amount of a compound of claim 1 or a pharmaceutically acceptable salt or prodrug thereof and a pharmaceutically acceptable carrier.

71. The pharmaceutical composition as recited in claim 70 for the treatment of osteoporosis wherein the therapeutically effective amount is an osteoporosis treating amount.

72. A pharmaceutical composition for the augmentation of bone mass which comprises a bone mass augmenting amount of a compound of claim 1 or a pharmaceutically acceptable salt or prodrug thereof and a pharmaceutically acceptable carrier.

73. The pharmaceutical composition as recited in claim 72 for the treatment of a bone fracture wherein a bone fracture treating amount of a compound of claim 1 or a pharmaceutically acceptable salt or prodrug thereof is used.

74. A pharmaceutical composition for the treatment of a condition which presents with low bone mass in a mammal which comprises a low bone mass condition treating amount of a compound of claim 1 or a pharmaceutically acceptable salt or prodrug thereof and a pharmaceutically acceptable carrier.

75. A pharmaceutical composition comprising:
   a. a therapeutically effective amount of a compound of claim 1 or a pharmaceutically acceptable salt or prodrug thereof;
   b. a therapeutically effective amount of an anti-resorptive agent; and
   c. a pharmaceutical carrier.

76. A pharmaceutical composition as recited in claim 75 wherein the anti-resorptive agent is droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]-naphthalen-2-ol, {4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone,
   Cis-6-(4-fluoro-phenyl)-5-[4-(2-piperidin-1-yl-ethoxy)-phenyl]-5,6,7,8-tetrahydro-naphthalen-2-ol;
   (−)-Cis-6-phenyl-5-[4-(2-pyrrolidin-1-yl-ethoxy)-phenyl]-5,6,7,8-tetrahydronaphthalene-2-ol;
   Cis-6-phenyl-5-[4-(2-pyrrolidin-1-yl-ethoxy)-phenyl]-5,6,7,8-tetrahydronaphthalene-2-ol;
   Cis-1-[6'-pyrrolodinoethoxy-3'-pyridyl]-2-phenyl-6-hydroxy-1,2,3,4-tetrahydrohaphthalene;
   1-(4'-Pyrrolidinoethoxyphenyl)-2-(4"-fluorophenyl)-6-hydroxy-1,2,3,4-tetrahydroisoquinoline;
   Cis-6-(4-hydroxyphenyl)-5-[4-(2-piperidin-1-yl-ethoxy)-phenyl]-5,6,7,8-tetrahydro-naphthalen-2-ol; or
   1-(4'-Pyrrolidinolethoxyphenyl)-2-phenyl-6-hydroxy-1,2,3,4-tetrahydroisoquinoline or a pharmaceutically acceptable salt thereof.

77. A pharmaceutical composition as recited in claim 75 wherein the anti-resorptive agent is tiludronic acid, alendronic acid, ibandronic acid, risedronic acid, etidronic acid, clodronic acid, and pamidronic Acid or a pharmaceutically acceptable salt thereof.

78. A method for treating a mammal having a condition which presents with low bone mass comprising administering to said mammal
   a. a therapeutically effective amount of a compound of claim 1 or a pharmaceutically acceptable salt or prodrug thereof; and
   b. a therapeutically effective amount of an anti-resorptive agent.

79. The method as recited in claim 78 wherein the anti-resorptive agent is droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]-naphthalen-2-ol, {4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone,
   Cis-6-(4-fluoro-phenyl)-5-[4-(2-piperidin-1-yl-ethoxy)-phenyl]-5,6,7,8-tetrahydro-naphthalen-2-ol;
   (−)-Cis-6-phenyl-5-[4-(2-pyrrolidin-1-yl-ethoxy)-phenyl]-5,6,7,8-tetrahydronaphthalene-2-ol;
   Cis-6-phenyl-5-[4-(2-pyrrolidin-1-yl-ethoxy)-phenyl]-5,6,7,8-tetrahydronaphthalene-2-ol;
   Cis-1-[6'-pyrrolodinoethoxy-3'-pyridyl]-2-phenyl-6-hydroxy-1,2,3,4-tetrahydrohaphthalene;
   1-(4'-Pyrrolidinoethoxyphenyl)-2-(4"-fluorophenyl)-6-hydroxy-1,2,3,4-tetrahydroisoquinoline;
   Cis-6-(4-hydroxyphenyl)-5-[4-(2-piperidin-1-yl-ethoxy)-phenyl]-5,6,7,8-tetrahydro-naphthalen-2-ol; or
   1-(4'-Pyrrolidinolethoxyphenyl)-2-phenyl-6-hydroxy-1,2,3,4-tetrahydroisoquinoline or a pharmaceutically acceptable salt thereof.

80. The method as recited in claim 78 wherein the anti-resorptive agent is, tiludronic acid, alendronic acid, ibandronic acid, risedronic acid, etidronic acid, clodronic acid, and pamidronic Acid or a pharmaceutically acceptable salt.

81. A kit comprising:
   a. a therapeutically effective amount of a compound of claim 1 or a pharmaceutically acceptable salt or prodrug thereof and a pharmaceutically acceptable carrier in a first unit dosage form;
   b. a therapeutically effective amount of an anti-resorptive agent and a pharmaceutically acceptable carrier in a second unit dosage form; and
   c. container means for containing said first and second dosage forms.

82. The kit as recited in claim 81 wherein the anti-resorptive agent is droloxifene, raloxifene, tamoxifen, 4-hydroxy-tamoxifen, toremifene, centchroman, levormeloxifene, idoxifene, 6-(4-hydroxy-phenyl)-5-[4-(2-piperidin-1-yl-ethoxy)-benzyl]-naphthalen-2-ol, {4-[2-(2-Aza-bicyclo[2.2.1 ]hept-2-yl)-ethoxy]-phenyl}-[6-hydroxy-2-(4-hydroxy-phenyl)-benzo[b]thiophen-3-yl]-methanone,
   Cis-6-(4-fluoro-phenyl)-5-[4-(2-piperidin-1-yl-ethoxy)-phenyl]-5,6,7,8-tetrahydro-naphthalen-2-ol;
   (−)-Cis-6-phenyl-5-[4-(2-pyrrolidin-1-yl-ethoxy)-phenyl]-5,6,7,8-tetrahydronaphthalene-2-ol;
   Cis-6-phenyl-5-[4-(2-pyrrolidin-1-yl-ethoxy)-phenyl]-5,6,7,8-tetrahydronaphthalene-2-ol;
   Cis-1-[6'-pyrrolodinoethoxy-3'-pyridyl]-2-phenyl-6-hydroxy-1,2,3,4-tetrahydrohaphthalene;
   1-(4'-Pyrrolidinoethoxyphenyl)-2-(4"-fluorophenyl)-6-hydroxy-1,2,3,4-tetrahydroisoquinoline;
   Cis-6-(4-hydroxyphenyl)-5-[4-(2-piperidin-1-yl-ethoxy)-phenyl]-5,6,7,8-tetrahydro-naphthalen-2-ol; or
   1-(4'-Pyrrolidinolethoxyphenyl)-2-phenyl-6-hydroxy-1,2,3,4-tetrahydroisoquinoline or a pharmaceutically acceptable salt thereof.

83. The kit as recited in 81 wherein the anti-resorptive agent is tiludronic acid, alendronic acid, ibandronic acid, risedronic acid, etidronic acid, clodronic acid, and pamidronic Acid or a pharmaceutically acceptable salt thereof.

84. A pharmaceutical composition comprising:
   a. a therapeutically effective amount of a compound of claim 1 or a pharmaceutically acceptable salt or prodrug thereof;

b. a therapeutically effective amount of an anabolic agent other than a compound of claim 1 or a pharmaceutically acceptable salt or prodrug thereof; and c. a pharmaceutical carrier.

85. The pharmaceutical composition as recited in claim 84 wherein the anabolic agent other than the claim 1 compound is IGF-1 optionally with IGF-1 binding protein 3 prostaglandin, prostaglandin agonist/antagonist, sodium fluoride, parathyroid hormone (PTH), active fragments of parathyroid hormone, growth hormone or growth hormone secretagogues or a pharmaceutically acceptable salt thereof.

86. A method for treating a mammal which presents with low bone mass comprising administering to said a. a therapeutically effective amount of a compound of claim 1 or a pharmaceutically acceptable salt or prodrug thereof; and b. a therapeutically effective amount of a bone anabolic agent other than a compound of claim 1 or a pharmaceutically acceptable salt or prodrug thereof.

87. The method as recited in claim 86 wherein the anabolic agent other than the claim 1 compound is IGF-1, prostaglandin, prostaglandin agonist/antagonist, sodium fluoride, parathyroid hormone (PTH), active fragments of parathyroid hormone, growth hormone or growth hormone secretagogues or a pharmaceutically acceptable salt thereof.

88. A kit comprising:

a. a therapeutically effective amount of a compound of claim 1 or a pharmaceutically acceptable salt or prodrug thereof and a pharmaceutically acceptable carrier in a first unit dosage form;

b. a therapeutically effective amount of an anabolic agent other than a compound of claim 1 or a pharmaceutically acceptable salt or prodrug thereof and a pharmaceutically acceptable carrier in a second unit dosage form; and c. container means for containing said first and second dosage forms.

89. The kit as recited in claim 88 wherein the anabolic agent other than the claim 1 compound is IGF-1, prostaglandin, prostaglandin agonist/antagonist, sodium fluoride, parathyroid hormone (PTH), active fragments of parathyroid hormone, growth hormone or growth hormone secretagogues or a pharmaceutically acceptable salt thereof.

90. A compound as recited in claim 1 wherein

A is $(C_1-C_3)$ alkyl;

Q is

—$(C_3-C_5)$alkylene—O—$(C_1-C_3)$alkylene-,

—$(C_5-C_7)$alkylene-, said —$(C_5-C_7)$alkylene-optionally substituted with up to four substituents independently selected from fluoro or $(C_1-C_4)$alkyl, —$(C_2-C_4)$alkylene-X-, —$(CH_2)$-meta-phenylene-O-$(CH_2)$-optionally mono- or di- substituted independently with methoxy, trifluoromethyl, difluoromethoxy, trifluoromethoxy, chloro or fluoro or —$(CH_2)$-meta-phenylene-$(CH_2)$-optionally mono- or di- substituted independently with methoxy, trifluoromethyl, difluoromethoxy, trifluoromethoxy, chloro or fluoro;

M is —$Ar^1$—V—$Ar^2$ or —$Ar^1$—O—$Ar^2$;

V is a bond or —$CH_2$-;

Z is carboxyl, $(C_1-C_4)$alkoxycarbonyl or tetrazolyl;

X is thienyl, thiazolyl, or furanyl;

K is methylene;

$Ar^1$ is furanyl, thienyl, thiazolyl, or pyridyl;

$Ar^2$ is thienyl, thiazolyl, pyridyl, pyrimidyl, oxazolyl, furanyl, imidazolyl, isoxazolyl, pyrazinyl, triazolyl or pyrazolyl;

$R^1$ is chloro, fluoro, $(C_1-C_4)$alkyl or $(C_1-C_4)$alkoxy, said $(C_1-C_4)$alkyl and $(C_1-C_4)$alkoxy optionally mono-, di- or tri-substituted independently with hydroxy or fluoro; and $R^2$ and $R^3$ are each independently, methoxy, trifluoromethyl, difluoromethoxy, trifluoromethoxy, chloro or fluoro.

91. A compound as recited in claim 90 wherein

Q is

—$(CH_2)$-meta-phenylene-$(CH_2)$-,

M is —$Ar^1$—$Ar^2$, $Ar^1$ is phenyl;

$Ar^2$ is $(C_5-C_7)$cycloalkyl, phenyl, thienyl, thiazolyl, pyridyl, pyrimidyl, oxazolyl, furanyl, imidazolyl, isoxazolyl, pyrazinyl or pyrazolyl, said $Ar^2$ optionally mono- or di- substituted independently with $R^1$ or $R^2$;

$R^1$ is chloro, fluoro, methyl, methoxy, trifluoromethyl, difluoromethoxy or trifluoromethoxy; and $R^2$ is methoxy, chloro or fluoro.

92. A compound as recited in claim 90 wherein

Q is

—$(CH_2)$-meta-phenylene—O—$(CH_2)$-,

M is —$Ar^1$—$Ar^2$, $Ar^1$ is phenyl;

$Ar^2$ is $(C_5-C_7)$cycloalkyl, phenyl, thienyl, thiazolyl, pyridyl, pyrimidyl, oxazolyl, furanyl, imidazolyl, isoxazolyl, pyrazinyl or pyrazolyl, said $Ar^2$ optionally mono- or di- substituted independently with $R^1$ or $R^2$;

$R^1$ is chloro, fluoro, methyl, methoxy, trifluoromethyl, difluoromethoxy or trifluoromethoxy; and $R^2$ is methoxy, chloro or fluoro.

93. A compound of claim 91 wherein

A is methylsulfonyl;

Z is carboxyl; and

M is 4-(cyclohexyl)phenyl.

94. A compound of claim 91 wherein

A is methylsulfonyl;

Z is carboxyl; and

M is 4-(thiazol-2-yl)phenyl.

95. A compound of claim 91 wherein

A is methylsulfonyl;

Z is carboxyl; and

M is 4-(pyrazin-2-yl)phenyl.

96. A compound as recited in claim 91 wherein the compound is a. (3-{[(4-Cyclohexyl-benzyl)-methanesulfonyl-amino]-methyl}-phenyl)-acetic acid;

b. (3-{[Methanesulfonyl-(4-thiazol-2-yl-benzyl)-amino]-methyl}-phenyl)-acetic acid; or c. (3-{[Methanesulfonyl-(4-pyrazin-2-yl-benzyl)-amino]-methyl}-phenyl)-acetic acid.

97. A compound as recited in claim 1 wherein

A is $(C_1-C_3)$alkyl;

Q is —$(C_2-C_4)$alkylene-X-;

X is thiazolyl or furanyl; said thiazolyl or furanyl optionally mono- or di- substituted independently with methyl, methoxy, fluoro, chloro, trifluoromethyl, difluoromethoxy or trifluoromethoxy;

K is oxy-ethylene or propylene, said propylene optionally being mono-unsaturated;

M is —Ar, said —Ar is thienyl, pyridyl, thiazolyl, oxazolyl, isoxazolyl, pyrimidyl or imidazolyl;

$R^1$ is halo, $(C_1-C_6)$alkoxy, $(C_1-C_7)$alkyl, $(C_3-C_7)$cycloalkyl, $(C_1-C_7)$alkanoyl or $(C_3-C_7)$cycloalkyl$(C_1-C_4)$alkyl, said $(C_1-C_6)$alkoxy, $(C_1-C_7)$alkyl, $(C_3-C_7)$cycloalkyl, $(C_1-C_7)$alkanoyl or $(C_3-C_7)$cycloalkyl$(C_1-C_4)$alkyl, optionally mono-, di- or tri-substituted independently with hydroxy, fluoro or chloro; and $R^2$ and $R^3$ are each independently methoxy, trifluoromethyl, difluoromethoxy, trifluoromethoxy, chloro or fluoro.

98. A compound having the Formula IA

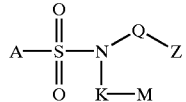

Formula 1A or a pharmaceutically acceptable salt or prodrug thereof wherein

A is $(C_1-C_6)$alkyl, $(C_3-C_7)$cycloalkyl or, $(C_3-C_7)$cycloalkyl$(C_1-C_6)$alkyl; said A moieties optionally mono-, di- or tri-substituted on carbon independently with hydroxy, $(C_1-C_4)$alkyl or halo;

Q is

—$(C_2-C_6)$alkylene-W—$(C_1-C_3)$alkylene-,

—$(C_3-C_8)$alkylene-, said —$(C_3-C_8)$alkylene- being straight chain with the proviso that $(C_3-C_8)$ alkylene may optionally substituted with up to four substituents independently selected from fluoro or $(C_1-C_4)$alkyl, —X—$(C_1-C_5)$alkylene-, —$(C_1-C_5)$alkylene-X-, —$(C_1-C_3)$alkylene-X—$(C_1-C_3)$alkylene-, —$(C_2-C_4)$alkylene-W-X—$(C_0-C_3)$alkylene-, —$(C_0-C_4)$alkylene-X-W—$(C_1-C_3)$alkylene-, —$(C_2-C_5)$alkylene-W-X-W—$(C_1-C_3)$alkylene-, wherein the two occurrences of W are independent of each other, —$(C_1-C_4)$alkylene-ethenylene—$(C_1-C_4)$alkylene-, —$(C_1-C_4)$alkylene-ethenylene—$(C_0-C_2)$alkylene-X—$(C_0-C_5)$alkylene-, —$(C_1-C_4)$alkylene-ethenylene—$(C_0-C_2)$alkylene-X-W—$(C_1-C_3)$alkylene-, —$(C_1-C_4)$alkylene-ethynylene—$(C_1-C_4)$alkylene-, or —$(C_1-C_4)$alkylene-ethynylene-X—$(C_0-C_3)$alkylene-;

W is oxy, thio, sulfino, sulfonyl, aminosulfonyl-, -mono-N—$(C_1-C_4)$alkyleneaminosulfonyl-, sulfonylamino, N—$(C_1-C_4)$alkylenesulfonylamino, carboxamido, N—$(C_1-C_4)$alkylenecarboxamido, carboxamidooxy, N—$(C_1-C_4)$ alkylenecarboxamidooxy, carbamoyl, -mono-N—$(C_1-C_4)$alkylenecarbamoyl, carbamoyloxy, or -mono-N—$(C_1-C_4)$alkylenecarbamoyloxy, wherein said W alkyl groups are optionally substituted on carbon with one to three fluorines;

X is tetrahydrofuranyl or a five or six membered aromatic ring optionally having one or two heteroatoms selected independently from oxygen, nitrogen, and sulfur; said ring optionally mono-, or di- substituted independently with halo, $(C_1-C_3)$alkyl, trifluoromethyl, trifluoromethyloxy, difluoromethyloxy, hydroxyl, $(C_1-C_4)$alkoxy, or carbamoyl;

Z is carboxyl, $(C_1-C_6)$alkoxycarbonyl, tetrazolyl, 1,2,4-oxadiazolyl, 5-oxo-1,2,4-oxadiazolyl, 5-oxo-1,2,4-thiadiazolyl, $(C_1-C_4)$alkylsulfonylcarbamoyl or phenylsulfonylcarbamoyl;

K is a bond, $(C_1-C_8)$alkylene, thio$(C_1-C_4)$alkylene or oxy$(C_1-C_4)$alkylene, said $(C_1-C_8)$alkylene optionally mono-unsaturated and wherein K is optionally mono-, di- or tri-substituted independently with fluoro, methyl or chloro;

M is —Ar, —$Ar^1$—V—$Ar^2$, —$Ar^1$—S—$Ar^2$, —$Ar^1$—O—$Ar^2$, —Ar—S—$(C_1-C_3)$—$Ar^2$-, —$Ar^1$—$(C_1-C_3)$—S—$Ar^2$— or —$Ar^1$—$(C_1-C_3)$—S—$(C_1-C_3)$—$Ar^2$, wherein Ar, $Ar^1$ and $Ar^2$ are each independently a partially saturated, fully saturated or fully unsaturated five to eight membered ring having one to four heteroatoms selected independently from oxygen, sulfur and nitrogen, or a bicyclic ring consisting of two fused partially saturated, fully saturated or fully unsaturated five or six membered rings, taken independently, having one to four heteroatoms selected independently from nitrogen, sulfur and oxygen;

said Ar, $Ar^1$ and $Ar^2$ moieties optionally substituted, on one ring if the moiety is monocyclic, or one or both rings if the moiety is bicyclic, on carbon, nitrogen or sulfur with up to three substituents independently selected from $R^1$, $R^2$ and $R^3$ wherein $R^1$, $R^2$ and $R^3$ are oxo, hydroxy, nitro, halo, $(C_1-C_6)$alkoxy, $(C_1-C_4)$alkoxy$(C_1-C_4)$alkyl, $(C_1-C_4)$alkoxycarbonyl, $(C_1-C_7)$alkyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, sulfonamido, $(C_1-C_4)$alkylsulfonamido, amino, mono-N- or di-N,N—$(C_1-C_4)$alkylamino, carbamoyl, mono-N- or di-N,N—$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N- or di-N,N—$(C_1-C_4)$alkylaminosulfinyl;

$R^1$, $R^2$ and $R^3$ are optionally mono-, di- or tri-substituted on carbon independently with halo or hydroxy; and V is a bond or $(C_1-C_3)$alkylene optionally mono-unsaturated and optionally mono- or di- substituted independently with hydroxy or fluoro.

99. A pharmaceutical composition comprising:

a. a therapeutically effective amount of a compound of claim 98 or a pharmaceutically acceptable salt or prodrug thereof;

b. a therapeutically effective amount of 2-(4-methoxyphenyl)-3-[4-(2-piperidin-1-yl-ethoxy)-phenoxy]-benzo[b]thiophen-6-ol or a pharmaceutically acceptable salt thereof or 3-[4-(1,2-diphenyl-but-1-enyl)-phenyl]-acrylic Acid or a pharmaceutically acceptable salt thereof and c. a pharmaceutical carrier.

100. A method for treating a mammal having a condition which presents with low bone mass comprising administering to said mammal a. a therapeutically effective amount of a compound of claim 98 or a pharmaceutically acceptable salt or prodrug thereof; and b. a therapeutically effective amount of 2-(4-methoxyphenyl)-3-[4-(2-piperidin-1-yl-ethoxy)-phenoxy]- benzo[b]thiophen-6-ol or a pharmaceutically acceptable salt thereof or 3-[4-(1,2-diphenyl-but-1-enyl)-phenyl]-acrylic Acid or pharmaceutically acceptable salt thereof.

101. A kit comprising:
a. a therapeutically effective amount of a compound of claim 98 or a pharmaceutically acceptable salt or prodrug thereof and a pharmaceutically acceptable carrier in a first unit dosage form;
b. a therapeutically effective amount of 2-(4-methoxy-phenyl)-3-[4-(2-piperidin-1-yl-ethoxy)-phenoxy]-benzo[b]thiophen-6-ol or a pharmaceutically acceptable salt thereof or 3-[4-(1,2-diphenyl-but-1-enyl)-phenyl]-acrylic Acid or a pharamceutically acceptable salt thereof and a pharmaceutically acceptable carrier in a second unit dosage form; and
c. container means for containing said first and second dosage forms.

102. A method for treating a mammal in need of kidney regeneration comprising administering to said mammal a therapeutically effective amount of a compound of claim 98 or a pharmaceutically acceptable salt or prodrug thereof.

103. A method for treating a mammal having a condition which presents with low bone mass comprising administering to said mammal a therapeutically effective amount of a compound of claim 98 or a pharmaceutically acceptable salt or prodrug thereof.

104. A pharmaceutical composition which comprises a therapeutically effective amount of a compound of claim 98 or a pharmaceutically acceptable salt or prodrug thereof and a pharmaceutically acceptable carrier.

* * * * *